US008304189B2

(12) United States Patent
Chesnut et al.

(10) Patent No.: US 8,304,189 B2
(45) Date of Patent: Nov. 6, 2012

(54) NUCLEIC ACID MOLECULES CONTAINING RECOMBINATION SITES AND METHODS OF USING THE SAME

(75) Inventors: Jon Chesnut, Carlsbad, CA (US); Louis Leong, Junction City, OR (US)

(73) Assignee: Life Technologies Corporation, Carlsbad, CA (US)

( * ) Notice: Subject to any disclaimer, the term of this patent is extended or adjusted under 35 U.S.C. 154(b) by 437 days.

(21) Appl. No.: 11/000,371

(22) Filed: Dec. 1, 2004

(65) Prior Publication Data

US 2005/0208530 A1 Sep. 22, 2005

Related U.S. Application Data

(60) Provisional application No. 60/525,672, filed on Dec. 1, 2003.

(51) Int. Cl.
C12Q 1/68 (2006.01)
C12N 15/87 (2006.01)
C12N 15/11 (2006.01)
C12N 15/64 (2006.01)

(52) U.S. Cl. ............... 435/6.11; 435/6.1; 435/320.1; 435/91.4; 435/462; 536/24.33

(58) Field of Classification Search ............... None
See application file for complete search history.

(56) References Cited

U.S. PATENT DOCUMENTS

| | | | |
|---|---|---|---|
| 462,505 A | 11/1891 | Parker et al. |
| 4,045,420 A | 8/1977 | Soffer et al. |
| 4,216,245 A | 8/1980 | Johnson |
| 4,293,652 A | 10/1981 | Cohen |
| 4,331,808 A | 5/1982 | Buckler et al. |
| 4,372,745 A | 2/1983 | Mandle et al. |
| 4,420,568 A | 12/1983 | Wang et al. |
| 4,458,066 A | 7/1984 | Caruthers et al. |
| 4,517,338 A | 5/1985 | Urdea et al. |
| 4,525,048 A | 6/1985 | Wong et al. |
| 4,555,166 A | 11/1985 | Enomoto |
| 4,585,862 A | 4/1986 | Wang et al. |
| 4,626,505 A | 12/1986 | Falco |
| 4,661,450 A | 4/1987 | Kempe et al. |
| 4,668,640 A | 5/1987 | Wang et al. |
| 4,670,572 A | 6/1987 | Hinshaw |
| 4,673,640 A | 6/1987 | Backman |
| 4,683,195 A | 7/1987 | Mullis et al. |
| 4,683,202 A | 7/1987 | Mullis |
| 4,736,866 A | 4/1988 | Leder et al. |
| 4,743,546 A | 5/1988 | Backman et al. |
| 4,745,051 A | 5/1988 | Smith et al. |
| 4,745,076 A | 5/1988 | Muller et al. |
| 4,795,699 A | 1/1989 | Tabor et al. |
| 4,797,368 A | 1/1989 | Carter et al. |
| 4,800,159 A | 1/1989 | Mullis et al. |
| 4,808,537 A | 2/1989 | Stroman et al. |
| 4,855,231 A | 8/1989 | Stroman et al. |
| 4,859,587 A | 8/1989 | Roizman |
| 4,873,191 A | 10/1989 | Wagner et al. |
| 4,879,239 A | 11/1989 | Daggett et al. |
| 4,889,818 A | 12/1989 | Gelfand et al. |
| 4,959,217 A | 9/1990 | Sanders et al. |
| 4,959,317 A | 9/1990 | Sauer |
| 4,960,707 A | 10/1990 | Lacks |
| 4,962,020 A | 10/1990 | Tabor et al. |
| 4,965,188 A | 10/1990 | Mullis et al. |
| 4,987,071 A | 1/1991 | Cech et al. |
| 5,047,342 A | 9/1991 | Chatterjee |
| 5,077,214 A | 12/1991 | Guarino et al. |
| 5,079,352 A | 1/1992 | Gelfand et al. |
| 5,082,784 A | 1/1992 | Chatterjee et al. |
| 5,093,257 A | 3/1992 | Gray |
| 5,098,839 A | 3/1992 | Polisson |
| 5,102,797 A | 4/1992 | Tucker et al. |
| 5,104,621 A | 4/1992 | Pfost et al. |
| 5,120,653 A | 6/1992 | Henderson |
| 5,125,748 A | 6/1992 | Bjornson et al. |
| 5,139,744 A | 8/1992 | Kowalski |
| 5,139,942 A | 8/1992 | Benner |
| 5,147,608 A | 9/1992 | Hudson et al. |
| 5,147,800 A | 9/1992 | Hammond et al. |
| 5,155,037 A | 10/1992 | Summers |
| 5,159,062 A | 10/1992 | Knapp et al. |
| 5,162,209 A | 11/1992 | Scheele |
| 5,162,222 A | 11/1992 | Guarino et al. |
| 5,169,784 A | 12/1992 | Summers et al. |
| 5,173,411 A | 12/1992 | Tabor et al. |

(Continued)

FOREIGN PATENT DOCUMENTS

CA 2141412 2/1994

(Continued)

OTHER PUBLICATIONS

Ohara and Temple, Directional cDNA library construction assisted by the in vitro recombination reaction, NAR, 2001, vol. 29 (4), pp. 1-8.*
Murphy, The Dropsophila Gateway Vector Clollection, 2003, downloaded Jul. 21, 2007, pp. 1-14.*
Hsu and Landy, Resolution of synthetic att-site Holliday structures by the integrase protein of bacteriophage λ, Nature. Oct. 25, 1984; 311(5988): 721-726.*
"Biochemistry", No. 43, 12746-12751.
"Honing your cloning", vol. 14, No. 16, *The Scientist* URL : http://www.the-scientist.com/yr2000/aug/profile1_000821.html Aug. 21, 2000, p. 29.
"The Echo(TM) cloning system: The Future of cloning is here", *Invitrogen Online Catalog* URL:http://web.archive.org/web/20000711064556/www.invitrogen.com/catalog_echo.html> Jul. 11, 2000.
"The EchoCTM) cloning system: The Future of cloning is here", *Invitrogen Online Catalog*, [Online] URL:http://invitrogen.com/content.cfm?pageid=3371&cfid=16767784&cftoken=62396683> Jul. 7, 2004, 6.

(Continued)

*Primary Examiner* — Maria Marvich

(57) ABSTRACT

The present invention relates to the fields of biotechnology and molecular biology. In particular, the present invention relates to the construction and use of nucleic acid molecules comprising cloning sites which differ in nucleotide sequence. In particular embodiments, the present invention relates to nucleic acid molecules which contain recombination sites with different primer binding sites. These different primer binding sites may be used to sequence different ends of nucleic acid segments located between the two recombination sites.

7 Claims, 14 Drawing Sheets

U.S. PATENT DOCUMENTS

| | | |
|---|---|---|
| 5,179,015 A | 1/1993 | Wilson et al. |
| 5,192,675 A | 3/1993 | Chatterjee et al. |
| 5,200,333 A | 4/1993 | Wilson |
| 5,202,248 A | 4/1993 | Vancott |
| 5,206,568 A | 4/1993 | Bjornson et al. |
| 5,221,623 A | 6/1993 | Legocki |
| 5,227,288 A | 7/1993 | Blattner |
| 5,231,021 A | 7/1993 | Chatterjee |
| 5,242,681 A | 9/1993 | Elgavish et al. |
| 5,244,797 A | 9/1993 | Kotewicz et al. |
| 5,244,805 A | 9/1993 | Miller |
| 5,248,605 A | 9/1993 | Chatterjee |
| 5,252,466 A | 10/1993 | Cronan, Jr. |
| 5,252,479 A | 10/1993 | Srivastava |
| 5,258,294 A | 11/1993 | Boyle et al. |
| 5,262,176 A | 11/1993 | Palmacci |
| 5,270,170 A | 12/1993 | Schatz et al. |
| 5,270,179 A | 12/1993 | Chatterjee |
| 5,283,173 A | 2/1994 | Fields et al. |
| 5,286,632 A | 2/1994 | Jones |
| 5,304,480 A | 4/1994 | Chatterjee |
| 5,312,746 A | 5/1994 | Longo |
| 5,334,375 A | 8/1994 | Nabi et al. |
| 5,334,526 A | 8/1994 | Smith et al. |
| 5,334,575 A | 8/1994 | Noonan et al. |
| 5,346,818 A | 9/1994 | Schafer |
| 5,348,886 A | 9/1994 | Lee et al. |
| 5,350,564 A | 9/1994 | Mazza et al. |
| 5,354,668 A | 10/1994 | Auerbach |
| 5,355,215 A | 10/1994 | Schroeder |
| 5,368,823 A | 11/1994 | McGraw |
| 5,374,553 A | 12/1994 | Gelfand et al. |
| 5,378,618 A | 1/1995 | Sternberg et al. |
| 5,409,818 A | 4/1995 | Davey et al. |
| 5,412,087 A | 5/1995 | McGall et al. |
| 5,434,006 A | 7/1995 | Goelff et al. |
| 5,434,049 A | 7/1995 | Okano et al. |
| 5,434,066 A | 7/1995 | Bebee et al. |
| 5,436,146 A | 7/1995 | Shenk |
| 5,436,327 A | 7/1995 | Southern et al. |
| 5,436,746 A | 7/1995 | Hirst |
| 5,445,934 A | 8/1995 | Fodor et al. |
| 5,451,513 A | 9/1995 | Maliga et al. |
| 5,464,764 A | 11/1995 | Capecchi et al. |
| 5,470,727 A | 11/1995 | Mascarenhas et al. |
| 5,470,740 A | 11/1995 | Longo |
| 5,487,933 A | 1/1996 | White |
| 5,487,993 A | 1/1996 | Herrnstadt |
| 5,492,841 A | 2/1996 | Craig |
| 5,512,462 A | 4/1996 | Cheng |
| H153100 | 5/1996 | Blumentals et al. |
| 5,527,695 A | 6/1996 | Hodges et al. |
| 5,534,428 A | 7/1996 | Longo |
| 5,538,848 A | 7/1996 | Livak et al. |
| 5,552,314 A | 9/1996 | Greener |
| 5,573,904 A | 11/1996 | Mattingly |
| 5,583,038 A | 12/1996 | Stover |
| 5,589,351 A | 12/1996 | Harootunian |
| 5,591,609 A | 1/1997 | Auerbach |
| 5,597,910 A | 1/1997 | Gudibande |
| 5,599,695 A | 2/1997 | Pease et al. |
| 5,601,980 A | 2/1997 | Gordon |
| 5,605,793 A | 2/1997 | Stemmer |
| 5,605,802 A | 2/1997 | Trono |
| 5,614,365 A | 3/1997 | Tabor et al. |
| 5,614,389 A | 3/1997 | Auerbach |
| 5,622,821 A | 4/1997 | Selvin et al. |
| 5,624,803 A | 4/1997 | Noonberg et al. |
| 5,624,826 A | 4/1997 | Kato et al. |
| 5,628,982 A | 5/1997 | Lauffer et al. |
| 5,631,153 A | 5/1997 | Capecchi et al. |
| 5,631,169 A | 5/1997 | Lakowicz |
| 5,635,381 A | 6/1997 | Hooykaas et al. |
| 5,637,685 A | 6/1997 | Soares et al. |
| 5,639,615 A | 6/1997 | Selvin |
| 5,650,289 A | 7/1997 | Wood |
| 5,650,308 A | 7/1997 | Baum |
| 5,650,557 A | 7/1997 | Hannah et al. |
| 5,654,149 A | 8/1997 | Mendoza et al. |
| 5,654,182 A | 8/1997 | Wahl et al. |
| 5,654,185 A | 8/1997 | Palsson et al. |
| 5,656,207 A | 8/1997 | Woodhead |
| 5,656,433 A | 8/1997 | Selvin et al. |
| 5,658,722 A | 8/1997 | Margolis-Nunno |
| 5,658,772 A | 8/1997 | Odell et al. |
| 5,672,344 A | 9/1997 | Kelley et al. |
| 5,674,713 A | 10/1997 | McElroy et al. |
| 5,677,170 A | 10/1997 | Devine et al. |
| 5,677,177 A | 10/1997 | Wahl et al. |
| 5,681,741 A | 10/1997 | Atwood |
| 5,683,888 A | 11/1997 | Campbell |
| 5,686,279 A | 11/1997 | Finer et al. |
| 5,695,971 A | 12/1997 | Kadokami et al. |
| 5,710,248 A | 1/1998 | Grose |
| 5,721,435 A | 2/1998 | Troll |
| 5,723,765 A | 3/1998 | Oliver et al. |
| 5,728,551 A | 3/1998 | Devine et al. |
| 5,731,149 A | 3/1998 | Selsted et al. |
| 5,733,733 A | 3/1998 | Auerbach |
| 5,733,743 A | 3/1998 | Johnson et al. |
| 5,736,388 A | 4/1998 | Chada et al. |
| 5,741,486 A | 4/1998 | Pathak et al. |
| 5,741,657 A | 4/1998 | Tsien et al. |
| 5,741,715 A | 4/1998 | Ghoshal et al. |
| 5,744,305 A | 4/1998 | Fodor et al. |
| 5,744,336 A | 4/1998 | Hodges et al. |
| 5,746,997 A | 5/1998 | Reed |
| 5,763,170 A | 6/1998 | Raybuck |
| 5,763,239 A | 6/1998 | Short |
| 5,766,891 A | 6/1998 | Shuman |
| 5,776,449 A | 7/1998 | Baum et al. |
| 5,777,079 A | 7/1998 | Tsien et al. |
| 5,786,139 A | 7/1998 | Burke et al. |
| 5,789,156 A | 8/1998 | Bujard et al. |
| 5,789,375 A | 8/1998 | Mukae |
| 5,800,992 A | 9/1998 | Fodor et al. |
| 5,800,999 A | 9/1998 | Bronstein et al. |
| 5,801,030 A | 9/1998 | McVey et al. |
| 5,804,387 A | 9/1998 | Cormack et al. |
| 5,804,395 A | 9/1998 | Schade et al. |
| 5,804,431 A | 9/1998 | Palsson |
| 5,807,522 A | 9/1998 | Brown et al. |
| 5,807,746 A | 9/1998 | Lin et al. |
| 5,811,252 A | 9/1998 | Verheijen |
| 5,811,274 A | 9/1998 | Palsson |
| 5,814,300 A | 9/1998 | Scott et al. |
| 5,827,657 A | 10/1998 | Herrnstadt et al. |
| 5,830,707 A | 11/1998 | Bushman |
| 5,834,256 A | 11/1998 | Finer et al. |
| 5,837,242 A | 11/1998 | Holliger et al. |
| 5,837,458 A | 11/1998 | Minshull et al. |
| 5,843,746 A | 12/1998 | Tatsumi et al. |
| 5,843,772 A | 12/1998 | Devine et al. |
| 5,846,721 A | 12/1998 | Soares et al. |
| 5,851,808 A | 12/1998 | Elledge et al. |
| 5,856,144 A | 1/1999 | Mierendorf et al. |
| 5,858,657 A | 1/1999 | Winter et al. |
| 5,858,740 A | 1/1999 | Finer et al. |
| 5,871,907 A | 2/1999 | Winter et al. |
| 5,874,259 A | 2/1999 | Szybalski |
| 5,876,946 A | 3/1999 | Burbaum et al. |
| 5,877,021 A | 3/1999 | Stinchcomb et al. |
| 5,888,732 A | 3/1999 | Hartley et al. |
| 5,888,795 A | 3/1999 | Hamilton |
| 5,889,165 A | 3/1999 | Fodor |
| 5,910,438 A | 6/1999 | Bernard et al. |
| 5,916,804 A | 6/1999 | Bushman |
| 5,917,012 A | 6/1999 | Nishikata |
| 5,919,676 A | 7/1999 | Graham et al. |
| 5,922,535 A | 7/1999 | Huo |
| 5,928,914 A | 7/1999 | Leboulch et al. |
| 5,929,307 A | 7/1999 | Hodges et al. |
| 5,932,474 A | 8/1999 | Tsien et al. |
| 5,939,301 A | 8/1999 | Hughes et al. |
| 5,948,653 A | 9/1999 | Pati et al. |
| 5,955,280 A | 9/1999 | Vidal |
| 5,955,604 A | 9/1999 | Tsien et al. |

| Patent No. | Date | Inventor |
|---|---|---|
| 5,958,681 A | 9/1999 | Wetmur et al. |
| 5,962,255 A | 10/1999 | Griffiths et al. |
| 5,965,408 A | 10/1999 | Short |
| 5,981,177 A | 11/1999 | Demirjian et al. |
| 5,981,182 A | 11/1999 | Jacobs et al. |
| 5,981,275 A | 11/1999 | Armentano et al. |
| 5,989,835 A | 11/1999 | Dunlay et al. |
| 5,989,872 A | 11/1999 | Luo et al. |
| 5,994,106 A | 11/1999 | Kovesdi et al. |
| 5,994,136 A | 11/1999 | Naldini et al. |
| 5,998,205 A | 12/1999 | Hallenbeck et al. |
| 5,998,208 A | 12/1999 | Fraefel et al. |
| 6,001,574 A | 12/1999 | Short et al. |
| 6,008,378 A | 12/1999 | Tsien et al. |
| 6,010,884 A | 1/2000 | Griffiths et al. |
| 6,013,440 A | 1/2000 | Lipshutz et al. |
| 6,013,516 A | 1/2000 | Verma et al. |
| 6,024,192 A | 2/2000 | Griffin |
| 6,025,192 A | 2/2000 | Beach et al. |
| 6,031,094 A | 2/2000 | Tsien et al. |
| 6,040,138 A | 3/2000 | Lockhart et al. |
| 6,040,174 A | 3/2000 | Imler et al. |
| 6,040,430 A | 3/2000 | Stewart |
| 6,051,427 A | 4/2000 | Finer et al. |
| 6,054,271 A | 4/2000 | Tsien et al. |
| 6,054,295 A | 4/2000 | Chen |
| 6,057,098 A | 5/2000 | Buechler et al. |
| 6,063,627 A | 5/2000 | McVey et al. |
| 6,066,776 A | 5/2000 | Goodwin |
| 6,066,778 A | 5/2000 | Ginsburg et al. |
| 6,072,046 A | 6/2000 | Reed et al. |
| 6,074,853 A | 6/2000 | Pati et al. |
| 6,080,576 A | 6/2000 | Zambrowicz et al. |
| 6,083,712 A | 7/2000 | Birch et al. |
| 6,086,902 A | 7/2000 | Zamb et al. |
| 6,088,214 A | 7/2000 | Dendy et al. |
| 6,090,590 A | 7/2000 | Kao |
| 6,096,551 A | 8/2000 | Barbas |
| 6,110,426 A | 8/2000 | Shalon et al. |
| 6,110,735 A | 8/2000 | Chartier et al. |
| 6,112,421 A | 9/2000 | Greene |
| 6,117,635 A | 9/2000 | Nazarenko et al. |
| 6,120,764 A | 9/2000 | Graham et al. |
| 6,121,043 A | 9/2000 | Cochran et al. |
| 6,127,175 A | 10/2000 | Vigne et al. |
| 6,130,364 A | 10/2000 | Jakobovits et al. |
| 6,133,028 A | 10/2000 | Imler et al. |
| 6,135,061 A | 10/2000 | Valcic |
| 6,136,594 A | 10/2000 | Dalemans et al. |
| 6,140,086 A | 10/2000 | Fox et al. |
| 6,140,087 A | 10/2000 | Graham et al. |
| 6,143,530 A | 11/2000 | Crouzet et al. |
| 6,143,557 A | 11/2000 | Hartley et al. |
| 6,156,497 A | 12/2000 | Kaleko |
| 6,165,782 A | 12/2000 | Naldini et al. |
| 6,171,820 B1 | 1/2001 | Short |
| 6,171,861 B1 | 1/2001 | Hartley et al. |
| 6,174,669 B1 | 1/2001 | Hayashizaki et al. |
| 6,180,407 B1 | 1/2001 | Bernard et al. |
| 6,190,907 B1 | 2/2001 | Kim |
| 6,190,908 B1 | 2/2001 | Kang et al. |
| 6,194,183 B1 | 2/2001 | Markvardsen |
| 6,194,191 B1 | 2/2001 | Zhang et al. |
| 6,197,584 B1 | 3/2001 | Bennett et al. |
| 6,200,812 B1 | 3/2001 | Pati et al. |
| 6,204,060 B1 | 3/2001 | Mehtali et al. |
| 6,218,128 B1 | 4/2001 | Klein et al. |
| 6,218,187 B1 | 4/2001 | Finer et al. |
| 6,225,121 B1 | 5/2001 | Savakis et al. |
| 6,227,620 B1 | 5/2001 | Page |
| 6,228,646 B1 | 5/2001 | Hardy |
| 6,238,884 B1 | 5/2001 | Short et al. |
| 6,248,520 B1 | 6/2001 | Roeder et al. |
| 6,248,526 B1 | 6/2001 | Weimer |
| 6,255,060 B1 | 7/2001 | Eberwine |
| 6,258,536 B1 | 7/2001 | Oliner et al. |
| 6,261,776 B1 | 7/2001 | Pirrung et al. |
| 6,261,797 B1 | 7/2001 | Sorge et al. |
| 6,261,807 B1 | 7/2001 | Crouzet et al. |
| 6,262,341 B1 | 7/2001 | Baszczynski et al. |
| 6,265,546 B1 | 7/2001 | Cohen et al. |
| 6,268,169 B1 | 7/2001 | Fahnestock |
| 6,270,969 B1 | 8/2001 | Hartley et al. |
| 6,271,436 B1 | 8/2001 | Piedrahita et al. |
| 6,277,608 B1 | 8/2001 | Hartley et al. |
| 6,277,620 B1 | 8/2001 | Gwynn et al. |
| 6,277,632 B1 | 8/2001 | Harney |
| 6,277,710 B1 | 8/2001 | Kim |
| 6,280,977 B1 | 8/2001 | Liang et al. |
| 6,281,000 B1 | 8/2001 | Chartier et al. |
| 6,291,162 B1 | 9/2001 | Tsien et al. |
| 6,291,183 B1 | 9/2001 | Pirrung et al. |
| 6,291,213 B1 | 9/2001 | Rothstein |
| 6,300,118 B1 | 10/2001 | Chavez et al. |
| 6,303,301 B1 | 10/2001 | Mack |
| 6,304,156 B1 | 10/2001 | Kushitani et al. |
| 6,309,822 B1 | 10/2001 | Fodor et al. |
| 6,316,608 B1 | 11/2001 | Reynolds et al. |
| 6,319,703 B1 | 11/2001 | Speck |
| 6,322,973 B1 | 11/2001 | Bostian et al. |
| 6,323,024 B1 | 11/2001 | Tracy et al. |
| 6,331,397 B1 | 12/2001 | Schindelhauer et al. |
| 6,333,155 B1 | 12/2001 | Lockhart et al. |
| 6,340,595 B1 | 1/2002 | Vogels et al. |
| 6,342,224 B1 | 1/2002 | Bruck et al. |
| 6,342,229 B2 | 1/2002 | O'Hare et al. |
| 6,346,413 B1 | 2/2002 | Fodor et al. |
| 6,352,842 B1 | 3/2002 | Short et al. |
| 6,355,412 B1 | 3/2002 | Stewart |
| 6,358,709 B1 | 3/2002 | Short et al. |
| 6,361,972 B1 | 3/2002 | Harrington et al. |
| 6,361,974 B1 | 3/2002 | Short et al. |
| 6,365,377 B1 | 4/2002 | Patten et al. |
| 6,379,967 B1 | 4/2002 | Meredith et al. |
| 6,395,524 B2 | 5/2002 | Loeb et al. |
| 6,410,255 B1 | 6/2002 | Pollok et al. |
| 6,410,266 B1 | 6/2002 | Harrington et al. |
| 6,410,311 B1 | 6/2002 | Cochran et al. |
| 6,410,317 B1 | 6/2002 | Farmer |
| 6,436,707 B1 | 8/2002 | Zambrowicz et al. |
| 6,451,536 B1 | 9/2002 | Fodor et al. |
| 6,451,569 B1 | 9/2002 | Tsien et al. |
| 6,455,254 B1 | 9/2002 | Short |
| 6,468,754 B1 | 10/2002 | Greene et al. |
| 6,472,205 B1 | 10/2002 | Tsien et al. |
| 6,476,209 B1 | 11/2002 | Glenn et al. |
| 6,479,258 B1 | 11/2002 | Short |
| 6,489,145 B1 | 12/2002 | Short |
| 6,495,318 B2 | 12/2002 | Harney |
| 6,506,559 B1 | 1/2003 | Fire et al. |
| 6,506,560 B1 | 1/2003 | Hughes et al. |
| 6,509,156 B1 | 1/2003 | Stewart |
| 6,537,776 B1 | 3/2003 | Short |
| 6,544,782 B1 | 4/2003 | Malo et al. |
| 6,544,790 B1 | 4/2003 | Sabatini |
| 6,548,277 B1 | 4/2003 | Shuman |
| 6,566,067 B2 | 5/2003 | Malo |
| 6,573,099 B2 | 6/2003 | Graham |
| 6,576,424 B2 | 6/2003 | Fodor et al. |
| 6,576,463 B1 | 6/2003 | Kasahara et al. |
| 6,576,464 B2 | 6/2003 | Gold et al. |
| 6,576,752 B1 | 6/2003 | Manoharan et al. |
| 6,586,180 B1 | 7/2003 | Ruffner et al. |
| 6,599,697 B1 | 7/2003 | Sodoyer et al. |
| 6,605,449 B1 | 8/2003 | Short |
| 6,610,482 B1 | 8/2003 | Fodor et al. |
| 6,630,333 B1 | 10/2003 | Hughes, Jr. |
| 6,632,600 B1 | 10/2003 | Short |
| 6,652,878 B2 | 11/2003 | Webb et al. |
| 6,653,106 B1 | 11/2003 | Shuman |
| 6,656,082 B1 | 12/2003 | Yamada et al. |
| 6,660,845 B1 | 12/2003 | Gall et al. |
| 6,670,129 B2 | 12/2003 | Webb et al. |
| 6,671,958 B2 | 1/2004 | Savolainen et al. |
| 6,709,841 B2 | 3/2004 | Short |
| 6,713,279 B2 | 3/2004 | Short |
| 6,713,282 B2 | 3/2004 | Short et al. |
| 6,720,140 B1 | 4/2004 | Hartley et al. |

| | | |
|---|---|---|
| 6,740,506 B2 | 5/2004 | Short |
| 6,773,900 B2 | 8/2004 | Short et al. |
| 6,835,561 B1 | 12/2004 | Gerard et al. |
| 6,838,285 B2 | 1/2005 | Farmer et al. |
| 6,872,551 B2 | 3/2005 | Lima |
| 6,884,612 B2 | 4/2005 | Maruyama et al. |
| 6,888,732 B2 | 5/2005 | Hu |
| 6,902,933 B2 | 6/2005 | Uhler |
| 6,916,632 B2 | 7/2005 | Chesnut et al. |
| 6,960,467 B2 | 11/2005 | Shieh |
| 6,964,861 B1 | 11/2005 | Gerard et al. |
| 6,977,165 B2 | 12/2005 | Farmer |
| 7,026,141 B2 | 4/2006 | Shuman |
| 7,078,501 B2 | 7/2006 | Heyman et al. |
| 7,109,178 B2 | 9/2006 | Ji et al. |
| 7,125,664 B2 | 10/2006 | Minc-Golomb |
| 7,175,806 B2 | 2/2007 | Deal |
| 7,176,029 B2 | 2/2007 | Bernard et al. |
| 7,179,644 B2 | 2/2007 | Farmer |
| 7,198,924 B2 | 4/2007 | Chesnut et al. |
| 7,214,515 B2 | 5/2007 | Chiocca et al. |
| 7,223,576 B2 | 5/2007 | Hartley et al. |
| 7,244,560 B2 | 7/2007 | Chestnut et al. |
| 7,282,326 B2 | 10/2007 | Hartley et al. |
| 7,304,130 B2 | 12/2007 | Hartley et al. |
| 7,351,578 B2 | 4/2008 | Cheo et al. |
| 7,393,632 B2 | 7/2008 | Cheo et al. |
| 7,408,049 B2 | 8/2008 | Hartley et al. |
| 7,670,823 B1 | 3/2010 | Hartley et al. |
| 2002/0006664 A1 | 1/2002 | Sabatini |
| 2002/0007051 A1 | 1/2002 | Cheo et al. |
| 2002/0025561 A1 | 2/2002 | Hodgson |
| 2002/0068290 A1 | 6/2002 | Yarovinsky |
| 2002/0094574 A1 | 7/2002 | Hartley et al. |
| 2002/0106797 A1 | 8/2002 | Miles et al. |
| 2002/0146741 A1 | 10/2002 | Halbleib et al. |
| 2002/0162126 A1 | 10/2002 | Beach et al. |
| 2002/0172997 A1 | 11/2002 | Hartley et al. |
| 2002/0182731 A1 | 12/2002 | Ji et al. |
| 2002/0186233 A1 | 12/2002 | Holtz et al. |
| 2002/0192819 A1 | 12/2002 | Hartley et al. |
| 2003/0022179 A1 | 1/2003 | Chesnut et al. |
| 2003/0027289 A1 | 2/2003 | Farmer |
| 2003/0027296 A1 | 2/2003 | Chatterjee |
| 2003/0027337 A1 | 2/2003 | Droge et al. |
| 2003/0032203 A1 | 2/2003 | Sabatini et al. |
| 2003/0054552 A1 | 3/2003 | Hartley et al. |
| 2003/0054555 A1 | 3/2003 | Farmer et al. |
| 2003/0059764 A1 | 3/2003 | Ravkin et al. |
| 2003/0059900 A1 | 3/2003 | Farmer |
| 2003/0064515 A1 | 4/2003 | Hartley et al. |
| 2003/0068799 A1 | 4/2003 | Hartley et al. |
| 2003/0077804 A1 | 4/2003 | Byrd et al. |
| 2003/0100110 A1 | 5/2003 | Hartley et al. |
| 2003/0102346 A1 | 6/2003 | Chen et al. |
| 2003/0124555 A1 | 7/2003 | Brasch et al. |
| 2003/0135888 A1 | 7/2003 | Zhu et al. |
| 2003/0139363 A1 | 7/2003 | Kay et al. |
| 2003/0153055 A1 | 8/2003 | Miles et al. |
| 2003/0157662 A1 | 8/2003 | Gerard et al. |
| 2003/0157716 A1 | 8/2003 | Hartley et al. |
| 2003/0175772 A1 | 9/2003 | Wang |
| 2003/0175970 A1 | 9/2003 | Hartley et al. |
| 2003/0176644 A1 | 9/2003 | Byrd et al. |
| 2003/0186233 A1 | 10/2003 | Chesnut et al. |
| 2003/0203486 A1 | 10/2003 | Sabatini |
| 2003/0219800 A1 | 11/2003 | Beske et al. |
| 2003/0220249 A1 | 11/2003 | Hackett et al. |
| 2004/0002077 A1 | 1/2004 | Taira et al. |
| 2004/0040053 A1* | 2/2004 | Nomura et al. ............... 800/278 |
| 2004/0053412 A1 | 3/2004 | Hartley et al. |
| 2004/0063207 A1 | 4/2004 | Hartley et al. |
| 2004/0132133 A1 | 7/2004 | Bennett |
| 2004/0171156 A1 | 9/2004 | Hartley et al. |
| 2004/0171157 A1 | 9/2004 | Hartley et al. |
| 2004/0219516 A1 | 11/2004 | Bennett et al. |
| 2004/0219673 A1 | 11/2004 | Hartley et al. |
| 2004/0229229 A1 | 11/2004 | Cheo et al. |
| 2004/0253620 A1 | 12/2004 | Leong |
| 2004/0253631 A1 | 12/2004 | Hartley et al. |
| 2004/0265863 A1 | 12/2004 | Chesnut et al. |
| 2005/0009091 A1 | 1/2005 | Hartley et al. |
| 2005/0045941 A1 | 3/2005 | Kurita et al. |
| 2005/0069929 A1 | 3/2005 | Chestnut et al. |
| 2005/0095615 A1 | 5/2005 | Welch et al. |
| 2005/0104027 A1 | 5/2005 | Lazarev |
| 2005/0156137 A1 | 7/2005 | Overkempe et al. |
| 2005/0176065 A1 | 8/2005 | Hanson |
| 2005/0181417 A1 | 8/2005 | Miles et al. |
| 2005/0208530 A1 | 9/2005 | Chesnut et al. |
| 2006/0008817 A1 | 1/2006 | Carrino |
| 2006/0035269 A1 | 2/2006 | Hartley et al. |
| 2006/0035272 A1 | 2/2006 | Brasch et al. |
| 2006/0073593 A1 | 4/2006 | Byrd et al. |
| 2006/0160072 A1 | 7/2006 | Shuman |
| 2006/0204979 A1 | 9/2006 | Gray et al. |
| 2007/0128724 A1 | 6/2007 | Miles et al. |
| 2007/0128725 A1 | 6/2007 | Brasch et al. |
| 2007/0184451 A1 | 8/2007 | Byrd et al. |
| 2007/0196838 A1 | 8/2007 | Chesnut et al. |
| 2008/0241889 A1 | 10/2008 | Chesnut et al. |
| 2009/0176975 A1 | 7/2009 | Yim et al. |
| 2009/0186387 A1 | 7/2009 | Hartley et al. |

FOREIGN PATENT DOCUMENTS

| | | |
|---|---|---|
| CA | 2141412 A1 | 2/1994 |
| CA | 2177367 | 6/1995 |
| CA | 2226463 | 12/1996 |
| EA | 386859 | 2/1995 |
| EP | 0160571 | 11/1985 |
| EP | 0220009 A2 | 4/1987 |
| EP | 0300422 A2 | 1/1989 |
| EP | 0351138 | 1/1990 |
| EP | 0373914 | 6/1990 |
| EP | 0427074 | 5/1991 |
| EP | 0516245 | 12/1992 |
| EP | 542466 | 5/1993 |
| EP | 0542466 A2 | 5/1993 |
| EP | 0625572 | 11/1994 |
| EP | 0655506 | 5/1995 |
| EP | 704534 | 4/1996 |
| EP | 1018549 | 1/1999 |
| EP | 1035208 A1 | 9/2000 |
| EP | 1079520 | 2/2001 |
| EP | 0672191 | 9/2001 |
| EP | 1215748 | 6/2002 |
| EP | 0937098 | 8/2002 |
| EP | 1227147 A3 | 8/2002 |
| EP | 1275735 | 1/2003 |
| JP | 11112986 | 4/1999 |
| JP | 2001-112986 | 4/2001 |
| JP | 2002-331431 | 11/2002 |
| JP | 2002331431 | 11/2002 |
| JP | 2006-087445 | 4/2006 |
| JP | 2006087445 | 4/2006 |
| WO | WO-85/04898 | 11/1985 |
| WO | WO-90/08839 | 8/1990 |
| WO | WO-90/11375 | 10/1990 |
| WO | WO-91/02090 | 2/1991 |
| WO | WO-91/02801 | 3/1991 |
| WO | WO-91/09957 | 4/1991 |
| WO | WO-91/09957 | 7/1991 |
| WO | WO-91/16427 | 10/1991 |
| WO | WO 91/16427 | 10/1991 |
| WO | WO-91/16446 | 10/1991 |
| WO | WO-92/01899 | 2/1992 |
| WO | WO-92/03556 | 3/1992 |
| WO | WO-92/06188 | 4/1992 |
| WO | WO-92/06200 | 4/1992 |
| WO | WO-92/06202 | 4/1992 |
| WO | WO-92/10577 | 6/1992 |
| WO | WO-92/13570 | 8/1992 |
| WO | WO-92/15694 | 9/1992 |
| WO | WO-92/20791 | 11/1992 |
| WO | WO-92/22650 | 12/1992 |
| WO | WO9222650 | * 12/1992 |
| WO | WO-93/00447 | 1/1993 |
| WO | WO-93/02212 | 2/1993 |

| | | |  | | | |
|---|---|---|---|---|---|---|
| WO | WO-93/07282 | 4/1993 | | WO | WO-99/49029 | 9/1999 |
| WO | WO-93/07283 | 4/1993 | | WO | WO-99/55851 | 11/1999 |
| WO | WO-93/10086 | 5/1993 | | WO | WO-99/55886 | 11/1999 |
| WO | WO-93/13423 | 7/1993 | | WO | WO-00/02900 | 1/2000 |
| WO | WO-93/15191 | 8/1993 | | WO | WO-00/12687 | 3/2000 |
| WO | WO-93/19172 | 9/1993 | | WO | WO-00/15779 | 3/2000 |
| WO | WO-93/19768 | 10/1993 | | WO | WO-00/29000 | 5/2000 |
| WO | WO-93/20612 | 10/1993 | | WO | WO-00/42206 | 7/2000 |
| WO | WO-94/01927 | 1/1994 | | WO | WO-00/49035 | 8/2000 |
| WO | WO-94/03624 | 2/1994 | | WO | WO0046401 * | 8/2000 |
| WO | WO94/03624 | 2/1994 | | WO | WO-00/52027 | 9/2000 |
| WO | WO-94/04696 | 3/1994 | | WO | WO-00/52141 | 9/2000 |
| WO | 94/09127 | 4/1994 | | WO | WO-00/56878 | 9/2000 |
| WO | WO-94/07921 | 4/1994 | | WO | WO-00/60091 | 10/2000 |
| WO | WO-94/08598 | 4/1994 | | WO | WO-00/63397 | 10/2000 |
| WO | WO-94/09127 | 4/1994 | | WO | WO-00/66722 | 11/2000 |
| WO | 95/00555 | 6/1994 | | WO | WO-01/05961 | 1/2001 |
| WO | WO-94/12649 | 6/1994 | | WO | WO-01/05961 A1 | 1/2001 |
| WO | 94/17176 | 8/1994 | | WO | WO-01/07572 | 2/2001 |
| WO | WO-94/17176 | 8/1994 | | WO | WO-01/07572 A2 | 2/2001 |
| WO | WO-94/18333 | 8/1994 | | WO | WO-01/11058 | 2/2001 |
| WO | WO-94/20604 | 9/1994 | | WO | WO-01/11058 A1 | 2/2001 |
| WO | WO-94/23751 | 10/1994 | | WO | WO-01/20015 | 3/2001 |
| WO | WO-94/29443 | 12/1994 | | WO | WO-01/25466 | 4/2001 |
| WO | WO-95/00555 | 1/1995 | | WO | WO-01/31039 | 5/2001 |
| WO | WO-95/00655 | 1/1995 | | WO | WO-01/42505 | 6/2001 |
| WO | WO-95/02397 | 1/1995 | | WO | WO-01/42509 | 6/2001 |
| WO | WO-95/16099 | 6/1995 | | WO | WO-01/53325 | 7/2001 |
| WO | WO-95/17373 | 6/1995 | | WO | WO-01/57242 | 8/2001 |
| WO | WO-95/33853 | 12/1995 | | WO | WO-01/62892 | 8/2001 |
| WO | 96/04393 | 2/1996 | | WO | WO-01/62892 A2 | 8/2001 |
| WO | WO-96/04393 | 2/1996 | | WO | WO-01/62943 | 8/2001 |
| WO | WO-96/05488 | 2/1996 | | WO | WO-01/68836 | 9/2001 |
| WO | WO-96/10640 | 4/1996 | | WO | WO-01/86001 | 11/2001 |
| WO | 96/19497 | 6/1996 | | WO | WO-02/00875 | 1/2002 |
| WO | WO-96/17053 | 6/1996 | | WO | WO-02/05294 | 1/2002 |
| WO | WO-96/19497 | 6/1996 | | WO | WO-02/05294 A1 | 1/2002 |
| WO | WO-96/20604 | 7/1996 | | WO | WO-02/08391 | 1/2002 |
| WO | WO-96/23569 | 8/1996 | | WO | WO-02/16594 | 2/2002 |
| WO | WO-96/23904 | 8/1996 | | WO | WO-02/42447 | 5/2002 |
| WO | WO-96/30498 | 10/1996 | | WO | WO-02/46372 | 6/2002 |
| WO | WO-96/34981 | 11/1996 | | WO | WO-0246372 | 6/2002 |
| WO | WO-96/38568 | 12/1996 | | WO | WO-02/061034 | 8/2002 |
| WO | WO-96/40722 | 12/1996 | | WO | WO-02/062957 | 8/2002 |
| WO | WO-96/40724 | 12/1996 | | WO | WO-02/077264 | 10/2002 |
| WO | WO-97/02357 | 1/1997 | | WO | WO-02/086114 | 10/2002 |
| WO | WO-97/06265 | 2/1997 | | WO | WO-02/086144 | 10/2002 |
| WO | WO-97/09436 | 3/1997 | | WO | WO-02/086744 | 10/2002 |
| WO | WO-97/09451 | 3/1997 | | WO | WO-02/090495 | 11/2002 |
| WO | WO-97/24455 | 7/1997 | | WO | WO-02/095055 | 11/2002 |
| WO | WO-97/25446 | 7/1997 | | WO | WO-03/025161 | 3/2003 |
| WO | WO-97/32481 | 9/1997 | | WO | WO-03/044207 | 5/2003 |
| WO | WO-97/40722 | 11/1997 | | WO | WO-03/046173 | 6/2003 |
| WO | WO-97/43450 | 11/1997 | | WO | WO-03046173 | 6/2003 |
| WO | 9747758 | 12/1997 | | WO | WO-03/089600 | 10/2003 |
| WO | WO-97/47758 | 12/1997 | | WO | WO-03/103600 | 12/2003 |
| WO | WO-97/48716 | 12/1997 | | WO | WO-2004/005482 | 1/2004 |
| WO | WO-98/05574 | 2/1998 | | WO | WO-2004/009768 | 1/2004 |
| WO | WO-98/09526 | 3/1998 | | WO | WO-2004/013290 | 2/2004 |
| WO | WO-98/10086 | 3/1998 | | WO | WO-2004/108897 | 12/2004 |
| WO | WO-98/11061 | 3/1998 | | WO | WO-2005/012487 | 2/2005 |
| WO | WO-98/12372 | 3/1998 | | WO | WO-2005/014796 | 2/2005 |
| WO | WO-99/10488 | 3/1998 | | WO | WO-2005/028615 | 3/2005 |
| WO | WO-98/20122 | 5/1998 | | WO | WO-2005/054438 A2 | 6/2005 |
| WO | WO-98/20967 | 5/1998 | | WO | WO-2005/054438 A3 | 7/2005 |
| WO | WO-98/38326 | 9/1998 | | | | |
| WO | WO-98/47912 | 10/1998 | | | | |
| WO | WO-98/53056 | 11/1998 | | | OTHER PUBLICATIONS | |
| WO | WO-98/53083 | 11/1998 | | | | |
| WO | WO-98/55502 | 12/1998 | | | | |
| WO | WO-98/56943 | 12/1998 | | | | |
| WO | WO-99/05591 | 2/1999 | | | | |
| WO | WO-99/10488 | 3/1999 | | | | |
| WO | WO-99/18124 | 4/1999 | | | | |
| WO | WO-99/21977 | 5/1999 | | | | |
| WO | WO-99/25851 | 5/1999 | | | | |
| WO | WO-99/27365 | 6/1999 | | | | |
| WO | WO-99/32619 | 7/1999 | | | | |
| WO | WO-99/40105 | 8/1999 | | | | |

OTHER PUBLICATIONS

98/53056, , "Dialog File 351 (Derwent World Patents Index) Language Abstract", *unverified English language abstract for WIPO/PCT Publication No. WO 98/53056 (Document No. AP4)* ; WPI Accession No. 1999-000502/199901 1999.

98/53056, , "Dialog File 351, Accession No. 12194396", *Dewent WPI English language Abstract for WO 98/53056 (Document AP4)*, 1-8.

98/53056, , "Dialog File 351, Derwent WPI English language abstract", *Derwent WPI English language abstract for WO 98/53056 (AO6)*Accession No. 1999-000502/199901 1998.

98/53056, , "Unverified english language abstract for PCT Publication No. 98/53056 Derwent World Patent Index, WPI Accession No. 1999-000502/199901, Dialog File 351", (ALB).

99/25851, , "Derwent World Patent Index, unverified English Language Abstract", PCT Patent No. WO 99/25851 (Document AO 7), WPI Accession No. 12541379, Dialog File 351, 1-8.

99/25851, , "Dialog File 351 (Derwent World Patents Index) ,", *unverified English lanquage abstract for WIPO/PCT Publication No. WO 99/25851* (Document No. AM4) ; WPI Accession No. 1999-347485/199929 1999.

99/25851, , "Dialog File 351 (Derwent WPI)", *Unverified English Language abstract for WO 99/25851* WPI Accession No. 1999-347485/199929 1999, 1-100.

99/25851, "Dialog File 351 Unverified English Language Abstract", *Derwent World Patent Index*, PCT Patent No. WO 99/25851 (Document AO7), WPI Accession No. 12541379.

Abbas-Terki, Toufik et al., "Lentiviral-Mediated RNA Interference", vol. 13, *Human Gene Therapy* Dec. 10, 2002, 2197-2201.

Abremski, Ken et al., "Bacteriophage P1 Cre-loxP site-specific recombination Site-specific DNA Topoisomerase Activity of the Cre Recombination Protein,", vol. 261, No. 1, *The Journal of Biological Chemistry* The American Society of Biochemistry and Molecular Biology Jan. 5, 1986, 391-396.

Abremski, Ken et al., "Bacteriophage P1 Site-specific Recombination-Purification and Properties of the Cre Recombinase Protein", *The Journal of Biological Chemistry* vol. 259, No. 3, American Society for Biochemistry and Molecular Biology, Inc. Feb. 10, 1984, 1509-1514.

Abremski, Ken et al., "Purification of the Bacteriophage lamda xis Gene Product Required for lamda Excisive Recombination", *The Journal of Biological Chemistry* vol. 256, No. 16, American Society for Biochemistry and Molecular Biology Aug. 25, 1982, 9658-9662.

Abremski, Ken et al., "Studies on the Properties of P1 Site-Specific Recombination: Evidence for Topologically Unlinked Products Following Recombination", vol. 32, *Cell* Cell Press Apr. 1993, 1301-1311.

Adams, David E. et al., "Cre-lox Recombination in *Escherichia coli* Cells: Mechanistic Differences from the in Vitro Reaction", *Journal of Molecular Biology* vol. 226, Academic Press 1992, 661-673.

Adams, Stephen R. et al., "New Biarsenical Ligands and Tetracysteine Motifs for Protein Labeling in Vitro and in Vivo: Synthesis and Biological Applications.", *Journal of the American Chemical Society* vol. 124 2002, 6063-6076.

Adelman, Zach N. et al., "RNA Silencing of Dengue Virus Type 2 Replication in Transformed C6/36 Mosquito Cells Transcribing an Inverted-Repeat RNA Derived from the Virus Genome.", *Journal of Virology* vol. 76, No. 24 Dec. 2002, 12925-12933.

Agah, Ramtin et al., "Gene Recombination in Postmitotic Cells. Targeted Expression of Cre Recombinase Provokes Cardiac-restricted, Site-specific Rearrangement in Adult Ventricular Muscle In Vivo", vol. 100, No. 1, *The Journal of Clinical Investigation* The American Society for Clinical Investigation, Inc. Jul. 1997, 169-179.

Airenne, Kari J. et al., "Avidin Is a Promising Tag for Fusion Proteins Produced in Baculovirus-Infected Insect Cells", *Protein Expression and Purification* vol. 17 1999, 139-145.

Akagi, Kiwamu et al., "Cre-mediated somatic site-specific recombination in mice", *Nucleic Acids Research* vol. 25, No. 9, Oxford University Press 1997, 1766-1773.

Aladjem, Mirit I. et al., "Positive Selection of FLP-Mediated Unequal Sister Chromatid Exchange Products in Mammalian Cells", *Molecular and Cellular Biology* vol. 17, No. 2, American Society for Microbiology Feb. 1997, 857-861.

Albert, Henrik et al., "Site-specific integration of DNA into wild-type and mutant lox sites placed in the plant genome", *The Plant Journal* vol. 7, No. 4, Blackwell Science Ltd. 1995, 649-659.

Aldrian-Herrada, Gudrun et al., "Solid-Phase Synthesis of Peptide Nucleic Acid (PNA) Monomers and Their Oligomerization Using Disulphite Anchoring Linkers.", *Journal of Peptide Science* vol. 4, John Wiley & Sons, Ltd. 1998, 266-281.

Alonso, Juan C., "Site-specific recombination in Gram-positive theta-replicating plasmids", *FEMS Microbiology Letters* col. 142, Elsevier Science B.V. Aug. 1996, 1-10.

Ambler, R. P., "The structure of B-lactamases", vol. 289, *Series B, Philosophical Transactions of the Royal Society of London.* vol. 289, Series B, Biological Sciences. The Royal Society Publishing 1980, 321-331.

Amin, Anthony A. et al., "Synthesis of an Enzymatically Active FLP Recombinase In Vitro: Search for a DNA-Binding Domain", *Molecular and Cellular Biology* vol. 9, No. 5, American Society for Microbiology May 1989, 1987-1995.

Andersen, P. A. et al., "Functional specificity of the replication fork-arrest complexes of *Bacillus subtilis* and *Escherichia coli*: significant specificity of Tus-Ter functioning in *E. coli*.", *Molecular Microbiology* vol. 36, No. 6 2000, 1327-1335.

Andersen, Anni H. et al., "Studies of the Topoisomerase II-mediated Cleavage and Religation AT 1 Reactions by Use of a Suicidal Double-stranded DNA Substrate", vol. 266, No. 14, *The Journal of Biological Chemistry* The American Society for Biochemistry and Molecular Biology, Inc May 15, 1991, 9203-9210.

Anderson, Richard A. et al., "DNA-mediated gene transfer: Recombination between cotransferred DNA sequences and recovery of recombinants in a plasmid", vol. 79, *Biochemistry* Proceedings of the National Academy of Sciences (PNAS) May 1982, 2748-2752.

Andersson, Stefan et al., "Cloning, Structure, and Expression of the Mitochondrial Cytochrome P-450 Sterol 26-Hydroxylase, a Bile Acid Biosynthetic Enzyme", vol. 264, No. 14, *The Journal of Biological Chemistry* American Society for Biochemistry and Molecular Biology, Inc. May 15, 1989, 8222-8229.

Andrews, Brenda J. et al., "Interaction of the FLP Recombinase of the *Saccharomyces cerevisiae* 2mum Plasmid with Mutated Target Sequences", *Molecular and Cellular Biology* vol. 6, No. 7 Jul. 1986, 2482-2489.

Andrews, Brenda J. et al., "The FLP Recombinase of the 2.mu. Circle DNA of Yeast: Interaction with Its Target Sequences", *Cell* vol. 40, Cell Press Apr. 1985, 795-803.

Angelastro, James M. et al., "Identification of diverse nerve growth factor-regulated genes by serial analysis of gene expression (SAGE) profiling", *Proceedings of the National Academy of Sciences (PNAS)* vol. 97, No. 19, National Academy of Sciences Sep. 12, 2000, 10424-10429.

Angrand, Pierre-Olivier et al., "Inducible expression based on regulated recombination: a single vector strategy for stable expression in cultured cells", *Nucleic Acids Research* vol. 26, No. 13, Oxford University Press 1998, 3263-3269.

Anton, Martina et al., "Site-Specific Recombination Mediated by an Adenovirus Vector Expressing the Cre Recombinase Protein: a Molecular Switch for Control of Gene Expression", *Journal of Virology* vol. 69, No. 8, American Society for Microbiology Aug. 1995, 4600-4606.

Aoki, Kazunori et al., "Efficient Generation of Recombinant Adenoviral Vectors by Cre-lox Recombination In Vitro", vol. 5, *Molecular Medicine* Picower Institute Press 1999, 224-231.

Araki, Hiroyuki et al., "Site-specific Recombinase, R, Encoded by Yeast Plasmid pSR1", vol. 225, *J. Mol. Biol.* Academic Press 1992, 25-37.

Argos, Patrick et al., "The integrase family of site-specific recombinases: regional similarities and global diversity", vol. 5, No. 2, *The EMBO Journal* IRL Press Limited 1986, 433-440.

Arnott, Struther et al., "DNA-RNA Hybrid Secondary Structures", *J. Mol. Biol.* vol. 188 1986, 631-640.

Askoxford, , "Dictionary definition for "in vitro"", AskOxford.com online dictionary concise_oed/invitro?view=uk, http://www.askoxford.com/ accessed Sep. 12, 2006, 1.

Astatke, Mekbib et al., "Deoxynucleoside Triphosphate and Pyrophosphate Binding Sites in the Catalytically Competent Ternary Complex for the Polymerase Reaction Catalyzed by DNA Polymerase I (Klenow Fragment)", vol. 270, No. 4, *The Journal of Biological Chemistry* Jan. 27, 1995, 1945-1954.

Astatke, Mekbib et al., "How *E. coli* DNA Polymerase I (Klenow fragment) distinguishes between Deoxy-and Dideoxynucleotides", *The Journal of Molecular Biology*, vol. 278, Academic Press Ltd., Apr. 1998, 147-165.

Astumian, Janette H. et al., "Site-specific recombination between cloned attp and attB sites from the *Haemophilus influenza* bacteriophage HP1 propagated in recombination deficient

*Escherichia coli"*, *Journal of Bacteriology* vol. 171, No. 3, American Society for Microbiology, Washington, D.C. Mar. 1989, 1747-1750.
Atlung, Tove et al., "A versatile method for integration of genes and gene fusions into the lambda attachment site of *Escherichia coli*", vol. 107, *Gene* Elsevier Science B.V. 1991, 11-17.
Ausubel, Frederick M. et al., "Current Protocols in Molecular Biology", *John Wiley & Sons, Inc.*, Boston, MA 1994-1998, 4.6.1-4.6.13.
Ausubel, Frederick et al., "Introduction to Expression by Fusion Protein Vectors", *Current Protocols in Molecular Biology*, John Wiley and Sons, Inc., 1994, 16.4.1-16.4.4.
Ausubel, Frederick M. et al., "Maps of Plasmids", *Current Protocols in Molecular Biology* John Wiley & Sons, Inc., Boston, MA 1995, 1.5.3-1.5.4.
Ausubel, Frederick M. et al., "Maps of Plasmids pBR322 and pUC19", *Short Protocols in Molecular Biology* Third Edition, John Wiley & Sons, Inc., Boston, MA 1995, 1.12-1.13.
Ausubel, Frederick M. et al., "Mutagenesis by the Polymerase Chain Reaction", *Current Protocols in Molecular Biology* John Wiley & Sons, Inc., Boston, MA 1995, 8.5.1-8.5.9.
Ausubel, Frederick et al., "vol. 1, Ch. 8", *Current Protocols in Immunology* Wiley & Sons 1994.
Ayres, Elaine K. et al., "Precise Deletions in Large Bacterial Genomes by Vector-mediated Excision (VEX). The trfA Gene of Promiscuous Plasmid RK2 is Essential for Replication in Several Gram-negative Hosts", *J. Mol. Biol.* vol. 230 1993, 174-185.
Babineau, Donna et al., "The FLP Protein of the 2-micron Plasmid of Yeast", *The Journal of Biological Chemistry* vol. 260, No. 22, American Society for Biochemistry and Molecular Biology, Inc. Oct. 5, 1985, 12313-12319.
Backman, K. et al., "Use of Synchronous Site-Specific Recombination In Vivo to Regulate Gene Expression", *Bio/Technology* vol. 2, No. 12, Nature Publishing Company Dec. 1984, 1045-1049.
Baek, Seung-Cheol et al., "Sustainable Systemic Delivery via a Single Injection of Lentivirus into Human Skin Tissue", vol. 12, *Human Gene Therapy* Mary Ann Liebert, Inc. Aug. 10, 2001, 1551-1558.
Bai, Chang et al., "SKP1 Connects Cell Cycle Regulators to the Ubiquitin Proteolysis Machinery through a Novel Motif, the F-Box", *Cell* vol. 86, Cell Press Jul. 26, 1996, 263-274.
Balakrishnan, R et al., "A gene cassette for adapting *Escherichia coli* strains as hosts for att-Int-mediated rearrangement and P1 expression vectors", *Gene* vol. 138 Jan. 1994, 101-104.
Baldwin, Thomas O. et al., "Cloning and expression of the luxY gene from *Vibrio fischeri* strain Y-1 in *Escherichia coli* and complete amino acid sequence of the yellow fluorescent protein", *Biochemistry* vol. 29, No. 23 1990, 5509-5515.
Ball, Catherine A. et al., "Dramatic Changes in Fis Levels Upon Nutrient Upshift in *Escherichia coli"*, *Journal of Bacteriology* vol. 174, No. 24 Dec. 1992, 8043-8056.
Ball, Catherine A. et al., "Efficient Excision of Phage Lambda from the *Escherichia coli* Chromosome Requires the Fis Protein", *Journal of Bacteriology*, vol. 173, No. 13 American Society for Microbiology Jul. 1991, 4027-4031.
Banerjee, Diya et al., "Control of developmental timing by small temporal RNAs: a paradigm for RNA mediated regulation of gene expression.", *Bioessays* vol. 24, No. 2 2002, 119-129.
Barbas, Carlos F. et al., "Assembly of combinatorial antibody libraries on phage surfaces: The gene III site.", *Proceedings of the National Academy of Sciences* (*PNAS*) vol. 88 Sep. 1991, 7978-7982.
Barbas, Carlos F. et al., "Semisynthetic Combinatorial Antibody Libraries: A Chemical Solution to the Diversity Problem", *Proceedings of the National Academy of Sciences* (*PNAS*) vol. 89 May 1992, 4457-4461.
Barnes, Georjana et al., "Regulated expression of endonuclease EcoRI in *Saccharomyces cerevisiae*: Nuclear entry and biological consequences", *Proceedings of the National Academy of Sciences* (*PNAS*) vol. 82, National Academy of Sciences Mar. 1985, 1354-1358.
Barnes, Wayne M., "The Fidelity of Taq Polymerase Catalyzing PCR is Improved by an N-Terminal Deletion", vol. 112, *Gene*, 1992, 29-35.
Bass, Brenda L., "Double-Stranded RNA as a Template for Gene Silencing", vol. 101, *Cell* Cell Press 2000 Apr. 28, 2000, 235-238.
Basu, Amaresh et al., "Identification and Amino Acid Sequence of the Deoxynucleoside Triphosphate Binding Site in *Escherichia coli* DNA Polymerase I", *Biochemistry* vol. 26, American Chemical Society 1987, 1704-1709.
Bath, Abigal J. et al., "Many Type IIs Restriction Endonucleases Interact with Two Recognition Sites before Cleaving DNA", *Journal of Biological Chemistry* vol. 277, No. 6 Feb. 8, 2002, 4024-4033.
Baubonis, Wendy et al., "Genomic targeting with purified Cre recombinase.", *Nucleic Acids Research* vol. 21. No. 9, Oxford Press. 1993, 2025-2029.
Bauer, Carl E. et al., "Extent of Sequence Homology Required for Bacteriophage Lambda Site-specific Recombination", *J. Mol. Biol.* vol. 181, Academic Press Inc. 1985, 187-197.
Baum, James A., "Tn5401, a New Class II Transposable Element From *Bacillus thuringiensis"*, *Journal of Bacteriology*, vol. 176, No. 10 American Society for Microbiology May 1994, 2835-2845.
Bayley, Christopher C. et al., "Exchange of gene activity in transgenic plants catalyzed by the Cre-lox site specific recombination system", *Plant Molecular Biology* vol. 18, Dordrecht Kluwer Academic 1992, 353-361.
Beese, Lorena S. et al., "Crystal Structures of the Klenow Fragment of DNA Polymerase I Complexed with Deoxynucleoside Triphosphate and Pyrophosphate", *Biochemistry* vol. 32, No. 51 1993, 14095-14101.
Belfort, Marlene et al., "Homing endonucleases: keeping the house in order", *Nucleic Acids Research* vol. 25, No. 17 1997, 3379-3388.
Benoist, Christophe et al., "In vivo sequence requirements of the SV40 early promoter region", vol. 290 *Nature* Mar. 26, 1981, 304-310.
Bergelson, Jeffrey M. et al., "Isolation of a Common Receptor for Coxsackie B Viruses and Adenoviruses 2 and 5,", vol. 275, No. 5304,*Science* The American Association for the Advancement of Science Feb. 28, 1997, 1320-1323.
Berger, James M. et al., "Structure of DNA topoisomerases", vol. 1400, *Biochimica et Biophysica Acta* Elsevier Science B.V. 1998, 3-18.
Bergquist, P. L. et al., "Ch 6: Genetics and Potential Biotechnological Applications of Thermophilic and Extremely Thermophilic Microorganisms", *Biotechnology and Genetic Engineering Reviews* vol. 5, editor Gordon E. Russell Sep. 1987, 199-244.
Berlman, Isadore B., "Energy Transfer Parameters of Aromatic Compounds", *Table of Contents, Academic Press* 1973, 1-4.
Bernad, Antonio et al., "A Conserved 3'-5' Exonuclease Active Site in Prokaryotic and Eukaryotic DNA Polymerases", *Cell* vol. 59 Oct. 6, 1989, 219-228.
Bernard, Philippe et al., "Cell Killing by the F plasmid Ccdb Protein Involves Poisoning of DNA-topoisomerase II Complexes", *J. Mol. Biol.* vol. 226, Academic Press, Inc. 1992, 735-745.
Bernard, Philippe, "Positive Selection of Recombinant DNA by CcdB", *BioTechniques* vol. 21, No. 2 Aug. 1996, 320-323.
Bernard, Philippe et al., "Positive-selection vectors using the F plasmid ccdB killer gene", *Gene* vol. 148, Elsevier Science B. V. Oct. 1994, 71-74.
Bernard, Philippe et al., "The F Plasmid CcdB Protein Induces Efficient ATP-dependent DNA Cleavage by Gyrase", *J. Mol. Biol.* vol. 234, Academic Press Limited 1993, 534-541.
Bernstein, Emily et al., "Role for a bidentate ribonuclease in the initiation step of RNA interference", *Nature* vol. 409 Jan. 18, 2001, 363-366.
Bernstein, Emily et al., "The rest is silence", vol. 7, *RNA* Cambridge University Press 2001, 1509-1521.
Bethke, Bruce et al., "Segmental genomic replacement by Cre-mediated recombination: genotoxic stress activation of the p53 promoter in single-copy transformants", vol. 25, No. 14, *Nucleic Acids Research* Oxford University Press 1997, 2828-2834.
Bett, Andrew J. et al., "An efficient and flexible system for construction of adenovirus vectors with insertions or deletions in early regions 1 and 3", vol. 91, *Proceedings of the National Academy of Sciences* (*PNAS*) The National Academy of Sciences Sep. 1994, 8802-8806.
Betz, Ulrich A. et al., "Bypass of lethality with mosaic mice generated by Cre-loxP-mediated recombination", *Current Biology Ltd.* vol. 6, No. 10 Oct. 1996, 1307-1316.

Bhandari, Poonam et al., "An *Escherichia coli* Host Strain Useful for Efficient Overproduction of Cloned Gene Products with NaCl as the Inducer", *Journal of Bacteriology* vol. 179, No. 13, American Society for Microbiology Jul. 1997 , 4403-4406.

Biocompare, "T-REx Expression System Support Kit from Invitrogen", www.biocompare.com/productdetails/382668/productdetails.html Oct. 21, 2008 , 1-2.

Black, Lindsay W. , "In vitro packaging into phage T4 particles and specific recircularization of phage lambda DNAs", *Gene* vol. 46, Elsevier Science 1986 , 97-101.

Blanco, Luis et al., "Evidence favouring the hypothesis of a conserved 3'-5' exonuclease active site in DNA-dependent DNA polymerases", *Gene* vol. 112 1992 , 139-144.

Bliska, James B. et al., "Use of Site-Specific Recombination as a Probe of DNA Structure and Metabolism in Vivo", *Journal of Molecular Biology* vol. 194, Academic Press Inc. 1987 , 205-218.

Blissard, Gary W. et al., "A Synthetic Early Promoter from a Baculovirus: Roles of the TATA Box and Conserved Start Site CAGT Sequence in Basal Levels of Transcription", vol. 190; *Virology* Academic Press, Inc. 1992 , 783-793.

Blissard, Gary W. et al., "Baculovirus gp64 Gene Expression: Analysis of Sequences Modulating Early Transcription and Transactivation by IE1", *Journal of Virology* vol. 65, No. 11, American Society for Microbiology 1991 , 5820-5827.

Blissard, Gary W. et al., "Location, Sequence, Transcriptional Mapping, and Temporal Expression of the gp64 Envelope Glycoprotein Gene of the *Orgyia pseudotsugata* Multicapsid Nuclear Polyhedrosis Virus", vol. 170, *Virology* Academic Press, Inc. 1989 , 537-555.

Bloch, Craig A. et al., "Purification of *Escherichia coli* Chromosomal Segments without Cloning", *Biochemical and Biophysical Research Communications* vol. 223, Academic Press, Inc. Jun. 1996 , 104-111.

Bochner, Barry R. et al., "Positive Selection for Loss of Tetracycline Resistance", *Journal of Bacteriology* vol. 143, No. 2 Aug. 1980 , 926-933.

Boesen, Jan J. et al., "Circumvention of chemotherapy-induced myelosuppression by transfer of the mdrl gene", *Biotherapy* vol. 6 1994 , 291-302.

Bokal, Anton J. et al., "The transcriptional activator protein FIS: DNA interactions and cooperative interactions with RNA polymerase at the *Escherichia coli* rrnB P1 promoter.", *Journal of Molecular Biology* vol. 245 1995 , 197-207.

Boshart, Michael et al., "A Very Strong Enhancer is Located Upstream of an Immediate Early Gene of Human Cytomegalovirus", vol. 41, *Cell* The MIT Press Jun. 1985 , 521-530.

Botstein, David et al., "Making Mutations In Vitro and Putting Them Back Into Yeast", vol. 19, *Miami Winter Symposia* From Gene to Protein: Translation into Biotechnology, Ahmad, F., et al., eds., Academic Press, New York, NY 1982 , 265-274.

Bouhassira, Eric E. et al., "Transcriptional Behavior of LCR Enhancer Elements Integrated at the Same Chromosomal Locus by Recombinase-Mediated Cassette Exchange", *Blood* vol. 90, No. 9, The American Society of Hematology Nov. 1, 1997 , 3332-3344.

Bout, Abraham et al., "Lung Gene Therapy: In Vivo Adenovirus-Mediated Gene Transfer to Rhesus Monley Airway Epithelium", vol. 5, *Human Gene Therapy* Mary Ann Liebert, Inc. 1994 , 3-10.

Boutla, Alexandra et al., "Short 5-phosphorylated double-stranded RNAs induce RNA interference in Drosophila.", *Current Biology* vol. 11; Elsevier Science Ltd. Nov. 13, 2001 , 1776-1780.

Boyd, A. C. et al., "Turbo cloning: a fast, efficient method for cloning PCR products and other blunt-ended DNA fragments into plasmids", *Nucleic Acids Research* vol. 21, No. 4,Oxford University Press 1993 , 817-821.

Braithwaite, Dan K. et al., "Compilation, alignment, and phylogenetic relationships of DNA polymerases", *Nucleic Acids Research* vol. 21, No. 4 1993, 787-802.

Brasch et al., "Pending U.S. Appl. No. 09/695,065, filed Oct. 25, 2000", Brasch, 1-81.

Brent, Roger et al., "A bacterial repressor protein or a yeast transcriptional terminator can block upstream activation of a yeast gene", *Nature* vol. 312, Macmillan Journals Ltd. Dec. 13, 1984 , 612-615.

Broach, James R. et al., "Recombination within the Yeast Plasmid, 2 mu Circle is Site Specific", vol. 29, *Cell* May 1982 , 227-234.

Broach, , "The Molecular Biology of the Yeast Saccharomyces: Life Cycle and Inheritance.", *Cold Spring Harbor Laboratory Press* 1981 , 445-570.

Broach, James R. , "The Yeast Plasmid 2u, Circle", vol. 28, *Cell* 1982 , 203-204.

Brousseau, R et al., "Synthesis of a Human Insulin Gene. V. Enzymatic Assembly Cloning and Characterization of the Human Proinsulin DNA.", *Gene* vol. 17 1982 , 279-289.

Brownstein, Michael J. et al., "Modulation of Non-Templated Nucleotide Addition by Tag DNA Polymerase: Primer Modifications that Facilitate Genotyping", *BioTechnigues* vol. 20, No. 6, Eaton Publishing Company Jun. 1, 1996, 1004, 1006, 1008.

Bruchez, Marcel et al., "Semiconductor Nanocrystals as Fluorescent Biological Labels", *Science*, vol. 281 1998 , 2013-2016.

Bruckner, Robert C. et al., "The Histone-like H Protein of *Escherichia coli* is ribosomal protein S3", *Nucleic Acids Research* vol. 17, No. 8, Oxford University Press 1989 , 3145-3161.

Brummelkamp, Thijn R. et al., "A System for Stable Expression of Short Interfering RNAs in Mammalian Cells.", *Science* vol. 296 Apr. 19, 2002 , 550-553.

Brunelli, Joseph P. et al., "A Series of Yeast/*Escherichia coli* lamda Expression Vectors Designed for Directional Cloning of cDNAs and cre/lox-Mediated Plasmid Excision", *Yeast* vol. 9, John Wiley & Sons 1993 , 1309-1318.

Brunelli, Joseph P. et al., "Lambda/Plasmid Vector Construction by In Vivo cre/lox-Mediated Recombination", *BioTechniques* vol. 16, No. 6 1994 , 1062-1064.

Brutlag, Douglas L. et al., "Improved sensitivity of biological sequence database searches", *Comp. Appl. Biosci.* vol. 6, No. 3 1990 , 237-245.

Bubeck, Peter et al., "Rapid cloning by homologous recombination in vivo", *Nucleic Acids Research* vol. 21, No. 15, Oxford University Press 1993 , 3601-3602.

Buchholz, Frank et al., "A simple assay to determine the functionality of Cre or FLP recombination targets in genomic manipulation constructs", *Nucleic Acids Research* vol. 24, No. 15, Oxford University Press Aug. 1996 , 3118-3119.

Buchholz, Frank et al., "Different thermostabilities of FLP and Cre recombinases: implications for applied site-specific recombination", *Nucleic Acids Research* vol. 24, No. 21, Oxford University Press 1996 , 4256-4262.

Buchschacher, Gary L. et al., "Development of lentiviral vectors for gene therapy for human diseases.", vol. 95, No. 8, *Blood* The American Society of Hematology Apr. 15, 2000 , 2499-2504.

Bundgaard, Hans , "Ch 1: Design of Prodrugs: Bioreversible derivatives for various functional groups and chemical entities", *Design of Prodrugs* Elsevier Science Publishers 1985 , 1-92.

Burcin, Mark M. et al., "Adenovirus-mediated regulable target gene expression in vivo", vol. 96, *Proceedings of the National Academy of Sciences (PNAS)* National Academy of Sciences Jan. 1999 , 355-360.

Burioni, R. et al., "An improved phage display vector for antibody repertoire cloning by construction of combinatorial libraries", *Res. Virol.* vol. 148, Elsevier Mar.-Apr. 1997 , 161-164.

Burns, Jane C. et al., "Vesicular Stomatitis Virus G. Glycoprotein Pseudotyped Retroviral Vectors: Concentration to Very High Titer and Efficient Gene Transfer into Mammalian and Nonmammalian Cells", vol. 90, *Proceedings of the National Academy of Sciences (PNAS)* The National Academy of Sciences Sep. 1993 , 8033-8037.

Bush, Karen et al., "A functional classification scheme for [beta]—lactamases and its correlation with molecular structure.", vol. 39, No. 6, *Antimicrobial Agents and Chemotherapy* American Society for Microbiology Jun. 1995 , 1211-1233.

Bushman, Wade et al., "Control of Directionality in Lambda Site Specific Recombination", *Science* vol. 230, American Association for the Advancement of Science 1985 , 906-911.

Buvoli, Massimo et al., "Suppression of Nonsense Mutations in Cell Culture and Mice by Multimerized Suppressor tRNA Genes", vol. 20, *Molecular and Cellular Biology* American Society for Microbiology May 2000 , 3116-3124.

CA2307016, , "Office Action mailed Feb. 9, 2009".

Caccio, Simone et al., "Establishing the *Cryptosporidium parvum* karyotype by NotI and SfiI restriction analysis and Southern hybridization.", *Gene* vol. 219 1998 , 73-79.

Cadwell, R. C. et al., "Randomization of Genes by PCR Mutagenesis", *PCR Methods Applications* vol. 2, Cold Spring Harbor Laboratory Press 1992, 28-33.

Campbell, Allan M., "Chromosomal insertion sites for phages and plasmids", vol. 174, No. 23, *Journal of Bacteriology* American Society for Microbiology Dec. 1992, 7495-7499.

Campbell, A, "Comparitive Molecular Biology of Lambdoid Phages", *Annu.Rev.Microbiol 48* 1994, 193-222.

Campbell, K. H. et al., "Sheep cloned by nuclear transfer from a cultured cell line", *Nature* vol. 380 1996, 64-66.

Campbell, Allan et al., "Specificity in DNA recognition by phage integrases", *Gene* vol. 300 Oct. 30, 2002, 13-18.

Cantor, Charles R. et al., "The Behavior of Biological Macromolecules: Their Biophysical Chemistry: pt. 3", W.H. Freeman & Co 1980, 1012-1036.

Caplen, Natasha J. et al., "Specific Inhibition of Gene Expression by Small Double-Stranded RNAs in Invertebrate and Vertebrate Systems.", *Proceedings of the National Academy of Sciences (PNAS)* vol. 98, No. 17 Aug. 14, 2001, 9742-9747.

Capone, John P. et al., "Amber, Ochre and Opal Suppressor tRNA Genes Derived from a Human Serine tRNA Gene.", vol. 4, No. 1, *EMBO Journal* IRL Press Limited 1985, 213-221.

Capone, John P. et al., "Introduction of UAG, UAA, and UGA Nonsense Mutations at a Specific Site in the *Escherichia coli* Chloramphenicol Acetyltransferase Gene: Use in Measurement of Amber, Ochre, and Opal Suppression in Mammalian Cells", vol. 6, No. 9, *Molecular and Cellular Biology* American Society for Microbiology Sep. 1986, 3059-3067.

Caravan, Peter et al., "Gadolinium (III) Chelates as MRI Contrast Agents: Structure, Dynamics, and Applications", *Chemical Reviews*, vol. 99, No. 9 1999, 2293-2352.

Carninci, Piero et al., "High Efficiency Full-Length cDNA Cloning by Biotinylated CAP Trapper", *Genomics* vol. 37, No. 3, Academic Press, Inc. Aug. 20, 1996, 327-336.

Carninci, Piero et al., "High Efficiency Selection of full-length cDNA by Improved Biotinylated Cap Trapper", *DNA Research* vol. 4, Universal Academy Press 1997, 61-66.

Carninci, Piero et al., "High-Efficiency Full-Length cDNA Cloning", *Methods in Enzymology* vol. 303, Academic Press 1999, 19-44.

Caron, Paul R. et al., "Appendix II: Alignment of primary sequences of DNA topoisomerases", vol. 29B *Advances in Pharmacology* 1994, 271-297.

Carver, Andrew S. et al., "Transgenic livestock as bioreactors: stable expression of human alpha-1-antitrypsin by a flock of sheep", *Biotechnology* vol. 11 Nov. 1993, 1263-1270.

Cenatiempo, Y., "Prokaryotic gene expression in vitro: transcription-translation coupled systems", *Biochimie*, vol. 68 Elsevier 1986, 505-515.

Chalfie, Martin et al., "Green fluorescent protein as a marker for gene expression", vol. 263, *Science* 1994, 802-805.

Chanock, Robert M. et al., "Human Monoclonal Antibody Fab Fragments Cloned from Combinatorial Libraries: Potential Usefulness in Prevention and/or Treatment of Major Human Viral Diseases", *Infectious Agents and Disease* vol. 2 1993, 118-131.

Chapin, Steven J. et al., "Differential expression of alternatively spliced forms of MAP4: a repertoire of structurally different microtubule-binding domains", *Biochemistry* vol. 34 Feb. 1995, 2289-2301.

Chapman-Smith, Anne et al., "Molecular Biology of Biotin Attachment to Proteins", *J. Nutr.* vol. 129 1999, 477S-484S.

Chartier, C et al., "Efficient Generation of Recombinant Adenovirus Vectors by Homologous Recombination in *Escherichia coli*", *Journal of Virology* vol. 70, No. 7 Jul. 1996, 4805-4810.

Chater, K F. et al., "Biological, Biochemical and Biomedical Aspects of Actinomycetes", *No. 34 of the FEMS Symposium Volumes. Akademiai Kaido; Sixth International Symposium on Actinomycetales Biology* Proceedings of the Sixth International Symposium on Actinomycetes Biology, Debrecen, Hungary, Aug. 26-30, 1985 1986, 45-54.

Chatterjee, Pradeep K. et al., "Isolating large nested deletions in bacterial and P1 artificial chromosomes by in vivo P1 packaging of products of Cre-catalyzed recombination between the endogenous and a transposed loxP site", *Nucleic Acids Research* vol. 25, No. 11, Jun. 1997, 2205-2212.

Chatterjee, Pradeep K. et al., "Retrofitting High Molecular Weight DNA Cloned in P1: Introduction of Reporter Genes, Markers Selectable in Mammalian Cells and Generation of Nested Deletions", *Genetic Analysis: Biomolecular Engineering* vol. 13, Elsevier Science B.V Jul. 1996, 33-42.

Chen, Hsiao-Huei et al., "DNA from Both High-Capacity and First-Generation Adenoviral Vectors", vol. 10, *Human Gene Therapy* Mary Ann Liebert, Inc. Feb. 10, 1999, 365-373.

Chen, Claudia et al., "High-Efficiency Transformation of Mammalian Cells by Plasmid DNA", vol. 7, No. 8,*Molecular and Cellular Biology* Aug. 1987, 2745-2752.

Cheng, Chonghui et al., "A catalytic domain of eukaryotic DNA topoisomerase I", *The Journal of Biological Chemistry* vol. 273, No. 19, The American Society for Biochemistry and Molecular Biology, Inc. May 8, 1988, 11589-11595.

Cheng, Chonghui et al., "Conservation of structure and mechanism between eukaryotic topoisomerase I and site-specific recombinases", vol. 92, No. 6, *Cell* Cell Press Mar. 20, 1998, 841-850.

Cheng, Chonghui et al., "DNA strand transfer catalyzed by vaccinia topoisomerase: ligation of DNAs containing a 3' mononucleotide overhang", vol. 28, No. 9, *Nucleic Acids Research* Oxford University Press 2000, 1893-1898.

Cheng, Chenghui et al., "Mutational analysis of 39 residues of vaccinia DNA topoisomerase identifies Lys-220, Arg-223, and Asn-228 as important for covalent catalysis", *The Journal of Biological Chemistry* vol. 272, No. 13, The American society for Biochemistry and Molecular Biology, Inc. Mar. 28, 1997, 8263-8269.

Cheng, Chonghui et al., "Recombinogenic flap ligation pathway for intrinsic repair of topoisomerase 1B-induced double-strand breaks", vol. 20, No. 21, *Molecular and Cellular Biology* American Society for Microbiology Nov. 2000, 8059-8068.

Cheng, Chonghui et al., "Site-specific DNA transesterification by vaccinia topoisomerase: Role of specific phosphates and nucleosides", *Biochemistry* vol. 38, No. 50, American Chemical Society 1999, 16599-16612.

Cherepanov, Peter P. et al., "Gene disruption in *Escherichia coli*: Tc R and KmR cassettes with the option of Flp-catalyzed excision of the antibiotic-resistance determinant", *Gene* vol. 158 1995, 9-14.

Chiba, Masatoshi et al., "Common sites for recombination and cleavage mediated by bacteriophage T4 DNA topoisomerase in Vitro", *The Journal of Biological Chemistry* vol. 264, No. 22 Aug. 5, 1989, 12785-12790.

Chong, Shaorong et al., "Single-column purification of free recombinant proteins using a self-cleavable affinity tag derived from a protein splicing element", vol. 192, *Gene* Elsevier Science B.V. 1997, 271-281.

Chou, Quin et al., "Use of Dark-Quenched FRET probes in Real-Time PCR", *American Biotechnology Laboratory* vol. 19, No. 8 Jul. 2001, 34.

Choulika, Andre et al., "Transfer of Single Gene-Containing Long Terminal Repeats into the Genome of Mammalian Cells by a Retroviral Vector Carrying the cre Gene and the IoxP site", *Journal of Virology* vol. 70, No. 3, American Society for Microbiology Mar. 1996, 1792-1798.

Christiansen, Bettina et al., "A Resolvase-Like Protein Is Required for the Site-Specific Integration of the Temperate Lactococcal Bacteriophage TP901-1", *Journal of Bacteriology*, vol. 178 No. 17 Sep. 1996, 5164-5173.

Christiansen, Bettina et al., "Characterization of the lactococcal temperate phage TP901-1 and its site-specific integration.", *Journal of Bacteriology* vol. 176, No. 4 Feb. 1994, 1069-1076.

Chu, Gilbert et al., "Electroporation for the efficient transfection of mammalian cells with DNA", vol. 15, No. 3, *Nucleic Acids Research* IRL Press Limited 1987, 1311-1326.

Chuang, Chiou-Feng et al., "Specific and heritable genetic interference by double-stranded RNA in *Arabidopsis thaliana*", vol. 97, No. 9, *Proceedings of the National Academy of Sciences (PNAS)* The National Academy of Sciences Apr. 25, 2000, 4985-4990.

Ciccarone, Valentina et al., "Lipofectamine 2000 Reagent for Rapid, Efficient Transfection of Eukaryotic Cells", vol. 21, No. 2, *Focus* Life Technologies 1999, 54-55.

Cigan, A. M. et al., "Mutational Analysis of the HIS4 Translational Initiator Region in *Saccharomyces cerevisiae*", *Molecular and Cellular Biology* vol. 8, No.7, American Society for Microbiology Jul. 1988, 2964-2975.

Cline, Martin J., "Perspectives for Gene Therapy: Inserting New Genetic Information into Mammalian Cells by Physical Techniques and Viral Vectors", *Pharmac. Ther.* vol. 29 1985, 69-92.

Clontech, "Creator Acceptor Vector Construction Kits", *CLONTECHniques* Oct. 2001, 2.

Clontech, , "Creator Gene Cloning & Expression System", *CLONTECHniques* CLONTECH Apr. 2000, 7-11.

Clontech, "Creator SMART Library Construction Kit", *CLONTECHniques16* Oct. 2001, 1-2.

Clontech, , "Creator: The Universal Platform for Analysis of Gene Function", *Powerpoint Presentation* Clontech, available at http://www.clontech.com/products/families/creator/popups/s1page1.html Jul. 24, 2001, 1-9.

Clontech, , "New Additions to the Creator Platform", http://www.clontech.com/archive/JAN01UPD/creator.shtml Jan. 2001, 1-4.

Clontech, , "New Creator-Compatible Expression Systems", *CLONTECHniques* Clontech Oct. 2000, 1-2.

Clowes, Monika M. et al., "Long-Term Biological Response of Injured Rat Carotid Artery Seeded with Smooth Muscle Cells Expressing Retrovirally Introduced Human Genes", *J. Clin. Invest.* vol. 93 Feb. 1994, 644-651.

Colby, Clarence et al., "Interferon Induction and Action", *Microbiology Section* The University of Connecticut, Storrs, Connecticut 06268 1971, 333-360.

Cole, Charles N. et al., "Identification of Sequences in the Herpes Simplex Virus Thymidine Kinase Gene Required for Efficient Processing and Polyadenylation", vol. 5, No. 8, *Molecular and Cellular Biology* American Society for Microbiology Aug. 1985, 2104-2113.

Collis, Christina M. et al., "Expression of Antibiotic Resistance Genes in the Integrated Cassettes of Integrons", *Antimicrobial Agents and Chemotherapy* vol. 39, No. 1 Jan. 1995, 155-162.

Compact Oxford English Dict., , "http://www.askford.com/concise_oed/invitro?view=uk", Accessed Jul. 19, 2006.

Cooper, Thomas A. et al., "Gene Regulation '97: The Regulation of Splice-Site Selection, and Its Role in Human Disease", vol. 61, *Am. J. Hum. Genet.* The American Society of Human Genetics 1997, 259-266.

Copeland, Neal G. et al., "Recombineering: A Powerful New Tool for Mouse Functional Genomics", *Nature Reviews |Genetics* vol. 2 Oct. 2001, 769-779.

Cormack, Brendan, "Directed Mutagenesis Using the Polymerase Chain Reaction", *Current Protocols in Molecular Biology* Ausubel, F.M., et al., eds., John Wiley & Sons, Inc., Boston, MA 1997, 8.5.1-8.5.10.

Cormack, Brendan, "Mutagenesis Using the Polymerase Chain Reaction", *Current Protcols in Molecular Biology* Ausubel, F.M., et al., eds., John Wiley & Sons, Inc., Boston, MA, 1991, 8.5.1-8.5.10.

Cotten, Matt et al., "High-Efficiency Receptor-Mediated Delivery of Small and Large (48 Kilobase Gene Constructs Using the Endosome-Disruption Activity of Defective or Chemically Inactivated Adenovirus Particles", vol. 89, *Proceedings of the National Academy of Sciences* (*PNAS*) The National Academy of Sciences Jul. 1992, 6094-6098.

Cotten, Matthew et al., "Receptor-Mediated Transport of DNA into Eukaryotic Cells", *Methods in Enzymology* vol. 217 1993, 618-644.

Cox, Michael M., "The FLP protein of the yeast 2-.micrometer plasmid: Expression of a eukaryotic genetic recombination system in *Escherichia coli*", *Proceedings of the National Academy of Sciences* (*PNAS*) vol. 80 Jul. 1983, 4223-4227.

Craig, Nancy L. et al., "The Mechanism of Phage lambda Site-Specific Recombination: Site-Specific Breakage of DNA by Int Topoisomerase", *Cell* vol. 35, Cell Press, Cambridge, MA Dec. 1983, 795-803.

Cramerie, A. et al., "Improved Green Fluorescent Protein by Molecular Evolution Using DNA Shuffling", vol. 14, *Nature Biotechnology* Mar. 1996, 315-319.

Crellin, Paul K. et al., "The Resolvase/Invertase Domain of the Site-Specific Recombinase TnpX Is Functional and Recognizes a Target Sequence That Resembles the Junction of the Circular Form of the Clostridium perfringens Transposon Tn4451", vol. 179, No. 16, *Journal of Bacteriology*, American Society for Microbiology Aug. 1997, 5148-5156.

Cronan, John E., "Biotination of Proteins in Vivo", *The Journal of Biological Chemistry* vol. 265, No. 18, The American Society for Biochemistry and Molecular Biology, Inc. Jun. 25, 1990, 10327-10333.

Crouzet, Joel et al., "Recombinational Construction in *Escherichia coli* of Infectious Adenoviral Genomes", vol. 94, *Proceedings of the National Academy of Sciences* (*PNAS*) The National Academy of Sciences Feb. 1997, 1414-1419.

Csordas-Toth, Eva et al., "Nucleotide sequence of a secondary attachment site for bacteriophage lambda on the *Escherichia coli* chromosome", *Nucleic Acids Research* vol. 7, No. 5 1979, 1335-1341.

Cubitt, Andrew B. et al., "Understanding structure-function relationships in the Aequorea victoria green fluorescent protein", *Methods in Cell Biology* vol. 58 1999, 19-30.

Curcio, M. J. et al., "Single-step selection for Ty1 element retrotransposition", *Proceedings of the National Academy of Sciences* (*PNAS*) vol. 88, National Academy of Sciences Feb. 1991, 936-940.

Curiel, David T. et al., "Adenovirus enhancement of transferrin-polylysine-mediated gene delivery", vol. 88, *Proceedings of the National Academy of Sciences* (*PNAS*) Oct. 1991, 8850-8854.

Curradi, Michela et al., "Molecular Mechanisms of Gene Silencing Mediated by DNA Methylation", vol. 22, No. 9, *Molecular and Cellular Biology* American Society for Microbiology May 2002, 3157-3173.

Dale, Emily C. et al., "Gene transfer with subsequent removal of the selection gene from the host genome", *Proceedings of the National Academy of Sciences* (*PNAS*) vol. 88 Dec. 1991, 10558-10562.

Dale, Emily C. et al., "Intra- and intermolecular site-specific recombination in plant cells mediated by bacteriophage P1 recombinase", *Gene* vol. 91 1990, 79-85.

Dale, Emily C. et al., "Mutations in the Cre/lox Recombination site Enhance the Stability of Recombination Products: Applications for Gene Targeting in Plants", *Journal of Cellular Biochemistry* abstract No. YI08 1992, 206.

Dang, Duyen T. et al., "Use of a Yeast Site-Specific Recombinase to Generate Embryonic Mosaics in Drosophila", *Developmental Genetics* vol. 13, Wiley-Liss, Inc. 1992, 367-375.

Datson, N. A. et al., "MicroSAGE: a modified procedure for serial analysis of gene expression in limited amounts of tissue", *Nucleic Acids Research* vol. 27, No. 5, Oxford University Press 1999, 1300-1307.

Davies, Julian et al., "An Antibody VH Domain with a lox-Cre Site Integrated Into its Coding Region: Bacterial Recombination within a Single Polypeptide Chain", *FEBS Letters* vol. 377, Federation of European Biochemical Societies 1995, 92-96.

Davis, Cynthia R. et al., "Analysis of the Mechanisms of Action of the *Saccharomyces cerevisiae* Dominant Lethal cdc42 G12V and Dominant Negative cdc42 D118A Mutations", *The Journal of Biological Chemistry* vol. 273, No. 2 Jan. 9, 1998, 849-858.

De Massy, B. et al., "Mutations of the phage .lambda. attachment site alter the directionality of resolution of Holliday structures", *EMBO J.* vol. 8:No. 5 1989, 1591-1599.

Degryse, Eric, "In vivo intermolecular recombination in *Escherichia coli*: application to plasmid constructions", *Gene* vol. 170, Elsevier Science 1996, 45-50.

Deng, Ming-De et al., "Ethanol Synthesis by Genetic Engineering in Cyanobacteria", *Applied and Environmental Microbiology* vol. 65, No. 2, American Society for Microbiology Feb. 1999, 523-528.

Der, Sandy D. et al., "A double-stranded RNA-activated protein kinase-dependent pathway mediating stress-induced apoptosis.", *Proceedings of the National Academy of Sciences* (*PNAS*) vol. 94 Apr. 1997, 3279-3283.

Derbyshire, Victoria et al., "Lightning strikes twice: Intron-intein coincidence", *Proceedings of the National Academy of Sciences* (*PNAS*) vol. 95, The National Academy of Sciences of the USA Feb. 1998, 1356-1357.

Devine, Scott E. et al., "Efficient integration of artificial transposons into plasmid targets in vitro: a useful tool for DNA mapping, sequencing and genetic analysis", *Nucleic Acids Research*, vol. 22, No. 18 1994, 3765-3772.

Di Virgilio, Francesco et al., "Fura-2 Secretion and Sequestration in Macrophages. A Blocker of Organic Anion Transport Reveals That These Processes Occur via a Membrane Transport System for Organic Anions", *The Journal of Immunology* vol. 140, No. 3, The American Association of Immunologists Feb. 1, 1988, 915-920.

Diederich, Ludger et al., "New Cloning vectors for Integration into the Lambda Attachment Site attB of the *Escherichia coli* Chromosome", *Plasmid*, vol. 28 Academic Press 1992, 14-24.

Digate, Russell J. et al., "Molecular Cloning and DNA Sequence Analysis of *Escherichia coli* topB, the Gene Encoding Topoisomerase III", *The Journal of Biological Chemistry* vol. 264, No. 30, The American society for Biochemistry and Molecular Biology, Inc. Oct. 25, 1989, 17924-17930.

Dijkema, R. et al., "Cloning and expression of the chromosomal immune interferon gene of the rat", *The EMBO Journal*, vol. 4, No. 3 IRL Press Limited 1985, 761-767.

Dion, L. D. et al., "Supernatant rescue assay vs. polymerase chain reaction for detection of", *Journal of Virological Methods* vol. 56, Elsevier Science B.V. 1996, 99-107.

Dirac, Annette M. et al., "Reversal of Senescence in Mouse Fibroblasts Through Lentiviral Suppression of p53", *The Journal of Biological Chemistry* vol. 278, No. 14 Apr. 4, 2003, 11731-11734.

Donoghue, Maria J. et al., "Rostrocaudal Gradient of Transgene Expression in Adult Skeletal Muscle", *Proceedings of the National Academy of Sciences (PNAS)* vol. 88 Jul. 1991, 5847-5851.

Dorgai, Laszlo et al., "Recognition of Core Binding Sites by Bacteriophage Integrases", *Journal of Molecular Biology*, vol. 277 Apr. 17, 1998, 1059-1070.

Douglas, et al., *Human Gene Therapy 10* 2001, 401-413.

Drocourt, Daniel et al., "Cassettes of the *Streptoalloteichus hindustanus* ble gene for transformation of lower and higher eukaryotes to pnleomycin resistance", *Nucleic Acids Research* vol. 18, No. 13, Oxford University Press 1990, 4009.

Dubendorff, John W. et al., "Controlling Basal Expression in an Inducible T7 Expression System by Blocking the Target T7 Promoter with lac Repressor", *J. Mol. Biol.* vol. 219, Academic Press, Ltd. 1991, 45-59.

Dull, Tom et al., "A Third-Generation Lentivirus Vector with a Conditional Packaging System", *Journal of Virology* vol. 72, No. 11, American Society for Microbiology Nov. 1998, 8463-8471.

Dykxhoorn, Derek M. et al., "Killing the Messenger: Short RNAs That Silence Gene Expression", *Nature Reviews, Molecular Cell Biology* vol. 4 Jun. 2003, 457-467.

Dymecki, Susan M., "A modular set of Flp, FRT and lacZ fusion vectors for manipulating genes by site-specific recombination", *Gene*, vol. 171 Elsevier Science B.V. 1996, 197-201.

Easter, Carla L. et al., "Contribution of Different Segments of the par Region to Stable Maintenance of the Broad-Host-Range Plasmid RK2", *Journal of Bacteriology* vol. 179, No. 20 Oct. 1997, 6472-6479.

Edery, Isaac et al., "An Efficient Strategy to Isolate Full-Length cDNAs Based on an mRNA Cap Retention Procedure (CAPture)", *Molecular and Cellular Biology* vol. 15, No. 6, American Society for Microbiology Jun. 1995, 3363-3371.

Edlund, Thomas et al., "Tandem Duplication Induced by an Unusual ampA1-, ampC-Transducing Lambda Phage: A Probe to Initiate Gene Amplification", *Molec. gen. Genet.* vol. 180, Department of Microbiology, University of Umea, S-901 87 Umea, Sweden 1980, 249-257.

Eggertsson, Gudmundur et al., "Transfer Ribonucleic Acid-Mediated Suppression of Termination Codons in *Escherichia coli*", *Microbiological Reviews* vol. 52, No. 3, American Society for Microbiology Sep. 1988, 354-374.

Einhauer, A. et al., "The FLAG peptide, a versatile fusion tag for purification of recombinant proteins.", *J. Biochem Bioptys Methods* vol. 49 2001, 455-465.

Elbashir, Sayda M. et al., "Duplexes of 21-nucleotide RNAs mediate RNA Interference in cultured mammalian cells", *Nature* vol. 411, 2001 Macmillan Magazines Ltd May 24, 2001, 494-499.

Elledge, Steven J. et al., "Lamda YES: A multifunctional cDNA expression vector for the isolation of genes by complementation of yeast and *Escherichia coli* mutations", *Proceedings of the National Academy of Sciences (PNAS)*, vol. 88 National Academy of Sciences Mar. 1991, 1731-1735.

Emi, Nobuhiko et al., "Pseudotype Formation of Murine Leukemia Virus with the G Protein of Vesicular Stomatitis Virus", *Journal of Virology* vol. 65, No. 3, American Society for Microbiology Mar. 1991, 1202-1207.

Engelberg-Kulka, Hanna et al., "Ch 60: Suppression of Termination Codons", *Escherichia coli and Samonella Cellular and Molecular Biology* Second Edition, vol. 1, No. 2, Ch. 60 American Society for Microbiology 1996, 909-921.

Engelhardt, John F. et al., "Direct gene transfer of human CFTR into bronchial epithelia of xenografts with E1-deleted adenoviruses", *Nature Genetics* vol. 4, Nature America, Inc. May 1993, 27-34.

Enquist, L. W. et al., "Strand exchange in site-specific recombination", *Proceedings of the National Academy of Sciences (PNAS)* vol. 76, No. 3 Mar. 1979, 1363-1367.

Enquist, L. W. et al., "The Red Plaque Test: A Rapid Method for Identification of Excision Defective Variants of Bacteriophage Lambda", *Virology* vol. 72 1976, 147-153.

Ericsson, Maria et al., "Characterization of ts 16, a Temperature-Sensitive Mutant of Vaccinia Virus", *Journal of Virology* vol. 69, No. 11, American Society for Microbiology Nov. 1995, 7072-7086.

Erlich, , "PRC Technology", *Stockton Press* Principles and Applications for DNA Amplications 1989, 23-30.

Esposito, Dominic et al., "The integrase family of tyrosine recombinases: evolution of a conserved active site domain", *Nucleic Acids Research*, vol. 25, No. 18 Oxford University Press 1997, 3605-3614.

Fallaux, Frits J. et al., "Characterization of 911: A New Helper Cell Line for the Titration and Propagation of Early Region 1-Deleted Adenoviral Vectors", *Human Gene Therapy* vol. 7, Mary Ann Liebert, Inc. Jan. 20, 1996, 215-222.

Fallaux, Frits J. et al., "New Helper Cells and Matched Early Region 1-Deleted Adenovirus Vectors Prevent Generation of Replication-Competent Adenoviruses", *Human Gene Therapy* vol. 9, Mary Ann Liebert, Inc. Sep. 1, 1998, 1909-1917.

Fan, Xiaolong et al., "Efficient Adenoviral Vector Transduction of Human Hematopoietic SCID-Repopulating and Long-Term Culture-Initiating Cells", *Human Gene Therapy* vol. 11, Mary Ann Liebert, Inc. Jun. 10, 2000, 1313-1327.

Feil, Robert et al., "Regulation of Cre Recombinase Activity by Mutated Estrogen Receptor Ligand-Binding Domains", *Biochemical and Biophysical Research Communications*, vol. 237 Academic Press 1997, 752-757.

Feinbaum, Rhonda, "Vectors Derived from Plasmids", *Current Protocols in Molecular Biology* John Wiley & Sons, Inc., Boston, MA 1998, 1:1.5.1-1.5.17.

Felgner, P. L. et al., "Cationic Liposome Mediated Transfection", *Proceedings West. Pharmacol. Soc.* vol. 32, Western Pharmacological Society 1989, 115-121.

Felgner, Philip L. et al., "Cationic liposome-mediated transfection", *Nature* vol. 337, No. 6205 Jan. 26, 1989, 387-388.

Ferguson, Jill et al., "Construction and characterization of three yeast-*Escherichia coli* shuttle vectors designed for rapid subcloning of yeast genes on small DNA fragments", *Gene*, vol. 16 Elsevier/North-Holland Biomedical Press 1981, 191-197.

Fermentas Life Sciences, , "pUC18/19 Description and Map", *Fermentas Life Sciences* http://www.fermentas.com/technifo/nucleicacids/mappuc1819.htm Aug. 2006, 1-2.

Ferrin, Lance J. et al., "Sequence-specific ligation of DNA using RecA protein", *Proceedings of the National Academy of Sciences (PNAS)* vol. 95 Mar. 1998, 2152-2157.

Fiering, Steven et al., "An "in-out" strategy using gene targeting and FLP recombinase for the functional dissection of complex DNA regulatory elements: Analysis of the Beta-globin locus control region", *Proceedings of the National Academy of Sciences (PNAS)*, vol. 90 Sep. 1993, 8469-8473.

Filutowicz, Marcin et al., "Involvement of Fis Protein in Replication of the *Escherichia coli* Chromosome", *Journal of Bacteriology* vol. 174, No. 2 Jan. 1992, 398-407.

Filutowicz, Marcin et al., "Purification of the *Escherichia coli* integration host factor (IHF) in one chromatographic step", *Gene*, vol. 147 Elsevier Science B.V. 1994, 149-150.

Fire, Andrew et al., "Potent and specific genetic interference by double-stranded RNA in Caenorhabditis elegans", *Nature* vol. 391, Nature Publishing Group Feb. 19, 1998, 806-811.

Flaman, Jean-Michel et al., "A rapid PCR fidelity assay", *Nucleic Acids Research*, vol. 22, No. 15, 1994, 3259-3260.

Flanagan, Peter M. et al., "Analysis of Inhibitors of the Site-specific Recombination Reaction Mediated by TN3 Resolvase", *J. Mol. Biol.*, vol. 206 Academic Press Limited 1989, 295-304.

Flores, A. et al., "A protein-protein interaction map of yeast RNA polymerase III", *Proceedings of the National Academy of Sciences (PNAS)*, vol. 96 Biochemistry Jul. 1999, 7815-7820.

Flowers, C. C. et al., "Inhibition of Recombinant Human Immunodeficiency Virus Type 1 Replication by a Site-Specific Recombinase", *Journal of Virology* Vo. 71, No. 4 Apr. 1997, 2685-2692.

FR 2 670 502, , "Dialog File 351, English Language Abstract", *Derwent World Patent Index* French Patent No. FR 2 670 502 (Document AL20) and PCT Patent No. WO 92/10577 (Document AM20), WPI Accession No. 9107201 1992.

Francia, M. V. et al., "Gene Integration in the *Escherichia coli* Chromosome Mediated by Tn21 Integrase (Int21)", *Journal of Bacteriology*, vol. 178, No. 3 American Society for Microbiology Feb. 1996, 894-898.

Francia, M. V. et al., "The Int1l Integron Integrase Preferentially Binds Single-Stranded DNA of the attC Site", *Journal of Bacteriology*, vol. 181, No. 21 American Society for Microbiology Nov. 1999, 6844-6849.

Freshney, R. I., "The Culture Environment: II. Media and Supplements", *Culture of Animal Cells: A Manual of Basic Technique* Alan R. Liss, Inc. 1983, 74-78.

Friesen, Paul D. et al., "Ch 6: Regulation of Baculovirus Early Gene Expression", *The Baculoviruses* Plenum Press, New York and London, Miller, Lois K., ed. 1997, 141-170.

Frolov, Ilya et al., "Alphavirus-based expression vectors: Strategies and applications", *Proceedings of the National Academy of Sciences (PNAS)* vol. 93 Oct. 1996, 11371-11377.

Fukushige, Shinichi et al., "Genomic targeting with a positive-selection lox integration vector allows highly reproducible gene expression in mammalian cells", *Proceedings of the National Academy of Sciences (PNAS)*, vol. 89 Sep. 1992, 7905-7909.

Gage, Philipe J. et al., "A Cell-Free Recombination System for Site-Specific Integration of Multigenic Shuttle Plasmids into Herpes Simplex Type 1 Genome", *Journal of Virology*, vol. 66, No. 9 American Society for Micobiology Sep. 1992, 5509-5515.

Gaietta, Guido et al., "Multicolor and Electron Microscopic Imaging of Connexin Trafficking", *Science* vol. 296, American Association for the Advancement of Science Apr. 19, 2002, 503-507.

Gallegos-Cuellar, Anabell et al., "Green Fluorescence Protein as a Transcriptional Reporter Gene in Epithelial Cells: Real-Time Studies of the Human Involucrin Promoter", *Focus* vol. 24 2002, 16-18.

Gallichan, W. S. et al., "Lentivirus-Mediated Transduction of Islet Grafts with Interleukin 4 Results in Sustained Gene Expression and Protection from Insulitis", *Human Gene Therapy* vol. 9, Mary Ann Liebert, Inc. Dec. 10, 1998, 2717-2726.

Gardner, J. F. et al., "Role of *Escherichia coli* IHF Protein in Lambda Site-specific Recombination- A Mutational Analysis of Binding Sites", *Journal of Molecular Biology*, London, GB,; vol. 19(2) Sep. 20, 1986, 181-189.

Gatz, Christiane et al., "Stringent repression and homogenous de-repression by tetracycline of a modified CaMV 35S promoter in intact transgenic tobacco plants", *The Plant Journal* vol. 2, No. 3, Blackwell Scientific Publishers.1992, 397-404.

Gay, Philippe et al., "Cloning Structural Gene sacB, Which Codes for Exoenzyme Levansucrase of *Bacillus subtilis*: Expression of the Gene in *Escherichia coli*", *Journal of Bacteriology* vol. 153, No. 3, American Society for Microbiology Mar. 1983, 1424-1431.

Gay, P. et al., "Positive Selection Procedure for Entrapment of Insertion Sequence Elements in Gram-Negative Bacteria", *Journal of Bacteriology* vol. 164, No. 2, American Society for Microbiology Nov. 1985, 918-921.

Gene, , vol. 150 1994, 51-56.

Geoffroy, Frederique et al., "A new phage display system to construct multicombinatorial libraries of very large antibody repertoires", *Gene* vol. 151, Elsevier Science B.V. 1994, 109-113.

Gerard, Gary F. et al., "cDNA Synthesis by Moloney Murine Leukemia Virus RNase H-Minus Reverse Transcriptase Possessing Full DNA Polymerase Activity", *Focus*, vol. 14, No. 3, 1992, 91-93.

Geysen, H. M. et al., "Use of peptide synthesis to probe antigens for epitopes to a resolution of a single amino acid", *Proceedings of the National Academy of Sciences (PNAS)* vol. 81 Jul. 1984, 3998-4002.

Gibco BRL, , "GatewayTM Cloning Technology, Version 1, Life Technologies Instructions Manual", http://www.lifetech.com/gateway 1999, 1-60.

Gilchrest, B. A. et al., "Characterization and Partial Purification of Keratinocyte Growth Factor From the Hypothalamus", *Journal of Cellular Physiology* vol. 120 1984, 377-383.

Gill, D. R. et al., "Increased persistence of lung gene expression using plasmids containing the ubiquitin C or elongation factor 1alpha promoter", *Gene Therapy* vol. 8, Nature Publishing Group 2001, 1539-1546.

Gilman, Michael Z. et al., "Isolation of sigma-28-specific promoters from *Bacillus subtilis* DNA", vol. 32, No. 1-2, *Gene* Elsevier Science Publishers Dec. 1984, 11-20.

Glasgow, Anna C. et al., "DNA-binding Properties of the Hin Recombinase", *The Journal of Biological Chemistry* vol. 264, No. 17, American Society for Biochemistry and Molecular Biology, Inc. Jun. 15, 1989, 10072-10082.

Glick, Bernard R. et al., "Factors affecting the expression of foreign proteins in *Escherichia coli*", *Journal Industrial Microbiology* vol. 1, Elsevier Science Publishers 1987, 277-282.

Godeau, Francois et al., "Replication inhibition by nucleoside analogues of a recombinant Autographa californica multicapsidnuclear polyhedrosis virus harboring the herpes thymidine kinase gene driven by the 1E-1 (0) promoter: a new way to select recombinant baculoviruses", *Nucleic Acids Research* vol. 20, No. 23, Oxford University Press 1992, 6239-6246.

Goldspiel, Barry R. et al., "Clinical Frontiers: Human gene therapy", *Clinical Pharmacy* vol. 12, American Society of Hospital Pharmacists, Inc. Jul. 1993, 488-505.

Golic, Kent G. et al., "Engineering the *Drosophila* Genome: Chromosome Rearrangements by Design", *Genetics* vol. 144 Dec. 1996, 1693-1711.

Golic, Kent G. et al., "The FLP Recombinase of Yeast Catalyzes Site-Specific Recombination in the *Drosophila* Genome", *Cell* vol. 59 Nov. 3, 1989, 499-509.

Gordon, Jon W. , "Transgenic Animals", *International Review of Cytology* vol. 115 1989, 171-229.

Gorman, Cornelia M. et al., "The *Rous sarcoma* virus long terminal repeat is a strong promoter when Introduced into a variety of eukaryotic cells by DNA-mediated transfection", *Proceedings of the National Academy of Sciences (PNAS)* vol. 79 Nov. 1982, 6777-6781.

Goshima, Naoki et al., "Development of high accuracy and high throughput production multi-purpose gateway entry clones production. I Improvement of the PCR condition for the construction of the entry clone", *Invitrogen Corp.* Abstract available online at http://biotech.nikkeibp.co.jp/netlink/Ito/gateway/newinfo/contents9.htrnl 2000, 1-2.

Gotou, Naoki et al., "Gateway Cloning Technology", *Experimental Medicine* vol. 18, No. 19 (in Japanese Language) Dec. 2000, 2716-2717.

Gottesman, Susan et al., "Bacterial Regulation: Global Regulatory Networks", vol. 18, *Ann. Rev. Genet.* Annual Reviews, Inc. 1984, 415-441.

Gotz, Frank et al., "*Escherichia coli* 30S mutants lacking protein S20 are defective in translation initiation", *Biochemica et Biophysica Acta* vol. 1050, Elsevier Science Publishing Co. 1990, 93-97.

Graham, F. L. et al., "Ch 16: Adenovirus-Based Expression Vectors and Recombinant Vaccines", *Vaccines: New Approaches to Immunological Problems* Ellis, R.W., ed. Butterworth-Heinemann, Stoneham, MA 1992, 363-390.

Graham, F. L. et al., "Characteristics of a Human Cell Line Transformed by DNA from Human Adenovirus Type 5", *J. gen. Virol.* vol. 36, Cambridge University Press 1977, 59-74.

Gram, Hermann et al., "In vitro selection and affinity maturation of antibodies from a naive combinatorial immunoglobulin library", *Proceedings of the National Academy of Sciences (PNAS)* vol. 89 Apr. 1992, 3576-3580.

Gray, et al., "U.S. Appl. No. 11/290,804, filed Dec. 1, 2005".

Green, N. M., "Avidin and Streptavidin", *Methods of Enzymology* vol. 184 1990, 51-67.

Green, Rachel et al., "Ribosomes and Translation", *Annu. Rev. Biochem* vol. 66, Annual Reviews, Inc. 1997, 679-716.

Griffin, B A. et al., "Specific Covalent Labeling of Recominant Protein Molecules Inside Live Cells", *Science* vol. 281 Jul. 10, 1998, 269-272.

Grindley, Nigel D. et al., "Effects of Different Alleles of the *E. coli* K12 polA Gene on the Replication of Non-transferring Plasmids", *Molec. gen. Genet.* vol. 143 1976, 311-318.

Gronostajski, Richard M. et al., "The FLP Protein of the 2-micron Plasmid of Yeast. Inter- and Intramolecular Reactions", *The Journal of Biological Chemistry* vol. 260, No. 22, The American Society of Biological Chemists, Inc. Oct. 5, 1985, 12328-12335.

Gross, Christian H. et al., "Vaccinia Virions Lacking the RNA Helicase Nucleoside Triphosphate Phosphohydrolase II Are Defective in Early Transcription", *Journal of Virology* vol. 70, No. 12, American Society for Microbiology Dec. 1996, 8549-8555.

Grossman, Mariann et al., "Retroviruses: delivery vehicle to the liver", *Current Osinion in Genetics and Development* vol. 3 1993, 110-114.

Grunden, Amy M. et al., "An Analysis of the Binding of Repressor Protein ModE to modABCD (Molybdate Transport) Operator/Promoter DNA of *Escherichia coli*", *The Journal of Biological Chemistry* vol. 274, No. 34, The American Society for Biochemistry and Molecular Biology, Inc. Aug. 20, 1999, 24308-24315.

Gryczan, Thomas J. et al., "Ch 10: Molecular Cloning in *Bacillus subtilis*", *Academic Press The Molecular Biology of Bacilli.* vol. I: *Bacilus subtilis* 1982, 307-329.

Gu, Hua et al., "Deletion of a DNA Polymerase Beta Gene Segment in T Cells Using Cell Type-Specific Gene Targeting", *Science* vol. 265, Association for the Advancement of Science Jul. 1, 1994, 103-106.

Guo, Feng et al., "Asymmetric DNA bending in the Cre-loxP site-specific recombination synapse", *Proceedings of the National Academy of Sciences (PNAS)*, vol. 96 Jun. 1999, 7143-7148.

Guo, Feng et al., "Structure of Cre recombinase complexed with DNA in a site-specific recombination synapse", *Nature* vol. 389, Nature Publishing Group Sep. 4, 1997, 40-46.

Gupta, Malini et al., "Eukaryotic DNA topoisomerases I", *Biochmica et Biophysica Acta* vol. 1262, Elsevier Science B.V. 1995, 1-14.

Guy, Jacqueline et al., "Delivery of DNA into Mammalian Cells by Receptor- Mediated Endocytosis and Gene Therapy" *Molecular Biotechnology* vol. 3 1995, 237-248.

Haffter, Pascal et al., "Enhancer-independent mutants of the Cin recombinise have a relaxed topological specificity", *The EMBO Journal* vol. 7, No. 12, IRL Press Limited 1988, 3991-3996.

Haghighat, Ashkan et al., "eIF4G Dramatically Enhances the Binding of eIF4E to the mRNA 5'-Cap Structure", *The Journal of Biological Chemistry* vol. 272, No. 35, The American Society for Biochemistry and Molecular Biology, Inc. 1997, 21677-21680.

Haghighat, Ashkan et al., "The eIF4G-eIF4E Complex is the Target for Direct Cleavage by the Rhinovirus 2A Proteinase", *Journal of Virology* vol. 70 Dec. 1996, 8444-8450.

Hall, Ruth M. et al., "Mobile Gene Cassettes and Integrons: Capture and Spread of Genes by Site-specific Recombination", *Mol. Microbiology* vol. 15, Blackwell Scientific Publication Ltd. 1995, 593-600.

Hallet, Bernard et al., "Transposition and site-specific recombination: adapting DNA cut-and-paste mechanisms to a variety of genetic rearrangements", *FEMS Microbiology Reviews* vol. 21, Elsevier Science B. V. Sep. 1997, 157-178.

Hallum, J. V. et al., "Quantitative Aspects of Inhibition of Virus Replication by Interferon in Chick Embryo Cell Cultures", *Journal of Bacteriology* vol. 92, No. 4 Oct. 1966, 1047-1050.

Hamer, Dean H. et al., "Regulation In Vivo of a Cloned Mammalian Gene: Cadmium Induces the Transcription of a Mouse Metallothionein Gene in SV40 Vectors", vol. 1, *Journal of Molecular and Applied Genetics* Raven Press 1982, 273-288.

Hammerling, Gunter J., "Production of Antibody-Producing Hybridomas in the Rodent Systems", *Monoclonal Antibodies and T-Cell Hybridomas: Perspectives and technical advances*, Elsevier/North-Holland Biomedical Press, 1981, 563-681.

Hanai, Ryo et al., "Human TOP3: A single-copy gene encoding DNA topoisomerase III", *Proceedings of the National Academy of Sciences (PNAS)* vol. 93, The National Academy of Sciences Apr. 1996, 3653-3657.

Hancock, Robert E. et al., "The role of antimicrobial peptides in animal defenses", *Proceedings of the National Academy of Sciences (PNAS)* vol. 97, No. 16 Aug. 1, 2000, 8856-8861.

Hanks, Steven K. et al., "Protein kinases 6. The eukaryotic protein kinase superfamily: kinase (catalytic) domain structure and classification", *The FASEB Journal*, vol. 9 May 1995, 576-596.

Hanson, "U.S. Appl. No. 10/970,635, filed Oct. 22, 2004".

Harbour, J. W. et al., "Rb function in cell-cycle regulation and apoptosis", *Nature Cell Biology* vol. 2 Apr. 2000, E65.

Hardy, Stephen et al., "Construction of Adenovirus Vectors though Cre-lox Recombination", *Journal of Virology* vol. 71, No. 3 American Society for Microbiology Mar. 1997, 1842-1849.

Harlow, Ed D. et al., "Antibodies: A Laboratory Manual", *Cold Spring Harbor Laboratory Press*, 2nd Edition, 1988, 116-120.

Harrison, Tim et al., "Host-Range Mutants of Adenovirus Type 5 Defective for Growth in HeLa Cells", *Virology* vol. 77, No. 1 Academic Press, Inc. 1977, 319-329.

Hartley, J. L. et al., "DNA Cloning Using In Vitro Site-Specific Recombination", Nov. 1, 2000, 1788-1795.

Hartley, James L. et al., "DNA Cloning Using In Vitro Site-Specific Recombination", vol. 10, No. 11, *Genome Research* Cold Spring Harbor Laboratory Press Nov. 2000, 1788-1795.

Harwood, Steven H. et al., "AcMNPV Late Expression Factor-5 Interacts with Itself and Contains a Zinc Ribbon Domain That Is Required for Maximal Late Transcription Activity and Is Homologous to Elongation Factor TFIIS", *Virology* vol. 250, Issue 1 Academic Press Oct. 10, 1998, 118-134.

Hasan, Noaman et al., "Control of cloned gene expression by promoter inversion in vivo: construction of improved vectors with multiple cloning site and the P.sub.tac promoter", *Gene* vol. 56, Elsevier Science 1987, 145-151.

Hasan, Noaman et al., "*Escherichia coli* genome targeting, I. Cre-lox-mediated in vitro generation of ori plasmids and their in vivo chromosomal integration and retrieval", *Gene* vol. 150, Elsevier Science B.V. 1994, 51-56.

Hashimoto-Gotoh, Tamotsu et al., "Improved vector, pHSG664, for direct streptomycin-resistance selection: cDNA cloning with G:C-tailing procedure and subcloning of double-digeste DNA fragments", *Gene* vol. 41, Elsevier Science 1986, 125-128.

He, Tong-Chuan et al., "A simplified system for generating recombinant adenoviruses", *Proceedings of the National Academy of Sciences (PNAS)* vol. 95 Mar. 1998, 2509-2514.

Hearing, Patrick et al., "Identification of a Repeated Sequence Element Required for Efficient Encapsidation of the Adenovirus Type 5 Chromosome", *Journal of Virology* vol. 61, No. 8 American Society for Microbiology Aug. 1987, 2555-2558.

Hearn, Milton T. et al., "Applications of novel affinity cassette methods: use of peptide fusion handles for the purification of recombinant proteins", *Journal of Molecular Recognition* vol. 14 2001, 323-369.

Hegedus, Dwayne D. et al., "A series of broad host range shuttle vectors for constitutive and inducible expression of heterologous proteins in insect cell lines", *Gene* vol. 207, Elsevier Science B.V. 1998, 241-249.

Hegedus, Dwayne D. et al., "Differences in the Expression and Localization of Human Melanotransferrin in Lepidopteran and Dipteran Insect Cell Lines", *Protein Expression and Purification* vol. 15, No. 3, Academic Press 1999, 296-307.

Hehl, Reinhard et al., "Structural analysis of Tam3, a transposable element from Antirrhinum majus, reveals homologies to the Ac element from maize", *Plant Molecular Biology* vol. 16, Kluwer Academic Publishers 1991, 369-371.

Henikoff, Steven, "Unidirectional digestion with exonuclease III creates targeted breakpoints for DNA sequencing", *Gene* vol. 28, Elsevier Science Publishers 1984, 351-359.

Henningfeld, Kristine A. et al., "A Model for Topoisomerase I-Mediated Insertions and Deletions with Duplex DNA Substrates Containing Branches, Nicks, and Gaps", *Biochemistry* vol. 34, No. 18 American Chemical Society 1995, 6120-6129.

Herman, Brian, "Ch 8: Resonance Energy Transfer Microscopy", *Methods in Cell Biology*, vol. 30 1989, 219-243.

Heyman, J. A. et al., "Genome-Scale Cloning and Expression of Individual Open Reading Frames Using Topoisomerase I-Mediated Ligation", vol. 9, No. 4, *Genome Research, Cold Spring Harbor Laboratory Press*, US, Apr. 1999, 383-392.

Heyman, John A. et al., "Genome-scale cloning and expression of individual open reading frames using topoisomerase I-mediated ligation", vol. 9, No. 4, *Genome Research*, Cold Spring Harbor Laboratory Press 1999, 383-392.

Hitt, Mary M. et al., "Human Adenovirus Vectors for Gene Transfer into Mammalian Cells", *Advances in Pharmacology* vol. 40 1997, 137-206.

Hitt, Mary M. et al., "Structure and Genetic Organization of Adenovirus Vectors", *The Development of Human Gene Therapy* Friedmann, T., ed., Cold Spring Harbor Laboratory Press, Cold Spring Harbor, NY 1999, 61-86.

Hochuli, E. et al., "Genetic Approach to Facilitate Purification of Recombinant Proteins with a Novel Metal Chelate Adsorbent", *Bio/Technology*, vol. 6 Nov. 1988, 1321-1325.

Hoekstra, Merl F. et al., "Shuttle Mutagenesis: Bacterial Transposons for Genetic Manipulations in Yeast", *Methods in Enzymology* vol. 194 1991, 329-342.

Hoess, Ronald H. et al., "Formation of small circular DNA molecules via an in vitro site-specific recombination system", *Gene* vol. 40 1985, 325-329.

Hoess, Ronald H. et al., "Interaction of the bacteriophage P1 recombinase Cre with the recombining site loxP", *Proceedings of the National Academy of Sciences (PNAS)* vol. 81 Feb. 1984, 1026-1029.

Hoess, Ronald H. et al., "Mechanism of Strand Cleavage and Exchange in the Cre-lox Site-specific Recombination System", *J. Mol. Biol.* vol. 181 1985, 351-362.

Hoess, Ronald H. et al., "P1 site-specific recombination: Nucleotide sequence of the recombining sites", vol. 79, No. 11, *Proceedings of the National Academy of Sciences (PNAS)* Jun. 1, 1982, 3398-3402.

Hoess, R. H. et al., "The Cre-lox Recombination System", *Nucleic Acids and Molecular Biology*, vol. 4 Eckstein, F., et al. 1990, 99-109.

Hoess, Ronald H. et al., "The role of the loxP spacer region in P1 site-specific recombination", *Nucleic Acids Research* vol. 14, No. 5 1986, 2287-2300.

Hollingshead, S et al., "NCBI Entrez", *Genbank Report* Accession No. X02340 M10241 1985, 1-2.

Hollingshead, Susan et al., "Nucleotide Sequence Analysis of a Gene Encoding a Streptomycin/Spectinomycin Adenyltransferase", vol. 13, *Plasmid* No. 1 Academic Press, Inc. 1985, 17-30.

Holt, Cydne L. et al., "A novel phage Lamda replacement Cre-lox vector that has automatic subcloning capabilities", *Gene* vol. 133 1993, 95-97.

Honda, Masao et al., "A replication-deficient adenovirus enhances liposome-mediated nucleic acid transfer into a stable cell line expressing T7 RNA polymerase", *Journal of Virological Methods* vol. 58, Elsevier Science B.V. 1996, 41-58.

Hoogenboom, Hennie R. et al., "Multi-subunit proteins on the surface of filamentous phage: methodologies for displaying antibody (Fab) heavy and light chains", *Nucleic Acids Research* vol. 19, No. 15, Oxford University Press 1991, 4133-4137.

Hopkins, , "High titers of retrovirus (vesicular stomatitis virus) pseudotypes", vol. 90 *PNAS* Proc. Natl. Acad. Sci. USA Oct. 1993, 8759-8760.

Horton, Robert M. et al., "Engineering hybrid genes without the use of restriction enzymes: gene splicing by overlap extension", *Gene* vol. 77 1989, 61-68.

Hu, Gengxi et al., "DNA Polymerase-Catalyzed Addition of Nontemplated Extra Nucleotides to the 3' End of a DNA Fragment", *DNA and Cell Biology* vol. 12, No. 8, Mary Ann Liebert, Inc. 1993, 763-770.

Huang, L. -. et al., "A bacterial model system for chromosomal targeting", *Nucleic Acids Research* vol. 19, No. 3 1991, 443-448.

Huang, Li-Chun et al., "Convenient and Reversible Site-Specific Targeting of Exogenous DNA into a Bacterial Chromosome by Use of the FLP Recombinase: the FLIRT System", *Journal of Bacteriology* vol. 179, No. 19 Oct. 1997, 6076-6083.

Hwang, E. S. et al., "Interaction of Integration Host Factor from *Escherichia coli* with the Integration Region of the *Haemophilus influenzae* Bacteriophage HPI", *Journal of Bacteriology*; vol. 172(9) Sep. 1990, 4852-4860.

Iida, Shigeru et al., "A site-specific, conservative recombination system carried by bacteriophage P1. Mapping of the recombinase gene cin and the crossover sites cix for the inversion of the C Segment", *The EMBO Journal* vol. 1, No. 11, Oxford University Press 1982, 1445-1453.

Iino, T. et al., "Trans-acting Genes of Bacteriophages P1 and Mu Mediate Inversion of a Specific DNA Segment Involved in Flagellar Phase Variation of Salmonella", *Cold Spring Harbor Symposia on Quantitative Biology* vol. 45, Cold Spring Harbor Laboratory Press 1981, 11-16.

Institut Pasteur, "Figure 1", http://www.pasteur.fr/recherche/unites/pmtg/integ/fig1.html http://www.pasteur.fr/recherche/unites/pmtg/integ/fig1.html Jun. 19, 2003, 1-2.

Institut Pasteur, "Figure 2", http://www.pasteur.fr/recherche/unites/pmtg/integ/fig2.html http://www.pasteur.fr/recherche/unites/pmtg/integ/fig2.html Jun. 19, 2003, 1.

Institut Pasteur, "Figure 3", http://www.pasteur.fr/recherche/unites/pmtg/integ/fig3.html http://www.pasteur.fr/recherche/unites/pmtg/integ/fig3.html Jun. 19, 2003.

Institut Pasteur, "Introduction", *Institut Pasteur Website*, http://www.pasteur.fr/recherche/unites/pmtg/integ/intro.html Jun. 19, 2003, 1-9.

Institut Pasteur, , "Introduction & Figures 1-3", *Institut Pasteur Integron System Website: Introduction*, figs. 1-3 and Contact Page, available at http://www.pasteur.fr/recherche/unites/pmtg/integ/intro.html (accessed Jun. 19, 2003). Jun. 19, 2003, 1-10.

Institut Pasteur, "Main Page", *Institut Pasteur Websites Main page* http://www.pasteur.fr/recherche/unites/pmtg (accessed Jun. 19, 2003) Jun. 19, 2003, 1.

Invitrogen, , *Invitrogen Online Catalogue*, http:invitrogen.com/content.cfm?pageid+3371&cfid=16767784&cftoken=62396683 This page no longer exists—site redesigned. as of Sep. 3, 2008—BJC Jul. 7, 2004.

Invitrogen, , "293A Cell Line Manual", *Catalogue No. R705-07, version B* Invitrogen Corporation, Carlsbad, CA Mar. 31, 2003, 1-2.

Invitrogen, , "Accelerate your research with TOPO Cloning and Gateway Technology", *Invitrogen Life Technologies* Product Information Sheets, 1-8.

Invitrogen, , "Bac to Bac Baculovirus Expression System Manual", *catalogue Nos. 11827-011, 11806-015, 11804-010 and 11807-013, version D* Invitrogen Corporation, Carlsbad, CA Oct. 3, 2003, 1-11.

Invitrogen, , "Bac to Bac Baculovirus Expression System Manual", *catalogue Nos. 10359-016, 10360-014, 10584-027, 10712-024, version C*, p. 27, Invitrogen Corporation, Carlsbad, CA Dec. 19, 2002, 1-11.

Invitrogen, , "Bac-n-Blue Manual", catalogue No. K855-01, version M, Invitrogen Corporation, Carlsbad, CA Dec. 10, 2002.

Invitrogen, , "Echo Cloning System 5-minute construction of a donor vector for recombination with an Echo-adapted acceptor expression vector", *5-minute construction of a donor vector for recombination with an Echo-adapted acceptor expression vector* Catalog Nos. ET001-XX Version G, 1-39.

Invitrogen, , "Five-minute, directional TOPO Cloning of blunt-end PCR products into an expression vector for the ViralPower", *pLenti6/V5 Directional TOPO Cloning Kit* Catalogue No. K4955-10, Version B Invitrogen Corporation, Carlsbad, CA Sep. 15, 2006, 1-56.

Invitrogen, , "Gateway-adapted destination vectors for cloning and high-level expression in mammalian cells using the Virapower Lentiviral Expression System", *pLenti4/V5-DEST, pLenti6/V5-DEET and pLenti6/UbC/V5-DEST Gateway Vector Kits* Catalogue Nos. V496-10, V498-10, V499-10, V368-20 Version H Invitrogen Corporation, Carlsbad, CA 2003, 1-55.

Invitrogen, , "Gateway Cloning Technology Instruction Manual, Version 1", *GibcoBRL, Life Technologies Inc.* http://www.lifetech.com/gateway Nov. 1999 , 1-64.

Invitrogen, , "Gateway entry vector pDONR221", accessed online at http://www.genome.wisc.edu/resources/cloneandmutlpdonr221.gbk available online Oct. 20, 2003 (accessed May 2, 2005), 1-3.

Invitrogen, , "Guide to Baculovirus Expression Systems (BEVS) and Insect Cell Culture Techniques Manual", *catalogue Nos. 10359016,10360014,10608016, 11827011* Invitrogen Corporation, Carlsbad, CA Feb. 27, 2002 , 1-26.

Invitrogen, , "pAd/CMVN5-Dest and pAd/PL-DESTT M Gateway Vector Manual", *Catalogue Nos. V493-20 and 494-20, Version C* Invitrogen Corporation, Carlsbad, CA Sep. 22, 2003 , 1-36.

Invitrogen, , "pAd/CMVN5-DEST and pAd/PL-DEST Gateway Vectors", *Catalogue Nos. V493-20 and V494-20 Version D* Sep. 28, 2004 , 1-36.

Invitrogen, , "pcDNA3.1/nV5-DEST gateway Vector Pack A gateway-adapted expression vector (destination vector) for cloning and expression of N-terminal V5 fusion proteins in mammalian cells", http://tools.invitrogen.com/content/sfs/manuals/pcdna3_1nv5dest_man.pdf Catalog No. 12290-010, Version A 2002 , 1-26.

Invitrogen, , "pCX TOPO TA Expression Kit", www.invitrogen.com/content/sfs/manuals/pcxtopota_man.pdf Catalog No. K6000-01 Jul. 12, 2002 , 1-42.

Invitrogen, , "pENTR Directional TOPO Cloning Kits Manual", *Catalogue Nos. K2400-20, K2400-480, K2400-500, K2420-20, K2420-80, K2r20-500, Version B.* Invitrogen Corporation, Carlsbad, CA 2002 , 1-12.

Invitrogen, , "pENTR Directional TOPO Cloning Kits Manual", *Catalogue Nos. K2400-20, K2400-480, K2400-500, K2420-20, K2420-480, K2420-500, Version B* Invitrogen Corporation, Carlsbad, CA 2002 , 1-52.

Invitrogen, , "pLenti4N5-DEST Gateway Vector Pack manual", *Catalogue Nos. V496-10, V498-10, and V499-10, Version C* Invitrogen Corporation, Carlsbad, CA Feb. 18, 2003 , 1-46.

Invitrogen, , "pLenti6/V5 Directional TOPO Cloning Kit", *Catalogue No. K4955-10, Version B* Invitrogen Corporation, Carlsbad, CA 2000 , 1-12.

Invitrogen, , "pLenti6/V5 Directional TOPO Cloning Kit Manual", *catalogue No. K4955-1 0, version B* Invitrogen Corporation, Carlsbad, CA Sep. 15, 2006 , 1-56.

Invitrogen, , "ProBond Resin Purification System Manual", *Catalogue Nos. R801-01, R801-15, Version B* Invitrogen Corporation, Carlsbad, CA Nov. 1997.

Invitrogen, , "The Echo Cloning System: The Future of Cloning is Here", *Invitrogen Online Catalogue* http://web.archive.org/web/20010112191100/www.invitrogen.com/catalogue_project/cat_echo.html Jul. 7, 2004 , 1-8.

Invitrogen, , "The fastest method of entry into Gateway Technology", www.invitrogen.com 2002 , 1-4.

Invitrogen, , "TOPO TA Cloning Kits with gateway Technology, downloaded May 30, 2005".

Invitrogen, , "ViraPower Lentiviral Expression System", *Catalogue Nos. K4950-00, K4960-00, K4970-00, K4975-00, K4980-00, K4985-00, K4990-00, K367-20, K370-20, and K371-20 Version G* Invitrogen Corporation, CA Apr. 14, 2006 , 1-56.

Invitrogen, , "ViraPower TM Adenoviral Expression System Manual", *catalogue Nos. K4930-00, and K4940-00, version A* Invitrogen Corporation, Carlsbad, CA Jul. 15, 2002 , 1-12.

Invitrogen, , "ViraPower TM Lentivirus Expression System Manual", *Catalog Nos. K4950-00, K496-0-00, K4970-00, Ver A* Invitrogen Corporation, Carlsbad Feb. 2002 , 1-45.

Invitrogen Corporation, , *Invitrogen Catalogue* 2007 , 20127-017.

Invitrogen Corporation, , *Invitrogen Catalogue* 2001 , 6-12.

Invitrogen Corporation, , "AcTEV TM Protease", *Invitrogen Catalogue* 2003 , 12575-015.

Invitrogen Corporation, , "Additional Cloning Products—Chapter 1", *K2000-01, Invitroien Catalogue* 2003.

Invitrogen Corporation, , "Cloning—Chapter 1", *K4550-40; Invitrogen Catalogue* 2003.

Invitrogen Corporation, , "Cloning—Chapter 1", *K4560-40; Invitrogen Catalogue* 2003.

Invitrogen Corporation, , "Cloning—Chapter 1", *K4500-05; Invitrogen Catalogue* HTP TOPO Cloning Kits 2003.

Invitrogen Corporation, , "Cloning—Chapter 1", *K4550-01; Invitrogen Catalogue* TOPO TA Cloning Kits 2003.

Invitrogen Corporation, , "Cloning—Chapter 1", *K4560-01; Invitrogen Catalogue* TOPO TA Cloning Kits 2003.

Invitrogen Corporation, , "Cloning (Chapter 11)—Gateway Destination Vectors", *Invitrogen Catalogue* V496-10 2004.

Invitrogen Corporation, , "DNA Purification—Chapter 9", *K1900-01; Invitrogen Catalogue* 2003.

Invitrogen Corporation, , "DNA Purification—Chapter 9", *K1999-25; Invitrogen Catalogue* 2003.

Invitrogen Corporation, , "Enzymes—Chapter—5", *Poly A Polymerase; Invitrosen Catalogue* 2003 , 15224-17.

Invitrogen Corporation, , "Enzymes—Chapter 8", *Invitrogen Catalogue* 2003 , 15224-025.

Invitrogen Corporation, , "Expression in *S. cerevisiae*", *Invitrogen Catalogue* Carlsbad, California 1998 , 18, 29, 43, 44, 49-52.

Invitrogen Corporation, , "Gateway Entry Vectors", *Invitrogen Catalogue* 2003 , 11813.

Invitrogen Corporation, , "Gateway R Technology", *Invitrogen Catalogue* 2003 , 11791-019.

Invitrogen Corporation, , "Gateway R Technology", *Invitrogen Catalogue* 2003 , 11824-026.

Invitrogen Corporation, , "Gateway Technology", *K2400-20; Invitrogen Catalogue* 2003.

Invitrogen Corporation, , "Gene Expression", *Invitrogen Catalogue* V494-20 2003.

Invitrogen Corporation, , "Gene Expression—Chapter 10", *K4944-00; Invitrogen Catalogue* 2004.

Invitrogen Corporation, , "Gene Expression—Chapter 10", *K4945-00; Invitrogen Catalogue* 2004.

Invitrogen Corporation, , "Gene Expression—Chapter 4", *K4950-00; Invitrogen Catalogue* 2003.

Invitrogen Corporation, , "Gene Expression—Chapter 4", *K4960-00; Invitrogen Catalogue* 2003.

Invitrogen Corporation, , "Gene Expression—Chapter 4", *K4970-00; Invitrogen Catalogue* 2003.

Invitrogen Corporation, , "Gene Expression—Chapter 4", *Invitrogen Catalogue* V790-20 2003.

Invitrogen Corporation, , "Gene Expression—Untagged pcDNA Vectors", *Invitrogen Catalogue* V795-20 2003.

Invitrogen Corporation, , "Invitrogen Online Ordering: CD 45 Mouse F(ab')2 Anti-Human, (Clone: HI30)", *Invitrogen Catalogue* https://catalog.invitrogen.com/index.cfm?fuseaction=viewCatalog.viewProductDetails&p . . . 1999 , 11.

Invitrogen Corporation, , "Invitrogen Online Ordering: DH10B Cells", *Invitrogen Catalogue* https://catalog.invitrogen.com/index.cfm?fuseaction=viewCatalog.viewProductDetails&p . . . 1999 , 18290-015.

Invitrogen Corporation, , "Invitrogen Online Ordering: Gateway Destination Vectors", *Invitrogen Catalog* https://catalog.invitrogen.com/index.cfm?fuseaction=viewCatalog.viewProductDetails&p . . . 1999 , 11801-016.

Invitrogen Corporation, , "Invitrogen Online Ordering: Gateway Destination Vectors", *Invitrogen Catalogue* https://catalog.invitrogen.com/index.cfm?fuseaction=viewCatalog.viewProductDetails&p . . . 1999 , 11804-010.

Invitrogen Corporation, , "Invitrogen Online Ordering: GripTite 293 MSR Cell Line", *Invitrogen Catalogue; R795-07* https://catalog.invitrogen.com/index.cfm?fuseaction=viewCatalog.viewProductDetails&pr . . . 2007.

Invitrogen Corporation, , "Invitrogen Online Ordering: PCR Cloning System with Gateway Technology", *Invitrogen Catalogue* https://catalog.invitrogen.com/index.cfm?fuseaction=viewCatalog.viewProductDetails&p . . . 1999 , 11798-014.

Invitrogen Corporation, , "Invitrogen Online Ordering: S.O.C. Medium", *Invitrogen Catalogue* https://catalog.invitrogen.com/index.cfm?fuseaction=viewCatalog.viewProductDetails&p . . . 1999 , 15544-034.

Invitrogen Corporation, , "Invitrogen Online Ordering: Uracil DNA Glycosylase", *Invitrogen Catalogue* https://catalog.invitrogen.com/index.cfm?fuseaction=viewCatalog.viewProductDetails&p . . . 1999 , 18054-015.

Invitrogen Corporation, , "K4500-04", *Invitrogen Catalogue* 2003.

Invitrogen Corporation, , "MultiSite Gateway Technology", *Invitrogen Catalogue* 2003 , 12537-023.

Invitrogen Corporation, , "MultiSite Gateway Technology", *Invitrogen Catalogue* 2003 , 12538-013.

Invitrogen Corporation, , "PCR Cloning System with Gateway R Technology", *Invitrogen Catalogue* 2003 , 11789-013.

Invitrogen Corporation, , "PCR Cloning System with Gateway R Technology", *Invitrogen Catalogue* 2003 , 12535-027.

Invitrogen Corporation, , "PCR Cloning System with Gateway Technology", *Invitrogen Catalogue* 2003 , 12535-019.

Invitrogen Corporation, , "PCR Cloning System with Gateway Technology", *Invitrogen Catalog* 2003 , 12536-017.

Invitrogen Corporation, , "Products for High-throughput", *K4500-01; Invitrogen Catalogue* 2003.

Invitrogen Corporation, , "Products for High-Throughput", *K4520-01; Invitrogen Catalogue* 2003.

Invitrogen Corporation, , "Products for High-Throughput", *K4520-40; Invitrogen Catalogue* 2003.

Invitrogen Corporation, , "Products for PCR and RT-PCR—Chapter 2", *K1220-01; Invitrogen Catalogue* 2003.

Invitrogen Corporation, , "Prokaryotic Expression", *Invitrogen Catalogue* 2003 , 12283-016.

Invitrogen Corporation, , "ProQuest TM Two-Hybrid System with Gateway Technology, continued", *Invitrogen Catalogue* 2003 , 10835-031.

Invitrogen Corporation, , "Sequencing Products", *N530-02; Invitrogen Catalogue* 2003.

Invitrogen Corporation, , "Transformation—Chapter 3", *C4040-03; Invitrogen Catalogue* 2003.

Invitrogen Corporation, , "Transformation—Chapter 3", *C4040-06; Invitrogen Catalogue* 2003.

Invitrogen Corporation, , "Transformation—Chapter 3", *C4040-10; Invitrogen Catalogue* 2003.

Invitrogen Corporation, , "Transformation—Chapter 3", *C409601; Invitrogen Catalogue* 2003.

Invitrogen Corporation, , "Transformation—Chapter 8", *C3030-06; Invitrogen Catalog* 2003.

Invitrogen Corporation, , "Transformation—Chapter 8", *C4040-52; Invitrogen Catalogue* 2003.

Invitrogen Corporation, , "Transformation—Chapter 8", *C8620-03; Invitrogen Catalogue* 2003.

Invitrogen Corporation, , "Transformation—Chapter 8", *C869601; Invitrogen Catalogue* 2003.

Invitrogen Corporation, , "Y90001", *Invitrogen Catalogue* 2007.

Invitrogen Life Technologies, , "Directional TOPO Entry Vectors", www.invitrogen.com/content.cfm?pageid=3799&cfid=2899760& cftoken=88086554 online catalogue-site redesigned, cannot find original page. Attachment is search on Directional TOPO Entry Vectors done Aug. 11, 2008 Sep. 27, 2002 , 1-9.

Iyer, Radhakrishnan P. et al., "Modified oligonucleotides—synthesis, properties, and applications", *Current Opinion in Molecular Therapeutics* vol. 1 No. 3 1999 , 344-358.

Izumi, Masako et al., "Blasticidin S-Resistance Gene (bsr): A Novel Selectable Marker for Mammalian Cells", *Experimental Cell Research* vol. 197, Academic Press, Inc. 1991 , 229-233.

Jaffe, Aline et al., "Effects of the ccd Function of the F Plasmid on Bacterial Growth", *Journal of Bacteriology* vol. 163, No. 3 Sep. 1985 , 841-849.

Jank, Matthias M. et al., "Expression and Biotinylation of a Mutant of the Transcarboxylase Carrier Protein from *Propioni shermanii*", *Protein Expression and Purification* vol. 17, Academic Press 1999 , 123-127.

Janknecht, Ralf et al., "Rapid and efficient purification of native histidine-tagged protein expressed by recombinant vaccinia virus", *Proceedings of the National Academy of Sciences (PNAS)* vol. 88 Oct. 1, 1991 , 8972-8976.

Jarvis, Donald L. et al., "Immediate-Early Baculovirus Vectors for Foreign Gene Expression in Transformed or Infected Insect Cells", *Protein Expression and Purification* vol. 8, Academic Press, Inc. 1996 , 191-203.

Jayaram, Makkuni , "The Int Family of Site-specific Recombinases: Some thoughts on a General Reaction Mechanism", *J. Genet.* vol. 67, No. 1, Indian Academy of Sciences Apr. 1988 , 29-36.

Jeong, Ja-Haeng et al., "Cloning and nucleotide sequencing of the genes, rplU and rpmA, for ribosomal proteins L21 and L27 of *Escherichia coli*", *DNA sequencing and Mapping* vol. 4, Harwood Academic Publishers 1993 , 59-67.

John, Joseph F. et al., "Plasmids as Epidemiologic Markers in Nosocomial Gram-Negative Bacilli: Experience at a University and Review of the Literature", vol. 8, No. 5, *Reviews of Infectious Diseases* The University of Chicago Sep. 1986 , 693-704.

Johnson, Reid C. et al., "Host Protein Requirements for in-Vitro Site-Specific DNA Inversion", vol. 46, *Cell* Aug. 15, 1986 , 531-539.

Johnson, Reid C. et al., "Isolation of the gene encoding the Hin recombinational enhancer binding protein", *Proceedings of the National Academy of Sciences (PNAS)* vol. 85, Genetics May 1988 , 3484-3488.

Johnston, Stephen A. et al., "Isolation of the yeast regulatory gene GAL4 and analysis of its dosage effects on the galactose/melibiose regulon", vol. 79, *Proceedings of the National Academy of Sciences (PNAS)* Genetics Nov. 1982 , 6971-6975.

JP 2002-548090, , "Office Action Mailed on Nov. 26, 2008".

JP 2006-273481, , "Office Action mailed Feb. 19, 2009".

JP 2007-175995, , "Response to Aug. 27, 2009 Office Action, Filed on Feb. 10, 2009".

Jung, Seung E. et al., "Cloning and Analysis of the DNA Polymerase-encoding Gene from *Thermus filiformis*", vol. 7, No. 6, *Molecules and Cells*, 1997 , 769-776.

Kafri, Tal et al., "Sustained expression of genes delivered directly into liver and muscle by lentiviral vectors", *Nature Genetics* vol. 17 Nov. 1997 , 314-317.

Kaizuka, Y. , "U.S. Appl. No. 09/517,446, filed Mar. 2, 2000".

Kanaar, Roland et al., "Gin-Mediated Recombination of Catenated and Knotted DNA Substrates: Implications for the Mechanism of Interaction Between Cis-Acting Sites", *Cell* vol. 58 Jul. 14, 1989 , 147-159.

Kane, Eileen M. et al., "Vaccinia Virus Morphogenesis Is Blocked by a Tmperature-Sensitive Mutation in the 17 Gene That Encodes a Virion Component", *Journal of Virology* vol. 67, No. 5 May 1993 , 2689-2698.

Kanegae, Yumi et al., "Efficient gene activation in mammalian cells by using recombinant adenovirus expressing site-specific Cre recombinase", *Nucleic Acids Research* vol. 23, No. 19 1995 , 3816-3821.

Kang, Angray S. et al., "Antibody redesign by chain shuffling from random combinatorial immunoglobulin libraries", *Proceedings of the National Academy of Sciences (PNAS)* vol. 88 Dec. 1991 , 11120-11123.

Kang, Angray S. et al., "Linkage of Recognition and Replication Functions by Assembling Combinatorial Antibody Fab Libraries Along Phage Surfaces", *Proceedings of the National Academy of Sciences (PNAS)* vol. 88 May 1991 , 4363-4366.

Kaniga, Kone et al., "A wide-host-range suicide vector for improving reverse genetics in Gram-negative bacteria: inactivation of the blaA gene of *Yersinia enterocolitica*", *Gene* vol. 109, Elsevier Science 1991 , 137-141.

Kappelman, James R. et al., "Sgf I, a new type-II restriction endonuclease that recognizes the octanucleotide sequence 5'-GCGAT/CGC-3'.", *Gene* vol. 160 1995 , 55-58.

Kasim, V. et al., "Control of siRNA expression utilizing Cre-loxP recombination system", *Nucleic Acids Research. Supplement* (2001) 2003, No. 3, XP002533697 2003 , 255-256 PGS.

Kato, Seishi et al., "Construction of a human full-length cDNA bank", *Gene* vol. 150, Elsevier Science 1994 , 243-250.

Katz, Leonard et al., "Site-specific recombination in *Esherichia coli* between the att sites of plasmid pSE211 from *Saccharopolyspora erhthraea*", *Mol. Gen. Genet.* vol. 227, Springer-Verlag 1991 , 155-159.

Kaufman, Peter B. et al., "Handbook of Molecular and Cellular Methods in Biology and Medicine", *CRC Press*, 1995 , 444-469.

Kawano, Yuji et al., "A Lentiviral cDNA Library Employing Lambda Recombination Used to Clone an Inhibitor of Human Immunodeficiency Virus Type 1-Induced Cell Death", *Journal of Virology* vol. 78, No. 20 Oct. 2004 , 11352-11359.

Kawasaki, Hiroaki et al., "siRNAs generated by recombinant human Dicer induce specific and significant but target site-independent gene silencing in human cells", *Nucleic Acids Research* vol. 31, No. 3 2003 , 981-987.

Kealey, James T. et al., "Production of polyketide natural product in nonpolyketide-producing prokaryotic and eukaryotic hosts", *Proceedings of the National Academy of Sciences (PNAS)* vol. 95 Jan. 1998 , 505-509.

Keil, Dietmar et al., "Synthesis and Characterization of 1,3 Bis-(2-dialkylamino 5 thienyl) substituted Squaraines—A Novel Class of Intensively Coloured Panchromatic Dyes", *Dyes and Pigments* vol. 17 1991 , 19-27.

Kendall, Kevin J. et al., "Plasmid Transfer in *Streptomyces lividans*: Identification of a kil-kor System Associated with the Transfer Region of plJ101", vol. 169, No. 9, *Journal of Bacteriology* American Society for Microbiology Sep. 1987 , 4177-4183.

Ketner, Gary et al., "Efficient manipulation of the human adenovirus genome as yeast artificial chromosome clone.", *Proceedings of the National Academy of Sciences (PNAS)* vol. 91, No. 13, The National Academy of Sciences Jun. 21, 1994 , 6186-6190.

Kholodenko, Boris N. et al., "Metabolic Design: How to Engineer a Living Cell to Desired Metabolite Concentrations and Fluxes", *Biotechnology and Bioengineering* vol. 59, No. 2, John Wiley & Son Jul. 20, 1998 , 239-247.

Khromykh, Alexander A. et al., "Subgenomic Replicons of the Flavivirus Kunjin: Construction and Applications", *Journal of Virology* vol. 71, No. 2 Feb. 1997 , 1497-1505.

Kiem, Hans-Peter et al., "Retrovirus-Mediated Gene Transduction Into Canine Peripheral Blood Repopulating Cells", *Blood* vol. 83, No. 6 Mar. 15, 1994 , 1467-1473.

Kiguchi, Joann S. et al., "Domain structure of vaccinia DNA ligase", *Nucleic Acids Research* vol. 25, No. 4, Kluwer Academic Publishers 1997 , 727-734.

Kijima, Takashi , "Application of the Cre Recombinase/loxP System Further Enhances Antitumor Effects in Cell Type-specific Gene Therapy against Carcinoembryonic Antigen-producing Cancer", *Cancer Research* vol. 59, American Association for Cancer Research Oct. 1, 1999 , 4906-4911.

Kilby, Nigel J. et al., "Site-specific recombinases: tools for genome engineering", *Trends Genet* vol. 9, No. 12 Dec. 1993 , 413-421.

Kim, Raymond A. et al., "Identification of the Yeast TOP3 Gene Product as a Single Strand-specific DNA Topoisomerase", *The Journal of Biological Chemistry* vol. 267, No. 24 Aug. 25, 1992 , 17178-17185.

Kim, Sunghoon et al., "Lambda Int Protein Bridges Between Higher Order Complexes at Two Distant Chromosomal Loci attL and attR", *Science* vol. 256, American Association for the Advancement of Science Apr. 10, 1992 , 198-203.

Kim, Raymond A. et al., "Molecular Cloning and DNA Sequence Analysis of *Escherichia coli* topB, the Gene Encoding Topoisomerase III", *The Journal of Biological Chemistry* 267 1992 , 17178-17185.

Kim, Dong W. et al., "Use of the human elongation factor 1a promoter as a versatile and efficient expression system", *Gene* vol . 91, Elsevier Science 1990 , 217-223.

Kimura, Makoto et al., "Blasticidin S deaminase gene from *Aspergillus terreus* (BSD): a new drug resistance gene for transfection of mammalian cells", *Biochimica et Biophysica Acta* vol. 1219, Elsevier Science B.V. 1994 , 653-659.

Kirby, Kim et al., "RNA interference-mediated silencing of Sod2 in Drosophila leads to early adult-onset mortality and elevated endogenous oxidative stress", *Proceedings of the National Academy of Sciences (PNAS)* vol. 99, No. 25 Dec. 10, 2002 , 16162-16167.

Kirik, Angela et al., "Species-specific double-strand break repair and genome evolution in plants.", *EMBO Journal* vol. 19, No. 20 2000 , 5562-5566.

Kisu, Yasutomo et al., "Development of high-throughput technology of entry clones of the multi-purpose Gateway cloning system (III): An improved method for high-efficient and high-fidelity construction of the entry clones", *Presented at the Annual Meeting of Japan Society of Molecular Biology* Abstract No. 2 Poster Session of the Annual Meeting of Japan Society of Molecular Biology, Abstract No. 2P-730 Dec. 2001 , 730.

Kitts, Paul A. et al., "A Method for Producing Recombinant Baculovirus Expression Vectors at High Frequency", *BioTechniques* vol. 14, No. 5 Eaton Publishing Co. 1993 , 810-812,814,816-817.

Kitts, Paul A. et al., "Bacteriophage Lambda Site-specific Recombination Proceeds with a Defined Order of Strand Exchanges", *J. Mol. Biol.* vol. 204 1988 , 95-107.

Kjems, Jorgen et al., "Structural analysis of the interaction between the human immunodeficiency virus Rev protein and the Rev response element", *Proceedings of the National Academy of Sciences (PNAS)* vol. 88, The National Academy of Sciences Feb. 1991 , 683-687.

Kleinschmidt, Walter J. et al., "Biochemistry of Interferon and its Inducers", *Annu. Rev. Biochem* vol. 41 1972 , 517.

Klemm, Martha et al., "Peptide Inhibitors of DNA Cleavage by Tyrosine Recombinases and Topoisomerases", *J. Mol. Biol.* vol. 299, No. 5, Academic Press, Inc. 2000 , 1203-1216.

Klemperer, Nancy et al., "Identification and Characterization of the orfVirus Type I Topoisomerase", *Virology* vol. 206, Academic Press, Inc. 1995 , 203-215.

Klippel, Anke et al., "Isolation and characterization of unusual gin mutants", vol. 7, No. 12, *The EMBO Journal* IRL Press Inc. 1988 , 3983-3989.

Koch, Christian et al., "*Escherichia coli* host factor for site-specific DNA inversion: Cloning and characterization of the fis gene", *Proceedings of the National Academy of Sciences (PNAS)* vol. 85 Jun. 1988 , 4237-4241.

Koch, Christian et al., "Purification and Properties of the *Escherichia coli* Host Factor Required for Inversion of the G Segment in Bacteriophage Mu", *The Journal of Biological Chemistry* vol. 261, No. 33 Nov. 25, 1986 , 15673-15678.

Koch, Christian et al., "The N-terminal part of the *E.coli* DNA binding protein FIS is essential for stimulating site-specific DNA inversion but is not required for specific DNA binding", *Nucleic Acids Research* vol. 19, No. 21 1991, 5915-5922.

Kochanek, Stefan et al., "A new adenoviral vector: Replacement of all viral coding sequences with 28 kb of DNA independently expressing both full-length dystrophin and B-galactosidase", *Proceedings of the National Academy of Sciences (PNAS)* vol. 93 Jun. 1996 , 5731-5736.

Kohler, G., et al., "Continuous cultures of fused cells secreting antibody of predefined specificity", *Nature*, vol. 256, Aug. 7, 1975 , 495-497.

Kohler, G., et al., "Fusion between immunoglobulin-secreting and nonsecreting myeloma cell lines", *Eur. J. Immunol*, vol. 6, No. 4, 1976 , 292-295.

Kolb, Andreas F. et al., "Genomic targeting with an MBP-Cre fusion protein", *Gene* vol. 183 Dec. 1996 , 53-60.

Konfortov, B. A. et al., "A High-Resolution HAPPY Map of Dictyostelium discoideum Chromosome 6", Nov. 1, 2000 , 1737-1742.

Kordower, Jeffrey H. et al., "Neurodegeneration Prevented by Lentiviral Vector Delivery of GDNF in Primate Models of Parkinson's Disease", *Science* vol. 290 Oct. 27, 2000 , 767-773.

Kostriken, R. et al., "The Product of the HO Gene is Nuclease: Purification and Characterization of the Enzyme", *Cold Spring Harbor Laboratory* Quant. Biol. 1984 , 89-96.

Kotewicz, Michael L. et al., "Isolation of cloned Moloney murine leukemia virus reverse transcriptase lacking ribonuclease H activity", *Nucleic Acids Research*, vol. 16, No. 1, Jan. 11, 1988 , 265-277.

Kouprina, Natalya et al., "Rescue of Targeted Regions of Mammalian Chromosomes by in Vivo Recombination in Yeast", *Genome Research* vol. 8, Cold Spring Harbor Research Laboratory Press 1998 , 666-672.

Kozak, Marilyn , "An analysis of 5'-noncoding sequences from 699 vertebrate messenger RNAs", *Nucleic Acids Research* vol. 15, No. 20, Oxford University Press 1987 , 8125-8132.

Kozak, Marilyn, "An Analysis of Vertebrate mRNA Sequences: Intimations of Translational Control", *The Journal of Cell Biology* vol. 115, No. 4, The Rockefeller University Press Nov. 1991, 887-903.

Kozak, Marilyn, "Comparison of initiation of protein synthesis in procaryotes, Eucaryotes, and organelles", *Microbiological Reviews* vol. 47, No. 1, American Society for Microbiology Mar. 1983, 1-45.

Kozak, Marilyn, "Downstream secondary structure facilitates recognition of initiator codons by eukaryotic ribosomes", *Proceedings of the National Academy of Sciences (PNAS)* vol. 87, The National Academy of Sciences Nov. 1990, 8301-8305.

Kozak, Marilyn, "Structural features in eukaryotic mRNAs that modulate the initiation of translation", *The Journal of Biological Chemistry* vol. 266, No. 30, American Society for Biochemistry and Molecular Biology Oct. 25, 1991, 19867-19870.

Kozarsky, Karen F. et al., "Gene Therapy: Adenovirus Vectors", *Current Opinion in Genetics and Development* vol. 3, Current Biology Ltd 1993, 499-503.

Krafte, Douglas S. et al., "Stable Expression and Functional Characterization of a Human Cardiac Na.sup.+ Channel Gene in Mammalian Cells", *J. Mol. Cell. Cardiol.* vol. 27 1995, 823-830.

Krautwald, Stefan et al., "Bacterially expressed murine CSF-1 possesses agonistic activity in its monomeric form", *Biochemican Biophysical Research Communications* vol. 192, No. 2, Academic Press, Inc. Apr. 30, 1993, 720-727.

Kreuzer, Karl-Anton et al., "Simultaneous Absolute Quantification of Target and Control Templates by Real-Time Fluorescence Reverse Transcription-PCR Using 4-(4'-Dimethylaminophenylazo) Benzoic Acid as a Dark Quencher Dye", *Clinical Chemistry* vol. 47, No. 3 2001, 486-490.

Krogh, Berit O. et al., "DNA strand transfer catalyzed by vaccinia topoisomerase: peroxidolysis and hydroxylaminolysis of the covalent protein-DNA intermediate", *Biochemistry* vol. 39, No. 21, American Chemical Society 2000, 6422-6432.

Krogh, Berit O. et al., "Effect of 2'-5' phosphodiesters on DNA transesterification by vaccinia topoisomerase", *The Journal of Biological Chemistry* vol. 276, No. 24, The American Society for Biochemistry and Molecular Biology, Inc. Jun. 15, 2001, 20907-20912.

Krogh, Berit O. et al., "*Melanoplus sanguinipes* entomopoxvirus DNA topoisomerase: site-specific DNA transesterification and effects of 5'-bridging phosphorothiolates", *Virology* vol. 264, No. 2, Academic Press, Inc. 1999, 441-451.

Krogh, Berit O. et al., "Vaccinia topoisomerase mutants illuminate conformational changes during closure of the protein clamp and assembly of a functional active site", *The Journal of Biological Chemistry* The American Society for Biochemistry and Molecular Biology, Inc. Jul. 5, 2001, 1-38.

Krougliak, Valeri et al., "Development of Cell Lines Capable of Complementing E1, E4, and Protein IX Defective Adenovirus Type 5 Mutants", *Human Gene Therapy* vol. 6, Mary Ann Liebert, Inc. Dec. 1995, 1575-1586.

Kudla, B. et al., "FR 2670502 (Document AL20)and PCT Patent No. WO 92/10577 (Document AM20), WPI Accession No. 9107201", Dialog File 351, Derwent World Patent Index, English Language Abstract for French Patent No. FR 2670502 (Document AL20)and PCT Patent No. WO 92/10577 (Document AM20), WPI Accession No. 9107201 2004.

Kuempel, Peter et al., "Use of a transposon (Tndif) to obtain suppressing and nonsuppressing insertions of the dif resolvase site of *Eschericia coli*", *Genes & Development*, vol. 10 Cold Spring Harbor Laboratory Press May 1, 1996, 1162-1171.

Kuhn, Ralf et al., "Inducible Gene Targeting in Mice", *Science* vol. 269, American Association for the Advancement of Science Sep. 8, 1995, 1427-1429.

Kunapuli, Prima et al., "Development of an inact cell reporter gene beta-lactamase assay for G protein-coupled receptors for high-throughput screening", *Analytical Biochemistry* vol. 314 2003, 16-29.

Lafontaine, Denis et al., "One-step PCR Mediated Strategy for the construction of Conditionally Expressed and Epitope Tagged Yeast Proteins", *Nucleic Acids Research* vol. 24, No. 17, Oxford University Press 1996, 3469-3472.

Lake, James A., "Evolving Ribosome Structure: Domains in Archaebacteria, Eubacteria, Eocytes and Eukaryotes", *Ann. Rev. Biochem.* vol. 54 1985, 507-530.

Lakowicz, Joseph R., *Topics in Fluorescence Spectroscopy* vols. 1-3, Plenum Press 1991-2000.

Lakowicz, Joseph R., "Emerging applications of fluorescence spectroscopy to cellular imaging: lifetime imaging, metal-ligand probes, multi-photon excitation and light quenching", *Scanning Microscopy Supplement*, vol. 10 1996, 213-224.

Lakso, M. et al., "Targeted Oncogene activation by site-specific recombination in transgenic mice", *Proceedings of the National Academy of Sciences (PNAS)* vol. 89, National Academy of Sciences Jul. 1992, 6232-6236.

Lampson, G P. et al., "Inducers of Interferon and Host Resistance, I. Double-Stranded RNA From Extracts of Penicillium Funiculosum", *Proceedings of the National Academy of Sciences (PNAS)* vol. 58, National Academy of Science 1967, 782-789.

Lander, Eric S., "The New Genomics: Global Views of Biology", *Science* vol. 274, American Association for the Advancement of Science Oct. 25, 1996, 536-539.

Landy, Arthur, "Dynamic, structural and regulatory aspects of lambda site-specific recombination.", *Annu. Rev. Biochem.* vol. 58, Annual Reviews Inc 1989, 913-949.

Landy, Arthur, "Mechanistic and structural complexity in the site-specific recombination pathways of Int and FLP.", *Current Opinion in Genetics and Development* vol. 3, Current Biology Ltd 1993, 699-707.

Langeveld, S. A. et al., "Expression of an *Escherichia coli* phr gene in the yeast *Saccharomyces cerevisiae*", *Mol. Gen. Genet.* vol. 199, Springer-Verlag.1985, 396-400.

Lauffer, Randall B., "Paramagnetic Metal Complexes as Water Proton Relaxation Agents for NMR Imaging: Theory and Design", *Chemical Reviews*, vol. 87, No. 5 1987, 901-927.

Lavitrano, Marialuisa et al., "Sperm Cells as Vectors for Introducing Foreign DNA into Eggs: Genetic Transformation of Mice", *Cell* vol. 57 Jun. 2, 1989, 717-723.

Lawyer, Frances C. et al., "High-level Expression, Purification, and Enzymatic characterization of Full-length *Thermus aquaticus* DNA polymerase and a Truncated Form Deficient in 5' to 3' Exonuclease activity", *PCR Methods and Applications*, vol. 2, No. 4, May 1993, 275-287.

Lebreton, Brigitte et al., "Mutations That Improve the Binding of Yeast FLP Recombinase to Its Substrate", *Genetics* vol. 118, Genetics Society of America Mar. 1988, 393-400.

Lee, E-Chiang et al., "A Highly Efficient *Escherichia coli*-Based Chromosome Engineering System Adapted for Recombinogenic Targeting and Subcloning of Bac DNA", *Genomics* vol. 73, No. 1 Apr. 1, 2001, 56-65.

Lee, Nan S. et al., "Expression of Small Interfering RNAs Targeted Against HIV-1 Rev Transcripts in Human Cells.", *Nature Biotechnology* vol. 20 May 2002, 500-505.

Lee, Eunhee C. et al., "Genetic Analysis of *Escherichia coli* Integration Host Factor Interactions with Its Bacteriophage lamda H' Recognition Site", *The Journal of Bacteriology* vol. 173, No. 2 Jan. 1991, 609-617.

Lee, Yoontae et al., "MiRNA maturation: stepwise processing and subcellular localization.", *The EMBO Journal* vol. 21, No. 17 2002, 4663-4670.

Lee, Gwang et al., "Role of Nucleotide Sequences of loxP Spacer Region in Cre-mediated Recombination", *Gene* vol. 216, Elsevier Science B.V. Aug. 1998, 55-65.

Lee, Mong H. et al., "Site-spectific integration of mycobacteriophage L5: Integration-proficient vectors for *Mycobacterium smegmatis, Mycobacterium tubercoulosis*, and bacille Calmette-Guerin", *Proceedings of the National Academy of Sciences (PNAS)*, vol. 88 National Academy of Sciences Apr. 1991, 3111-3115.

Lenski, Richard E. et al., "Genetic Analysis of a Plasmid-Encoded, Host Genotype-Specific Enhancement of Bacterial Fitness", *Journal of Bacteriology*, vol. 176, No. 11 American Society for Microbiology Jun. 1994, 3140-3147.

Leon, Ronald P. et al., "Adenoviral-mediated gene transfer in lymphocytes", *Proceedings of the National Academy of Sciences (PNAS)* vol. 95, National Academy of Sciences Oct. 1998, 13159-13164.

Leong, John M. et al., "Generation of single base-pair deletions, insertions, and substitutions by a site-specific recombination system", *Proceedings of the National Academy of Sciences (PNAS)* vol. 82 Oct. 1985, 6990-6994.

Leslie, Nicholas R. et al., "Site-specific Recombination in the Replication Terminus Region of *Escherichia coli*: Functional Replacement of dif", *The EMBO Journal* vol. 14, No. 7 1995, 1561-1570.

Leung, David W. et al., "A method for random mutagenesis of a defined DNA segment using a modified polymerase chain reaction.", *Technique—A Journal of Methods in Cell and Molecular Biology* vol. 1, No. 1, Sounders Co. Aug. 1989, 11-15.

Leung, Lawrence L., "Application of Combinatorial Libraries and Protein Engineering to the Discovery of Novel Anti-Thrombotic Drugs", *Thrombosis and Haemostasis* vol. 74, No. 1 1995, 373-376.

Lewis, Paul F. et al., "Passage through Mitosis Is Required for Oncoretroviruses but Not for the Human Immunodeficiency Virus", *The Journal of Virology* vol. 68, No. 1, American Society for Microbiology Jan. 1994, 510-516.

Li, Zhi-Wei et al., "Generation of mice with a 200-kb amyloid precursor protein gene deletion by Cre recombinase-medicated site-specific recombination in embryonic stem cells", *Proceedings of the National Academy of Sciences (PNAS)* vol. 93, National Academy of Sciences Jun. 1996, 6158-6162.

Li, Zhiyu et al., "The traE Gene of Plasmid RP4 Encodes a Homologue of *Escherichia coli* DNA Topoisomerase III", *The Journal of Biological Chemistry* vol. 272, No. 31, The American Society for Biochemistry and Molecular Biology, Inc. Aug. 1, 1997, 19582-19587.

Lieber, Andre et al., "Recombinant Adenoviruses with Large Deletions Generated by Cre-Mediated Excision Exhibit Different Biological Properties Compared with First-Generation Vectors in Vitro and in Vivo", *Journal of Virology* vol. 70, No. 12, American Society for Microbiology Dec. 1996, 8944-8960.

Lin, Jhy-Jhu et al., "AFLP(TM): A Novel PCR-Based Assay for Plant and Bacterial DNA Fingerprinting", *Focus*, vol. 17, No. 2, 1995, 66-70.

Lindner, P et al.,. "Specific Detection of His-Tagged Proteins With Recombinant Anti-his Tag scFv-Phosphatase or scFv-Phage Fusions", *Biotechniques* vol. 22 No. 1 Jan. 1997, 140-149.

Liu, Xiuwen et al., "Mapping the 5' and 3' Ends of Tetrahymena thermophelia mRNAs Using RNA Ligase Mediated Amplification of cDNA Ends (RLM-RACE)", *Nucleic Acids Research* vol. 21, No. 21, Oxford University Press 1993, 4954-4960.

Liu, Q. et al., "The univector plasmid-fusion system, a method for rapid construction of recombinant DNA without restriction enzymes", *Current Biology*, vol. 8 (24) 1998, 1300-1309.

Liu, Qinghua et al., "The univector plasmid-fusion system, a method for rapid construction of recombinant DNA without restriction enzymes.", *Current Biology* vol. 8 Nov. 19, 1998, 1300-1309.

Lo, Cecilia W., "Transformation by iontophoretic microinjection of DNA: multiple integrations without tandem insertions.", *Molecular and Cellular Biology* vol. 3, No. 10 Oct. 1983, 1803-1814.

Lochmuller, H et al., "Emergence of Early Region 1-Containing Replication-Competent Adenovirus in Stocks of Replication-Defective Adenovirus Recombinants (Delta E1 + Delta E3) During Multiple Passages in 293 Cells", *Human Gene Therapy* vol. 5, Mary Ann Liebert, Inc. Dec. 1994, 1485-1491.

Lockard, Raymond E. et al., "Labeling of Eukaryotic Messenger RNA 5' Terminus with Phosphorus-32: Use of Tobacco Acid Pyrophosphatase for Removal of Cap Structures", *Gene Amplification and Analysis* vol. 2, Elsevier Science 1981, 229-251.

Loeffler, Jean-Philippe et al., "Gene Transfer into Primary and Established Mammalian Cell Lines with Lipopolyamine-Coated DNA", *Methods in Enzymology* vol. 217, Academic Press, Inc. 1993, 599-618.

Loftus, Stacie K. et al., "Generation of RCAS Vectors Useful for Functional Genomic Analysis", vol. 8, No. 5, *DNA Research* 2001, 221-226.

Logan, John et al., "The Use of Adenovirus Recombinants to Study Viral Gene Expression", *Genetically Altered Viruses and the Environment* Cold Spring Harbor Laboratory Press, Cold Spring Harbor, NY, Fields, B., et el., eds. 1985, 313-318.

Lois, Carlos et al., "Germline Transmission and Tissue-Specific Expression of Transgenes Delivered by Lentiviral Vectors", *Science* vol. 295, American Association for the Advancement of Science Feb. 1, 2002, 868-872.

Lomniczi, B et al., "Biological properties of avian coronavirus RNA.", *Journal of General Virology* vol. 36 1977, 531-533.

Lorbach, Elke et al., "Site-specific Recombination in Human cells Catalyzed by Phage Lamda Integrase Mutants", *J. Mol. Biol.* vol. 296, Academic Press Mar. 2000, 1175-1181.

Lu, Fang et al., "Conjugative transposition : Tn916 integrase contains two independent DNA binding domains that recognize different DNA sequences", *The EMBO Journal* vol. 13, No. 7, Oxford University Press 1994, 1541-1548.

Luciw, Paul A. et al., "Ch 60: Human Immunodeficiency Viruses and Their Replication", *Fields Virology, Third Edition* Fields, B.N., etal., eds., Lippincott-Raven Publishers, Philadelphia, PA 1996, 1881-1952.

Luckow, Verne A. et al., "Efficient Generation of Infectious recombinant Baculoviruses by Site-Specific Transposon-Mediated Insertion of Foreign Genes into a Baculovirus Genome Propagated in *Escherichia coli*", *Journal of Virology* vol. 67, No. 8, American Society for Microbiology Aug. 1993, 4566-4579.

Luetke, Karen H. et al., "Asymmetry in Flp-mediated cleavage", vol. 25, No. 21, *Nucleic Acids Research* 1997, 4240-4249.

Lunnen, Keith D. et al., "Cloning Type-II Restriction and Modification Genes", vol. 74, *Gene* Elsevier Science Publishers B.V. 1988, 25-32.

Luo, B. et al., "Small i nterferi ng RNA production by enzymatic engineering of DNA (SPEED)", *Proceedings of the National Academy of Sciences of USA, National Academy of Science*, Washington, DC., US, vol. 101, No. 15 XP002991703 Apr. 13, 2004, 5494-5499 pgs.

Lyznik, Leszek A. et al., "Activity of yeast FLP recombinase in maize and rice protoplasts", *Nucleic Acids Research* vol. 21, No. 4, Oxford University Press 1993, 969-975.

MacDonald, P. R. et al., "A multipurpose transposon system for analyzing protein production, localization, and function in *Saccharomyces cerevisiae*", *Proc. Natl. Acad. Sci.* ,94 Jan. 1997, 190-195.

Machattie, L A. et al., "Chromosomal integration of phage [lambda] by means of a DNA insertion element", *Proceedings of the National Academy of Sciences (PNAS)* vol. 75, No. 3 Mar. 1978, 1490-1494.

Mackie, George A. et al., "Nucleotide Sequence of the Gene for Ribosomal Protein S20 and Its Flanking Regions", *The Journal of Biological Chemistry* vol. 256, No. 15, American Society for Biochemistry and Molecular Biology, Inc. Aug. 10, 1981, 8177-8182.

Madison, Lara L. et al., "Metabolic Engineering of Poly(3-Hydroxyalkanoates): From DNA to Plastic", *Microbiology and Molecular Biology Reviews* vol. 63, No. 1, American Society for Microbiology Mar. 1999, 21-53.

Maemura, Koji et al., "Generation of a Dominant-negative Mutant of Endothelial PAS Domain Protein 1 by Deletion of a Potent C-terminal Transactivation Domain", *The Journal of Biological Chemistry* vol. 274, No. 44, American Society for Biochemistry and Molecular Biology, Inc. Oct. 29, 1999, 31565-31570.

Maeser, Stefan et al., "The Gin Recombinase of Phage Mu Can Catalyse Site-Specific Recombination in Plant Protoplasts.", *Mol. Gen. Genet.* vol. 230, Springer-Verlag 1991, 170-176.

Mahillon, J et al., "IS231 and other *Bacillus thuringiensis* elements: a review.", *Genetica* vol. 93 1994, 13-26.

Mahillon, Jacques et al., "Subdivision of the *Escherichia coli* K-12 genome for sequencing: manipulation and DNA sequence of transposable elements introducing unique restriction sites", *Gene* vol. 223, Elsevier Science B.V. 1998, 47-54.

Malim, Michael H. et al., "The HIV-1 rev trans-activator acts through a structured target sequence to activate nuclear export of unspliced viral mRNA", *Nature* vol. 338, MacMillan Magazines Ltd. 1989, 254-257.

Malynn, Barbara A. et al., "The Scid Defect Affects the Final Step of the Immunoglobulin VDJ Recombinase Mechanism", *Cell* vol. 54, Cell Press Aug. 12, 1988, 453-460.

Maniatis, Tom, "Ch 11: Recombinant DNA Procedures in the Study of Eukaryotic Genes", *Cell Biology: A Comprehensive Treatise* vol.

3, Gene Expression: The Production of RNA's,Goldstein, L., and Prescott, D.M., eds. 1980, 563-608.

Maniatis, Tom et al., "Regulation of Inducible and Tissue-Specific Gene Expression", *Science* vol. 236, American Association for the Advancement of Science Jun. 5, 1987, 1237-1245.

Maniatis, T., et al., "Synthesis of cDNA", *Molecular Cloning: A Laboratory Manual*, Cold Spring Harbor Laboratory Press, 1982, 213 & 231.

Manning, Paul A. et al., "Gene capture in Vibrio cholerae", *Trends in Microbiology*, vol. 7 No. 3 Elsevier Science Mar. 1999, 93-95.

Manstein, Dietmar J. et al., "Cloning vectors for the production of proteins in *Dictyostelium discoideum*", *Gene* vol. 162, Elsevier Science B.V. 1995, 129-134.

Marayama, Nobuhiro et al., "Evidence for Involvement of *Escherichia coli* Genes pmbA, csrA and a Previously unrecognized Gene tldD, in the Control of DNA Gyrase by letD (ccdB) of Sex Factor F", vol. 256, *J. Mol. Biol.* Academic Press Limited 1996, 483-502.

Marinovic, Anne C. et al., "Tools for Evaluating Ubiquitin (UbC) Gene Expression: Characterization of the Rat UbC Promoter and Use of a Unique 3' mRNA Sequence", *Biochemical and Biophysical Research Communication* vol. 274, No. 2, Academic Press 2000, 537-541.

Martin, Robin et al., "Codon context effects on nonsense suppression in human cells.", *Biochemical Society Transactions* vol. 21, Portland Press Ltd. 1993, 846-851.

Martinek, Sebastian et al., "Specific Genetic Interference With Behavioral Rhythms in Drosophila by Expression of Inverted Repeats", vol. 156, *Genetics* Dec. 2000, 1717-1725.

Martinez-Salas, Encarnacion, "Internal ribosome entry site (IRES) biology and its use in gene expression vectors.", *Current Opinion in Biotechnology* vol. 10 1999, 458-464.

Maruyama, Kazao et al., "Oligo-Capping: A Simple Method to Replace the Cap Structure of Eukaryotic mRNAs with Oligoribonucleotides", *Gene* vol. 138 1994, 171-174.

Mastrangeli, Andrea et al., "Diversity of airway Epithelial Cell targets for In Vivo Recombinant Adenovirus-mediated Gene Transfer", *Journal of Clinical Investigation* vol. 91, American Society for Clinical Investigation Jan. 1993, 225-234.

Matsuzaki, Hiroaki et al., "Chromsome Engineering in *Saccharomyces cerevisiae* by Using a Site-Specific Recombination System of a Yeast Plasmid", *The Journal of Bacteriology* vol. 172, No. 2, American Society for Microbiology Feb. 1990, 610-618.

Matta, Hittu et al., "Use of Lentiviral Vectors for Delivery of Small Interfering RNA.", *Cancer & Biology Therapy* vol. 2, No. 2 Mar. 2003, 206-210.

Matthews, Jayne A. et al., "Analytical Strategies for the Use of DNA Probes", *Analytical Biochemistry* vol. 169 1988, 1-25.

Mayer, Bruce J. et al., "Signalling through SH2 and SH3 domains", *Trends Cell Biology* vol. 3, Elsevier Science Jan. 3, 1993, 8-13.

McCarthy, John E. et al., "Prokaryotic translation: the interactive pathway leading to initiation", *Trends Genet* vol. 10, No. 11, Elsevier Trends Journals Nov. 1994, 402-407.

McKnight, Steven L., "Functional Relationships between Transcriptional Control Signals of the Thymidine Kinase Gene of Herpes Simplex Virus", vol. 31, *Cell* MIT Dec. 1982, 355-365.

Medberry, Scott L. et al., "Intra-chromosomal rearrangements generated by Cre-lox site-specific recombination", *Nucleic Acids Research* vol. 23, No. 3, Oxford University Press 1995, 485-490.

Melchner, H. et al., "Retrovirus mediated gene transfer into hemopoietic cells", vol. 57 *Blut* 1988, 1-5.

Mendiola, M. W. et al., "Specificity of Insertion of IS91, an Insertion Sequence Present in .alpha.-haemolysis Plasmids of *Escherichia coli*", *Molecular Microbiology* vol. 3, No. 7 1989, 979-984.

Mercier, Josee et al., "Structural and Functional Characterization of tnpl, a Recombinase Locus in Tn21 and Related .beta.-Lactamase Transposons", *Journal of Bacteriology* vol. 172, No. 7, American Society for Microbiology Jul. 1990, 3745-3757.

Merkulov, G. V., "Libraries of Green Fluorescent Protein Fusions Generated by Transposition in Vivo", *Gene* vol. 222 1998, 213-222.

Merriam-Webster, "Dictionary definition of "In vitro"", *Merriam-Webster online dictionary* Merriam-Webster http://www.m-w.com/cgi-bin/dictionary?book=Dictionary&va=in+vitro, accessed Sep. 12, 2006, 1.

Merwin, June R. et al., "CDS-Mediated Specific Delivery of DNA to T Lymphocytes: Compartmentalization Augmented by Adenovirus", *Journal of Immunological Methods* vol. 186, No. 2, Elsevier Science B.V. 1995, 257-266.

Metcalf, William W. et al., "Conditionally Replicative and Conjugative Plasmids Carrying lacZ.alpha. for Cloning, Mutagenesis, and Allele Replacement in Bacteria", *Plasmid* vol. 35, No. 0001, Academic Press 1996, 1-13.

Mette, M. F. et al., "Transcriptional silencing and promoter methylation triggered by double-stranded RNA", *The EMBO Journal* vol. 19, No. 19, European Molecular Biology Organization 2000, 5194-5201.

Meyer-Leon, Leslie et al., "Purification of the FLP Site-Specific Recombinase by Affinity Chromatography and Re-Examination of Basic Properties of the System", *Nucleic Acids Research* vol. 15, No. 16, IRL Press Limited 1987, 6469-6488.

Miki, Takeyoshi et al., "Control of Segregation of Chromosomal DNA by Sex Factor P in *Escherichia coli*. Mutants of DNA Gyrase Subunit A Suppress letD (ccdB) Product Growth Inhibition", *J. Mol. Biol.* vol. 225, Academic Press 1992, 39-52.

Miller, Harvey I. et al., "Direct Role of the himA Gene Product in Phage lambda Integration", *Nature* vol. 290 Apr. 9, 1981, 523-526.

Miller, Daniel G. et al., "Gene Transfer by Retrovirus Vectors Occurs Only in Cells that are Actively Replicating At the Time of Infection", *Molecular and Cellular Biology* vol. 10, No. 8 Aug. 1990, 4239-4242.

Miller, A D. et al., "Improved Retroviral Vectors for Gene Transfer and Expression", *BioTechniques* vol. 7, No. 9 Eaton Publishing Co. 1989, 980-982,984,986,989-990.

Miller, Harvey I. et al., "int-h: an int Mutation of Phage A That Enhances Site Specific Recombination", *Cell* vol. 20 Jul. 1980, 721-729.

Miller, A. D. et al., "Use of retroviral vectors for gene transfer and expression", *Methods in Enzymology* vol. 217 1993, 581-599.

Mills, Alea A., "Changing colors in mice: an inducible system that delivers", *Genes & Development* vol. 15, Cold Spring Harbor Laboratory Press Jun. 2001, 1461-1467.

Miyake, Sanae et al., "Efficient generation of recombinant adenoviruses using adenovirus DNA-terminal protein complex and a cosmid bearing the full-length virus genome", *Proceedings of the National Academy of Sciences (PNAS)* vol. 93, National Academy of Sciences Feb. 1996, 1320-1324.

Miyoshi, Hiroyuki et al., "Stable and efficient gene transfer into the retina using an HIV-based lentiviral vector", *Proceedings of the National Academy of Sciences (PNAS)* vol. 94, The National Academy of Sciences Sep. 1997, 10319-10323.

Mizushima, Seiichi et al., "pEF-Bos, a Powerful Mammalian Expression Vector", *Nucleic Acids Research* vol. 18, No. 17, Oxford University Press 1990, 5322.

Mizuuchi, Michiyo et al., "Integrative recombination of bacteriophage lambda: Extent of the DNA sequence involved in attachment site function", vol. 77, No. 6, *Proceedings of the National Academy of Sciences (PNAS)* Jun. 1980, 3220-3224.

Mizuuchi, K. et al., "Integrative Recombination of Bacteriophage Lamda: In Vitro Study of the Intermolecular Reaction", *Cold Spring Harbor Symposia on Quantitative Biology* vol. 43, Cold Spring Harbor Laboratory Press 1979, 1111-1114.

Mizuuchi, Michiyo et al., "The extent of DNA sequence required for a functional bacterial attachment site of phage lambda", *Nucleic Acids Research* vol. 13, No. 4, Oxford University Press 1985, 1193-1208.

Mochizuki, Hideki et al., "High-Titer Human Immunodeficiency Virus Type 1-Based Vector Systems for Gene Delivery into Nondividing Cells", *Journal of Virology* vol. 72, No. 11, American Society for Microbiology Nov. 1998, 8873-8883.

Morgan, Richard A. et al., "Human Gene Therapy", *Ann. Rev. Biochem.* vol. 62, Annual Reviews Inc. 1993, 191-217.

Morham, Scott G. et al., "Covalent and Noncovalent DNA Binding by Mutants of Vaccinia DNA Topoisomerase I", *Journal of Biologi-* cal Chemistry vol. 267, No. 22, The American Society for Biochemistry and Molecular Biology, Inc. Aug. 5, 1992, 15984-15992.

Morham, Scott G. et al., "Phenotypic selection and characterization of mutant alleles of a eukaryotic DNA topoisomerase I", Genes & Development vol. 4, No. 4, Cold Spring Harbor Laboratory Press 1990, 515-524.

Morsy, Manal A. et al., "An adenoviral vector deleted for all viral coding sequences results in enhanced safety and extended expression of a leptin transgene", Proceedings of the National Academy of Sciences (PNAS) vol. 95, National Academy of Sciences Jul. 1998, 7866-7871.

Moss, Bernard et al., "Overview of the vaccinia virus expression system", in Current Protocols in Molecular Biology Ausubel, F.M., et et., eds., John Wiley & Sons, New York, NY 1997, 16.15-16.18.

Mottagui-Tabar, Salim, "Quantitative analysis of in vivo ribosomal events at UGA and UAG stop codons", Nucleic Acids Research vol. 26, No. 11, Oxford.University Press 1998, 2789-2796.

Mount, Stephen M. et al., "A catalogue of splice junction sequences", Nucleic Acids. Research vol. 10, No. 2, IRL Press Limited 1982, 459-472.

Mozo, Teresa et al., "Design of a novel system for the construction of vectors for Agrobacterium-mediated plant transformation", Mol. Gen. Genet vol. 236, No. 1, Springer-Verlag 1992, 1-7.

MSN Encarta, "Dictionary entry for "in vitro"", Encarta.msn.com http://Encarta.msn.com/encnet/features/dictionaryresults. aspx?refid=18616222 . . . accessed Sep. 12, 2006, 1.

Muller, Heiko et al., "The E2F transcription factors: key regulators of cell proliferation.", Biochimica et Biophysica Acta vol. 1470 2000, 1-12.

Mulligan, Richard C., "The Basic Science of Gene Therapy", Science vol. 260, No. 5110, American Association for the Advancement of Science May 14, 1993, 926-932.

Mullins, Linda J. et al., "Efficient Cre-lox linearisation of BACs: applications to physical mapping and generation of transgenic animals", Nucleic Acids Research vol. 25, No. 12 1997, 2539-2540.

Mullis, K. et al., "Specific Enzymatic Amplification of DNA In Vitro: The Polymerase Chain Reaction", Cold Spring Harbor Symposia on Quantitative Biology, vol. 51 Cold Spring Harbor Laboratory Press 1986, 263-273.

Mulsant, Philippe et al., "Phleomycin Resistance as a Dominant Selectable Marker in CHO Cells", Somatic Cell and Molecular Genetics vol. 14, No. 3, Plenum Publishing Corporation 1988, 243-252.

Munir, Khan M. et al., "Permissible amino acid substitutions within the putative nucleoside binding site of herpes simplex virus type 1 established by random sequence mutagenesis", The Journal of Biological Chemistry vol. 267, No. 10 Apr. 5, 1992, 6584-6589.

Murayama, N. et al., "Evidence for Involvement of Escherichia coli Genes pmbA, csrA and a Previously unrecognized Gene tldD, in the Control of Gyrase by letD (ccdB) of Sex Factor F", vol. 256, J. Mol. biol Academic Press Limited 1996, 483-502.

Murphy, Cheryl I. et al., "Expression and Purification of Recombinant Proteins Using the Baculovirus System", Current Protocols in Molecular Biology 2004, 16.11.1-16.11.14.

Murphy, Kenan C., "Use of Bacteriophage Lambda Recombination Functions to Promote Gene Replacement in Escherichia coli", Journal of Bacteriology vol. 180, No. 8 Apr. 1998, 2063-2071.

Murray, Peter J. et al., "Epitope Tagging of the Human Endoplasmic Reticulum HSP70 Protein, BiP, to Facilitate Analysis of BiP—Substrate Interactions", Analytical Biochemistry vol. 229, Academic Press, Inc. 1995, 170-179.

Murtif, Vicki L. et al., "Cloning and expression of the 1.3S biotin-containing subunit of transcarboxylase", Proceedings of the National Academy of Sciences (PNAS) vol. 82, National Academy Press Sep. 1985, 5617-5621.

Muskhelishvili, G. et al., "SSVI-encoded site-specific recombination system in Suliolobus shibatse", Molecular and General Genetics; vol. 237(3) 1993, 334-342.

Muyrers, Joep P. et al., "Rapid Modification of Bacterial Artificial Chromosomes by ET-Recombination", Nucleic Acids Research vol. 27, No. 6, Oxford University Press Mar. 15, 1999, 1555-1557.

Nagaraja, Ramaiah et al., "Specificity Determinants in the Attachment Sites of Bacteriophages HK022 and .lamda", The Journal of Bacteriology vol. 172, No. 11, American Society for Microbiology Nov. 1990, 6540-6550.

Nagy, Andras, "Cre Recombinase: The Universal Reagent for Genome Tailoring", Genesis vol. 26, Wiley-Liss, Inc. 2000, 99-109.

Naldini, Luigi et al., "Ch 3: Lentiviral Vectors", The Development of Human Gene Therapy Friedmann, T., ed., Cold Spring Harbor Laboratory Press Cold Spring Harbor NY 1999, 47-60.

Naldini, Luigi et al., "Efficient transfer, integration, and sustained long-term expression of the transgene in adult rat brains injected with a lentiviral vector", Proceedings of the National Academy of Sciences (PNAS) vol. 93, The National Academy of Sciences Oct. 1996, 11382-11388.

Naldini, Luigi, "Lentiviruses as gene transfer agents for delivery to non-dividing cells", Current Opinion in Biotechnology vol. 9 1998, 457-463.

Nash, Howard A., "Bending and supercoiling of DNA at the attachment site of bacteriophage lambda", Trends in Biochemical Science vol. 15 Jun. 1990, 222-227.

Nash, Howard A. et al., "Heteroduplex substrates for bacteriophage lambda site-specific recombinantion: cleavage and strand transfer products", vol. 8, No. 11, The EMBO Journal Oxford University Press 1989, 3523-3533.

Nash, Howard A., "Integrative Recombination of Bacteriophage Lambda DNA In Vitro", vol. 72, No. 3, Proceedings of the National Academy of Sciences (PNAS) National Academy of Sciences Mar. 1975, 1072-1076.

Nash, Howard A. et al., "Purification and Properties of the Bacteriophage Lambda Int Protein", Methods in Enzymology vol. 100 1983, 210-216.

Nash, Howard A. et al., "Purification and properties of the Escherichia coli protein factor required for lambda integrative recombination", The Journal of Biological Chemistry vol. 256, No. 17 Sep. 10, 1981, 9246-9253.

Nash, Howard A. et al., "Role of homology in site-specific recombination of bacteriophage .lamda.: Evidence against joining of cohesive ends", Proceedings of the National Academy of Sciences (PNAS) vol. 84 Jun. 1987, 4049-4053.

Nature Biotechnology, "New products", vol. 18, Nature Biotechnology http://biotech.nature.com Mar. 2000, 356.

Navarro, V. et al., "Efficient gene transfer and long-term expression in neurons using a recombinant adenovirus with a neuron-specific promoter", Gene Therapy vol. 6, Stockton Press 1999, 1884-1892.

NCBI Entrez, , "Accession No. BC000141", Genbank Report Strausberg, R.L., et et. 2002, 1-3.

NCBI Entrez, , "Accession No. BCOOO141", NCBI Entrez, GenBank Report Accession No. BCOOO141, Entry Date 2001, Last Updated Jun. 2004.

Nelson, Jay A. et al., "Negative and Positive Regulation by a Short Segment in the 5'-Flanking Region of the Human Cytomegalovirus Major Immediate-Early Gene", Molecular and Cellular Biology vol. 7, No. 11, American Society for Mocrobiology Nov. 1987, 4125-4129.

Nelson, Kristin K. et al., "Splice site selection and ribonucleoprotein complex assembly during in vitro pre-mRNA splicing", Genes and Development vol. 2, No. 3, Cold Spring Harbor Laboratory 1988, 319-329.

Nenoi, Mitsuru et al., "Heterogeneous structure of the polyubiquitin gene UbC of HeLa S3 cells", Gene vol. 175, Elsevier Science B.V. 1996, 179-185.

New England Biolabs, , "pUC18/19 Description and map", #N3041S http://www.neb.com/nebecomm/products/productN3041.asp 2006, 1-2.

New England Biolabs, Inc., , "New England Biolabs Catalogue", M0202S http://www.neb.com/nebecomm/default.asp 2003, 1.

Ng, P. et al., "A High-Efficiency Cre/loxP-Based System for Construction of Adenoviral Vectors", Human Gene Therapy vol. 10, Mary Ann Liebert, Inc. Nov. 1, 1999, 2667-2672.

Nickoloff, Jac A. et al., "A 24-Base-Pair DNA Sequence from the MAT Locus Stimulates Intergenic Recombination in Yeast", Proceedings of the National Academy of Sciences (PNAS) vol. 83 Oct. 1986, 7831-7835.

Nilsson, Bjorn et al., "Immobilization and Purification of enzymes with staphylococcal protein A gene fusion vectors", *EMBO Journal* vol. 4, No. 4 1985, 1075-1080.

Nomura, Masayasu et al., "Regulation of the Synthesis of Ribosomes and Ribosomal Components", *Ann. Rev. Biochem.* vol. 53, Annual Reviews, Inc. 1984, 75-117.

Norris, Belinda J. et al., "Nucleotide sequence of a cDNA clone encoding the precursor of the peridinin-chlorophyll a-binding protein from the dinoflagellate *Symbiodinium* sp.", *Plant Molecular Biology*, vol. 24 No. 4 Feb. 1994, 673-677.

Novagen Corporation, "BugBuster Plus Benzonase from Novagen", *Novagen Catalogue #70750-3* http://www.biocompare.com/ProductDetails/23301/ProductDetails.html Oct. 20, 2008, 1-2.

Numrych, Thomas E. et al., "A comparison of the effects of single-base and triple-base changes in the integrase arm-type binding sites on the site-specific recombination of bacteriophage lambda", *Nucleic Acids Research* vol. 18, No. 13, Oxford University Press 1990, 3953-3959.

Numrych, Thomas E. et al., "Characterization of the bacteriophage lambda exisionase (Xis) protein: the C-terminus is required for Xis-integrase cooperativity but not for DNA binding", *The EMBO Journal* vol. 11, No. 10, Oxford University Press 1992, 3797-3806.

Nunes-Duby, Simone E. et al., "Half-att Site Substrates Reveal the Homology Independence and Minimal Protein Requirements for Productive Synapsis in .lamda. Excisive Recombination", *Cell* vol. 59 Oct. 6, 1989, 197-206.

Nunes-Duby, Simone E. et al., "Lambda Integrase cleaves DNA in cis", *The EMBO Journal* vol. 13 1994, 4421-4430.

Nunes-Duby, Simone E. et al., "Similarities and differences among 105 members of the Int family of site-specific recombinases", *Nucleic Acids Research* vol. 26, No. 2, Oxford University Press 1998, 391-406.

Oberto, Jacques et al., "A segment of the phage HK022 chromosome is a mosaic of other lambdoid chromosomes", *Nucleic Acids Research* vol. 22, No. 3, Oxford University Press 1994, 354-356.

Odell, Joan T. et al., "Seed-Specific Gene Activation Mediated by the Cre/lox Site Specific Recombination System", *Plant Physiol.* vol. 106, American Society of Plant Physiologists 1994, 447-458.

Odell, Joan et al., "Site-directed recombination in the genome of transgenic tobacco", *Mol. Gen. Genet.* vol. 223, Springer-Verlag 1990, 369-378.

O'Gara, James P. et al., "Identification and Molecular Genetic Analysis of Multiple Loci Contributing to High-Level Tellurite Resistance in Rhodobacter sphaeroides 2.4.1", *Applied and Environmental Microbiology* vol. 63, No. 12, American Society for Microbiology Dec. 1997, 4713-4720.

Ohkawa, Jun et al., "Control of the Functional Activity of an Antisense RNA by a Tetracycline-Responsive Derivative of the Human U6 snRNA Promoter", *Human Gene Therapy* vol. 11 Mar. 1, 2000, 577-585.

Ohtani, Kiyoshi, "Implication of transcription factor E2F in regulation of DNA replication", *Frontiers in Bioscience* vol. 4 Dec. 1, 1999, 793-804.

Okayama, Hiroto et al., "Bacteriophage Lambda Vector for Transducing a cDNA Clone Library into Mammalian Cells", *Molecular and Cellular Biology* vol. 5, American Society for Microbiology May 1985, 1136-1142.

Old, R. W., "Basic Techniques", *Principles of Gene Manipulation, An Introduction to Genetic Engineering* 1981, 26-27.

Oliner, Jonathan D. et al., "In vivo cloning of PCR products in *E. coli*", *Nucleic Acids Research* vol. 21, No. 22, Oxford University Press 1993, 5192-5197.

Orban, Paul C. et al., "Tissue- and site-specific DNA recombination in transgenic mice", *Proceedings of the National Academy of Sciences (PNAS)* vol. 89, National Academy of Sciences Aug. 1992, 6861-6865.

Orosz, Andras et al., "Analysis of the complex transcription termination region of the *Escherichia coli* rrnB gene", *Eur. J. Biochem* vol. 201, Blackwell Science Ltd. 1991, 653-659.

Osborne, Brian I. et al., "A system for insertional mutagenesis and chromosomal rearrangement using the Ds transposon and Cre-lox", *The Plant Journal* vol. 7, No. 4, Blackwell Scientific Publishers and BIOS Scientific Publishers 1995, 687-701.

Osuna, Robert et al., "Identification of two functional regions in Fis: the N-terminus is required to promote Hin-mediated DNA inversion but not Lambda excision", *The EMBO Journal* vol. 10, No. 6, Oxford University Press 1991, 1593-1603.

Paabo, Svante et al., "Ch 20: Amplifying Ancient DNA", *PCR Protocols: A Guide to Methods and Applications* Academic Press 1990, 159-166.

Paddison, Patrick J. et al., "Short hairpin RNAs (shRNAs) induce sequence-specific silencing in mammalian cells", *Genes & Development* vol. 16 2002, 948-958.

Padgett, K. A. et al., "Creat i ng seaml ess junctions independent of restriction sites in PCR cloning", *Gene, Elsevier*, Amsterdam, NL, vol. 168, No. 1, XP004042930 Feb. 2, 1996, 31-35 Pgs.

Padgett, Kerstein A. et al., "Creating seamless junctions independent of restricition sites in PCR cloning", *Gene* vol. 168, Elsevier/North-Holland, Netherlands 1996, 31-35.

Pal, Subrata K. et al., "P1 Plasmid Replication. Role of Initiator Titration in Copy Number Control", *Journal of Molecular Biology* vol. 192, Academic Press Inc. 1986, 275-285.

Palaniyar, Nades et al., "SFV topoisomerase: sequence specificity in a genetically mapped interval", *Virology* vol. 221, American Press, Inc. 1996, 351-354.

Palazzolo, Michael J. et al., "Phage lambda cDNA cloning vectors for subtractive hybridization, fusion-protein synthesis and Cre-loxP automatic plasmid subcloning", *Gene* vol. 88 1990, 25-36.

Pan, Clark Q. et al., "Identification of new Fis binding sites by DNA scission with Fis-1,10-phenanthroline-copper(I) chimeras", *Biochemistry* vol. 35 1996, 4326-33.

Pan, Guohua et al., "Ligation of Synthetic Activation DNA Substrates by Site-specific Recombinases and Topoisomerase I", *The Journal of Biological Chemistry* vol. 268, No. 5, American Society for Biochemestry and Molecular Biology, Inc. Feb. 15, 1993, 3683-3689.

Pan, Clark Q. et al., "Variable structures of Fis-DNA complexes determined by flanking DNA-protein contacts.", *Journal of Molecular Biology* 264 1996, 675-95.

Panke, Sven et al., "Engineering of Quasi-Natural *Pseudomonas putida* Strains for Toluene Metabolism through an Ortho-Cleavage Degradation Pathway", *Applied and Environmental Microbiology* vol. 64, No. 2, American Society for Microbiology Feb. 1998, 748-751.

Park, Frank et al., "Modified HIV-1 based lentiviral vectors have an effect on viral transduction efficiency and gene expression in vitro and in vivo.", vol. 4, No. 3, *Molecular Therapy* The American Society of Gene Therapy Sep. 3, 2001, 164-173.

Parker, L. T. et al., "AmpliTaq DNA Polymerase, FS Dye-Terminator Sequencing: Analysis of Peak Height Patterns", *BioTechniques* vol. 21, No. 4, PJB Publications, London. Oct. 1996, 694-699.

Parks, Robin J. et al., "A Helper-Dependent System for Adenovirus Vector Production Helps Define a Lower Limit for Efficient DNA Packaging", vol. 71, No. 4, *Journal of Virology* Apr. 1997, 3293-3298.

Parr, Rebecca D. et al., "New Donor vector for generation of histidine- tagged fusion protiens using the gateway cloning system", vol. 49, *Plasmid Elsevier Science (USA)* 2003, 179-183.

Parrott, M. B. et al., "Metabolic Biotinylation of Recombinant Proteins in Mammalian Cells and in Mice", *Molecular Therapy* vol. 1, No. 1, The American Society of Gene Therapy Jan. 2000, 96-104.

Parrott, M. B. et al., "Metabolic Biotinylation of Secreted and Cell Surface Proteins from Mammalian Cells", *Biochemical and Biophysical Research Communications* vol. 281, No. 4, Academic Press Mar. 2001, 993-1000.

Patanjali, Sankhavaram R. et al., "Construction of a Uniform-Abundance (Normalized) cDNA Library", vol. 88, *Proceedings of the National Academy of Sciences (PNAS)* Mar. 1991, 1943-1947.

Patel, Premal H. et al., "DNA polymerase active site is highly mutable: Evolutionary consequences", *Proceedings of the National Academy of Sciences (PNAS)* vol. 97, No. 10, National Academy of Sciences May 9, 2000, 5095-5100.

Paterson, Trevor et al., "Approaches to maximizing stable expression of alpha1-antitrypsin in transformed CHO cells", *Appl. Microbiol. Biotechnol.* vol. 40 1994, 691-698.

Paul, Cynthia P. et al., "Effective Expression of Small Interfering RNA in human cells.", *Nature Biotechnology* vol. 20 May 2002, 505-508.

Paull, Tanya T. et al., "DNA Looping by *Saccharomyces cerevisiae* High Mobility Group Proteins NHP6A/B", *The Journal of Biological Chemistry* vol. 270, No. 15 Apr. 14, 1995, 8744-54.

Peakman, Timothy C. et al., "Highly efficient generation of recombinant baculovirus by enzymatically mediated site-specific in vitro recombination", *Nucleic Acids Research* vol. 20, No. 3, Oxford University Press 1992, 495-500.

Peng, K-W et al., "Organ distribution of gene expression after intravenous infusion of the targeted and untargeted lentiviral vectors", *Gene Therapy* vol. 8, Nature Publishing Group 2001, 1456-1463.

Peredelchuk, Michael Y. et al., "A method for construction of *E. coli* strains with multiple DNA insertions in the Chromosome", *Gene* vol. 187 1997, 231-238.

Perler, Francine B., "InBase, the New England Biolabs Intein Database", *Nucleic Acids Research* vol. 27, No. 1, Oxford University Press 1999, 346-347.

Persson, Mats A., "Combinatorial Libraries", *Intern. Rev. Immunol.* vol. 10 1993, 153-163.

Petersen, Birgitte O. et al., "Characterization of a DNA Topoisomerase Encoded by *Amsacta moorei* Entomopoxvirus", *Virology* vol. 230, Academic Press 1997, 197-206.

Petersen, Birgitte O. et al., "DNA strand transfer reactions catalyzed by vaccinia topoisomerase: hydrolysis and glycerololysis of the covalent protein-DNA intermediate", *Nucleic Acids Research* vol. 25, No. 11, Oxford University Press 1997, 2091-2097.

Petersen, Birgitte O. et al., "Histidine 265 is Important for Covalent Catalysis by Vaccinia Topoisormerase and is Conserved in all Eukaryotic Type I Enzymes", *Journal of Biological Chemistry* vol. 272, No. 7 Feb. 14, 1997, 3891-3896.

Petersen, B. O. et al., "Mutations within a conserved region of vaccinia topoisomerase affect the DNA cleavage-religation equilibrium", *J. Mol. Biol.* vol. 263, No. 2, Academic Press Limited 1996, 181-195.

Pfeifer, Tom A. et al., "Baculovirus immediate-early promoter-mediated expression of the ZeocinTM resistance gene for use as a dominant selectable marker in Dipteran and Lepidopteran insect cell lines", *Gene* vol. 188, Elsevier Science B.V. 1997, 183-190.

Pfeifer, Alexander et al., "Delivery of the Cre Recombinase by a Self-Deleting Lentiviral Vector: Efficient Gene Targeting in Vivo", *Proceedings of the National Academy of Sciences (PNAS)* vol. 98, No. 20, National Academy of Sciences Sep. 25, 2001, 11450-11455.

Pfeifer, Alexander et al., "Transduction of Liver Cells by Lentiviral Vectors: Analysis in Living Animals by Fluorescence Imaging", *Molecular Therapy* vol. 3, The American Society of Gene Therapy Mar. 2001, 319-322.

Phillips-Jones, Mary K. et al., "Context effects on misreading and suppression of UAG codons in human cells.", *Molecular and Cellular Biology* vol. 15, No. 12, American Society for Microbiology Dec. 1995, 6593-6600.

Pichel, Jose G. et al., "Timing of SV40 oncongene activation by site-specific recombination determines subsequent tumor progression during murine lens development", *Oncogene* vol. 8 1993, 3333-3342.

Pierce, James C. et al., "A positive selection vector for cloning high molecular weight DNA by the bacteriophage P1 system: Improved cloning efficacy", *Proceedings of the National Academy of Sciences (PNAS)* vol. 89 Mar. 1992, 2056-2060.

Pierce, M. L. et al., "Construction of a Directed Hammerhead Ribozyme Library Towards the Identification of Optimal Target Sites for Antisense-Mediated Gene Inhibition", *Nucleic Acids Research Oxford University Press*, Surrey, GB vol. 26, No. 22, XP002919160 Jan. 1, 1998, 5093-5101 pgs.

Pings, et al., "Dynamics of RNA-protein interactions in the HIV-1 Rev-RRE complex visualized by 6-thyoguanosine-mediated photocrosslinking", vol. 3, RNA Cambridge University Press, Printed in USA. 1997, 850-860.

Pittelkow, M. R. et al., "New techniques for the in vitro culture of human skin keratinocytes and perspectives on their use for grafting of patients with extensive burns.", *Mayo Clin. Proc* vol. 61, Mayo Foundation 1986, 771-777.

Podhajska, Anna J. et al., "Control of cloned gene expression by promoter inversion in vivo: construction of the heat-pulse-activated att-nutL-p-att-N module", *Gene* vol. 40 1985, 163-168.

Posfai, Gyorgy et al., "In vivo excision and amplification of large segmentsof the *Escherichia coli* genome", *Nucleic Acids Research* vol. 22, No. 12, Oxford University Press 1994, 2392-2398.

Powell, J., "Enhanced concatemer cloning—a modification to the SAGE (Serial Analysis of Gene Expression) Technique", *Nucleic Acids Research* vol. 26, No. 14, Oxford University Press 1998, 3445-3446.

Prasad, P. V. et al., "Substrate Recognition by the 2um Circle Site-Specific Recombinase: Effect of Mutations within the Symmetry Elements of the Minimal Substrate", vol. 6, No. 12, *Molecular and Cellular Biology* American Society for Microbiology, Washington, D.C. Dec. 1986, 4329-4334.

Prasher, Douglas C. et al., "Primary structure of the *Aequorea victoria* green fluorescent protein", *Gene*, vol. 111 1992, 229-233.

Prieto, Maria A. et al., "Molecular Characterization of the 4-Hydroxyphenylacetate Catabolic Pathway of *Escherichia coli* W: Engineering a Mobile Aromatic Degradative Cluster", *Journal of Bacteriology* vol. 178, No. 1 Jan. 1996, 111-120.

Qian, Xiao-Hong et al., "Reactions between Half- and Full-FLP Recombination Target Sites: A Model System for Analyzing Early Steps in FLP Protein-Mediated Site-Specific Recombination", *The Journal of Biological Chemistry* vol. 267, No. 1, American Society for Biochemistry and Molecular Biology Apr. 15, 1992, 7794-7805.

Qin, Minmin et al., "Cre recombinase-mediated site-specific recombination between plant chromosomes", *Proceedings of the National Academy of Sciences (PNAS)* vol. 91, National Academ of Sciences Mar. 1994, 1706-1710.

Qin, Xiao-Feng et al., "Inhibiting HIV-1 Infection in Human T Cells by Lentiviral-Mediated Delivery of Small Interfering RNA Against CCR5", *Proceedings of the National Academy of Sciences (PNAS)* vol. 100, No. 1 Jan. 7, 2003, 183-188.

Qin, Minmin et al., "Site-specific cleavage of chromosomes in vitro through Cre-lox recombination", *Nucleic Acids Research* vol. 23, No. 11, Oxford University Press 1995, 1923-1927.

Qinghua, L. et al., "The Univector Plasmid-Fusion System Amethod for Rapid Constructionof Recombinant DNA Without Restriction Enzymes", vol. 8, No. 24, *Current Biology, Current Science* GB Dec. 3, 1998, 1300-1309.

Rao, Anjana, "Sampling the Universe of Gene Expression", *Nature Biotechnology* vol. 16 Dec. 1998, 1311.

Rausch, Helmut et al., "Structural Analysis of the actinophage phi C31 attachment site", Nucleic Acids Research vol. 19, No. 19, IRL Press 1991, 5187-5189.

Ravenscroft, Neil et al., "Identification, isolation, and structural studies of the outer membrane lipopolysaccharide of Caulobacter crescentus.", *Journal of Bacteriology* vol. 174, No. 23 Dec. 1992, 7595-7605.

Recchia, Alessandra et al., "Site-specific integration mediated by a hybrid adenovirus/adeno-associated virus vector", *Proceedings of the National Academy of Sciences (PNAS)* vol. 96, National Academy of Sciences Mar. 1999, 2615-2620.

Reed, R., "Initial splice-site recognition and pairing during pre-mRNA splicing", *Curro Opin. Genet. Devel.* vol. 6, Current Biology Ltd. 1996, 215-220.

Reed, Randall R. et al., "Transposon-Mediated Site-Specific Recombination in vitro: DNA Cleavage and Protein-DNA Linkage at the Recombination Site", *Cell* vol. 25, No. 3, Cell Press Sep. 1981, 721-728.

Reed, Randall R., "Transposon-Mediated Site-Specific Recombination: A Defined in Vitro System", vol. 25, *Cell* Sep. 1981, 713-719.

Rheinwald, James G., "Ch 15: Serial Cultivation of Normal Human Epidermal Keratinocytes", *Methods in Cell Biology*, vol. 21A Academic Press, Inc. 1980, 229-254.

Richet, Evelyne et al., "Synapsis of Attachment Sites during Lambda Integrative Recombination Involves Capture of a Naked DNA by a Protein-DNA Complex", *Cell* vol. 52, Cell Press Jan. 15, 1988, 9-17.

Richet, Evelyne et al., "The Interaction of Recombination Proteins with Supercoiled DNA: Defining the Role of Supercoiling in Lambda Integrative Recombination", *Cell* vol. 46, Cell Press Sep. 26, 1986, 1011-1021.

Rietveld, Luc E. et al., "In vivo repression of an erythroid-specific gene by distinct corepressor complexes", *The EMBO Journal* vol. 21, No. 6, European Molecular Biology Organization 2002, 1389-1397.

Robinson, Donald F. et al., "Suppression of Single and Double Nonsense Mutations Introduced into the Diphtheria Toxin A-Chain Gene: A Potential Binary System for Toxin Gene Therapy", *Human Gene Therapy* vol. 6, Mary Ann Liebert, Inc., Publishers Feb. 1995, 137-143.

Roca, Joaquim et al., "The capture of a DNA double helix by an ATP-dependent protein clamp: A key step in DNA transport by type II DNA topoisomerases.", *Cell* vol. 71, Cell Press Nov. 27, 1992, 833-840.

Rodems, Steven M. et al., "A FRET-Based Assay Platform for Ultra-high density drug Screening of protein kinases and phosphatases", *Assay and Drug Development Technologies*, vol. 1, No. 1-1 2002, 9-19.

Rogers, Yu-Hui et al., "Immobilization of Oligonucleotides onto a Glass Support Via Disulfide Bonds: A Method for Preparation of DNA Microarrays", *Analytical Biochemistry* vol. 266 1999, 23-30.

Rosano, Camillo et al., "The X-ray three-dimensional structure of avidin", *Biomolecular Engineering* vol. 16, Elsevier Science B.V. 1999, 5-12.

Rosenberg, Alan H. et al., "Vectors for selective expression of cloned DNAs by T7 RNA polymerase", *Gene* vol. 56 1987, 125-135.

Rosenfeld, Melissa A. et al., "Adenovirus-Mediated Transfer of a Recombinant alpha1-Antitrypsin Gene to the Lung Epithelium in Vivo", *Science* vol. 252 Apr. 19, 1991, 431-434.

Rosenfeld, Melissa A. et al., "In Vivo Transfer of the Human Cystic Fibrosis Transmembrane Conductance Regulator Gene to the Airway Epithelium", *Cell* vol. 68 Jan. 10, 1992, 143-155.

Ross, Wilma et al., "*E. coli* Fis protein activates ribosomal RNA transcription in vitro and in vivo", *The EMBO Journal* vol. 9, No. 11 1990, 3733-42.

Ross, Wilma et al., "Interaction of Int Protein with Specific Sites on lambda att DNA", *Cell* vol. 18 Oct. 1979, 297-307.

Ross, Wilma et al., "Patterns of Lamda Int Recognition in the Regions of Strand Exchange", *Cell* vol. 33, MIT Press May 1983, 261-272.

Rubenstein, J.L. R. et al., "Subtractive Hybridization System Using Single-Stranded Phagemids With Directional Inserts", *Nucleic Acids Research* vol. 18, No. 16 1990, 4833-4842.

Rubinson, Douglas A. et al., "A Lentivirus-Based System to Functionally Silence Genes in Primary Mammalian Cells, Stem Cells and Transgenic Mice by RNA Interference", *Nature Genetics* vol. 33 Mar. 2003, 401-406.

Rubinson, D. A. et al., "A lentivirus-based system to functionally silence genes inprimary mammalian cells, stem cells and transgenic mice by RNA interference", *Nature Genetics, Nature Publishing Group* New York, US vol. 33 XP002973404 Mar. 1, 2003, 401-406 pgs.

Russell, M., "A recombination-based cloning system that decreases time to protein analysis", *American Biotechnology Laboratory*, vol. 18(7) Jun. 30, 2000, 8 & 10.

Russell, Marijane, "A recombination-based cloning system that decreases time to protein analysis", vol. 18, No. 7, *American Biotechnology Laboratory* Jun. 2000, 8,10.

Russell, M., "A recombination-based cloning system that decreases time to protein analysis", *American Biotechnology Laboratory*, vol. 18(7) Jun. 2000, 8-10.

Russell, Marijane, "A recombination-based cloning system that decreases time to protein analysis", vol. 18, No. 7, *American Biotechnol. Lab.* International Scientific Communications, Inc. Jun. 2000, 8-10.

Russell, W. C., "Update on adenovirus and its vectors", *Journal of General Virology* vol. 81, SGM 2000, 2573-2604.

Sadowski, Ivan et al., "A Noncatalytic Domain Conserved among Cytoplasmic Protein-Tyrosine Kinases Modifies the Kinase Function and Transforming Activity of Fujinami Sarcoma Virus P130.sup.gag-fps", *Molecular and Cellular Biology*, vol. 6, No. 12, American Society for Microbiology Dec. 1986, 4396-4408.

Sadowski, Paul D., "Site-Specific Genetic Recombination: Hops, Flips and Flops", *FASEB Journal* vol. 7, No. 9 Jun. 1993, 760-767.

Sadowski, Paul, "Site-Specific Recombinases: Changing Partners and Doing the Twist", *The Journal of Bacteriology* vol. 165, No. 2, American Society for Microbiology Feb. 1986, 341-347.

Sadowski, Paul D., "The Flp recombinase of the 2-microns plasmid of *Saccharomyces cerevisiae*", *Progress in Nucleic Acid Research and Molecular Biology* vol. 51 1995, 53-91.

Saiki, Randall K. et al., "Primer-Directed Enzymatic Amplification of DNA with a Thermostable DNA Polymerase", *Science*, vol. 239 Jan. 20, 1988, 487-491.

Salazar, Miguel et al., "The DNA strand in DNA.RNA hybrid duplexes is neither B-form nor A-form in solution", *Biochemistry* vol. 32, No. 16, American Chemical Society 1993, 4207-4215.

Salmons, Brian et al., "Targeting of Retroviral Vectors for Gene Therapy", *Human Gene Therapy* vol. 4 1993, 129-141.

Sambrook, Joseph et al., "Ch: 16.30-16.60—Introduction of Recombinant Vectors into Mammalian Cells", *Molecular Cloning, a Laboratory Manual* 2nd ed., Cold Spring Harbor Laboratory Press, Cold Spring Harbor, NY 1989, 16.30-16.60.

Sambrook, Joseph et al., "Ch: 16.6-16.8—Termination and Polyadenylation Signals", *Molecular Cloning: A Laboratory Manual* Second Edition,Cold Spring Harbor Laboratory Press 1989, 16.6-16.8.

Sandhu, Jasbir S., "Protein Engineering of Antibodies", *Critical Reviews in Biotechnology* vol. 12, No. 5/6, CRC Press, Inc. 1992, 437-462.

Santoro, Stephen W. et al., "Directed evolution of the site specificity of Cre recombinase", *Proceedings of the National Academy of Sciences (PNAS)* vol. 99, No. 7 Apr. 2, 2002, 4185-4190.

Sato, Tsutomo et al., "The cisA Cistron of *Bacillus subtilis* Sporulation Gene spolVC Encodes a Protein Homologous to a Site-Specific Recombinase", *Journal of Bacteriology* vol. 172, No. 2, American Society for Microbiology Feb. 1990, 1092-1098.

Sauer, Brian et al., "Construction of Isogenic Cell Lines Expressing Human and Rat Angiotensin II AT1 Receptors by Cre-Mediated Site-Specific Recombination", *Methods: A Companion to Methods in Enzymology* vol. 4, Academic Press, Inc. 1992, 143-149.

Sauer, Brian et al., "Cre-stimulated recombination at loxP-containing DNA sequences placed into the mammalian genome", *Nucleic Acids Research* vol. 17, No. 1, Oxford University Press 1989, 147-161.

Sauer, Brian et al., "Expression and Functioning in Yeast of a Bacterial Site Specific Recombination System", *Journal of Cellular Biochemistry* Supplement 10B, Abstract # I340, Alan R. Liss, Inc. 1986, 242.

Sauer, Brian, "Functional Expression of the cre-lox Site-Specific Recombination System in the Yeast *Saccharomyces cerevisiae*", *Molecular and Cellular Biology* vol. 7, No. 6, American Society for Microbiology Jun. 1987, 2087-2096.

Sauer, Brian, "Inducible gene targeting in mice using the Cre/lox system", *Methods: A Companion to Methods in Enzymology* vol. 14, Academic Press Apr. 1998, 381-392.

Sauer, Brian, "Manipulation of Transgenes by Site-Specific Recombination: Use of Cre Recombinase", *Methods in Enzymology* vol. 225, Academic Press, Inc. 1993, 890-900.

Sauer, Brian, "Multiplex Cre/lox recombination permits selective site-specific DNA targeting to both a natural and an engineered site in the yeast genome", *Nucleic Acids Research* vol. 24, No. 23, Oxford University Press 1996, 4608-4613.

Sauer, Brian et al., "Site-specific DNA Recombination in mammalian cells by the Cre recombinase of bacteriophage P1", *Proceedings of the National Academy of Sciences (PNAS)* vol. 85, National Academy of Science Jul. 1988, 5166-5170.

Sauer, Brian et al., "Site-specific insertion of DNA into a pseudorabies virus vector", *Proceedings of the National Academy of Sciences (PNAS)* vol. 84, National Academy of Sciences Dec. 1987, 9108-9112.

Sauer, Brian, "Site-specific recombination: developments and applications.", *Current Opinion in Biotechnology* vol. 5, Current Biology Ltd. 1994, 521-527.

Sauer, Brian et al., "Targeted Insertion of Exogenous DNA into the Eukaryotic Genome by the Cre Recombinase", *The New Biologist*, vol. 2, No. 5 May 1990, 441-449.

Sauer, Brian et al., "The Cyclization of linear DNA in *Escherichia coli* by site-specific recombination", *Gene* vol. 70, Elsevier Science B.V. 1988, 331-341.

Schild, David et al., "Cloning of Three Human Multifunction de novo Purine Biosynthetic Genes by Functional Complementation of Yeast Mutations", *Proceedings of the National Academy of Sciences (PNAS)* vol. 87, National Academy of Sciences Apr. 1990, 2916-2920.

Schindelhauer, Dirk et al., "Efficient combination of large DNA in vitro: in gel site specific recombination (IGSSR) of PAC fragments containing a satellite DNA and the human HPRT gene locus", *Nucleic Acids Research* vol. 25, No. 11, Oxford University Press 1997, 2241-2243.

Schlake, T. et al., "Biochemistry", vol. 33 1994, 12746-12751.

Schlake, Thomas et al., "Use of Mutated FLP Recognition Target (FRT) Sites for the Exchange of Expression Cassettes at Defined Chromosomal Loci", vol. 33, *Biochemistry* American Chemical Society Nov. 1994, 12746-12751.

Schmitt, et al., "Affinity purification of histidine-tagged proteins", Molecular Biology Reports vol. 18 (3) Jan. 1, 1993, 223-230.

Schnepf, E. et al., "*Bacillus thuringiensis* and Its Pesticidal Crystal Proteins", *Microbiology and Molecular Biology Reviews* vol. 62, No. 3, American Society for Microbiology Sep. 1998, 775-806.

Schorpp, Marina et al., "The human ubiquitin C promoter directs high ubiquitous expression of transgenes in mice", *Nucleic Acids Research* vol. 24, No. 9, Oxford University Press 1996, 1787-1788.

Schwartz, D. C. et al., "New Techniques for Purifying Large DNAs and Studying Their Properties and Packaging", *Cold Spring Harbor Symposia on Quantitative Biology* vol. 47 1983, 189-195.

Schwartz, David C. et al., "Separation of Yeast Chromosomesized DNAs by Pulsed Field Gradient Gel Electrophoresis.", *Cell* vol. 37 May 1984, 67-75.

Schwarz, Elisabeth et al., "The Sodium Ion Translocating Oxalcetate Decarboxylase of *Klebsiella pneumoniae*", *The Journal of Biological Chemistry* vol. 263, No. 20 Jul. 15, 1988, 9650-9645.

Scott, S. D. et al., "Comment on the use of the cre/loxP recombinase system for gene therapy vectors", *Gene Therapy* vol. 7 2000, 1706.

Sedivy, John M. et al., "An inducible mammalian amber suppressor: propagation of a poliovirus mutant.", Cell vol. 50, Cell Press Jul. 31, 1987, 379-389.

Segall, Anca M. et al., "Architectural Elements in Nucleoprotein Complexes: Interchangeability of Specific and Non-specific DNA Binding Proteins", *The EMBO Journal* vol. 13, No. 19 1994, 4536-4548.

Segall, Anca M. et al., "Architectural flexibility in lambda site-specific recombination: three Alternate conformations channel the attL site into three distinct pathways", *Genes to Cells* vol. 1, Blackwell Science Ltd. May 1996, 453-463.

Segall, Anca M. et al., "Synaptic intermediates in bacteriophage lambda site-specific recombination: integrase can align pairs of attachment sites", *The EMBO Journal* vol. 12, No. 12, Oxford University Press 1993, 4567-4576.

Seki, Shuji et al., "Differential Effects of Aphidicolin on Replicative DNA Synthesis and Unscheduled DNA Synthesis in Permeable Mouse Sarcoma Cells", *Biochemica et Biophysica Acta* vol. 610, Elsevier/North-Holland Biomedical Press 1980, 413-420.

Sekiguchi, Joann et al., "Covalent DNA binding by vaccinia topoisomerase results in unpairing of the thymine base 5' of the scissile bond and Shuman", *Journal of Biological Chemistry* vol. 271, No. 32, The American Society for Biochemistry and Molecular Biology, Inc. Aug. 9, 1996, 19436-19442.

Sekiguchi, Joann et al., "Identification of contacts between topoisomerase I and its target DNA by site-specific photocrosslinking", *The EMBO Journal* vol. 15, No. 13, Oxford University Press 1996, 3448-3457.

Sekiguchi, Joann et al., "Kinetic analysis of DNA and RNA strand transfer reactions catalyzed by vaccinia topoisomerase", *The Journal of Biological Chemistry* vol. 272, No. 25, The American Society for Biochemistry and Molecular Biology, Inc. Jun. 20, 1997, 15721-15728.

Sekiguchi, Joann et al., "Mechanism of inhibition of vaccinia DNA topoisomerase by novobiocin and coumermycin", *The Journal of Biological Chemistry* vol. 271, No. 4, The American Society for Biochemistry and Molecular Biology, Inc. Jan. 26, 1996, 2313-2322.

Sekiguchi, Joann et al., "Mutational analysis of vaccinia virus topoisomerase identifies residues involved in DNA binding", *Nucleic Acids Research* vol. 25, No. 18, Oxford University Press 1997, 3649-3656.

Sekiguchi, Joann et al., "Nick sensing by vaccinia virus DNA ligase requires a 5' phosphate at the nick and occupancy of the adenylate binding site on the enzyme", *The Journal of Virology* vol. 71, No. 12, American Society for Microbiology Dec. 1997, 9679-9684.

Sekiguchi, Joann et al., "Proteolytic footprinting of vaccinia topoisomerase bound to DNA", *The Journal of Biological Chemistry* vol. 270, No. 19, The American Society for Biochemistry and Molecular Biology, Inc. May 12, 1995, 11636-11645.

Sekiguchi, Joann et al., "Requirements for noncovalent binding of vaccina topoisomerase I to duplex DNA", *Nucleic Acids Research* vol. 22, No. 24, Oxford University Press Dec. 11, 1994, 5360-5365.

Sekiguchi, Joann et al., "Resolution of a Holliday junction by vaccinia topoisomerase requires a spacer DNA segment 3' of the CCCTT/cleavage sites", *Nucleic Acids Research* vol. 28, No. 14, Oxford University Press 2000, 2658-2663.

Sekiguchi, Joann et al., "Resolution of Holliday junctions by eukaryotic DNA topoisomerase I", *Proceedings of the National Academy of Sciences (PNAS)* vol. 93, No. 2, National Academy of Sciences Jan. 1996, 785-789.

Sekiguchi, Joann et al., "Site-specific ribonuclease activity of eukaryotic DNA topoisomerase I", *Molecular Cell* vol. 1, No. 1, Cell Press Dec. 1997, 89-97.

Sekiguchi, Joann et al., "Stimulation of vaccinia topoisomerase I by nucleoside triphosphates", *Journal of Biological Chemistry* vol. 269, No. 47, The American Society for Biochemistry and Molecular Biology, Inc. Nov. 25, 1994, 29760-29764.

Sekiguchi, Joann et al., "Vaccinia topoisomerase binds circumferentially to DNA", *Journal of Biological Chemistry* vol. 269, No. 50, The American Society for Biochemistry and Molecular Biology, Inc. Dec. 16, 1994, 31731-31734.

Sen, G. et al., "Restriction enzyme-generated siRNA (REGS) vectors and libraries", *Nature Genetics*, Nature Publishing Group New York, US vol. 36, No. 2, XP002323763 Jan. 1, 2004, 183-189 Pgs.

Senecoff, Julie F. et al., "DNA Recognition by the FLP Recombinase of the Yeast 2 micro Plasmid—A Mutational Analysis of the FLP Binding Site", J. Mol. Biol. vol. 201 1988, 405-421.

Senecoff, Julie F. et al., "The FLP recombinase of the yeast 2-um plasmid: Characterization of its recombination site", *Proceedings of the National Academy of Sciences (PNAS)*, vol. 82 National Academy of Sciences Nov. 1985, 7270-7274.

Shaikh, A. C. et al., "The Cre Recombinase Cleaves the lox Site in trans", *The Journal of Biological Chemistry*, vol. 272 American Society for Biochemistry and Molecular Biology, Inc. Feb. 1997, 5695-5702.

Sharp, Philip A. et al., "Detection of Two Restriction Endonuclease Activities in Haemophilus Parainfluenzae Using Analytical Agarose-Ethidium Bromide Electrophoresis", *Biochemistry* vol. 12, No. 16 1973, 3055-3063.

Sharp, Philip A., "RNAi and double-strand RNA", *Genes & Development* vol. 13 1999, 139-141.

Sharp, Philip A., "Split Genes and RNA Splicing", *Cell* vol. 77, Cell Press Jun. 17, 1994, 805-815.

Shashikant, Cooduvalli S. et al., "Recombinogenic Targeting: A New Approach to Genomic Analysis—A Review", *Gene* vol. 223 1998, 9-20.

Shatkin, A. J. et al., "Capping of Eucaryotic mRNAs", *Cell* vol. 9 Dec. 1976, 645-653.

Sheffield, Peter et al., "Overcoming expression and purification problems of RhoGDI using a Family of "Parallel" expression vectors", *Protein Expression and Purification* vol. 15, Academic Press 1999, 34-39.

Shibata, K. et al., "RIKEN Integrated Sequence Analysis (RISA) System-384-Format Sequencing Pipeline with 384 Multicapillary Sequencer", Nov. 1, 2000, 1757-1771.

Shigekawa, Katherine et al., "Electroporation of Eukaryotes and Prokaryotes: A General Approach to the Introduction of Macromolecules into Cells", *BioTechniques* vol. 6, No. 8, Eaton Publishing Company 1988 , 742-751.
Shim, Jaegal et al., "Distinct and Redundant Functions of .mu.1 Medium Chains of the AP-1 Clathrin-Associated Protein Complex in the Nematode Caenorhabditis elegans", *Molecular Biology of the Cell* vol. 11, American Society for Biology Aug. 2000 , 2743-2756.
Shima, Yasufumi et al., "Construction and Characterization of N-Terminally Truncated DNA Polymerase from *Thermus thermophilus*", *Journal of Fermentation and Bioengineering* vol. 81., No. 6., 1996. XP002300266 ISSN:0922-338X, Elsevier B.V., New York 1996 , 504-510.
Shirai, Makoto et al., "Site-Specific Integration of the Actinophage R4 Genome into the Chromosome of *Streptomyces parvulus* upon Lysogenization", *Journal of Bacteriology*, vol. 173, No. 13, American Society for Microbiology Jul. 1991 , 4237-4239.
Short, Jay M. et al., "ZAP: a bacteriophage expression vector with in vivo excision properties", vol. 16, No. 15, *Nucleic Acids Research* IRL Press Limited Aug. 11, 1988 , 7583-7600.
Shuman, Stewart , "Analysis of topoisomerase-DNA interactions by electrophoretic mobility shift assay", *Methods in Molecular Biology* vol. 95, Hunana Press, Inc. 2001 , 65-74.
Shuman, Stewart et al., "Characterization of Vaccinia Virus DNA Topoisomerase I Expressed in *Escherichia coli*", *Journal of Biological Chemistry*, vol. 263 The American Society for Biochemistry and Molecular Biology, Inc. Nov. 5, 1988 , 16401-16407.
Shuman, Stewart , "DNA Strand Transfer Reactions Catalyzed by Vaccinia Topoisomerase I", *The Journal of Biological Chemistry* vol. 267, No. 12, The American Society for Biochemistry and Molecular Biology, Inc. Apr. 25, 1992 , 8620-8627.
Shuman, Stewart et al., "Identification of a Vaccinia Virus Gene Encoding a Type I DNA Topoisomerase", *Proceedings of the National Academy of Sciences (PNAS)* vol. 84, National Academic of Sciences Nov. 1987 , 7478-7482.
Shuman, Stewart et al., "Insertional mutagenesis of the vaccinia virus gene encoding a type I DNA topoisomerase: evidence that the gene is essential for virus growth", *Virology* vol. 170, No. 1, Academic Press, Inc. 1989 , 302-306.
Shuman, Stewart et al., "Intramolecular synapsis of duplex DNA by vaccinia topoisomerase", *The EMBO Journal* vol. 16, No. 21, Oxford University Press 1997 , 6584-6589.
Shuman, Stewart et al., "Mapping the active-site tyrosine of vaccinia virus DNA topoisomerase I", *Proceedings of the National Academy of Sciences (PNAS)* vol. 86, No. 24, National Academic of Sciences Dec. 1989 , 9793-9797.
Shuman, Stewart , "Novel Approach to molecular cloning and polynucleotide synthesis using vaccinia DNA Topoisomerase", vol. 269, No. 51, *The Journal of Biological Chemistry*, American Society for Biochemistry and Molecular Biology, Inc. Dec. 23, 1994 , 32678-32684.
Shuman, Stewart , "Polynucleotide ligase activity of eukaryotic topoisomerase I", *Molecular Cell* vol. 1, No. 5, Cell Press Apr. 1998 , 741-748.
Shuman, Stewart , "Recombination mediated by vaccinia virus DNA topoisomerase I in *Escherichia coli* is sequence specific", vol. 88, No. 22, *Proceedings of the National Academy of Sciences (PNAS)* National Academy of Sciences of the USA, Washington, D.C. Nov. 1991 , 10104-10108.
Shuman, Stewart , "Site-specific DNA cleavage by vaccinia virus DNA topoisomerase I. Role of nucleotide sequence and DNA secondary structure", *The Journal of Biological Chemistry* vol. 266, No. 17, The American Society for Biochemistry and Molecular Biology, Inc. Jan. 15, 1991 , 1796-1803.
Shuman, Stewart et al., "Site-specific interaction of vaccinia virus topoisomerase I with base and sugar moieties in duplex DNA", *Journal of Biological Chemistry* vol. 268, No. 25, The American Society for Biochemistry and Molecular Biology, Inc. Sep. 5, 1993 , 18943-18950.
Shuman, Stewart , "Site-specific Interaction of Vaccinia Virus Topoisomerase I with Duplex DNA. Minimal DNA Substrate for Strand Cleavage In Vitro", *The Journal of Biological Chemistry* vol. 266 No. 30 Erratum for: J Biol Chem. Jun. 15, 1991;266(17):11372-9. Oct. 25, 1991 , 20576-20577.
Shuman, Stewart , "Site-specific interaction of Vaccinia Virus Topoisomerase I with Duplex DNA.Minimal DNA Substrate for Strand Cleavage In Vitro", *Journal of Biological Chemistry*, vol. 266, No. 17 The American Society for Biochemistry and Molecular Biology, Inc. Jun. 15, 1991 , 11372-11379.
Shuman, Stewart et al., "Specific DNA Cleavage and Binding of Vaccinia Virus DNA Topoisomerase I", *The Journal of Biological Chemistry* vol. 265, No. 29, The American Society for Biochemistry and Molecular Biology, Inc. Oct. 15, 1990 , 17826-17836.
Shuman, Stewart , "Two Classes of DNA End-Joining Reactions Catalyzed by Vaccinia Topoisomerase I", *The Journal of Biological Chemistry* vol. 267, No. 24, The American Society for Biochemistry and Molecular Biology, Inc. Aug. 25, 1992 , 16755-16758.
Shuman, Stewart , "Vaccinia DNA topoisomerase I promotes illegitimate recombination in *Escherichia coli*", *Proceedings of the National Academy of Sciences (PNAS)* vol. 86, No. 10, National Academic of Sciences May 1989 , 3489-3493.
Shuman, Stewart , "Vaccinia virus DNA ligase: specificity, fidelity, and inhibition", *Biochemistry* vol. 34, American Chemical Society 1995 , 16138-16147.
Shuman, Stewart , "Vaccinia virus DNA topoisomerase: a model eukaryotic type IB enzyme", *Biochimica et Biophysica Acta* vol. 1400, Elsevier Science B. V. 1998 , 321-337.
Sigma, , "Item S4014", *Sigma Catalogue; S4014* http://www.sigmaaldrich.com/catalog/search/ProductDetail/SIGMA/S4014 2003 , 1-2.
Silver, Pamela A. et al., "Amino terminus of the yeast GAL4 gene product is sufficient for nuclear localization", vol. 81, *Proceedings of the National Academy of Sciences (PNAS)* Oct. 1984 , 5951-5955.
Simpson, Jeremy C. et al., "Systematic Subcellular Localization of Novel Proteins Identified by Large-scale cDNA Sequencing", *EMBO Reports* vol. 1, No. 3 2000 , 287-292.
Sinclair, Bob , "Honing your cloning", *The Scientist*, vol. 14(16) URL:http://www.the-scientist.com/yr2000/aug/profile1_000821.html> Aug. 21, 2008 , 29.
Sinclair, Bob , "Honing Your Cloning. New cloning systems give protein expression studies a boost", *The Scientist*, vol. 14, No. 16 Aug. 21, 2000 , 28-29.
Sioud, M. , "Therapeutic potential of small interfering RNAs", *Drugs of the Future* vol. 29, No. 7, XP002533698 Jul. 2004 741-750 pgs.
Sizemore, Christine et al., "Quantitative analysis of Tn10 Tet repressor binding to a complete set of tet operator mutants", *Nucleic Acids Research* vol. 18, No. 10, Oxford University Press 1990 , 2875-2880.
Skraly, Frank A. et al., "Construction and Characterization of a 1,3-Propanediol Operon", *Applied and Environmental Microbiology* vol. 64, No. 1, American Society for Microbiology Jan. 1998 , 98-105.
Smith, Andrew J. et al., "A site-directed chromosmal translocation induced in embryonic stem cells by Cre-loxP recombination", *Nature Genetics* vol. 9 Apr. 1995 , 376-385.
Smith, Temple F. et al., "Comparison of Biosequences", *Advances in Applied Mathematics* vol. 2, Academic Press, Inc. 1981 , 482-489.
Smith, Donald B. et al., "Single-step purification of polypeptides expressed in *Escherichia coli*", *Gene* vol. 67 1988 , 31-40.
Snaith, Michael R. et al., "Multiple cloning sites carrying loxP and FRT recognition sites for the Cre and Flp site-specific recombinases", *Gene* vol. 166, Elsevier Science B.V. Dec. 1995 , 173-174.
Soderlund, C. et al., "Contigs Built with Fingerprints, Markers, and FPC V4.7", 1772-1787 , Nov. 8, 2000.
Soltis, Daniel A. et al., "The Alpha and Beta Chains of Avian Retrovirus Reverse Transcriptase Independently Expressed in *Escherichia coli*: Characterization of Enzymatic Activities", *Proceedings of the National Academy of Sciences (PNAS)*, vol. 85, May 1988 , 3372-3376.
Southern, J. A. et al., "Identification of an epitope on the P and V proteins of simian virus 5 that distinguishes between two isolates with different biological characteristics", *Journal of General Virology* vol. 72, Society for General Microbiology 1991 , 1551-1557.

Southern, P. J. et al., "Transformation of Mammalian Cells to Antibiotic Resistance with a Bacterial Gene Under Control of the SV40 Early Region Promoter", *Journal of Molecular and Applied Genetics* vol. 1, Raven Press 1982.

Spatola, Arno F. et al., "Ch 5: Peptide Backbone Modifications: A Structure—Activity Analysis of Peptides Containing Amide Bond Surrogates, Conformational Constraints, and Rela", *Chemistry and Biochemistry of Amino Acids, Peptides and Proteins*, vol. 7 1983, 267-357.

Spengler, Sylvia J. et al., "The stereostructure of knots and catenanes produced by phage lambda integrative recombination: implications for mechanism and DNA structure", *Cell* vol. 42, Cell Press Aug. 1985, 325-334.

Spinella, Dominic G. et al., "Tandem arrayed ligation of expressed sequence tags (TALEST): a new method for generating global gene expression profiles", *Nucleic Acids Research* vol. 27, No. 18, Oxford University Press 1999, i-viii.

Stammers, D. K. et al., "Rapid purification and characterisation of HIV-1 reverse transciptase and RNaseH engineered to incorporate a C-terminal tripeptide a-tubulin epitope", *FEBS Letters* vol. 283, No. 2, Elsevier Science Publishers B.V. Jun. 1991, 298-302.

Stark, W. M. et al., "Catalysis by site-specific recombinases", vol. 8, No. 12, *Trends in Genetics* Elsevier Science Dec. 1992, 432-439.

Stark, W. M. et al., "Site-specific Recombination by TN3 Resolvase: Topological Changes in the Forward and Reverse Reactions", *Cell* vol. 58, Cell Press Aug. 25, 1989, 779-790.

Stassi, D. L. et al., "Ethyl-substituted erythromycin derivatives produced by directed metabolic engineering", *Proceedings of the National Academy of Sciences (PNAS)* vol. 95 Jun. 1998, 7305-7309.

Stedman's Online Medical Dict., , "http://216.251.232.159/semdweb/internetsomd/ASP/1529936.asp", 27th Edition, Accessed Jul. 19, 2006.

Steinberg, M et al., "Retrovirus-mediated transduction of primary ZAP-70-deficient human T cells results in the selective growth advantage of gene-corrected cells: implications for gene therapy.", *Gene Therapy* vol. 7 2000, 1392-14000.

Stellwagen, Anne E. et al., "Mobile DNA elements: controlling transposition with ATP-dependent molecular switches", *Trends in Biochemical Science* vol. 23 Dec. 1998, 486-490.

Stemple, Derek L. et al., "Isolation of a Stem Cell for Neurons and Glia from the Mammalian Neural Crest", *Cell* vol. 71, Cell Press Dec. 11, 1992, 973-985.

Stenzel, Timothy T. et al., "The Integration Host Factor of *Escherichia coli* Binds to Bent DNA at the Origin of Replication of the Plasmid pSC01", *Cell* vol. 49 Jun. 5, 1987, 709-717.

Sternberg, Nat, "Bacteriophage P1 cloning system for the isolation, amplification, and recovery of DNA fragments as large as 100 kilobase pairs", *Proceedings of the National Academy of Sciences (PNAS)* vol. 87, National Academy of Sciences Jan. 1990, 103-107.

Sternberg, Nat et al., "Bacteriophage P1 cre Gene and its Regulatory Region. Evidence for Multiple Promoters and for Regulation by DNA Methylation", *J. Mol. Biol.* vol. 187 1986, 197-212.

Sternberg, Edward A. et al., "Identification of Upstream and Intragenic Regulatory Elements that Confer Cell-Type-Restricted and Differentiation-Specific Expression on the Muscle Creatine Kinase Gene.", *Molecular and Cellular Biology* vol. 8, No. 7 Jul. 1988, 2896-2909.

Sternberg, N. et al., "Site-specific Recombination and Its Role in the Life Cycle of Bacteriophage P1", *Cold Spring Harbor Symp. Quant. Biol.* vol. 45, Cold Spring Harbor Laboratory Press 1981, 297-309.

Stewart, Sheila A. et al., "Lentivirus-Delivered Stable Gene Silencing by RNAi in Primary Cells", *RNA* vol. 9, No. 4 2003, 493-501.

Stivers, James T. et al., "Stereochemical outcome and kinetic effects of Rp-and Sp-phosphorothioate substitution at the cleavage site of vaccinia type I DNA topoisomerase", *Biochemistry* vol. 39, No. 18, American Chemical Society 2000, 5561-5572.

Stivers, James T. et al., "Vaccinia DNA topoisomerase I: kinetic evidence for general acid-base catalysis and a conformational step", *Biochemistry* vol. 33, No. 51, American Chemical Society 1994, 15449-15458.

Stivers, James T. et al., "Vaccinia DNA topoisomerase I: single-turnover and steady-state kinetic analysis of the DNA strand cleavage and ligation reactions", *Biochemistry* vol. 33, No. 1, American Chemical Society 1994, 327-339.

Stolz, Jurgen et al., "Bacteriophage lambda surface display of a bacterial biotin acceptor domain reveals the minimal peptide size required for biotinylation", *FEBS Letters* vol. 440 1998, 213-217.

Storck, Thorsten et al., "Rapid construction in yeast of complex targeting vectors for gene manipulation in the mouse", *Nucleic Acids Research* vol. 24, No. 22, Oxford University Press 1996, 4594-4596.

Stratagene, "Gene Characterization Kits", *1988 Catalog* 1988, 39.

Strathmann, Michael et al., "Transposon-facilitated DNA sequencing", *Proceedings of the National Academy of Sciences (PNAS)* vol. 88, National Academy of Sciences Feb. 1991, 1247-1250.

Strizhov, N. et al., "Functional analysis of hybrid plasmids carrying genes for lambda site-specific recombination", *Gene* vol. 12 1980, 201-214.

Stryer, Lubert, "The DNA Template Contains Stop Signals for transcription", *Biochemistry*, 2nd ed. W.H. Freeman and Co., San Francisco 1981, 610.

Studier, F. W. et al., "Use of Bacteriophage T7 RNA Polymerase to Direct Selective High-Level Expression of Cloned Genes", *Journal of Molecular Biology* vol. 189 1986, 113-130.

Studier, F. W. et al., "Use of T7 RNA Polymerase to Direct Expression of Cloned Genes", *Methods in Enzymology: Gene Expression Technology* vol. 185, Academic Press, Inc. 1990, 60-89.

Stuurman, Jeroen et al., "Single-site manipulation of tomato chromosomes in vitro and in vivo using Cre-lox site-specific recombination", *Plant Molecular Biology*, vol. 32 Kluwer Academic Publishers May 21, 1996, 901-913.

Sugiura, Shigeki et al., "Minimal Essential Origin of Plasmid pSC101 Replication: Requirement of a Region Downstream of Iterons", *Journal of Bacteriology* vol. 175, No. 18 Sep. 1993, 5993-6001.

Sutcliffe, J. G. et al., "Antibodies That React with Predetermined Sites on Proteins", *Science* vol. 219 1983, 660-666.

Sutcliffe, J. G., "Nucleotide sequence of the ampicillin resistance gene of *Escherichia coli* plasmid pBR322", *Proceedings of the National Academy of Sciences (PNAS)* vol. 75, No. 8, The National Academy of Sciences Aug. 1978, 3737-3741.

Svoboda, Petr et al., "RNAi in mouse oocytes and preimplantation embryos: effectiveness of hairpin dsRNA.", *Biochemical and Biophysical Research Communications* vol. 287 2001, 1099-1104.

Sykes, Kathryn F. et al., "Linear Expression Elements: a rapid, in vivo, method to screen for gene functions.", *Nature Biotechnology* vol. 17 Apr. 1999, 355-359.

Szybalski, Waclaw et al., "Class-IIS Restriction Enzymes—a review", *Gene* vol. 100 1991, 13-26.

Takahashi, Masayo et al., "Rescue from Photoreceptor Degeneration in the rd Mouse by Human Immunodeficiency Virus Vector-Mediated Gene Transfer", *Journal of Virology* vol. 73, No. 9, American Society for Microbiology Sep. 1999, 7812-7816.

Takeuchi, Setsuo et al., "Blasticidin S, A New Antibiotic", *The Journal of Antibiotics* vol. 11, No. 1, Japan Antibiotics Research Association Jan. 1958, 1-5.

Tan, Brenton T. et al., "An Adenovirus-Epstein-Barr Virus Hybrid Vector That Stably Transforms Cultured Cells with High Efficiency", *Journal of Virology* vol. 73, No. 9, American Society for Microbiology Sep. 1999, 7582-7589.

Tawfik, Dan S. et al., "Man-made cell-like compartments for molecular evolution", *Nature Biotechnology* vol. 16 Jul. 1998, 652-656.

Temple, Gary F. et al., "Construction of a functional human suppressor tRNA gene: an approach to gene therapy for beta-thalassaemia.", *Nature* vol. 296, Macmillan Journals Ltd. Apr. 8, 1982, 537-540.

Theilmann, David A. et al., "Molecular Analysis of the trans-Activating IE-2 Gene of Orgyia pseudotsugata Multicapsid Nuclear Polyhedrosis Virus", *Virology* vol. 187, Academic Press, Inc. 1992, 84-96.

Theus, Sue A. et al., "A Simple Assay for Determining the Capping Efficiencies of RNA Polymerases Used for Inv Vitro Transcription", *BioTechniques* vol. 9, No. 5 1990, 610-615.

Thompson, John F. et al., "Cellular Factors Couple Recombination with Growth Phase: Characterization of a New Component in the Lamda Site-Specific Recombination Pathway", *Cell* vol. 50 Sep. 11, 1987, 901-908.

Thompson, Julie D. et al., "Clustal W: improving the sensitivity of progressive multiple sequence alignment through sequence weighting, position-specific gap penalties and weight matrix choice.", *Nucleic Acids Research* vol. 22, No. 22 1994, 4673-4680.

Thompson, John F. et al., "Empirical estimation of protein-induced DNA bending angles: applications to site-specific recombination complexes", *Nucleic Acids Research* vol. 16, No. 20 1988, 9687-9705.

Thompson, Simon et al., "Germ line transmission and expression of a corrected HPRT gene produced by gene targeting in embryonic stem cells", *Cell* vol. 56 Jan. 27, 1989, 313-321.

Thompson, John F. et al., "Helical-repeat dependence of integrative recombination of bacteriophage lambda: Role P1 and H1 protein binding sites", *Proceedings of the National Academy of Sciences (PNAS)* vol. 85 Sep. 1988, 6323-6327.

Thompson, John F. et al., "Mutations in an Integration Host Factor-Binding Site: Effect on Lambda Site-Specific Recombination and Regulatory Implications", *Journal of Bacteriology* vol. 168, No. 3, American Society for Microbiology Dec. 1986, 1343-1351.

Thomson, T. M. et al., "Fusion of the Human Gene for the Polyubiquitination Coeffector UEVI with Kua, a Newly Identified Gene", Nov. 1, 2000, 1743-1756.

Thorpe, Helena M. et al., "In vitro site-specific integration of bacteriophage DNA catalyzed by a recombinase of the resolvase/invertase family", *Proceedings of the National Academy of Sciences (PNAS)* vol. 95, National Academy of Sciences May 1998, 5505-5510.

Tiscornia, Gustavo et al., "A General Method for Gene Knockdown in Mice by Using Lentiviral Vectors Exprerssing Small Interfering RNA", *Proceedings of the National Academy of Sciences (PNAS)* vol. 100, No. 4 Feb. 18, 2003, 1844-1848.

Tolstoshev, Paul, "Gene Therapy, Concepts, Current Trials and Future Directions", *Ann. Rev. Pharmacol. Toxicol.* vol. 32, Annual Reviews Inc. 1993, 573-596.

Traunecker, Andre et al., "Soluble CD4 molecules neutralize human immunodeficiency virus type 1", *Nature* vol. 331 Jan. 7, 1988, 84-86.

Tsien, Roger Y. et al., "Ch 16: Fluorophores for Confocal Microscopy, Photophysics and Photochemistry", *Handbook of Biological Confocal Microscopy* 1990, 169-178.

Tsurushita, Naoya et al., "Phage display vectors for in vivo recombination of immunoglobulin heavy and light chain genes to make large combinatorial libraries", *Gene* vol. 172, Elsevier Science B.V. 1996, 59-63.

Turro, Nicholas J., "Ch 9.1: An Energy-Surface Description of Electronic Energy Transfer and Energy Degradation", *Modern Molecular Photochemistry* Menlo Park: Benjamin/Cummings Publishing Col, Inc 1978, 296-361.

Tymms, M. J., "Methods in Molecular Biology", *In Vitro Transcription and Translation Protocols* 37 1995.

Uetsuki, Taichi et al., "Isolation and Characterization of the Human Chromosomal Gene for Polypeptide Chain Elongation Factor-1alpha", *The Journal of Biological Chemistry* vol. 264, No. 10, The American Society for Biochemistry and Molecular Biology, Inc. Apr. 5, 1989, 5791-5798.

Ulmanen, I et al., "Transcription and Translation of Foreign Genes in *Bacillus subtilis* by the Aid of a Secretion Vector", vol. 162, No. 1, *Journal of Bacteriology* American Society for Microbiology Apr. 1985, 176-182.

Ulmer, Jeffrey B. et al., "Heterologous Protection Against Influenza by Injection of DNA Encoding a Viral Protein", *Science* vol. 259 Mar. 19, 1993, 1745-1749.

Urdea, Mickey S. et al., "Chemical Synthesis of a Gene for Human Epidermal Growth Factor Urogastrone and Its Expression in Yeast", *Proceedings of the National Academy of Sciences (PNAS)* vol. 80 Dec. 1983, 7461-7465.

Valeur, B, "Molecular Fluorescence: Principles and Applications", (*Textbook*) Wiley VCH 2002.

Van Den Berg, Anke et al., "Serial analysis of gene expression: rapid RT-PCR analysis of unknown SAGE tags", *Nucleic Acids Research* vol. 27, No. 17, Oxford University Press 1999, i-iii.

Van Der Putten, Herman et al., "Efficient Insertion of Genes into the Mouse Germ Line Via Retroviral Vectors", *Proceedings of the National Academy of Sciences (PNAS)* vol. 82 Sep. 1985, 6148-6152.

Van Deursen, J. et al., "Cre-mediated site-specific translocation between nonhomologous mouse chromosomes", *Proceedings of the National Academy of Sciences (PNAS)*, vol. 92 National Academy of Sciences Aug. 1995, 7376-7380.

Vanin, Elio F. et al., "Development of High-Titer Retroviral Producer Cell Lines by Using Cre-Mediated Recombination", *Journal of Virology* vol. 71, No. 10 Oct. 1997, 7820-7826.

Various, , "Trends in Biotechnology", (*Textbook*) *Elsevier Science Publishers Ltd.* vol. 11, No. 5, Science Direct May 1993, 155-215.

Venkatesh, T. V. et al., "Ribosomal Protein S1 and NusA Protein Complexed to Recombination protein beta of Phage lambda", *Journal of Bacteriology* vol. 175, No. 6 Mar. 1993, 1844-1846.

Vergunst, Annette C. et al., "Site-specific integration of Agrobacterium T-DNA in *Arabidopsis thaliana* mediated by Cre recombinase", *Nucleic Acids Research* vol. 26 No. 11, Oxford University Press 1998, 2729-2734.

Verma, Sandeep et al., "Modified Oligonucleotides: Synthesis and Strategy for Users", *Annual Rev. Biochem.* vol. 67 1998, 99-134.

Vetter, Dan et al., "Site-specific recombination of yeast 2-um DNA in vitro", *Proceedings of the National Academy of Sciences (PNAS)* vol. 80, National Academy of Sciences Dec. 1983, 7284-7288.

Voss, Stephan D. et al., "The Role of Enhancers in the Regulation of Cell-type-specific Transcriptional Control", *Trends Biochem. Sci.* vol. 11, Elsevier Science Jul. 1986, 287-289.

Voziyanov, Yuri et al., "A general model for site-specific recombination by the integrase family recombinases", *Nucleic Acids Research* vol. 27, No. 4, Oxford University Press 1999, 930-941.

Wagstaff, Mjd et al., "Gene Transfer Using a Disabled Herpes Virus Vector Containing the EMCV IRES allows Multiple Gene Expression In Vitro and In Vivo", *Gene Therapy* vol. 5 1998, 1566-1570.

Walhout, Albertha J., "Gateway Recombinational cloning: Application to the cloning of large numbers of open reading frames or ORFeomes", *Methods in Enzymology* vol. 328, Academic Press 2000, 575-592.

Walhout, Albertha J., "Protein Interaction Mapping in C. elegans Using Proteins Involved in Vulval Development", *Science* vol. 287, American Association for the Advancement of Science Jan. 7, 2000, 116-122.

Walsh, Christopher E. et al., "Gene Therapy for Human Hemoglobinopathies.", *Proceedings of the Society for Experimental Biology and Medicine* vol. 204, No. 3 Dec. 1993, 289-300.

Wang, Q et al., "A packaging cell line for propagation of recombinant adenovirus vectors containing two lethal gene-region deletions", *Gene Therapy* vol. 2, No. 10 1995, 775-783.

Wang, Yibin et al., "Adenovirus technology for gene manipulation and functional studies", *Drug Discovery Today* vol. 5, No. 1, Elsevier Science Ltd. Jan. 2000, 10-16.

Wang, Li K. et al., "Deletions at the carboxyl terminus of vaccinia DNA topoisomerase affect DNA binding and enhance distributivity in DNA relaxation", *Biochemistry* vol. 36, No. 13, American Chemical Society 1997, 3909-3916.

Wang, James C. et al., "DNA Topoisomerases: Why So Many?", *The Journal of Biological Chemistry*; vol. 266 (11); Issue of Apr. 15, 1991, 6659-6662.

Wang, L. K. et al., "Mutational analysis of 26 residues of vaccinia DNA topoisomerase identifies Ser-204 as important for DNA binding and cleavage", *Biochemistry*; vol. 36, No. 26, *American Chemical Society* 1997, 7944-7950.

Wang, Gan et al., "pDUAL: A transposon-based cosmid cloning vector for generating nested deletions and DNA sequencing templates in vivo", *Proceedings of the National Academy of Sciences (PNAS)* vol. 90 Aug. 1993, 7874-7878.

Wang, Y. et al., "Targeted DNA recombination in vivo using an adenovirus carrying the cre recombinase gene", *Proceedings of the National Academy of Sciences (PNAS)* vol. 93 Apr. 1996, 3932-3936.

Ward, Judith M. et al., "Construction and characterisation of a series of multi-copy promoter-probe plasmid vectors for Streptomyces using the aminoglycoside phosphotransferase gene from Tn5 as indicator", vol. 203, *Mol. Gen. Genet.* 1986, 468-478.

Wasserman, Steven A. et al., "The helical repeat of double-stranded DNA varies as a function of catenation and supercoiling", *Nature* vol. 334, No. 4 Aug. 1988, 448-450.

Waterhouse, Peter et al., "Combinatorial infection and in vivo recombination: a strategy for making large phage antibody repertoires", *Nucleic Acids Research* vol. 21, No. 9 1993, 2265-2266.

Waterhouse, P. et al., "Nucleic Acids Research", vol. 21 1993, 2265-2266.

Watson, James D. et al., "Ch 12: Transferring Genes into Mammalian Cells", *Recombinant DNA, 2nd Ed.; W.H. Freeman and Co.* 1992, 213-234.

Weber, Gregorio, "Ch 8: Polarization of the Fluorescence of Solutions", *Fluorescence and Phosphorescence Analysis: Principles and Applications* 1966, 217-240.

Weinberg, D. H. et al., "A cell line that supports the growth of a defective early region 4 deletion mutant of human adenovirus type 2", *Proceedings of the National Academy of Sciences (PNAS)*; vol. 80, The National Academy of Sciences 1983, 5383-5386.

Weisberg, Robert A. et al., "Site-specific Recombination in Phage Lambda", *Lambda II* Hendrix, R.W., et al., eds., Cold Spring Harbor Laboratory, Cold Spring Harbor, NY 1983, 211-250.

Welker, E. et al., "Vectors With Hidden Cloning Sites", *Biochemical and Biophysical Research Communications, Academic Press Inc* Orlando, FL, US vol. 271, No. 2 XP002909410 Jan. 1, 2000, 534-536 Pgs.

Wexler, et al., "A Procedure to Amplify cDNA from dsRNA Templates Using the Polymerase Chain Reaction", Methods in Molecular and Cellular Biology 2 1991, 273-279.

White, S. M., "Lentivirus vectors using human and Simian Immunodeficiency Virus Elements", *Journal of Virology* vol. 73, No. 5 411999, 2832.

Whitney, Mike et al., "A Genome-Wide Functional Assay of Signal Transduction in Living Mammalian Cells", *Nature Biotechnology* vol. 16, Nature America Inc. Dec. 1998, 1329-1333.

Wierzbicki, Anna et al., "A Mutational Analysis of the Bacteriophage P1 Recombinase Cre", *J. Mol. Biol.* vol. 195 1987, 785-794.

Wigler, Michael et al., "Transfer of Purified Herpes Virus Thymidine Kinase Gene to Cultured Mouse Cells", *Cell*; vol. 11, The MIT Press May 1977, 223-232.

Wilbanks, Sigurd M. et al., "Rod structure of a phycoerythrin II-containing phycobilisome", *Journal of Biological Chemistry*, vol. 268, No. 2 Jan. 15, 1993, 1226-1235.

Wilchek, Meir et al., "Introduction to Avidin-Biotin Technology", *Methods in Enzymology*; vol. 184, Academic Press, Inc. 1990, 5-13.

Wild, Jadwiga et al., "A broad-host-range in vivo pop-out and amplification system for generating large quantities of 50- to 100-kb genomic fragments for direct DNA sequencing", *Gene* vol. 179 1996, 181-188.

Wild, J et al., "Targeting and retrofitting pre-existing libraries of transposon insertions with FRT and on V elements for in-vivo generation of large quantities of any genomic fragment 1", Jan. 12, 1998, 55-66.

Wild, Jadwiga et al., "Targeting and retrofitting pre-existing libraries of transposon insertions with FRT and oriV elements for in-vivo generation of large quantities of any genomic fragment", *Gene* vol. 223 1998, 55-66.

Wilmut, et al., "Viable offspring derived from fetal and adult mammalian cells.", *Nature*; vol. 385 1997, 810-813.

Wilson, Tina M. et al., "Cloning and Characterization of Drosophila Topoisomerase IIIβ", *The Journal of Biological Chemistry* vol. 275, No. 3 Jan. 21, 2000, 1533-1540.

Wilson, Geoffrey G., "Organization of restriction-modification systems", *Nucleic Acids Research*, vol. 19 (10), Oxford University Press 1991, 2539-2566.

Wilson, I. A. et al., "The Structure of an Antigenic Determinant in a Protein", *Cell*; vol. 37 1984, 767-778.

Winnacker, E. L., *From Genes to Clones* Paperback, VCH Publishers Aug. 1987, 1-634.

Winoto, Astar et al., "Directional Control of Site-specific Recombintation by Bacteriophage lambda: Evidence that a Binding Site for Int Protein Far from the Crossover Point is Required for Integrative but not Excisive Recombination", *J. Mol. Biol.* vol. 192 1986, 677-680.

Wittman, H. G., "Components of Bacterial Ribosomes", *Ann Rev. Biochem* vol. 51, Annual Reviews, Inc. 1982, 155-183.

Wittmann, H. G., "Architecture of Prokaryotic Ribosomes", *Ann. Rev. Biochem.* vol. 52, Annual Reviews, Inc. 1983, 35-65.

Wittmann, H.G., "Architecture of Prokaryotic Ribosomes", *Ann. Rev. Biochem.* vol. 52, Annual Reviews, Inc. 1983, 35-65.

Wittschieben, John et al., "Mechanism of DNA transesterification by vaccinia topoisomerase: catalytic contributions of essential residues Arg-130, Gly-132, Tyr-136 and Lys-167", *Nucleic Acids Res. 25(15)* Oxford University Press 1997, 3001-3008.

Wittschieben, John et al., "Mutational analysis of vaccinia DNA topoisomerase defines amino acid residues essential for covalent catalysis", *J. Biol. Chem. 269(47)* The American Society for Biochemistry and Molecular Biology, Inc. 1994, 29978-29983.

Wittschieben, et al., "Replacement of the active site tyrosine of vaccinia DNA topoisomerase by glutamate, cysteine or histidine converts the enzyme into a site-specific endonuclease", Nucleic Acids Res., vol. 26, No. 2, Oxford University Press 1998, 490-496.

Wivel, N. A. et al., "Adenovirus Vectors", *The Development of Human Gene Therapy* Friedmann, T., ed., Cold Spring Harbor Laboratory Press, Cold Spring Harbor NY 1999, 87-110.

WO 91/00363, , "English abstract of WO 91/00363 (document AL4)", WPI Accession No. 1991-010244/199102. Dialog File No. 351, Derwent WPI Jan. 10, 1991, 1.

WO2005/054438, , Jun. 16, 2005.

Woodfield, et al., "Vaccinia topoisomerase and Cre recombinase catalyze direct ligation of activated DNA substrates containing a 3'-para-nitrophenyl phosphate ester", *Nucleic Acids Res.* vol. 28, No. 17, Oxford University Press 2000, 3323-3331.

Wright, et al., "High level Expression of Active Human Alpha-1-Antitrypsin in the Milk of Transgenic Sheep", *Biotechnology* vol. 9 Sep. 1991, 830-834.

Wu, George Y. et al., "Delivery systems for gene therapy", *Biotherapy* vol. 3, Kluwer Academic Publishers 1991, 87-95.

Wulff, Birgitte S. et al., "Partial processing of the neuropeptide Y precursor in transfected CHO cells", *FEBS Letters* vol. 261, No. 1 Elsevier Science Publishers BV. Feb. 1990, 101-105.

Xu, Jimin et al., "Fis activates the RpoS-dependent stationary-phase expression of proP in *Escherichia coli*", *Journal of Bacteriology* vol. 177, No. 18 Sep. 1995, 5222-52231.

Xu, Jimin et al., "Identification of genes negatively regulated by Fis: Fis and RpoS comodulate growth-phase-dependent gene expression in *Escherichia coli*", *Journal of Bacteriology* vol. 177, No. 4 Feb. 1995, 938-947.

Yahata, K et al., "Development of high accuracy and high through put production of multi purpose Gateway entry clones. liVery low mutation frequency in constructing 60 entry clones of human full length cDNAs", *Experimental Medicine* vol. 18, No. 19, Abstract available online at <http://biotech.nikkeibp.co.jp/netlink/Ito/gateway/newinfo/contents9.htrnl> Dec. 2000, 1-4.

Yahata, K et al., "Development of high accuracy and high-throughput production method of entry clone of multi-purpose Gateway system. (IV) Improvement ofDNA sequencing method for Gateway entry clones", *Unverified English language abstract* Poster Session of the Annual Meeting of the Japan Society of Molecular Biology, Abstract No. 2P-731 2001, 1.

Yamaguchi, Hideyo et al., "Inhibition of Protein Synthesis by Blasticidin S", *The Journal of Biochemistry* vol. 57, No. 5, The Japanese Biochemical Society 1965, 667-677.

Yang, Shu-Wei et al., "A eukaryotic enzyme that can disjoin dead-end covalent complexes between DNA and type I topoisomerases", *Proceedings of the National Academy of Sciences (PNAS)* vol. 93, No. 21 Oct. 1996, 11534-11539.

Yang, Shu-Wei et al., "Mutant Thermotoga neopolitana DNA polymerase I: altered catalytic properties for non-templated nucleotide addition and incorporation of correct nucleotides", *Nucleic Acids Research* vol. 30, No. 19, Oxford University Press, London Oct. 1, 2002, 4314-4320.

Yang, Wei et al., "Site-specific recombination in plane view", *Structure* vol. 5, No. 11, Cell Press Nov. 15, 1997, 1401-1406.

Yang, Shicheng et al., "Specific Double-Stranded RNA Interference in Undifferentiated Mouse Embryonic Stem Cells", *Molecular and Cellular Biology* vol. 21, No. 22, American Society for Microbiology Nov. 2001, 7807-7816.

Yanisch-Perron, Celeste et al., "Improved M13 phage cloning vectors and host strains: nucleotide sequences of the M13mp18 and pUC19 vectors", *Gene* vol. 33, Science 1985, 103-119.

Yarovinsky, Timur O., "Application of DNA Topoisomerase-Activated Adapters to Riboprobe Synthesis.", *BioTechniques* vol. 28, No. 6 Jun. 2000, 1160-1165.

Yavuzer, U et al., "pWITCH: A Versatile Two-Hybrid Assay Vector for the Production of Epitope/Activation Domain-Tagged Proteins Both in Vitro and in Yeast.", *Gene* vol. 165 1995, 93-96.

Yee, Jiing-Kuan et al., "A general method for the generation of high-titer, pantropic retroviral vectors: Highly efficient infection of primary hepatocytes", *Proceedings of the National Academy of Sciences (PNAS)* vol. 91 Sep. 1994, 9564-9568.

Yee, Jiing-Kuan, "Ch 2: Retroviral Vectors", *The development of Human Gene therapy* Friedmann, T., ed., Code spring Harbor Laboratory Press, Cold Spring harbor, NY 1999, 21-45.

Yee, Jiing-Kuan et al., "Gene expression from transcriptionally disabled retroviral vectors", *Proceedings of the National Academy of Sciences (PNAS)* vol. 84 Aug. 1987, 5197-5201.

Yew, Nelson S. et al., "High and Sustained Transgene Expression in Vivo from Plasmid Vectors Containing a Hybrid Ubiquitin Promoter", *Molecular Therapy* vol. 4, No. 1 Jul. 2001, 75-82.

Yi, Christopher E. et al., "Specific and Potent RNA Interference in Terminally Differentiated Myotubes.", *Journal of Biological Chemistry* vol. 278, No. 2 Jan. 10, 2003, 934-939.

Yon, Jeff et al., "Precise gene fusion by PCR", *Nucleic Acids Research* vol. 17, No. 12 1989, 4895.

Yoon, Young G. et al., "Cre/loxP-mediated in vivo excision of large segments from yeast genome and their amplification based on the 2 .mu.m plasmid-derived system", *Gene* vol. 223, Elsevier Science 1998, 67-76.

Yoon, Heejeong et al., "SSL1, a Suppressor of a HIS4 5'-UTR Stem-loop Mutation, is Essential for Translation Initiation and Affects UV Resistance in Yeast", *Genes and Development* vol. 6, Cold Spring Harbor Laboratory Press 1992, 2463-2477.

York, Dona et al., "Simple and efficient generation in vitro of nested deletions and inversions: Tn5 intramolecular transposition", *Nucleic Acids Research* vol. 26, No. 8 1998, 1927-1933.

Yu, Jenn-Yah et al., "RNA interference by expression of short-interfering RNAs and hairpin RNAs in mammalian cells.", *Proceedings of the National Academy of Sciences (PNAS)* vol. 99, No. 9 Apr. 30, 2002, 6047-6052.

Yu, Sheau-Fung et al., "Self-inactivating retroviral vectors designed for transfer of whole genes into mammalian cells", *Proceedings of the National Academy of Sciences (PNAS)* vol. 83 May 1986, 3194-3198.

Zahra, David G. et al., "Selectable in-vivo recombination to Increase Antibody Library Size-an Improved Phage Display Vector System", *Gene* vol. 227 1999, 49-54.

Zatloukal, K. et al., "Genetic Modification of Cells by Receptor-Mediated Adenovirus-augmented Gene Delivery: A New Approach for Immunotherapy of Cancer", *Verh. Dtsch. Ges. Pathol.* vol. 78 1994, 171-176.

Zechiedrich, E. L. et al., "Topoisomerase IV, not gyrase, decatenates products of site-specific recombination in *Escherichia coli*", *Genes & Development*, vol. 11 Cold Spring Harbor Laboratory Press 1997, 2580-2592.

Zhang, Youming et al., "A new logic for DNA engineering using recombination in *Escherichia coli*", *Nature Genetics* vol. 20 Oct. 1998, 123-128.

Zhang, Youming et al., "A new logic for DNA engineering using recombination in *Escherichia coli*", *Nature Genetics* vol. 20, No. 2, Nature Publishing Company Oct. 1998, 123-128.

Zhang, W-W et al., "Detection of Wild-Type Contamination in a Recombinant Adenoviral Preparation by PCR", *BioTechniques* vol. 18, No. 3 Mar. 1995, 444-447.

Zhang, Hong L. et al., "*Escherichia coli* DNA Topoisomerase III Is a Site-specific DNA Binding Protein That Binds Asymmetrically to Its Cleavage Site.", *The Journal of Biological Chemistry* vol. 270, No. 40, The American Society for Biochemistry and Molecular Biology, Inc. Oct. 6, 1995, 23700-23705.

Zhu, Xu-Dong et al., "Homology requirements for ligation and strand exchange by the FLP recombinase", *The Journal of Biological Chemistry* vol. 270, No. 19, American Society for Biochemistry and Molecular Biology May 12, 1995, 11646-11653.

Zhu, Xuemei et al., "Mouse cone arrestin gene characterization: promoter targets expression to cone photoreceptors", *Febs Letters* vol. 524, No. 1-3 Jul. 31, 2002, 116-122.

Ziauddin, Junaid et al., "Microarrays of Cells Expressing Defined cDNAs", *Nature* vol. 411 May 3, 2001, 107-110.

Zlokarnik, Gregor et al., "Quantitation of Transcription and Clonal Selection of Single Living Cells with B-Lactamase as Reporter", *Science* vol. 279 Jan. 2, 1998, 84-88.

Zou, Hanfa et al., "Affinity membrane chromatography for the analysis and purification of proteins", *Journal of Biochemical and Biophysical Methods* vol. 49, No. 1-3 Oct. 30, 2001, 199-240.

Zufferey, Romain et al., "Self-Inactivating Lentivirus Vector for Safe and Efficient In Vivo Gene Delivery" *Journal of Virology* vol. 72, No. 12 Dec. 1998, 9873-9880.

Zusman, R. et al., "Glass fibers covered with sol-gel glass as a new support for affinity chromatography columns: a review", *Journal of Biochemical and Biophysical Methods* vol. 49 Oct. 2001, 175-187.

Zylka, Mark J. et al., "Optimized Filter Set and Viewing Conditions for the S65T Mutant of GFP in Living Cells", *BioTechniques* vol. 21, No. 2, Eaton Publishing Co. Aug. 1996, 220-226.

U.S. Appl. No. 09/984,239, filed Oct. 29, 2001, Brasch, Michael et al.

Ohara et al., "Directional cDNA library construction assisted by the in vitro recombination reaction", *Nucleic Acids Research*, vol. 29, No. 4, Feb. 2001, e22.

\* cited by examiner

NUCLEIC ACID MOLECULES CONTAINING RECOMBINATION SITES AND METHODS OF USING THE SAME

CROSS REFERENCE TO RELATED APPLICATIONS

The present application claims the benefit of the filing date of U.S. Provisional Application No. 60/525,672, filed Dec. 1, 2003, the disclosure of which is incorporated by reference herein in its entirety.

BACKGROUND OF THE INVENTION

1. Field of the Invention

The present invention relates to the fields of biotechnology and molecular biology. In particular, the present invention relates to the construction and use of nucleic acid molecules comprising cloning sites which differ in nucleotide sequence. In particular embodiments, the present invention relates to nucleic acid molecules which contain recombination sites with different primer binding sites. These different primer binding sites may be used to sequence different ends of nucleic acid segments located between the two recombination sites.

2. Related Art

Site-specific recombinases are proteins that are present in many organisms (e.g. viruses and bacteria) and have been characterized as having both endonuclease and ligase properties. These recombinases (along with associated proteins in some cases) recognize specific sequences of bases in a nucleic acid molecule and exchange the nucleic acid segments flanking those sequences. The recombinases and associated proteins are collectively referred to as "recombination proteins" (see, e.g., Landy, A., *Current Opinion in Biotechnology* 3:699-707 (1993)).

Numerous recombination systems from various organisms have been described. See, e.g., Hoess, et al., *Nucleic Acids Research* 14(6):2287 (1986); Abremski, et al., *J. Biol. Chem.* 261(1):391 (1986); Campbell, *J. Bacteriol.* 174(23):7495 (1992); Qian, et al., *J. Biol. Chem.* 267(11):7794 (1992); Araki, et al., *J. Mol. Biol.* 225(1):25 (1992); Maeser and Kahnmann, *Mol. Gen. Genet.* 230:170-176) (1991); Esposito, et al., *Nucl. Acids Res.* 25(18):3605 (1997). Many of these belong to the integrase family of recombinases (Argos, et al., *EMBO J.* 5:433-440 (1986); Voziyanov, et al., *Nucl. Acids Res.* 27:930 (1999)). Perhaps the best studied of these are the Integrase/att system from bacteriophage ((Landy, A. *Current Opinions in Genetics and Devel.* 3:699-707 (1993)), the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90-109), and the FLP/FRT system from the *Saccharomyces cerevisiae* 2 Φ circle plasmid (Broach, et al., *Cell* 29:227-234 (1982)).

Recombination Sites

Whether the reactions discussed above are termed recombination, transposition or integration and are catalyzed by a recombinase, transposase or integrase, they share the key feature of specific recognition sequences, often termed "recombination sites," on the nucleic acid molecules participating in the reactions. These recombination sites are sections or segments of nucleic acid on the participating nucleic acid molecules that are recognized and bound by the recombination proteins during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence. See FIG. 1 of Sauer, B., *Curr. Opin. Biotech.* 5:521-527 (1994). Other examples of recognition sequences include the attB, attP, attL, and attR sequences which are recognized by the recombination protein (Int. attB is an approximately 25 base pair sequence containing two 9 base pair core-type Int binding sites and a 7 base pair overlap region, while attP is an approximately 240 base pair sequence containing core-type Int binding sites and arm-type Int binding sites as well as sites for auxiliary proteins integration host factor (IHF), FIS and excisionase (Xis). See Landy, *Curr. Opin. Biotech.* 3:699-707 (1993).

Conventional Nucleic Acid Cloning

The cloning of nucleic acid segments currently occurs as a daily routine in many research labs and as a prerequisite step in many genetic analyses. The purposes of these clonings are various, however, two general purposes can be considered: (1) the initial cloning of nucleic acid from large DNA or RNA segments (chromosomes, YACs, PCR fragments, mRNA, etc.), done in a relative handful of known vectors such as pUC, pGem, pBlueScript, and (2) the subcloning of these nucleic acid segments into specialized vectors for functional analysis. A great deal of time and effort is expended both in the transfer of nucleic acid segments from the initial cloning vectors to the more specialized vectors. This transfer is called subcloning.

The basic methods for cloning have been known for many years and have changed little during that time. A typical cloning protocol is as follows:

(1) digest the nucleic acid of interest with one or two restriction enzymes;

(2) gel purify the nucleic acid segment of interest when known;

(3) prepare the vector by cutting with appropriate restriction enzymes, treating with alkaline phosphatase, gel purify etc., as appropriate;

(4) ligate the nucleic acid segment to the vector, with appropriate controls to eliminate background of uncut and self-ligated vector;

(5) introduce the resulting vector into an *E. coli* host cell;

(6) pick selected colonies and grow small cultures overnight;

(7) make nucleic acid minipreps; and (8) analyze the isolated plasmid on agarose gels (often after diagnostic restriction enzyme digestions) or by PCR.

The specialized vectors used for subcloning nucleic acid segments are functionally diverse. These include but are not limited to: vectors for expressing nucleic acid molecules in various organisms; for regulating nucleic acid molecule expression; for providing tags to aid in protein purification or to allow tracking of proteins in cells; for modifying the cloned nucleic acid segment (e.g., generating deletions); for the synthesis of probes (e.g., riboprobes); for the preparation of templates for nucleic acid sequencing; for the identification of protein coding regions; for the fusion of various protein-coding regions; to provide large amounts of the nucleic acid of interest, etc. It is common that a particular investigation will involve subcloning the nucleic acid segment of interest into several different specialized vectors.

As known in the art, simple subclonings can be done in one day (e.g., the nucleic acid segment is not large and the restriction sites are compatible with those of the subcloning vector). However, many other subclonings can take several weeks, especially those involving unknown sequences, long fragments, toxic genes, unsuitable placement of restriction sites, high backgrounds, impure enzymes, etc. One of the most tedious and time consuming type of subcloning involves the sequential addition of several nucleic acid segments to a vector in order to construct a desired clone. One example of this type of cloning is in the construction of gene targeting vectors. Gene targeting vectors typically include two nucleic acid segments, each identical to a portion of the target gene, flanking a selectable marker. In order to construct such a vector, it may be necessary to clone each segment sequentially, i.e., first one gene fragment is inserted into the vector, then the selectable marker and then the second fragment of the target gene. This may require a number of digestion, purification, ligation and isolation steps for each fragment cloned. Subcloning nucleic acid fragments is thus often viewed as a chore to be done as few times as possible.

Several methods for facilitating the cloning of nucleic acid segments have been described, e.g., as in the following references.

Ferguson, J., et al., *Gene* 16:191 (1981), disclose a family of vectors for subcloning fragments of yeast nucleic acids. The vectors encode kanamycin resistance. Clones of longer yeast nucleic acid segments can be partially digested and ligated into the subcloning vectors. If the original cloning vector conveys resistance to ampicillin, no purification is necessary prior to transformation, since the selection will be for kanamycin.

Hashimoto-Gotoh, T., et al., *Gene* 41:125 (1986), disclose a subcloning vector with unique cloning sites within a streptomycin sensitivity gene; in a streptomycin-resistant host, only plasmids with inserts or deletions in the dominant sensitivity gene will survive streptomycin selection.

Notwithstanding the improvements provided by these methods, traditional subclonings using restriction and ligase enzymes are time consuming and relatively unreliable. Considerable labor is expended, and if two or more days later the desired subclone can not be found among the candidate plasmids, the entire process must then be repeated with alternative conditions attempted.

Recombinational Cloning

Cloning systems that utilize recombination at defined recombination sites have been previously described in U.S. Pat. Nos. 5,888,732, 6,143,557, 6,171,861, 6,270,969, and 6,277,608 which are specifically incorporated herein by reference. In brief, the GATEWAY® Cloning System, described in this application and the applications referred to in the related applications section, utilizes vectors that contain at least one and preferably at least two different site-specific recombination sites based on the bacteriophage lambda system (e.g., att1 and att2) that are mutated from the wild type (att0) sites. Each mutated site has a unique specificity for its cognate partner att site of the same type (for example attB1 with attP1, or attL1 with attR1) and will not cross-react with recombination sites of the other mutant type or with the wild-type att0 site. Nucleic acid fragments flanked by recombination sites are cloned and subcloned using the GATEWAY® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

Mutating specific residues in the core region of the att site can generate a large number of different att sites. As with the att1 and att2 sites utilized in GATEWAY®, each additional mutation potentially creates a novel att site with unique specificity that will recombine only with its cognate partner att site bearing the same mutation and will not cross-react with any other mutant or wild-type att site. Novel mutated att sites (e.g., attB 1-10, attP 1-10, attR 1-10 and attL 1-10) are described in previous patent application Ser. No. 60/136,744, filed May 28, 1999 and Ser. No. 09/517,466, filed Mar. 2, 2000, the entire disclosures of which are specifically incorporated herein by reference. Other recombination sites having unique specificity (i.e., a first site will recombine with its corresponding site and will not recombine or not substantially recombine with a second site having a different specificity) may be used to practice the present invention. Examples of suitable recombination sites include, but are not limited to, loxP sites and derivatives such as loxP511 (see U.S. Pat. No. 5,851,808), frt sites and derivatives, dif sites and derivatives, psi sites and derivatives and cer sites and derivatives. The present invention provides novel methods using such recombination sites to join or link multiple nucleic acid molecules or segments and more specifically to clone such multiple segments into one or more vectors containing one or more recombination sites (such as any GATEWAY® Vector including Destination Vectors).

SUMMARY OF THE INVENTION

The present invention relates, in part, to nucleic acids which comprise at least one cloning site. The invention also includes nucleic acids which contain two or more primer binding sites which share sufficient sequence identity such that a single primer (e.g., a sequencing primer, a PCR primer, etc.) will bind to both sites but will only function with respect to one or more functional activity when bound to one of the two or more binding sites. Further, when two primer binding sites are present, one or both of these sites may (1) be contained within a cloning site, (2) encompass all of a cloning site, or (3) encompass only the cloning site and no additional nucleic acid. In some instances, these cloning sites will contain primer binding sites which allow for a primer to bind to one primer binding site but not the other primer binding site. Thus, in particular embodiments, nucleic acid molecules of the invention comprise two cloning sites to which primers having different nucleotide sequences can bind. In many instances, one or more of these cloning sites will be recombination sites.

The invention further includes nucleic acid molecules which contain a single cloning site and methods for using such nucleic acid molecules in molecular cloning processes and other processes which employ primers.

The invention further includes methods for using nucleic acid molecules of the invention for molecular biological processes (e.g., polymerase mediated amplification, molecular cloning, vector construction, etc.), as well as nucleic acid molecules generated by such processes. In particular embodiments, the invention includes nucleic acid molecules in which a nucleic acid segment is flanked by one or more cloning sites. These cloning sites may contain one or more nucleotide sequences to which primers can bind. In particular embodiments, these nucleic acid molecules will contain cloning sites to which different primers can bind. In some embodiments, a single primer will be capable of binding to both primer binding sites but this primer will only function with respect to a particular activity when bound to only one of the two primer binding sites.

The invention further includes compositions, such as reaction mixtures, which contain nucleic acid molecules described herein. These reaction mixtures may contain in addition to one or more nucleic acid molecules of the invention, one or more of the following components: (1) one or more primers (e.g., one or more sequencing primers, one or more PCR primers, etc.), (2) one or more buffers (e.g., Tris-HCl, tri-sodium phosphate, etc.), (3), one or more nucleotides (e.g., ATP, UTP, CTP, GTP, TTP, etc.), (4) one or more enzymes (e.g., one or more polymerases), (5) one or more additional components.

In particular embodiments, the invention includes method for sequencing all or part of a nucleic acid segment comprising:

(a) performing a recombination reaction upon the nucleic acid segment which results in the generation of a product nucleic acid molecule comprising sequencing primer binding sites which flank all or part the nucleic acid segment and allow for sequencing of the nucleic acid segment from either end;

(b) hybridizing the product nucleic acid molecule of (a) with a sequencing primer under conditions which allows for the sequencing primer to hybridize to both of the primer binding sites of the product nucleic acid molecule; and (c) performing a sequencing reaction, wherein the sequencing primer is capable of binding to both primer binding sites but mediates 5' to 3' extension only when bound to one of the two primer binding sites.

In specific embodiment, the recombination reaction of (a) occurs between two nucleic acid molecule which differ in nucleotide sequence. In particular instances, both of the nucleic acid molecules are circular. In other instances, where each of the two nucleic acid molecules contain two recombination sites, the two recombination sites in each individual nucleic acid molecule will often not substantially under go recombination with each other, and each of the two recombination sites in one of the nucleic acid molecules will undergo recombination under suitable conditions with at least one of the recombination sites in the other nucleic acid molecule.

In particular instances, one or more of the recombination sites are selected from the group consisting of: (a) attB sites, (b) attP sites, (c) attL sites, (d) attR sites, (e) lox sites, (f) psi sites, (g) dif sites, (h) cer sites, and (i) frt sites, as well as mutants, variants, and derivatives of the recombination sites of (a), (b), (c), (d), (e), (f), (g), (h) or (i) which, in many instances, retain the ability to undergo recombination.

In many instances, one of the nucleic acid molecules used in methods and/or forming compositions of the invention will contain two attB recombination sites and the other nucleic acid molecule will contain two attP recombination sites. Further, the two sequencing primer binding sites may be located within the attP sites in such embodiments.

In certain instances, the product nucleic acid molecule of (a), referred to above and elsewhere herein, may comprise a nucleic acid segment which is flanked by attL recombination sites. In such instances, as well as in other embodiments of the invention, two sequencing primer binding sites may be located within the attL sites.

When a primer binding site (e.g., a sequencing primer binding site) falls within all or part of an attP recombination site or an attL recombination sites, this primer binding site may encompass all or part of the IHF site (see FIG. 4).

When two primer binding sites are located within the same nucleic acid molecule, these primer binding sites may differ by one, two, three, or four nucleotides. In many instances, when the two sequencing primer binding sites differ by more than one nucleotide, the nucleotides which are different are located adjacent to each other.

Primers used in method and compositions of the invention may be of any length including between 12 to 40, 10 to 60, 15 to 60, 20 to 60, 20 to 40, 25 to 60, 25 to 40, and 35 to 60 nucleotides in length.

In many instances, (for example, when one seeks to determine the nucleotide sequence of all or part of a nucleic acid segment), at least one primer binding site will be located near the nucleic acid segment. When flanking primer binding sites are present on each end of the nucleic acid segment, one or both of these primer binding sites will often be located near the nucleic acid segment. The location of primer binding sites to nucleic acid segments is especially pertinent when one seeks to sequence all or part of these nucleic acid segments. This is so because it is normally desirable to sequence a relatively small number (e.g., 5 to 10) of nucleotides before reaching the nucleic acid segment. The reason this is normally desirable is because nucleotide sequence data can only be determined so many nucleotides away from the primer binding site. On the other hand, it is often advantageous to determine the sequence of at least a short stretch of nucleotides before reaching the nucleic acid segment so that sequence data corresponding to the beginning of the nucleic acid segment can be identified. In many instances, the primer binding site will be located 5 to 100, 10 to 100, 20 to 100, 30 to 100, 40 to 100, 50 to 100, 60 to 100, 70 to 100, 80 to 100, 5 to 80, 10 to 80, 20 to 80, 30 to 80, 40 to 80, 50 to 80, 60 to 80, 70 to 80, 5 to 70, 10 to 70, 20 to 70, 30 to 70, 40 to 70, 50 to 70, 60 to 70, 5 to 60, 10 to 60, 20 to 60, 30 to 60, 40 to 60, 50 to 60, 5 to 50, 10 to 50, 20 to 50, 30 to 50, 40 to 50, 5 to 30, 10 to 30, 20 to 30, 35 to 45, 25 to 55, or 35 to 55 nucleotides from the nucleic acid segment to be sequenced. For example, when topoisomerase (also referred to herein as "TOPO") mediated ligation is used to connect a nucleic acid segment to a cloning site which also contains a primer binding site, the unique primer site or sites will often be within 35 to 45 base pairs of the topoisomerase recognition site. When a cloning site which contains the primer binding site is an attL recombination site, in many instances the primer binding site will be within the attL arms.

The invention also includes methods for sequencing all or part of a nucleic acid segment comprising:

(a) performing a recombination reaction upon the nucleic acid segment which results in the generation of a product nucleic acid molecule comprising sequencing primer binding sites which flank all or part the nucleic acid segment and allow for sequencing of the nucleic acid segment from either end;

(b) contacting a first subportion of the product nucleic acid molecule of (a) with a first sequencing primer under conditions which allows for the first sequencing primer to hybridize to both of the primer binding sites of the product nucleic acid molecule; and (c) performing a sequencing reaction, wherein the first sequencing primer binds to both primer binding sites but mediates 5' to 3' extension only when bound to one of the two binding sites.

In related embodiments, the invention provide methods further comprising, in addition to the above, the steps of:

(e) contacting a second subportion of the product nucleic acid molecule of (a) with a second sequencing primer which under conditions which allow for the second sequencing primer to hybridize to the primer binding sites of the product nucleic acid molecule; and (f) performing a sequencing reaction, wherein the second sequencing primer binds to both primer binding sites but only mediates 5' to 3' extension only when bound to one of the two binding sites and this primer binding site is located at the opposite end of the nucleic acid segment from which the first sequencing primer mediates 5' to 3' extension.

In specific embodiments, first sequencing primer and the second sequencing primer are each between 15 and 45 nucleotides in length. Further, the lengths of the first primer and second primer may be independent of each other. In other words, the first primer may be 32 nucleotides in length and the second primer may be 29 nucleotides in length.

Further, the first sequencing primer and the second sequencing primer may differ in nucleotide sequence from each other by any number of nucleotides (e.g., one, two, three, or four nucleotides).

In particular embodiments, the first sequencing primer and the second sequencing primer may differ in nucleotide sequence at or near (e.g., within 3 nucleotides) their 5' or 3' termini. In many instances, the first primer and second primer will differ in nucleotides sequence in one, two, three, four or five nucleotides at their 3' termini. In particular instances, the difference between the first primer and the second primer will all be localized in the same area (e.g., when the two primers differ by more than one nucleotide, all of the different nucleotides may be adjacent to each other).

In particular methods and compositions of the invention, the first sequencing primer comprises the nucleotide sequence 5' GTTGCAACAAATTGATGAGCAATTA 3' (SEQ ID NO: 1) and second sequencing primer comprises the nucleotide sequence 5' GTTGCAACAAATTGATGAG-CAATGC 3' (SEQ ID NO: 2). The invention further includes nucleic acid molecules which comprise these nucleotide sequences.

The invention also provides composition comprising isolated nucleic acid molecules (e.g., vectors such as plasmids), the nucleic acid molecules comprising:

(a) a first recombination site and a second recombination site, (b) a nucleic acid segment located between the first and second recombination sites, and (c) a primer which is capable of binding to two primer binding sites which differ in nucleotide sequence, wherein one the primer binding sites is located within the first recombination site and the other primer binding site is located within the second recombination site.

In particular instances, the nucleic acid molecule present in these compositions is single stranded except for the primer binding sites where the primer is bound. Further, the two different primer binding sites present in compositions which comprise these nucleic acid molecules may differ in nucleotide sequence from each other by one, two, three, or four nucleotides.

The invention further includes reaction mixtures which comprise compositions of the invention described herein and one or more components selected from the group consisting of:

(a) one or more nucleotide triphosphates,
(b) one of more polymerase,
(c) one or more deoxynucleotide triphosphates, and
(d) at least one dideoxynucleotides triphosphate.

The invention further includes nucleic acid molecules (e.g., isolated nucleic acid molecules) comprising the nucleotide sequence 5' GAAAATATTG 3' (SEQ ID NO: 3). Such nucleic acid molecules may be vectors (e.g., plasmids). One example of such a nucleic acid molecule is the vector pCR2.1 EcoRI/RV, which is represented schematically in FIG. 3. These isolated nucleic acid molecules may be, for example, vectors, such as plasmids.

The invention also include kits for practicing methods of the invention and/or containing compositions of the invention. In certain embodiments, kits of the invention comprise an isolated nucleic acid molecule, the nucleic acid molecule comprising:

(a) a first recombination site and a second recombination site, (b) a nucleic acid segment located between the first and second recombination sites, and (c) a primer which is capable of binding to two primer binding sites which differ in nucleotide sequence, wherein one the primer binding sites is located within the first recombination site and the other primer binding site is located within the second recombination site.

Kits of the invention may also comprise one or more component selected from the group consisting of:

(a) one or more nucleotides (e.g., one or more nucleotide triphosphates such as ATP, CTP, TTP, GTP, UTP, etc.), (b) one of more polymerase, (c) one or more deoxynucleotide (e.g., one or more deoxynucleotide triphosphates,), (d) at least one dideoxynucleotide (e.g., at least one dideoxynucleotide triphosphate), (e) one or more buffers, (f) one or more additional primers or other nucleic acid molecules, and (f) one or more sets of instructions.

These instructions may, for example, describe methods for using kit components in methods described herein (e.g., methods for sequencing nucleic acid segments).

The invention further provides instructions which are separate from kits of the invention. Such instructions may or may not be in printed form. In certain embodiments, the invention provides instructions for performing methods and/or preparing compositions described herein and these instructions are in printed form. In other words, the invention includes compositions comprising printed instructions. These instruction may be in the form, for example, of a booklet or pamphlet. Further, these instruction may provide step-by-step guidance regarding how to perform methods of the invention and/or how to prepare compositions of the invention.

Other embodiments of the invention will be apparent to one of ordinary skill in the art in light of what is known in the art, in light of the following drawings and description of the invention, and in light of the claims.

BRIEF DESCRIPTION OF THE DRAWINGS/FIGURES

FIG. 1 is a schematic representation of a basic recombinational cloning reaction.

FIG. 2 is a schematic representation of nucleic acid molecules of the invention. "CS1" and "CS2" refer to two different cloning sites. "P1" and "P2" refer to primer binding sites, which differ in nucleotide sequence. "NAS" refers to a nucleic acid segment. FIG. 2A: a nucleic acid molecule with two cloning sites and two primer binding sites. FIGS. 2B and 2C: a nucleic acid molecule with one cloning site and two primer binding sites.

FIG. 3 is a schematic representation of pCR2.1 EcoRI/RV. The 711 bp fragment from pDONR221, discussed in the examples below, includes a portion of the coding region of the CAT gene.

FIG. 4 is a representation of the creation of the attP2 mut12 site. A section of the attP2 site is represented by the double stranded sequence. The hatched arrows represent the mutagenic primers used to mutate the GC pairs (underlined) to AT pairs with the arrowheads in the 3' position of the primers. The boxed sequences on the left and right, respectively, contain 11 base pairs of the attB2 sequence found in attP2 and 12 base pairs of the proximal IHF protein binding site. The solid arrow represents the placement of the L-reverse sequencing primer. The top strand is SEQ ID NO:4 shown in the 5' to 3' orientation. The bottom strand is SEQ ID NO: 5 shown in the 3' to 5' orientation.

FIG. 5 shows a vector map of pCR8/GW and particular features of this vector. The vector map of supercoiled pCR8/GW is shown in FIG. 5A. A map of TOPO adapted cloning sites is shown in FIG. 5B. These sites are incorporated into pCR8/GW/TOPO, a vector map of which is shown in FIG. 8. L-forward (GW-1) and L-reverse primers (GW-2) are indicated with the specific base mutations in bold. The TOPO cloning sites are boxed. The top strand is SEQ ID NO: 6 shown in the 5' to 3' orientation. The bottom strand is SEQ ID NO: 7 shown in the 3' to 5' orientation. The nucleotide sequence of the pCR/GW vector is shown in Table 19 (SEQ ID NO: 71). The nucleotide sequence of the pCR8/GW/TOPO vector is shown in Table 20 (SEQ ID NO: 10).

FIG. 6 shows sequencing data obtained using attL primers and pCR8/GW/TOPO. The CAT ORF was amplified with Platinum taq then used in a TOPO cloning reaction with pCR8/GW/TOPO. Miniprep DNA was used for sequencing. A) Sequencing data obtained using the L-forward primer. The sequence shown at the top of the FIG. 6A is SEQ ID NO: 8. B) Sequencing obtained data using L-reverse primer. Shown are the first and the last clearly readable series of bases from each reaction. The sequence shown at the top of FIG. 6B is SEQ ID NO: 9. The EcoRI adaptation sites are underlined and the TOPO cloning sites appear in boxes.

FIG. 7 is a Analysis of Mach I and TOP10 growth rates. A) Culture densities from picked colonies of either Mach I or TOP10 cells containing pENTR vectors with kanamycin (221), ampicillin (223), or spectinomycin (228). B) Normalized culture growth rates of pENTER D-TOPO and pCR8/GW/TOPO in either Mach I or TOP10 cells. C) Normalized culture growth rates of pENTER vectors (kan, amp, or spec) in Mach I or TOP10 cells.

FIG. 8 shows a vector map of pCR8/GW/TOPO and particular features of this vector. The nucleotide sequence of pCR8/GW/TOPO is shown in Table 20 (SEQ ID NO: 10). While the vector map shows this vector in circular form, this vector may be linear. For example, a linear form of this vector may have termini which correspond to nucleotides 683 and 684 in Table 20. Further, the 3' ends of such a linear vector may contain covalently bound topoisomerase proteins.

DETAILED DESCRIPTION OF THE INVENTION

Definitions

Figure 1:
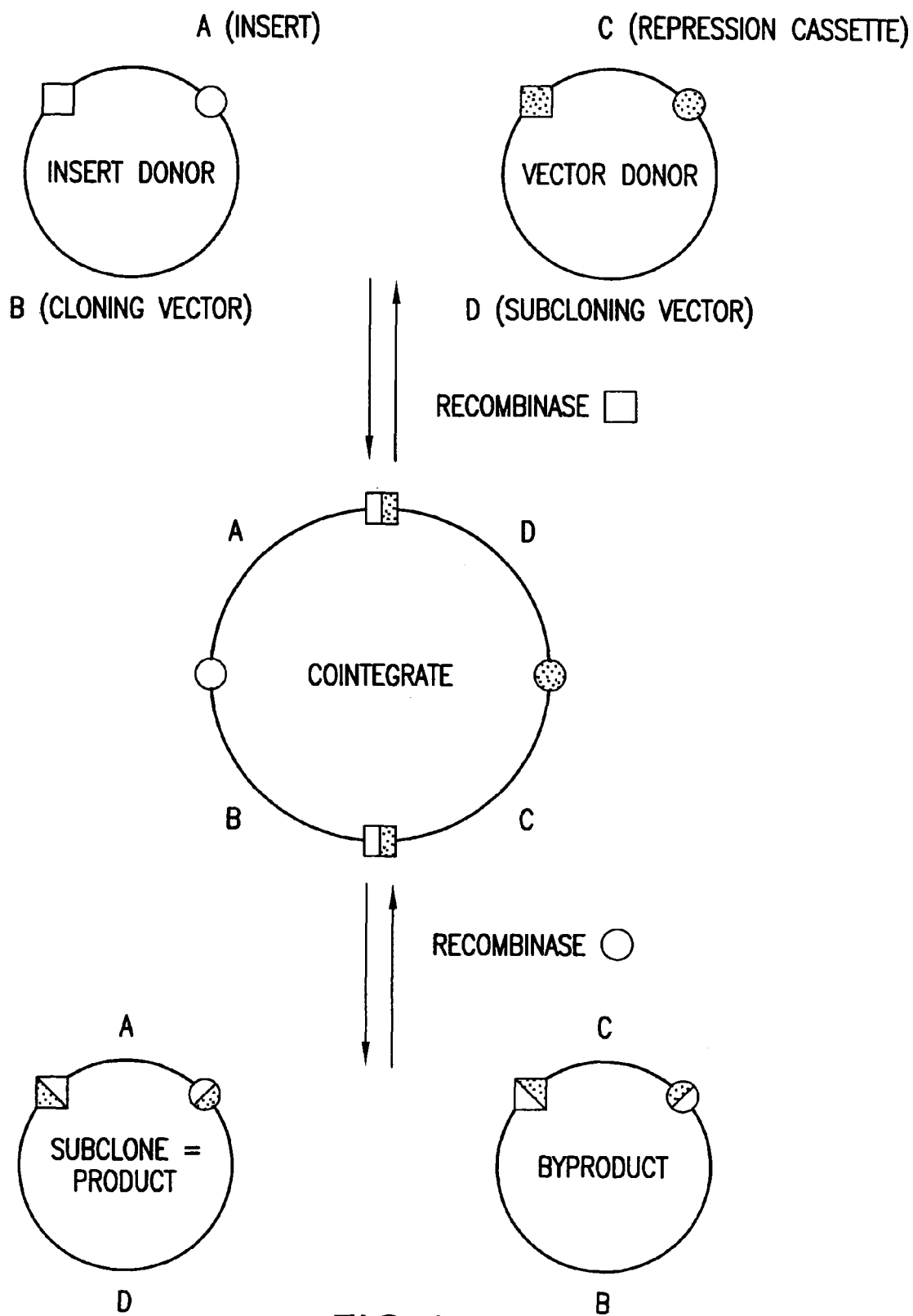

In the description that follows, a number of terms used in recombinant nucleic acid technology are utilized extensively. In order to provide a clear and more consistent understanding of the specification and claims, including the scope to be given such terms, the following definitions are provided.

As used herein, the following is the set of 20 naturally occurring amino acids commonly found in proteins and the one and three letter codes associated with each amino acid:

| Full name | Three-letter Code | One-letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Gene: As used herein, the term "gene" refers to a nucleic acid that contains information necessary for expression of a polypeptide, protein, or untranslated RNA (e.g., rRNA, tRNA, anti-sense RNA). When the gene encodes a protein, it includes the promoter and the structural gene open reading frame sequence (ORF), as well as other sequences involved in expression of the protein. When the gene encodes an untranslated RNA, it includes the promoter and the nucleic acid that encodes the untranslated RNA.

Structural Gene: As used herein, the phrase "structural gene" refers to refers to a nucleic acid that is transcribed into messenger RNA that is then translated into a sequence of amino acids characteristic of a specific polypeptide.

Cloning Site: As used herein, the term "cloning site" refers to a specific location in a nucleic acid molecule which may be used to connect the nucleic acid molecule to another nucleic acid molecule. Examples of cloning sites include restriction endonuclease recognition sites, recombination sites, topoisomerase recognition sites, and, in appropriate instances, and "sticky ends" of nucleic acid molecules (e.g., a 3' terminal thymidine overhang, a 3' terminal adenine overhang, etc.). Cloning sites include multiple cloning sites (MCSs), which include clusters of more than three restriction endonuclease sites within a region of 15 consecutive nucleotides.

Host: As used herein, the term "host" refers to any prokaryotic or eukaryotic (e.g., mammalian, insect, yeast, plant, avian, animal, etc.) organism that is a recipient of a replicable expression vector, cloning vector or any nucleic acid molecule. The nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see Sambrook, et al., Molecular Cloning: A Laboratory Manual, Cold Spring Harbor Laboratory, Cold Spring Harbor, N.Y.

Transcriptional Regulatory Sequence: As used herein, the phrase "transcriptional regulatory sequence" refers to a functional stretch of nucleotides contained on a nucleic acid molecule, in any configuration or geometry, that act to regulate the transcription of (1) one or more structural genes (e.g., two, three, four, five, seven, ten, etc.) into messenger RNA or (2) one or more genes into untranslated RNA. Examples of transcriptional regulatory sequences include, but are not limited to, promoters, enhancers, repressors, operators (e.g., the tet operator), and the like.

Promoter: As used herein, a promoter is an example of a transcriptional regulatory sequence, and is specifically a nucleic acid generally described as the 5'-region of a gene located proximal to the start codon or nucleic acid that encodes untranslated RNA. The transcription of an adjacent nucleic acid segment is initiated at or near the promoter. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Insert Donor: As used herein, the phrase "Insert Donor" refers to one of the two parental nucleic acid molecules (e.g., RNA or DNA) of the present invention that carries an insert (see FIG. 1). The Insert Donor molecule comprises the insert flanked on both sides with recombination sites. The Insert Donor can be linear or circular. In one embodiment of the invention, the Insert Donor is a circular nucleic acid molecule, optionally supercoiled, and further comprises a cloning vector sequence outside of the recombination signals. When a population of inserts or population of nucleic acid segments are used to make the Insert Donor, a population of Insert Donors result and may be used in accordance with the invention.

Insert: As used herein, the term "insert" refers to a desired nucleic acid segment that is a part of a larger nucleic acid molecule. In many instances, the insert will be introduced into the larger nucleic acid molecule. For example, the nucleic acid segments labeled A in FIG. 1, is an insert with respect to the larger nucleic acid molecule (labeled B) shown therein. In most instances, the insert will be flanked by recombination sites, topoisomerase sites and/or other recognition sequences (e.g., at least one recognition sequence will be located at each end). In certain embodiments, however, the insert will only contain a recognition sequence on one end.

Product: As used herein, the term "Product" refers to one the desired daughter molecules comprising the A and D sequences that is produced after the second recombination event during the recombinational cloning process (see FIG. 1). The Product contains the nucleic acid that was to be cloned or subcloned. In accordance with the invention, when a population of Insert Donors are used, the resulting population of Product molecules will contain all or a portion of the population of Inserts of the Insert Donors and often will contain a representative population of the original molecules of the Insert Donors.

Byproduct: As used herein, the term "Byproduct" refers to a daughter molecule (a new clone produced after the second recombination event during the recombinational cloning process) lacking the segment that is desired to be cloned or subcloned.

Cointegrate: As used herein, the term "Cointegrate" refers to at least one recombination intermediate nucleic acid molecule of the present invention that contains both parental (starting) molecules. Cointegrates may be linear or circular. RNA and polypeptides may be expressed from cointegrates using an appropriate host cell strain, for example E. coli DB3.1 (particularly E. coli LIBRARY EFFICIENCY® DB3.1™ Competent Cells), and selecting for both selection markers found on the cointegrate molecule.

Recognition Sequence: As used herein, the phrase "recognition sequence" or "recognition site" refers to a particular sequence to which a protein, chemical compound, DNA, or RNA molecule (e.g., restriction endonuclease, a modification methylase, topoisomerases, or a recombinase) recognizes and binds. In some embodiments of the present invention, a recognition sequence may refer to a recombination site or topoisomerases site. For example, the recognition sequence for Cre recombinase is loxP which is a 34 base pair sequence comprising two 13 base pair inverted repeats (serving as the recombinase binding sites) flanking an 8 base pair core sequence (see FIG. 1 of Sauer, B., Current Opinion in Biotechnology 5:521-527 (1994)). Other examples of recognition sequences are the attB, attP, attL, and attR sequences, which are recognized by the recombinase enzyme λ Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (Xis) (see Landy, Current Opinion in Biotechnology 3:699-707 (1993)). Such sites may also be engineered according to the present invention to enhance production of products in the methods of the invention. For example, when such engineered sites lack the P1 or H1 domains to make the recombination reactions irreversible (e.g., attR or attP), such sites may be designated attR' or attP' to show that the domains of these sites have been modified in some way.

Recombination Proteins: As used herein, the phrase "recombination proteins" includes excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in *Biotechnology* 3:699-707 (1993)), or mutants, derivatives (e.g., fusion proteins containing the recombination protein sequences or fragments thereof), fragments, and variants thereof. Examples of recombination proteins include Cre, Int, IHF, Xis, Flp, Fis, Hin, Gin, ΦC31, Cin, Tn3 resolvase, TndX, XerC, XerD, TnpX, Hjc, SpCCE1, and ParA.

Recombinases: As used herein, the term "recombinases" is used to refer to the protein that catalyzes strand cleavage and re-ligation in a recombination reaction. Site-specific recombinases are proteins that are present in many organisms (e.g., viruses and bacteria) and have been characterized as having both endonuclease and ligase properties. These recombinases (along with associated proteins in some cases) recognize specific sequences of bases in a nucleic acid molecule and exchange the nucleic acid segments flanking those sequences. The recombinases and associated proteins are collectively referred to as "recombination proteins" (see, e.g., Landy, A., Current Opinion in *Biotechnology* 3:699-707 (1993)).

Numerous recombination systems from various organisms have been described. See, e.g., Hoess, et al., *Nucleic Acids Research* 14(6):2287 (1986); Abremski, et al., *J. Biol. Chem.* 261(1):391 (1986); Campbell, *J. Bacteriol.* 174(23):7495 (1992); Qian, et al., *J. Biol. Chem.* 267(11):7794 (1992); Araki, et al., *J. Mol. Biol.* 225(1):25 (1992); Maeser and Kahnmann, *Mol. Gen. Genet.* 230:170-176) (1991); Esposito, et al., *Nucl. Acids Res.* 25(18):3605 (1997). Many of these belong to the integrase family of recombinases (Argos, et al., *EMBO J.* 5:433-440 (1986); Voziyanov, et al., *Nucl. Acids Res.* 27:930 (1999)). Perhaps the best studied of these are the Integrase/att system from bacteriophage λ (Landy, A. Current Opinions in Genetics and Devel. 3:699-707 (1993)), the Cre/loxP system from bacteriophage P1 (Hoess and Abremski (1990) In *Nucleic Acids and Molecular Biology*, vol. 4. Eds.: Eckstein and Lilley, Berlin-Heidelberg:

Springer-Verlag; pp. 90-109), and the FLP/FRT system from the *Saccharomyces cerevisiae* 2µ circle plasmid (Broach, et al., *Cell* 29:227-234 (1982)).

Recombination Site: A used herein, the phrase "recombination site" refers to a recognition sequence on a nucleic acid molecule that participates in an integration/recombination reaction by recombination proteins. Recombination sites are discrete sections or segments of nucleic acid on the participating nucleic acid molecules that are recognized and bound by a site-specific recombination protein during the initial stages of integration or recombination. For example, the recombination site for Cre recombinase is loxP, which is a 34 base pair sequence comprised of two 13 base pair inverted repeats (serving as the recombinase binding sites) flanking an 8 base pair core sequence (see FIG. 1 of Sauer, B., *Curr. Opin. Biotech.* 5:521-527 (1994)). Other examples of recombination sites include the attB, attP, attL, and attR sequences described in U.S. provisional patent applications 60/136,744, filed May 28, 1999, and 60/188,000, filed Mar. 9, 2000, and in co-pending U.S. patent application Ser. Nos. 09/517,466 and 09/732,91—all of which are specifically incorporated herein by reference—and mutants, fragments, variants and derivatives thereof, which are recognized by the recombination protein λ Int and by the auxiliary proteins integration host factor (IHF), FIS and excisionase (Xis) (see Landy, *Curr. Opin. Biotech.* 3:699-707 (1993)).

Recombination sites may be added to molecules by any number of known methods. For example, recombination sites can be added to nucleic acid molecules by blunt end ligation, PCR performed with fully or partially random primers, or inserting the nucleic acid molecules into an vector using a restriction site flanked by recombination sites.

Isolated. As used herein, the term "isolated," when used in reference to a molecule, means that the molecule is in a form other than that in which it exists in nature. In general, an isolated nucleic acid molecule, for example, can be any nucleic acid molecule that is not part of a genome in a cell, or is separated physically from a cell that normally contains the nucleic acid molecule. Of course, a nucleic acid molecule which is integrated into the genome of a cell is "isolated" if the nucleic acid molecule is not naturally found either in that genome or in that particular location in that genome. It should be recognized that various compositions of the invention comprise a mixture of isolated nucleic acid molecules. As such, it will be understood that the term "isolated" only is used in respect to the isolation of the molecule from its natural state, but does not indicate that the molecule is the only constituent present.

Topoisomerase recognition site. As used herein, the term "topoisomerase recognition site" or "topoisomerase site" means a defined nucleotide sequence that is recognized and bound by a site specific topoisomerase. For example, the nucleotide sequence 5'-(C/T)CCTT-3' is a topoisomerase recognition site that is bound specifically by most poxvirus topoisomerases, including *Vaccinia* virus DNA topoisomerase I, which then can cleave the strand after the 3'-most thymidine of the recognition site to produce a nucleotide sequence comprising 5'-(C/T)CCTT-PO4-TOPO, i.e., a complex of the topoisomerase covalently bound to the 3' phosphate through a tyrosine residue in the topoisomerase (see Shuman, *J. Biol. Chem.* 266:11372-11379, 1991; Sekiguchi and Shuman, *Nucl. Acids Res.* 22:5360-5365, 1994; each of which is incorporated herein by reference; see, also, U.S. Pat. No. 5,766,891; PCT/US95/16099; and PCT/US98/12372 also incorporated herein by reference). In comparison, the nucleotide sequence 5'-GCAACTT-3' is the topoisomerase recognition site for type IA *E. coli* topoisomerase III.

Recombinational Cloning: As used herein, the phrase "recombinational cloning" refers to a method, such as that described in U.S. Pat. Nos. 5,888,732; 6,143,557; 6,171,861; 6,270,969; and 6,277,608 (the contents of which are fully incorporated herein by reference), whereby segments of nucleic acid molecules or populations of such molecules are exchanged, inserted, replaced, substituted or modified, in vitro or in vivo. In many instances, the cloning method is an in vitro method.

Cloning systems that utilize recombination at defined recombination sites have been previously described in U.S. Pat. Nos. 5,888,732, 6,143,557, 6,171,861, 6,270,969, and U.S. Pat. No. 6,277,608, and in pending U.S. application Ser. No. 09/517,466 filed Mar. 2, 2000, and in published U.S. application no. 2002 0007051-A1, all assigned to the Invitrogen Corporation, Carlsbad, Calif., the disclosures of which are specifically incorporated herein in their entirety. In brief, the Gateway® Cloning System described in these patents and applications utilizes vectors that contain at least one recombination site to clone desired nucleic acid molecules in vivo or in vitro. In some embodiments, the system utilizes vectors that contain at least two different site-specific recombination sites that may be based on the bacteriophage lambda system (e.g., att1 and att2) that are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

Mutating specific residues in the core region of the att site can generate a large number of different att sites. As with the att1 and att2 sites utilized in Gateway®, each additional mutation potentially creates a novel att site with unique specificity that will recombine only with its cognate partner att site bearing the same mutation and will not cross-react with any other mutant or wild-type att site. Novel mutated att sites (e.g., attB 1-10, attP 1-10, attR 1-10 and attL 1-10) are described in previous patent application Ser. No. 09/517,466, filed Mar. 2, 2000, which is specifically incorporated herein by reference. Other recombination sites having unique specificity (i.e., a first site will recombine with its corresponding site and will not recombine or not substantially recombine with a second site having a different specificity) may be used to practice the present invention. Examples of suitable recombination sites include, but are not limited to, loxP sites; loxP site mutants, variants or derivatives such as loxP511 (see U.S. Pat. No. 5,851,808); frt sites; frt site mutants, variants or derivatives; dif sites; dif site mutants, variants or derivatives; psi sites; psi site mutants, variants or derivatives; cer sites; and cer site mutants, variants or derivatives.

Repression Cassette: As used herein, the phrase "repression cassette" refers to a nucleic acid segment that contains a repressor or a selectable marker present in the subcloning vector.

Selectable Marker: As used herein, the phrase "selectable marker" refers to a nucleic acid segment that allows one to select for or against a molecule (e.g., a replicon) or a cell that contains it and/or permits identification of a cell or organism that contains or does not contain the nucleic acid segment. Frequently, selection and/or identification occur under particular conditions and do not occur under other conditions.

Markers can encode an activity, such as, but not limited to, production of RNA, peptide, or protein, or can provide a binding site for RNA, peptides, proteins, inorganic and organic compounds or compositions and the like. Examples of selectable markers include but are not limited to: (1) nucleic acid segments that encode products that provide resistance against otherwise toxic compounds (e.g., antibiotics); (2) nucleic acid segments that encode products that are otherwise lacking in the recipient cell (e.g., tRNA genes, auxotrophic markers); (3) nucleic acid segments that encode products that suppress the activity of a gene product; (4) nucleic acid segments that encode products that can be readily identified (e.g., phenotypic markers such as β-lactamase, β-galactosidase, green fluorescent protein (GFP), yellow flourescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; and/or (11) nucleic acid segments that encode products that either are toxic (e.g., Diphtheria toxin) or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, etc.).

Selection and/or identification may be accomplished using techniques well known in the art. For example, a selectable marker may confer resistance to an otherwise toxic compound and selection may be accomplished by contacting a population of host cells with the toxic compound under conditions in which only those host cells containing the selectable marker are viable. In another example, a selectable marker may confer sensitivity to an otherwise benign compound and selection may be accomplished by contacting a population of host cells with the benign compound under conditions in which only those host cells that do not contain the selectable marker are viable. A selectable marker may make it possible to identify host cells containing or not containing the marker by selection of appropriate conditions. In one aspect, a selectable marker may enable visual screening of host cells to determine the presence or absence of the marker. For example, a selectable marker may alter the color and/or fluorescence characteristics of a cell containing it. This alteration may occur in the presence of one or more compounds, for example, as a result of an interaction between a polypeptide encoded by the selectable marker and the compound (e.g., an enzymatic reaction using the compound as a substrate). Such alterations in visual characteristics can be used to physically separate the cells containing the selectable marker from those not contain it by, for example, fluorescent activated cell sorting (FACS).

Multiple selectable markers may be simultaneously used to distinguish various populations of cells. For example, a nucleic acid molecule of the invention may have multiple selectable markers, one or more of which may be removed from the nucleic acid molecule by a suitable reaction (e.g., a recombination reaction). After the reaction, the nucleic acid molecules may be introduced into a host cell population and those host cells comprising nucleic acid molecules having all of the selectable markers may be distinguished from host cells comprising nucleic acid molecules in which one or more selectable markers have been removed (e.g., by the recombination reaction). For example, a nucleic acid molecule of the invention may have a blasticidin resistance marker outside a pair of recombination sites and a β-lactamase encoding selectable marker inside the recombination sites. After a recombination reaction and introduction of the reaction mixture into a cell population, cells comprising any nucleic acid molecule can be selected for by contacting the cell population with blasticidin. Those cell comprising a nucleic acid molecule that has undergone a recombination reaction can be distinguished from those containing an unreacted nucleic acid molecules by contacting the cell population with a fluorogenic β-lactamase substrate as described below and observing the fluorescence of the cell population. Optionally, the desired cells can be physically separated from undesirable cells, for example, by FACS.

Selection Scheme: As used herein, the phrase "selection scheme" refers to any method that allows selection, enrichment, or identification of a desired nucleic acid molecules or host cells containing them (in particular Product or Product(s) from a mixture containing an Entry Clone or Vector, a Destination Vector, a Donor Vector, an Expression Clone or Vector, any intermediates (e.g., a Cointegrate or a replicon), and/or Byproducts). In one aspect, selection schemes of the invention rely on one or more selectable markers. The selection schemes of one embodiment have at least two components that are either linked or unlinked during recombinational cloning. One component is a selectable marker. The other component controls the expression in vitro or in vivo of the selectable marker, or survival of the cell (or the nucleic acid molecule, e.g., a replicon) harboring the plasmid carrying the selectable marker. Generally, this controlling element will be a repressor or inducer of the selectable marker, but other means for controlling expression or activity of the selectable marker can be used. Whether a repressor or activator is used will depend on whether the marker is for a positive or negative selection, and the exact arrangement of the various nucleic acid segments, as will be readily apparent to those skilled in the art. In some embodiments, the selection scheme results in selection of, or enrichment for, only one or more desired nucleic acid molecules (such as Products). As defined herein, selecting for a nucleic acid molecule includes (a) selecting or enriching for the presence of the desired nucleic acid molecule (referred to as a "positive selection scheme"), and (b) selecting or enriching against the presence of nucleic acid molecules that are not the desired nucleic acid molecule (referred to as a "negative selection scheme").

In one embodiment, the selection schemes (which can be carried out in reverse) will take one of three forms, which will be discussed in terms of FIG. 1. The first, exemplified herein with a selectable marker and a repressor therefore, selects for molecules having segment D and lacking segment C. The second selects against molecules having segment C and for molecules having segment D. Possible embodiments of the second form would have a nucleic acid segment carrying a gene toxic to cells into which the in vitro reaction products are to be introduced. A toxic gene can be a nucleic acid that is expressed as a toxic gene product (a toxic protein or RNA), or can be toxic in and of itself. (In the latter case, the toxic gene is understood to carry its classical definition of "heritable trait.")

Examples of such toxic gene products are well known in the art, and include, but are not limited to, restriction endonucleases (e.g., DpnI, Nla3, etc.); apoptosis-related genes (e.g., ASK1 or members of the bcl-2/ced-9 family); retroviral genes; including those of the human immunodeficiency virus (HIV); defensins such as NP-1; inverted repeats or paired palindromic nucleic acid sequences; bacteriophage lytic genes such as those from ΦX174 or bacteriophage T4; antibiotic sensitivity genes such as rpsL; antimicrobial sensitivity genes such as pheS; plasmid killer genes' eukaryotic transcriptional vector genes that produce a gene product toxic to bacteria, such as GATA-1; genes that kill hosts in the absence of a suppressing function, e.g., kicB, ccdB, ΦX174 E (Liu, Q., et al., Curr. Biol. 8:1300-1309 (1998)); and other genes that negatively affect replicon stability and/or replication. A toxic gene can alternatively be selectable in vitro, e.g., a restriction site.

Many genes coding for restriction endonucleases operably linked to inducible promoters are known, and may be used in the present invention (see, e.g., U.S. Pat. No. 4,960,707 (DpnI and DpnII); U.S. Pat. Nos. 5,082,784 and 5,192,675 (KpnI); U.S. Pat. No. 5,147,800 (NgoAIII and NgoAI); U.S. Pat. No. 5,179,015 (FspI and HaeIII): U.S. Pat. No. 5,200,333 (HaeII and TaqI); U.S. Pat. No. 5,248,605 (HpaII); U.S. Pat. No. 5,312,746 (ClaI); U.S. Pat. Nos. 5,231,021 and 5,304,480 (XhoI and XhoII); U.S. Pat. No. 5,334,526 (AluI); U.S. Pat. No. 5,470,740 (NsiI); U.S. Pat. No. 5,534,428 (SstI/SacI); U.S. Pat. No. 5,202,248 (NcoI); U.S. Pat. No. 5,139,942 (NdeI); and U.S. Pat. No. 5,098,839 (PacI). (See also Wilson, G. G., Nucl. Acids Res. 19:2539-2566 (1991); and Lunnen, K. D., et al., Gene 74:25-32 (1988)).

In the second form, segment D carries a selectable marker. The toxic gene would eliminate transformants harboring the Vector Donor, Cointegrate, and Byproduct molecules, while the selectable marker can be used to select for cells containing the Product and against cells harboring only the Insert Donor.

The third form selects for cells that have both segments A and D in cis on the same molecule, but not for cells that have both segments in trans on different molecules. This could be embodied by a selectable marker that is split into two inactive fragments, one each on segments A and D.

The fragments are so arranged relative to the recombination sites that when the segments are brought together by the recombination event, they reconstitute a functional selectable marker. For example, the recombinational event can link a promoter with a structural nucleic acid molecule (e.g., a gene), can link two fragments of a structural nucleic acid molecule, or can link nucleic acid molecules that encode a heterodimeric gene product needed for survival, or can link portions of a replicon.

Site-Specific Recombinase: As used herein, the phrase "site-specific recombinase" refers to a type of recombinase that typically has at least the following four activities (or combinations thereof): (1) recognition of specific nucleic acid sequences; (2) cleavage of said sequence or sequences; (3) topoisomerase activity involved in strand exchange; and (4) ligase activity to reseal the cleaved strands of nucleic acid (see Sauer, B., Current Opinions in Biotechnology 5:521-527 (1994)). Conservative site-specific recombination is distinguished from homologous recombination and transposition by a high degree of sequence specificity for both partners. The strand exchange mechanism involves the cleavage and rejoining of specific nucleic acid sequences in the absence of DNA synthesis (Landy, A. (1989) Ann. Rev. Biochem. 58:913-949).

Homologous Recombination: As used herein, the phrase "homologous recombination" refers to the process in which nucleic acid molecules with similar nucleotide sequences associate and exchange nucleotide strands. A nucleotide sequence of a first nucleic acid molecule that is effective for engaging in homologous recombination at a predefined position of a second nucleic acid molecule will therefore have a nucleotide sequence that facilitates the exchange of nucleotide strands between the first nucleic acid molecule and a defined position of the second nucleic acid molecule. Thus, the first nucleic acid will generally have a nucleotide sequence that is sufficiently complementary to a portion of the second nucleic acid molecule to promote nucleotide base pairing. Nucleic acid molecules of the invention may be integrated into host cell genomes by homologous of non-homologous recombination.

Homologous recombination requires homologous sequences in the two recombining partner nucleic acids but does not require any specific sequences. As indicated above, site-specific recombination that occurs, for example, at recombination sites such as att sites, is not considered to be "homologous recombination," as the phrase is used herein.

Vector: As used herein, the term "vector" refers to a nucleic acid molecule (e.g., DNA) that provides a useful biological or biochemical property to an insert. Examples include plasmids, phages, autonomously replicating sequences (ARS), centromeres, and other sequences that are able to replicate or be replicated in vitro or in a host cell, or to convey a desired nucleic acid segment to a desired location within a host cell. A vector can have one or more recognition sites (e.g., two, three, four, five, seven, ten, etc. recombination sites, restriction sites, and/or topoisomerases sites) at which the sequences can be manipulated in a determinable fashion without loss of an essential biological function of the vector, and into which a nucleic acid fragment can be spliced in order to bring about its replication and cloning. Vectors can further provide primer sites (e.g., for PCR), transcriptional and/or translational initiation and/or regulation sites, recombinational signals, replicons, selectable markers, etc. Clearly, methods of inserting a desired nucleic acid fragment that do not require the use of recombination, transpositions or restriction enzymes (such as, but not limited to, uracil N-glycosylase (UDG) cloning of PCR fragments (U.S. Pat. Nos. 5,334,575 and 5,888,795, both of which are entirely incorporated herein by reference), T:A cloning, and the like) can also be applied to clone a fragment into a cloning vector to be used according to the present invention. The cloning vector can further contain one or more selectable markers (e.g., two, three, four, five, seven, ten, etc.) suitable for use in the identification of cells transformed with the cloning vector.

Subcloning Vector: As used herein, the phrase "subcloning vector" refers to a cloning vector comprising a circular or linear nucleic acid molecule that includes, in many instances, an appropriate replicon. In the present invention, the subcloning vector (segment D in FIG. 1) can also contain functional and/or regulatory elements that are desired to be incorporated into the final product to act upon or with the cloned nucleic acid insert (segment A in FIG. 1). The subcloning vector can also contain a selectable marker (e.g., DNA).

Vector Donor: As used herein, the phrase "Vector Donor" refers to one of the two parental nucleic acid molecules (e.g., RNA or DNA) of the present invention that carries the nucleic acid segments comprising the nucleic acid vector that is to become part of the desired Product. The Vector Donor comprises a subcloning vector D (or it can be called the cloning vector if the Insert Donor does not already contain a cloning vector) and a segment C flanked by recombination sites (see FIG. 1). Segments C and/or D can contain elements that contribute to selection for the desired Product daughter molecule, as described above for selection schemes. The recombination signals can be the same or different, and can be acted upon by the same or different recombinases. In addition, the Vector Donor can be linear or circular.

Primer: As used herein, the term "primer" refers to a single stranded or double stranded oligonucleotide which may be extended by covalent bonding of nucleotide monomers during amplification or polymerization of a nucleic acid molecule (e.g., a DNA molecule). In one aspect, the primer may be a sequencing primer (for example, a universal sequencing primer). In another aspect, the primer may comprise a recombination site or portion thereof.

Adapter: As used herein, the term "adapter" refers to an oligonucleotide or nucleic acid fragment or segment (e.g., DNA) that comprises one or more recombination sites and/or topoisomerase site (or portions of such sites) that can be added to a circular or linear Insert Donor molecule as well as to other nucleic acid molecules described herein. When using portions of sites, the missing portion may be provided by the Insert Donor molecule. Such adapters may be added at any location within a circular or linear molecule, although the adapters are typically added at or near one or both termini of a linear molecule. Adapters may be positioned, for example, to be located on both sides (flanking) a particular nucleic acid molecule of interest. In accordance with the invention, adapters may be added to nucleic acid molecules of interest by standard recombinant techniques (e.g., restriction digest and ligation). For example, adapters may be added to a circular molecule by first digesting the molecule with an appropriate restriction enzyme, adding the adapter at the cleavage site and reforming the circular molecule that contains the adapter(s) at the site of cleavage. In other aspects, adapters may be added by homologous recombination, by integration of RNA molecules, and the like. Alternatively, adapters may be ligated directly to one or more terminus or both termini of a linear molecule thereby resulting in linear molecule(s) having adapters at one or both termini. In one aspect of the invention, adapters may be added to a population of linear molecules, (e.g., a cDNA library or genomic DNA that has been cleaved or digested) to form a population of linear molecules containing adapters at one terminus or both termini of all or substantial portion of said population.

Adapter-Primer: As used herein, the phrase "adapter-primer" refers to a primer molecule that comprises one or more recombination sites (or portions of such recombination sites) that can be added to a circular or to a linear nucleic acid molecule described herein. When using portions of recombination sites, the missing portion may be provided by a nucleic acid molecule (e.g., an adapter) of the invention. Such adapter-primers may be added at any location within a circular or linear molecule, although the adapter-primers may be added at or near one or both termini of a linear molecule. Such adapter-primers may be used to add one or more recombination sites or portions thereof to circular or linear nucleic acid molecules in a variety of contexts and by a variety of techniques, including but not limited to amplification (e.g., PCR), ligation (e.g., enzymatic or chemical/synthetic ligation), recombination (e.g., homologous or non-homologous (illegitimate) recombination) and the like.

Template: As used herein, the term "template" refers to a double stranded or single stranded nucleic acid molecule that is to be amplified, synthesized or sequenced. In the case of a double-stranded DNA molecule, denaturation of its strands to form a first and a second strand may be performed before these molecules may be amplified, synthesized or sequenced, or the double stranded molecule may be used directly as a template. For single stranded templates, a primer complementary to at least a portion of the template hybridizes under appropriate conditions and one or more polypeptides having polymerase activity (e.g., two, three, four, five, or seven DNA polymerases and/or reverse transcriptases) may then synthesize a molecule complementary to all or a portion of the template. Alternatively, for double stranded templates, one or more transcriptional regulatory sequences (e.g., two, three, four, five, seven or more promoters) may be used in combination with one or more polymerases to make nucleic acid molecules complementary to all or a portion of the template. The newly synthesized molecule, according to the invention, may be of equal or shorter length compared to the original template. Mismatch incorporation or strand slippage during the synthesis or extension of the newly synthesized molecule may result in one or a number of mismatched base pairs. Thus, the synthesized molecule need not be exactly complementary to the template. Additionally, a population of nucleic acid templates may be used during synthesis or amplification to produce a population of nucleic acid molecules typically representative of the original template population.

Incorporating: As used herein, the term "incorporating" means becoming a part of a nucleic acid (e.g., DNA) molecule or primer.

Amplification: As used herein, the term "amplification" refers to any in vitro method for increasing the number of copies of a nucleic acid molecule with the use of one or more polypeptides having polymerase activity (e.g., one, two, three, four or more nucleic acid polymerases or reverse transcriptases). Nucleic acid amplification results in the incorporation of nucleotides into a DNA and/or RNA molecule or primer thereby forming a new nucleic acid molecule complementary to a template. The formed nucleic acid molecule and its template can be used as templates to synthesize additional nucleic acid molecules. As used herein, one amplification reaction may consist of many rounds of nucleic acid replication. DNA amplification reactions include, for example, polymerase chain reaction (PCR). One PCR reaction may consist of 5 to 100 cycles of denaturation and synthesis of a DNA molecule.

Nucleotide: As used herein, the term "nucleotide" refers to a base-sugar-phosphate combination. Nucleotides are monomeric units of a nucleic acid molecule (DNA and RNA). The term nucleotide includes ribonucleotide triphosphates ATP, UTP, CTG, GTP and deoxyribonucleotide triphosphates such as dATP, dCTP, dITP, dUTP, dGTP, dTTP, or derivatives thereof. Such derivatives include, for example, [α-S]dATP, 7-deaza-dGTP and 7-deaza-dATP. The term nucleotide as used herein also refers to dideoxyribonucleotide triphosphates (ddNTPs) and their derivatives. Illustrated examples of dideoxyribonucleotide triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Nucleic Acid Molecule: As used herein, the phrase "nucleic acid molecule" refers to a sequence of contiguous nucleotides (riboNTPs, dNTPs, ddNTPs, or combinations thereof) of any length. A nucleic acid molecule may encode a full-length polypeptide or a fragment of any length thereof, or may be non-coding. As used herein, the terms "nucleic acid molecule" and "polynucleotide" may be used interchangeably and include both RNA and DNA.

Nucleic Acid Segment: As used herein, the phrase "nucleic acid segment" refers to all or part of a nucleic acid molecule (e.g., RNA or DNA) which is involved in methods of the invention (e.g., is amplified or sequenced). In suitable embodiments, nucleic acid segments will be flanked by primer binding sites. Typically, when primer binding sites are added to a nucleic acid segment, nucleic acid other than the primer binding sites which is added to the nucleic acid segment along with the primer binding sites is not considered to be part of the nucleic acid segment.

Oligonucleotide: As used herein, the term "oligonucleotide" refers to a synthetic or natural molecule comprising a covalently linked sequence of nucleotides that are joined by a phosphodiester bond between the 3' position of the pentose of one nucleotide and the 5' position of the pentose of the adjacent nucleotide.

Polypeptide: As used herein, the term "polypeptide" refers to a sequence of contiguous amino acids of any length. The terms "peptide," "oligopeptide," or "protein" may be used interchangeably herein with the term "polypeptide."

Hybridization: As used herein, the terms "hybridization" and "hybridizing" refer to base pairing of two complementary single-stranded nucleic acid molecules (RNA and/or DNA) to give a double stranded molecule. As used herein, two nucleic acid molecules may hybridize, although the base pairing is not completely complementary. Accordingly, mismatched bases do not prevent hybridization of two nucleic acid molecules provided that appropriate conditions, well known in the art, are used. In some aspects, hybridization is said to be under "stringent conditions." By "stringent conditions," as the phrase is used herein, is meant overnight incubation at 42° C. in a solution comprising: 50% formamide, 5× SSC (750 mM NaCl, 75 m M trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1× SSC at about 65° C.

Derivative: As used herein the term "derivative", when used in reference to a vector, means that the derivative vector contains one or more (e.g., one, two, three, four five, etc.) nucleic acid segments which share sequence similar to at least one vector represented in one or more of FIG. 3, 5, 8, 9 or 10. In particular embodiments, a derivative vector (1) may be obtained by alteration of a vector represented in FIG. 3, 5, 8, 9 or 10, or (2) may contain one or more elements (e.g., ampicillin resistance marker, attL1 recombination site, TOPO site, etc.) of a vector represented in FIG. 3, 5, 8, 9 or 10. Further, as noted above, a derivative vector may contain one or more element which shares sequence similarity (e.g., at least 50%, at least 60%, at least 70%, at least 80%, at least 90%, at least 95%, etc. sequence identity at the nucleotide level) to one or more element of a vector represented in FIG. 3, 5, 8, 9 or 10. Derivative vectors may also share at least at least 50%, at least 60%, at least 70%, at least 80%, at least 90%, at least 95%, etc. sequence identity at the nucleotide level to the complete nucleotide sequence of a vector represented in FIG. 3, 5, 8, 9 or 10. Derivative vectors also include progeny of any of the vectors referred to above, as well as vectors referred to above which have been subjected to mutagenesis (e.g., random mutagenesis). The invention includes the vector shown in FIGS. 3, 5, 8, 9 and 10, as well as derivatives of these vectors. The invention further includes the nucleic acid molecules which contain one or more elements of the vectors shown in FIGS. 3, 5, 8, 9 and 10, as well as nucleic acid molecules which contain (1) elements which shares sequence similarity and/or (2) elements which perform similar functions.

Other terms used in the fields of recombinant nucleic acid technology and molecular and cell biology as used herein will be generally understood by one of ordinary skill in the applicable arts.

Overview

The present invention relates to nucleic acid molecules comprising at least one cloning site. In many instances, these nucleic acid molecules will contain two primer binding sites. The invention also relates to compositions comprising nucleic acid molecules of the invention, polypeptides encoded by such nucleic acid molecules, vectors comprising such nucleic acid molecules and derivatives thereof, and kits comprising such compositions. These invention further relates to methods employing nucleic acid molecules of the invention. Often these methods will employ one or more primers which bind to the nucleic acid molecules. Such methods include methods for amplifying and/or sequencing all of part of a nucleic acid molecule of the invention.

Nucleic Acid Molecules of the Invention

Nucleic acid molecules of the invention include those which are useful for performing two types of processes: molecular cloning processes and/or primer mediated processes. These nucleic acid molecules will often contain at least one cloning site and/or at least one site to which a primer can bind. Typically, primer binding activity will be assessed under particular conditions which will differ with the particular primers used and the nucleotide sequences to which they hybridize.

Figure 2A:
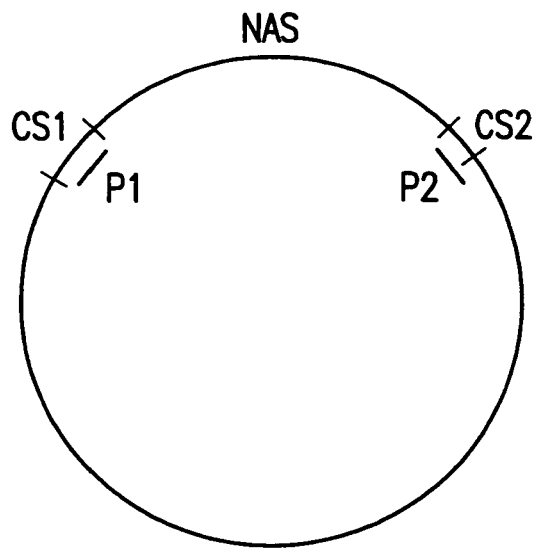

Examples of nucleic acid molecules of the invention are show schematically in FIG. 2. FIG. 2A shows a nucleic acid molecule which contains two cloning sites and two primer binding sites. Located between the two cloning sites is a nucleic acid segment. As an example, a nucleic acid molecule such as that shown in FIG. 2A may be generated by use of the cloning sites to position the nucleic acid segment which is located therein between. Thus, in instances wherein CS1 is a recombination site and CS2 is a TOPO site, the nucleic acid segment located between these sites may have been introduced into the nucleic acid molecule by a combination of recombinational cloning and topoisomerase mediated ligation. Further, the resulting nucleic acid molecule may be used, for example, for sequencing the nucleic acid segment located between the cloning sites from each end of the segment. In other words, a sequencing primer may be annealed to the nucleic acid molecule at the primer binding site P1 and used to sequence one end of the nucleic acid segment. Further, a sequencing primer may be annealed to the nucleic acid molecule at the primer binding site P2 and used to sequence the other end of the nucleic acid segment. Thus, nucleic acid molecules with a structure similar to that shown in FIG. 2A may be used for generating sequence data from both ends of a segment located between the primer binding sites.

Figure 2B:
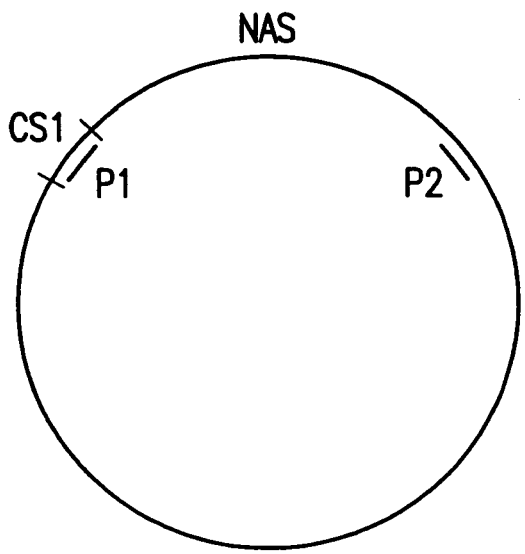
Figure 2C:

FIG. 2B shows a nucleic acid molecule which is similar to that shown in FIG. 2A and contains two primer binding sites but only one cloning site. FIG. 2C shows a linear nucleic acid molecule which may be used to prepare a nucleic acid molecule such as that shown in FIG. 2B. More specifically, the linear nucleic acid molecule shown in FIG. 2C contains a cloning site on one end and primer binding sites on both ends. Assuming for purposes of illustration that the cloning site is a recombination site, the molecule may be circularized, for example, by performing a recombination reaction between CS1 and a cognate recombination site on a separate nucleic acid molecule, which may also be referred to as a nucleic acid segment. This recombination reaction links the two nucleic acid molecules to form a linear nucleic acid molecule comprising both of the original nucleic acid molecules. The new linear nucleic acid molecule may then be circularized by ligating the free ends using, for example, an enzyme such as a ligase, resulting in a circular nucleic acid molecule having the structure shown in FIG. 2B. The nucleic acid molecule shown in FIG. 2B may then be used, for example, to sequence the nucleic acid segment located between the primer binding sites essentially as described above for the nucleic acid molecule shown in FIG. 2A.

As shown in FIG. 2, primer binding sites of nucleic acid molecules of the invention may fall within a cloning site or may encompass all of a cloning site and additional nucleotide sequences. Additionally, these primers binding sites may encompass all of a cloning site and no more or less.

Nucleic acid molecules of the invention include those which contain one or more of the recombination sites referred to herein.

Nucleic acid molecules used in methods of the invention may be prepared by any number of means. As examples, nucleic acid molecules which contain a nucleic acid segment located between two primer binding sites may be prepared by restriction enzyme digestion followed by ligase mediated ligation, recombination, topoisomerase mediated ligation, T/A cloning, or by amplification (e.g., PCR) with primers designed to add primer binding sites to the amplification products. Further, a primer binding site may be added to one end of a nucleic acid segments by one method (e.g., a recombination reaction) and another primer binding site may be added to the other end of the same nucleic acid segment by another method (e.g., topoisomerase mediated ligation)

Primers and Primer Binding Sites

Primers used in the practice of the invention may have any number of characteristics. These characteristics include containing or comprising nucleotide sequences, GC/AT content (e.g., 10%-20%, 10%-30%, 10%-40%, 10%-50%, 10%-60%, 10%-70%, 10%-80%, 20%-30%, 20%-40%, 20%-50% 20%-60%, 20%-70%, 20%-80%, 30%-40%, 30%-50%, 30%-60%, 30%-70% 30%-80%, 40%-50%, 40%-60%, 40%-70%, 40%-80%, 50%-60%, 50%-70% 50%-80%, 60%-70%, 60%-80%, etc. GCs) and length. The characteristics selected for these primers will vary with a number of factors including the application for and conditions under which they are to be used. For example, the sequence of primers used will often directly relate to the sequence of the nucleic acid molecule to which they are intended to hybridize. Further, the GC/AT content and the length of the primers will often directly relate to the stringency of the hybridization conditions used which the primers are to be used. In addition, the stringency of the hybridization conditions used will often relate to the particular methods being performed (e.g., PCR, sequencing, etc.).

In many instances, nucleic acid molecules of the invention will contain two primer binding sites which differ in nucleotide sequence by at least one nucleotide. The nucleotide sequence of these primer binding sites may differ, for example, by 1 to 10, 2 to 10, 3 to 10, 4 to 10, 1 to 8, 1 to 5, 1 to 3, 1 to 2, 2 to 3, 2 to 5, 2 to 8, or 2 to 10 nucleotides. Additionally, these primer binding sites and primers which bind to these sites may vary in length from 10 to 100, 10 to 75, 10 to 60, 10 to 50, 10 to 40, 10 to 30, 10 to 25, 15 to 100, 15 to 75, 15 to 60, 15 to 50, 15 to 40, 15 to 30, 15 to 25, 20 to 100, 20 to 75, 20 to 60, 20 to 50, 20 to 40, 20 to 30, 20 to 25, 30 to 100, 30 to 75, 30 to 60, 30 to 50, or 30 to 40 nucleotides.

Further, when one nucleic acid molecule contains more than one primer binding site, these primer binding sites need not be of the same length. Also, the lengths of the primer binding sites will often be determined, at least in part, by the length of primers designed to hybridize to these sites. In other words, there is a close relationship between what constitutes a primer binding site and the primers which are designed to bind to the site.

In many instances, primers used in the practice of the invention will be able to bind to two primer binding sites located in nucleic acid molecules of the invention but will only function with respect to a particular activity when bound to one of the sites. For example, when a primer binds to a primer binding site and one or more nucleotides on the 3' terminus of the primer do not hybridize, often the primer will not mediate 5' to 3' extension reactions. Examples of such primers and primer binding sites are set out below in Example 1. Thus, in many instances where methods of the invention employ two or more primers, often these primers will differ in nucleotide sequence by one or more nucleotide. Also, in many instances, the location where at least one of the nucleotide difference will be found will often be at or near (e.g., with 3 nucleotides) the 3' terminus of the primers.

Primer binding sites used in conjunction with the invention will often, either encompass or be located within cloning sites. Also, when more than one primer binding site is present in a nucleic acid molecule used in the practice of the invention or comprising a nucleic acid molecule of the invention, in many instances at least one of these primer binding sites encompass or be located within a cloning site. The invention further includes compositions (e.g., reaction mixtures) which contain and methods which employ such nucleic acid molecules.

Further, primer binding sites and cloning sites of the invention may reside, for example, in host cell chromosomes. For example, recombination sites located in a host cell chromosome, and which further contain primer binding sites, may be used to position a nucleic acid segment between the primer binding sites by in vivo recombination. These chromosomes may then be used in methods of the invention. Methods for performing in vivo recombination reactions are described in Droge et al., U.S. Patent Publication 2003/0027337A1, the entire disclosure of which is incorporated herein by reference.

In particular, the invention includes nucleic acid molecules which contain, in addition to the primer binding sites discussed herein, (1) at least one recombination site (e.g., one, two, three or four recombination sites), (2) at least one recombination site and at least one topoisomerase recognition sequence (e.g., one, two, three or four topoisomerase recognition sequences), and (3) at least one recombination site, at least one topoisomerase recognition sequence, and at least one T overhang (e.g., a linear nucleic acid molecule with a single nucleotide T overhang on the 3' termini at each end).

Primers which are suitable for practicing methods of the invention will often be identified by designing such primers which are predicted to function in a particular way and then testing the primers to determine if they function as predicted. Using such methods, primers which have been found to function in sequencing reactions when used in conjunction with a particular vector are set out in Example 1. pDONR223 mut34 mutant vector was created using a method similar to that described in Example 1 employing the phosphorylated primers GCTA3 (5'-AAATG CTTTT TTATA ATGCC AACTT TG-3') (SEQ ID NO: 12) and GCTA4 (5'-ATCAT CAATT TGTTG CAACG AACAG G-3') (SEQ ID NO: 13). However, sequencing reactions using the mut34 sequencing primer (5'-TGTTC GTTGC AACAA ATTGA TGAT-3') (SEQ ID NO: 14) did not yield any legible sequence data. The reason for the failure to obtain legible sequencing using this primer was not determined.

Recombination Sites

Recombination sites for use in the invention may be any nucleic acid that can serve as a substrate in a recombination reaction. Such recombination sites may be wild-type or naturally occurring recombination sites, or modified, variant, derivative, or mutant recombination sites. Examples of recombination sites for use in the invention include, but are not limited to, phage-lambda recombination sites (such as attP, attB, attL, and attR and mutants or derivatives thereof) and recombination sites from other bacteriophages such as phi80, P22, P2, 186, P4 and P1 (including lox sites such as loxP and loxP511).

Recombination proteins and mutant, modified, variant, or derivative recombination sites for use in the invention include those described in U.S. Pat. Nos. 5,888,732, 6,143,557, 6,171,861, 6,270,969, and 6,277,608 and in U.S. application Ser. No. 09/438,358, filed Nov. 12, 1999, which are specifically incorporated herein by reference. Mutated att sites (e.g., attB 1-10, attP 1-10, attR 1-10 and attL 1-10) are described in U.S. application Ser. No. 09/517,466, filed Mar. 2, 2000, and Ser. No. 09/732,914, filed Dec. 11, 2000 (published as US 2002/0007051-A1) the disclosures of which are specifically incorporated herein by reference in their entirety. Other suitable recombination sites and proteins are those associated with the GATEWAY® Cloning Technology systems available from Invitrogen Corporation, Carlsbad, Calif., and are described in the associated product literature (see, e.g., cat. nos. 10835-031, 12537-023, 12535-019, and 12535-027), the entire disclosures of all of which are specifically incorporated herein by reference in their entireties.

Recombination sites that may be used in the present invention include att sites. The 15 bp core region of the wild-type att site (GCTTTTTTAT ACTAA) (SEQ ID NO: 15), which is identical in all wild-type att sites, may be mutated in one or more positions. Engineered att sites that specifically recombine with other engineered att sites can be constructed by altering nucleotides in and near the 7 base pair overlap region, bases 6-12, of the core region. Thus, recombination sites suitable for use in the methods, molecules, compositions, and vectors of the invention include, but are not limited to, those with insertions, deletions or substitutions of one, two, three, four, or more nucleotide bases within the 15 base pair core region (see U.S. Pat. Nos. 5,888,732 and 6,277,608, which describe the core region in further detail, and the disclosures of which are incorporated herein by reference in their entireties). Recombination sites suitable for use in the methods, compositions, and vectors of the invention also include those with insertions, deletions or substitutions of one, two, three, four, or more nucleotide bases within the 15 base pair core region that are at least 50% identical, at least 55% identical, at least 60% identical, at least 65% identical, at least 70% identical, at least 75% identical, at least 80% identical, at least 85% identical, at least 90% identical, or at least 95% identical to this 15 base pair core region.

As a practical matter, whether any particular nucleic acid molecule is at least 50%, 60%, 70%, 75%, 80%, 85%, 90%, 95%, 96%, 97%, 98% or 99% identical to, for instance, a given recombination site nucleotide sequence or portion thereof can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments. Alternatively, such determinations may be accomplished using the BESTFIT program (Wisconsin Sequence Analysis Package, Genetics Computer Group, University Research Park, 575 Science Drive, Madison, Wis. 53711), which employs a local homology algorithm (Smith and Waterman, *Advances in Applied Mathematics* 2: 482-489 (1981)) to find the best segment of homology between two sequences. When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed. Computer programs such as those discussed above may also be used to determine percent identity and homology between two proteins at the amino acid level.

Analogously, the core regions in attB1, attP1, attL1 and attR1 are identical to one another, as are the core regions in attB2, attP2, attL2 and attR2. Nucleic acid molecules suitable for use with the invention also include those comprising insertions, deletions or substitutions of one, two, three, four, or more nucleotides within the seven base pair overlap region (TTTATAC, bases 6-12 in the core region). The overlap region is defined by the cut sites for the integrase protein and is the region where strand exchange takes place. Examples of such mutants, fragments, variants and derivatives include, but are not limited to, nucleic acid molecules in which (1) the thymine at position 1 of the seven bp overlap region has been deleted or substituted with a guanine, cytosine, or adenine; (2) the thymine at position 2 of the seven bp overlap region has been deleted or substituted with a guanine, cytosine, or adenine; (3) the thymine at position 3 of the seven bp overlap region has been deleted or substituted with a guanine, cytosine, or adenine; (4) the adenine at position 4 of the seven bp overlap region has been deleted or substituted with a guanine, cytosine, or thymine; (5) the thymine at position 5 of the seven bp overlap region has been deleted or substituted with a guanine, cytosine, or adenine; (6) the adenine at position 6 of the seven bp overlap region has been deleted or substituted with a guanine, cytosine, or thymine; and (7) the cytosine at position 7 of the seven bp overlap region has been deleted or substituted with a guanine, thymine, or adenine; or any combination of one or more (e.g., two, three, four, five, etc.) such deletions and/or substitutions within this seven bp overlap region. The nucleotide sequences of representative seven base pair core regions are set out below.

Altered att sites have been constructed that demonstrate that (1) substitutions made within the first three positions of the seven base pair overlap (TTTATAC) strongly affect the specificity of recombination, (2) substitutions made in the last four positions (TTTATAC) only partially alter recombination specificity, and (3) nucleotide substitutions outside of the seven bp overlap, but elsewhere within the 15 base pair core region, do not affect specificity of recombination but do influence the efficiency of recombination. Thus, nucleic acid molecules and methods of the invention include those comprising or employing one, two, three, four, five, six, eight, ten, or more recombination sites which affect recombination specificity, particularly one or more (e.g., one, two, three, four, five, six, eight, ten, twenty, thirty, forty, fifty, etc.) different recombination sites that may correspond substantially to the seven base pair overlap within the 15 base pair core region, having one or more mutations that affect recombination specificity. Such molecules may comprise a consensus sequence such as NNNATAC wherein "N" refers to any nucleotide (i.e., may be A, G, T/U or C, or an analogue or derivative thereof). In particular embodiments, if one of the first three nucleotides in the consensus sequence is a T/U, then at least one of the other two of the first three nucleotides is not a T/U.

The core sequence of each att site (attB, attP, attL and attR) can be divided into functional units consisting of integrase binding sites, integrase cleavage sites and sequences that determine specificity. Specificity determinants are defined by the first three positions following the integrase top strand cleavage site. These three positions are shown with underlining in the following reference sequence: CAAC TTTTTTATAC AAAGTTG (SEQ ID NO: 16). Modification of these three positions (64 possible combinations) can be used to generate att sites that recombine with high specificity with other att sites having the same sequence for the first three nucleotides of the seven base pair overlap region. The possible combinations of first three nucleotides of the overlap region are shown in Table 1.

TABLE 1

Modifications of the First Three Nucleotides of the att Site Seven Base Pair Overlap Region that Alter Recombination Specificity.

| AAA | CAA | GAA | TAA |
|---|---|---|---|
| AAC | CAC | GAC | TAC |
| AAG | CAG | GAG | TAG |
| AAT | CAT | GAT | TAT |
| ACA | CCA | GCA | TCA |
| ACC | CCC | GCC | TCC |
| ACG | CCG | GCG | TCG |
| ACT | CCT | GCT | TCT |
| AGA | CGA | GGA | TGA |
| AGC | CGC | GGC | TGC |
| AGG | CGG | GGG | TGG |
| AGT | CGT | GGT | TGT |
| ATA | CTA | GTA | TTA |
| ATC | CTC | GTC | TTC |
| ATG | CTG | GTG | TTG |
| ATT | CTT | GTT | TTT |

Representative examples of seven base pair att site overlap regions suitable for use in methods, compositions and vectors of the invention are shown in Table 2. The invention further includes nucleic acid molecules comprising one or more (e.g., one, two, three, four, five, six, eight, ten, twenty, thirty, forty, fifty, etc.) nucleotides sequences set out in Table 1. Thus, for example, in one aspect, the invention provides nucleic acid molecules comprising the nucleotide sequence GAAATAC, GATATAC, ACAATAC, or TGCATAC.

TABLE 2

Representative Examples of Seven Base Pair att Site Overlap Regions Suitable for use in the recombination sites of the Invention.

| AAAATAC | CAAATAC | GAAATAC | TAAATAC |
|---|---|---|---|
| AACATAC | CACATAC | GACATAC | TACATAC |
| AAGATAC | CAGATAC | GAGATAC | TAGATAC |

TABLE 2-continued

Representative Examples of Seven Base Pair att Site Overlap Regions Suitable for use in the recombination sites of the Invention.

| AATATAC | CATATAC | GATATAC | TATATAC |
|---|---|---|---|
| ACAATAC | CCAATAC | GCAATAC | TCAATAC |
| ACCATAC | CCCATAC | GCCATAC | TCCATAC |
| ACGATAC | CCGATAC | GCGATAC | TCGATAC |
| ACTATAC | CCTATAC | GCTATAC | TCTATAC |
| AGAATAC | CGAATAC | GGAATAC | TGAATAC |
| AGCATAC | CGCATAC | GGCATAC | TGCATAC |
| AGGATAC | CGGATAC | GGGATAC | TGGATAC |
| AGTATAC | CGTATAC | GGTATAC | TGTATAC |
| ATAATAC | CTAATAC | GTAATAC | TTAATAC |
| ATCATAC | CTCATAC | GTCATAC | TTCATAC |
| ATGATAC | CTGATAC | GTGATAC | TTGATAC |
| ATTATAC | CTTATAC | GTTATAC | TTTATAC |

As noted above, alterations of nucleotides located 3' to the three base pair region discussed above can also affect recombination specificity. For example, alterations within the last four positions of the seven base pair overlap can also affect recombination specificity.

For example, mutated att sites that may be used in the practice of the present invention include attB1 (AGCCT-GCTTT TTTGTACAAA CTTGT (SEQ ID NO:17)), attP1 (TACAGGTCAC TAATACCATC TAAGTAGTTG ATTCATAGTG ACTGGATATG TTGTGTTTTA CAGTAT-TATG TAGTCTGTTT TTTATGCAAA ATCTAATTTA ATATATTGAT ATTTATATCA TTTTACGTTT CTCGT-TCAGC TTTTTTGTAC AAAGTTGGCA TTATAAAAAA GCATTGCTCA TCAATTTGTT GCAACGAACA GGT-CACTATC AGTCAAAATA AAATCATTAT TTG (SEQ ID NO: 18)), attL1 (CAAATAATGA TTTTATTTTG ACTGAT-AGTG ACCTGTTCGT TGCAACAAAT TGATAAGCAA TGCTTTTTTA TAATGCCAAC TTTGTACAAA AAAG-CAGGCT (SEQ ID NO: 19)), and attR1 (ACAAGTTTGT ACAAAAAAGC TGAACGAGAA ACGTAAAATG ATATAAATAT CAATATATTA AATTAGATTT TGCAT-AAAAA ACAGACTACA TAATACTGTA AAACACAACA TATCCAGTCA CTATG (SEQ ID NO: 20)). Table 3 provides the sequences of the regions surrounding the core region for the wild type att sites (attB0, P0, R0, and L0) as well as a variety of other suitable recombination sites. Those skilled in the art will appreciated that the remainder of the site may be the same as the corresponding site (B, P, L, or R) listed above.

TABLE 3

Nucleotide sequences of att sites.

| attB0 | AGCCTGCTTT TTTATACTAA CTTGAGC | (SEQ ID NO: 21) |
|---|---|---|
| attP0 | GTTCAGCTTT TTTATACTAA GTTGGCA | (SEQ ID NO: 22) |

TABLE 3-continued

Nucleotide sequences of att sites.

| | | |
|---|---|---|
| attL0 | AGCCTGCTTT TTTATACTAA GTTGGCA | (SEQ ID NO: 23) |
| attR0 | GTTCAGCTTT TTTATACTAA CTTGAGC | (SEQ ID NO: 24) |
| attB1 | AGCCTGCTTT TTTGTACAAA CTTGT | (SEQ ID NO: 25) |
| attP1 | GTTCAGCTTT TTTGTACAAA GTTGGCA | (SEQ ID NO: 26) |
| attL1 | AGCCTGCTTT TTTGTACAAA GTTGGCA | (SEQ ID NO: 27) |
| attR1 | GTTCAGCTTT TTTGTACAAA CTTGT | (SEQ ID NO: 28) |
| attB2 | ACCCAGCTTT CTTGTACAAA GTGGT | (SEQ ID NO: 29) |
| attP2 | GTTCAGCTTT CTTGTACAAA GTTGGCA | (SEQ ID NO: 30) |
| attL2 | ACCCAGCTTT CTTGTACAAA GTTGGCA | (SEQ ID NO: 31) |
| attR2 | GTTCAGCTTT CTTGTACAAA GTGGT | (SEQ ID NO: 32) |
| attB5 | CAACTTTATT ATACAAAGTT GT | (SEQ ID NO: 33) |
| attP5 | GTTCAACTTT ATTATACAAA GTTGGCA | (SEQ ID NO: 34) |
| attL5 | CAACTTTATT ATACAAAGTT GGCA | (SEQ ID NO: 35) |
| attR5 | GTTCAACTTT ATTATACAAA GTTGT | (SEQ ID NO: 36) |
| attB11 | CAACTTTTCT ATACAAAGTT GT | (SEQ ID NO: 37) |
| attP11 | GTTCAACTTT TCTATACAAA GTTGGCA | (SEQ ID NO: 38) |
| attL11 | CAACTTTTCT ATACAAAGTT GGCA | (SEQ ID NO: 39) |
| attR11 | GTTCAACTTT TCTATACAAA GTTGT | (SEQ ID NO: 40) |
| attB17 | CAACTTTTGT ATACAAAGTT GT | (SEQ ID NO: 41) |
| attP17 | GTTCAACTTT TGTATACAAA GTTGGCA | (SEQ ID NO: 42) |
| attL17 | CAACTTTTGT ATACAAAGTT GGCA | (SEQ ID NO: 43) |
| attR17 | GTTCAACTTT TGTATACAAA GTTGT | (SEQ ID NO: 44) |
| attB19 | CAACTTTTTC GTACAAAGTT GT | (SEQ ID NO: 45) |
| attP19 | GTTCAACTTT TTCGTACAAA GTTGGCA | (SEQ ID NO: 46) |
| attL19 | CAACTTTTTC GTACAAAGTT GGCA | (SEQ ID NO: 47) |
| attR19 | GTTCAACTTT TTCGTACAAA GTTGT | (SEQ ID NO: 48) |
| attB20 | CAACTTTTTG GTACAAAGTT GT | (SEQ ID NO: 49) |
| attP20 | GTTCAACTTT TTGGTACAAA GTTGGCA | (SEQ ID NO: 50) |
| attL20 | CAACTTTTTG GTACAAAGTT GGCA | (SEQ ID NO: 51) |
| attR20 | GTTCAACTTT TTGGTACAAA GTTGT | (SEQ ID NO: 52) |
| attB21 | CAACTTTTTA ATACAAAGTT GT | (SEQ ID NO: 53) |
| attP21 | GTTCAACTTT TTAATACAAA GTTGGCA | (SEQ ID NO: 54) |
| attL21 | CAACTTTTTA ATACAAAGTT GGCA | (SEQ ID NO: 55) |
| attR21 | GTTCAACTTT TTAATACAAA GTTGT | (SEQ ID NO: 56) |

Other recombination sites having unique specificity (i.e., a first site will recombine with its corresponding site and will not substantially recombine with a second site having a different specificity) are known to those skilled in the art and may be used to practice the present invention. Corresponding recombination proteins for these systems may be used in accordance with the invention with the indicated recombination sites. Other systems providing recombination sites and recombination proteins for use in the invention include the FLP/FRT system from *Saccharomyces cerevisiae*, the resolvase family (e.g., γδ, TndX, TnpX, Tn3 resolvase, Hin, Hjc, Gin, SpCCE1, ParA, and Cin), and IS231 and other *Bacillus thuringiensis* transposable elements. Other suitable recombination systems for use in the present invention include the XerC and XerD recombinases and the psi, dif and cer recombination sites in *E. coli*. Other suitable recombination sites may be found in U.S. Pat. No. 5,851,808 issued to Elledge and Liu which is specifically incorporated herein by reference.

Recombination Reactions

Those skilled in the art can readily optimize the conditions for conducting the recombination reactions described herein without the use of undue experimentation, based on the guidance provided herein and available in the art (see, e.g., U.S. Pat. Nos. 5,888,732 and 6,277,608, which are specifically incorporated herein by reference in their entireties). In a typical reaction from, about 50 ng to about 1000 ng of a second nucleic acid molecule may be contacted with a first nucleic acid molecule under suitable reaction conditions. Each nucleic acid molecule may be present in a molar ratio of from about 25:1 to about 1:25 first nucleic acid molecule:second nucleic acid molecule. In some embodiments, a first nucleic acid molecule may be present at a molar ratio of from about 10:1 to 1:10 first nucleic acid molecule:second nucleic acid molecule. In one embodiment, each nucleic acid molecule may be present at a molar ratio of about 1:1 first nucleic acid molecule:second nucleic acid molecule.

Typically, the nucleic acid molecules may be dissolved in an aqueous buffer and added to the reaction mixture. One suitable set of conditions is 4 μl CLONASE™ enzyme mixture (e.g., Invitrogen Corporation, Cat. Nos. 11791-019 and 11789-013), 4 μl 5× reaction buffer and nucleic acid and water to a final volume of 20 μl. This will typically result in the inclusion of about 200 ng of Int and about 80 ng of IHF in a 20 μl BP reaction and about 150 ng Int, about 25 ng IHF and about 30 ng Xis in a 20 μl LR reaction.

Proteins for conducting an LR reaction may be stored in a suitable buffer, for example, LR Storage Buffer, which may comprise about 50 mM Tris at about pH 7.5, about 50 mM NaCl, about 0.25 mM EDTA, about 2.5 mM Spermidine, and about 0.2 mg/ml BSA. When stored, proteins for an LR reaction may be stored at a concentration of about 37.5 ng/μl INT, 10 ng/μl IHF and 15 ng/μl XIS. Proteins for conducting a BP reaction may be stored in a suitable buffer, for example, BP Storage Buffer, which may comprise about 25 mM Tris at about pH 7.5, about 22 mM NaCl, about 5 mM EDTA, about 5 mM Spermidine, about 1 mg/ml BSA, and about 0.0025% Triton X-100. When stored, proteins for an BP reaction may be stored at a concentration of about 37.5 ng/μl INT and 20 ng/μl IHF. One skilled in the art will recognize that enzymatic activity may vary in different preparations of enzymes. The amounts suggested above may be modified to adjust for the amount of activity in any specific preparation of enzymes.

A suitable 5× reaction buffer for conducting recombination reactions may comprise 100 mM Tris pH 7.5, 88 mM NaCl, 20 mM EDTA, 20 mM Spermidine, and 4 mg/ml BSA. Thus, in a recombination reaction, the final buffer concentrations may be 20 mM Tris pH 7.5, 17.6 mM NaCl, 4 mM EDTA, 4 mM Spermidine, and 0.8 mg/ml BSA. Those skilled in the art will appreciate that the final reaction mixture may incorporate additional components added with the reagents used to prepare the mixture, for example, a BP reaction may include 0.005% Triton X-100 incorporated from the BP CLONASE™.

In some embodiments, particularly those in which attL sites are to be recombined with attR sites, the final reaction mixture may include about 50 mM Tris HCl, pH 7.5, about 1 mM EDTA, about 1 mg/ml BSA, about 75 mM NaCl and about 7.5 mM spermidine in addition to recombination enzymes and the nucleic acids to be combined. In other embodiments, particularly those in which an attB site is to be recombined with an attP site, the final reaction mixture may include about 25 mM Tris HCl, pH 7.5, about 5 mM EDTA, about 1 mg/ml bovine serum albumin (BSA), about 22 mM NaCl, and about 5 mM spermidine.

In some embodiments, particularly those in which attL sites are to be recombined with attR sites, the final reaction mixture may include about 40 mM Tris HCl, pH 7.5, about 1 mM EDTA, about 1 mg/ml BSA, about 64 mM NaCl and about 8 mM spermidine in addition to recombination enzymes and the nucleic acids to be combined. One of skill in the art will appreciate that the reaction conditions may be varied somewhat without departing from the invention. For example, the pH of the reaction may be varied from about 7.0 to about 8.0; the concentration of buffer may be varied from about 25 mM to about 100 mM; the concentration of EDTA may be varied from about 0.5 mM to about 2 mM; the concentration of NaCl may be varied from about 25 mM to about 150 mM; and the concentration of BSA may be varied from 0.5 mg/ml to about 5 mg/ml. In other embodiments, particularly those in which an attB site is to be recombined with an attP site, the final reaction mixture may include about 25 mM Tris HCl, pH 7.5, about 5 mM EDTA, about 1 mg/ml bovine serum albumin (BSA), about 22 mM NaCl, about 5 mM spermidine and about 0.005% detergent (e.g., Triton X-100).

Topoisomerase Cloning

The present invention also includes methods of using one or more topoisomerases to generate a recombinant nucleic acid molecule from two or more nucleotide sequences. In a first aspect, the invention includes a method for generating a ds recombinant nucleic acid molecule that is covalently linked in one strand. Such a method is directed to linking a first and at least a second nucleotide sequence with at least one (e.g., one, two, three, four, etc.) topoisomerase (e.g., a type IA, type IB, and/or type II topoisomerase) such that one strand, but not both strands, is covalently linked. In a second aspect, the invention includes a method for generating a ds recombinant nucleic acid molecule covalently linked in both strands. Such a method is directed to linking a first and at least a second nucleotide sequence with at least one topoisomerase, such that ligated ends are covalently linked in both strands (i.e., the ds recombinant nucleic acid molecule contain no nicks at the positions where ends were ligated. In a third aspect, the invention includes a method for generating a recombinant nucleic acid molecule covalently linked in one strand, wherein the substrate nucleotide sequences linked according to the method include at least one single stranded nucleotide sequence, which can be covalently linked to a second (or more) single stranded nucleotide sequence or to a nucleic acid molecule. Topoisomerase mediated methods for linking nucleic acids are described, for example, in U.S. Pat. Nos. 5,766,891 and 6,548,277 and U.S. Patent Publications 2003/0022179A1 and 2003/0186233A1, the entire disclosures of which are incorporated herein by reference.

A method for generating a ds recombinant nucleic acid molecule covalently linked in one strand can be performed by contacting a first nucleic acid molecule which has a site-specific topoisomerase recognition site (e.g., a type IA or a type II topoisomerase recognition site), or a cleavage product thereof, at a 5' or 3' terminus, with a second (or other) nucleic acid molecule, and optionally, a topoisomerase (e.g., a type IA, type IB, and/or type II topoisomerase), such that the second nucleotide sequence can be covalently attached to the first nucleotide sequence. Topoisomerase mediated can be performed using any number of nucleotide sequences, typically nucleic acid molecules wherein at least one of the nucleotide sequences has a site-specific topoisomerase recognition site (e.g., a type IA, or type II topoisomerase), or cleavage product thereof, at one or both 5' termini.

A method for generating a ds recombinant nucleic acid molecule covalently linked in both strands can be performed, for example, by contacting a first nucleic acid molecule having a first end and a second end, wherein, at the first end or second end or both, the first nucleic acid molecule has a topoisomerase recognition site (or cleavage product thereof) at or near the 3' terminus; at least a second nucleic acid molecule having a first end and a second end, wherein, at the first end or second end or both, the at least second double stranded nucleotide sequence has a topoisomerase recognition site (or cleavage product thereof) at or near a 3' terminus; and at least one site specific topoisomerase (e.g., a type IA and/or a type IB topoisomerase), under conditions such that all components are in contact and the topoisomerase can effect its activity. A covalently linked ds recombinant nucleic acid generated according to such a method of is characterized, in part, in that it does not contain a nick in either strand at the position where the nucleic acid molecules are joined. In one embodiment, the method may be performed by contacting a first nucleic acid molecule and a second (or other) nucleic acid molecule, each of which has a topoisomerase recognition site, or a cleavage product thereof, at the 3' termini or at the 5' termini of two ends to be covalently linked. In another embodiment, the method may be performed by contacting a first nucleic acid molecule having a topoisomerase recognition site, or cleavage product thereof, at the 5' terminus and the 3' terminus of at least one end, and a second (or other) nucleic acid molecule having a 3' hydroxyl group and a 5' hydroxyl group at the end to be linked to the end of the first nucleic acid molecule containing the recognition sites.

Topoisomerases are categorized as type I, including type IA and type IB topoisomerases, which cleave a single strand of a double stranded nucleic acid molecule, and type II topoisomerases (gyrases), which cleave both strands of a nucleic acid molecule. Type IA and IB topoisomerases cleave one strand of a nucleic acid molecule. Cleavage of a nucleic acid molecule by type IA topoisomerases generates a 5' phosphate and a 3' hydroxyl at the cleavage site, with the type IA topoisomerase covalently binding to the 5' terminus of a cleaved strand. In comparison, cleavage of a nucleic acid molecule by type IB topoisomerases generates a 3' phosphate and a 5' hydroxyl at the cleavage site, with the type IB topoisomerase covalently binding to the 3' terminus of a cleaved strand. As disclosed herein, type I and type II topoisomerases, as well as catalytic domains and mutant forms thereof, are useful for generating ds recombinant nucleic acid molecules covalently linked in both strands according to a method of the invention.

Type IA topoisomerases include *E. coli* topoisomerase I, *E. coli* topoisomerase III, eukaryotic topoisomerase II, archeal reverse gyrase, yeast topoisomerase III, *Drosophila* topoisomerase III, human topoisomerase III, *Streptococcus pneumoniae* topoisomerase III, and the like, including other type IA topoisomerases (see Berger, *Biochim. Biophys. Acta* 1400: 3-18, 1998; DiGate and Marians, *J. Biol. Chem.* 264:17924-17930, 1989; Kim and Wang, *J. Biol. Chem.* 267:17178-17185, 1992; Wilson et al., *J. Biol. Chem.* 275:1533-1540, 2000; Hanai et al., *Proc. Natl. Acad. Sci., USA* 93:3653-3657, 1996, U.S. Pat. No. 6,277,620, each of which is incorporated herein by reference). *E. coli* topoisomerase III, which is a type IA topoisomerase that recognizes, binds to and cleaves the sequence 5'-GCAACTT-3', can be particularly useful in a method of the invention (Zhang et al., *J. Biol. Chem.* 270: 23700-23705, 1995, which is incorporated herein by reference). A homolog, the traE protein of plasmid RP4, has been described by Li et al., *J. Biol. Chem.* 272:19582-19587 (1997) and can also be used in the practice of the invention. A DNA-protein adduct is formed with the enzyme covalently binding to the 5'-thymidine residue, with cleavage occurring between the two thymidine residues.

Type IB topoisomerases include the nuclear type I topoisomerases present in all eukaryotic cells and those encoded by *vaccinia* and other cellular poxviruses (see Cheng et al., *Cell* 92:841-850, 1998, which is incorporated herein by reference). The eukaryotic type IB topoisomerases are exemplified by those expressed in yeast, *Drosophila* and mammalian cells, including human cells (see Caron and Wang, *Adv. Pharmacol.* 29B,:271-297, 1994; Gupta et al., *Biochim. Biophys. Acta* 1262:1-14, 1995, each of which is incorporated herein by reference; see, also, Berger, supra, 1998). Viral type IB topoisomerases are exemplified by those produced by the vertebrate poxviruses (*vaccinia*, Shope fibroma virus, ORF virus, fowlpox virus, and molluscum contagiosum virus), and the insect poxvirus (*Amsacta moorei* entomopoxvirus) (see Shuman, *Biochim. Biophys. Acta* 1400:321-337, 1998; Petersen et al., *Virology* 230:197-206, 1997; Shuman and Prescott, *Proc. Natl. Acad. Sci., USA* 84:7478-7482, 1987; Shuman, *J. Biol. Chem.* 269:32678-32684, 1994; U.S. Pat. No. 5,766,891; PCT/US95/16099; PCT/US98/12372, each of which is incorporated herein by reference; see, also, Cheng et al., supra, 1998).

Type II topoisomerases include, for example, bacterial gyrase, bacterial DNA topoisomerase IV, eukaryotic DNA topoisomerase II, and T-even phage encoded DNA topoisomerases (Roca and Wang, *Cell* 71:833-840, 1992; Wang, *J. Biol. Chem.* 266:6659-6662, 1991, each of which is incorporated herein by reference; Berger, supra, 1998;). Like the type IB topoisomerases, the type II topoisomerases have both cleaving and ligating activities. In addition, like type IB topoisomerase, substrate nucleic acid molecules can be prepared such that the type II topoisomerase can form a covalent linkage to one strand at a cleavage site. For example, calf thymus type II topoisomerase can cleave a substrate nucleic acid molecule containing a 5' recessed topoisomerase recognition site positioned three nucleotides from the 5' end, resulting in dissociation of the three nucleotide sequence 5' to the cleavage site and covalent binding the of the topoisomerase to the 5' terminus of the nucleic acid molecule (Andersen et al., supra, 1991). Furthermore, upon contacting such a type II topoisomerase charged nucleic acid molecule with a second nucleotide sequence containing a 3' hydroxyl group, the type II topoisomerase can ligate the sequences together, and then is released from the recombinant nucleic acid molecule. As such, type II topoisomerases also are useful for performing methods of the invention.

Structural analysis of topoisomerases indicates that the members of each particular topoisomerase families, including type IA, type IB and type II topoisomerases, share common structural features with other members of the family (Berger, supra, 1998). In addition, sequence analysis of various type IB topoisomerases indicates that the structures are highly conserved, particularly in the catalytic domain (Shuman, supra, 1998; Cheng et al., supra, 1998; Petersen et al., supra, 1997). For example, a domain comprising amino acids 81 to 314 of the 314 amino acid *vaccinia* topoisomerase shares substantial homology with other type IB topoisomerases, and the isolated domain has essentially the same activity as the full length topoisomerase, although the isolated domain has a slower turnover rate and lower binding affinity to the recognition site (see Shuman, supra, 1998; Cheng et al., supra, 1998). In addition, a mutant *vaccinia* topoisomerase, which is mutated in the amino terminal domain (at amino acid residues 70 and 72) displays identical properties as the full length topoisomerase (Cheng et al., supra, 1998). In fact, mutation analysis of *vaccinia* type IB topoisomerase reveals a large number of amino acid residues that can be mutated without affecting the activity of the topoisomerase, and has identified several amino acids that are required for activity (Shuman, supra, 1998). In view of the high homology shared among the *vaccinia* topoisomerase catalytic domain and the other type IB topoisomerases, and the detailed mutation analysis of *vaccinia* topoisomerase, it will be recognized that isolated catalytic domains of the type IB topoisomerases and type IB topoisomerases having various amino acid mutations can be used in the methods of the invention.

The various topoisomerases exhibit a range of sequence specificity. For example, type II topoisomerases can bind to a variety of sequences, but cleave at a highly specific recognition site (see Andersen et al., *J. Biol. Chem.* 266:9203-9210, 1991, which is incorporated herein by reference.). In comparison, the type IB topoisomerases include site specific topoisomerases, which bind to and cleave a specific nucleotide sequence ("topoisomerase recognition site"). Upon cleavage of a nucleic acid molecule by a topoisomerase, for example, a type IB topoisomerase, the energy of the phosphodiester bond is conserved via the formation of a phosphotyrosyl linkage between a specific tyrosine residue in the topoisomerase and the 3' nucleotide of the topoisomerase recognition site. Where the topoisomerase cleavage site is near the 3' terminus of the nucleic acid molecule, the downstream sequence (3' to the cleavage site) can dissociate, leaving a nucleic acid molecule having the topoisomerase covalently bound to the newly generated 3' end.

A method for generating a ds recombinant nucleic acid molecule covalently linked in one strand, can be performed by contacting 1) a first nucleic acid molecule having a first end and a second end, wherein the first nucleic acid molecule has a site-specific topoisomerase recognition site (e.g., a type IA or a type II topoisomerase recognition site) at or near the 5' terminus of the first end or the second end or both and, optionally, comprising one or more recombination sites; 2) at least a second nucleic acid molecule that has, or can be made to have, a first end and a second end; and 3) at least one (e.g., 1, 2, 3, 4, 5, 6, 7, 8, 9, 10, etc.) site-specific topoisomerase (e.g., a type IA or a type IB topoisomerase), under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a nucleic acid molecule, the topoisomerase preferably is stably bound to the 5' terminus. Upon cleavage by the topoisomerase, the cleaved nucleic acid molecule often may comprise a 3' overhanging sequence. Once nucleic acid molecules are joined by the methods described above, the resulting molecules may then be used in recombination reactions, such as those described elsewhere herein.

A method for generating a ds recombinant nucleic acid molecule covalently linked in one strand can be performed such that any combination of ends are linked, and wherein one strand at the ends being linked is covalently linked and the other strand is not covalently linked, but contains a nick. For example, the first nucleic acid molecule can comprise a coding sequence, wherein the ATG start codon is at or near the first end and a poly A signal is encoded at or near the second end; and a second nucleic acid molecule can comprise a promoter element, which functions when positioned upstream of a coding sequence, and the first end is upstream of the second end, the method can be performed wherein a site-specific topoisomerase recognition site (e.g., a type IA or a type II topoisomerase recognition site) is at or near the 5' terminus of the first end of the first nucleic acid molecule, and wherein the contacting is performed under conditions such that the topoisomerase (e.g., a type IA or a type II topoisomerase) can covalently link the 5' terminus of the first end of the first nucleic acid molecule to the 3' terminus of the first end of the second nucleic acid molecule, thereby generating a ds recombinant nucleic acid molecule, in which a polypeptide can be expressed from the coding sequence. Alternatively, the method can be performed wherein the topoisomerase recognition site (e.g., a type IA or a type II topoisomerase recognition site) is at or near the 5' terminus of the second end of the first nucleic acid molecule, and wherein the contacting is performed under conditions such that the topoisomerase (e.g., a type IA or a type II topoisomerase recognition site) can covalently link the 5' terminus of the second end of the first nucleic acid molecule to the 3' terminus of the first end of the second nucleic acid molecule, thereby generating a ds recombinant nucleic acid molecule from which an antisense molecule can be expressed. Once nucleic acid molecules are joined by the methods described above, the resulting molecules may then be used in recombination reactions, such as those described elsewhere herein.

As another example using the first nucleic acid molecule and second nucleic acid molecule described above, the method can be performed, wherein the topoisomerase recognition site (e.g., a type IA or a type II topoisomerase recognition site) is at or near the 5' terminus of each of the first end and the second end of the first nucleic acid molecule, and wherein the contacting is performed under conditions such that the type IA topoisomerase can covalently link the 5' terminus of the first end of the first nucleic acid molecule to the 3' terminus of the first end of the second nucleic acid molecule, and the 5' terminus of the second end of the first nucleic acid molecule to the 3' terminus of the second end of the second nucleic acid molecule. As such, the ds recombinant nucleic acid molecule generated by the method is circularized, and includes a nick in each strand opposite the location where a strand was covalently linked by a topoisomerase (e.g., a type IA or a type II topoisomerase). Furthermore, the promoter of the second nucleic acid molecule can initiate expression of the first nucleic acid molecule. In one embodiment, the circularized ds recombinant nucleic acid molecule comprises a vector. Once nucleic acid molecules are joined by the methods described above, the resulting molecules may then be used in recombination reactions, such as those described elsewhere herein.

As another example using the first nucleic acid molecule and second nucleic acid molecule described above, the method can be performed, wherein the topoisomerase recognition site (e.g., a type IA or a type II topoisomerase recognition site) is at or near the 5' terminus of each of the first end and the second end of the first nucleic acid molecule, and wherein the contacting is performed under conditions such that the topoisomerase (e.g., a type IA or a type II topoisomerase) can covalently link the 5' terminus of the first end of the first nucleic acid molecule to the 3' terminus of the second end of the second nucleic acid molecule, and the 5' terminus of the second end of the first nucleic acid molecule to the 3' terminus of the first end of the second nucleic acid molecule. As such, the ds recombinant nucleic acid molecule generated by the method is circularized, and includes a nick in each strand opposite the location where a strand was covalently linked by topoisomerase (e.g., a type IA or a type II topoisomerase recognition site). Furthermore, the promoter of the second nucleic acid molecule can initiate expression of an antisense sequence. In one embodiment, the circularized ds recombinant nucleic acid molecule comprises a vector. Once nucleic acid molecules are joined by the methods described above, the resulting molecules may then be used in recombination reactions, such as those described elsewhere herein.

A method of generating a ds recombinant nucleic acid molecule covalently linked in one strand also can be performed by contacting 1) a first nucleic acid molecule having a first end and a second end, wherein the first nucleic acid molecule has a site-specific topoisomerase recognition site (e.g., a type IA or a type II topoisomerase recognition site) at or near the 5' terminus of the first end or the second end or both; 2) at least a second nucleic acid molecule that has, or can be made to have, a first end and a second end; 3) at least a third nucleic acid molecule which has, or can be made to have, a first end and a second end, each end further comprising a 5' terminus and a 3' terminus; and 4) at least one (e.g., 1, 2, 3, 4, 5, 6, 7, 8, 9, 10, etc.) site-specific topoisomerase (e.g., a type IA or a type II topoisomerase), under conditions such that all components are in contact and the at least one topoisomerase can effect its activity. For example, the topoisomerase can be a type IA topoisomerase such as E. coli topoisomerase I, E. coli topoisomerase III, or a eukaryotic topoisomerase III. Upon cleavage of a nucleic acid molecule, the topoisomerase preferably is stably bound to the 5' terminus. Preferably, upon cleavage by the topoisomerase, the cleaved nucleic acid molecule comprises a 3' overhanging sequence. Once nucleic acid molecules are joined by the methods described above, the resulting molecules may then be used in recombination reactions or other processes, such as those described elsewhere herein.

A method of the invention for generating a ds recombinant nucleic acid molecule covalently linked in one strand, involving a first nucleic acid molecule that contains a site-specific topoisomerase recognition site (e.g., a type IA or a type IB topoisomerase recognition site), or cleavage product thereof, at least a second nucleic acid molecule, and at least a third nucleic acid molecule can be performed such that any combination of ends are linked, and one strand at the ends being linked is covalently linked and one strand is nicked. According to this embodiment, any of the ends can contain a type IA, type II, or type IB topoisomerase recognition site, or can comprise a cleavage product thereof, provided that the first ds recombinant nucleotide molecule contains a topoisomerase recognition site (e.g., a type IA or a type II topoisomerase recognition site) at or near a 5' terminus, or a cleavage product thereof, and only one topoisomerase or topoisomerase recognition site is present at the ends that are to be linked. For example, where the first nucleic acid molecule comprises a site-specific type IA topoisomerase recognition site at or near each of the first end and the second end, the method further can include contacting the first nucleic acid molecule and the second nucleic acid molecule with at least a third nucleic acid molecule which has, or can be made to have, a first end and a second end, each end further comprising a 5' terminus and a 3' terminus, under conditions such that the topoisomerase (e.g., a type IA or a type II topoisomerase) can covalently link the 5' terminus of the first end of the first nucleic acid molecule with the 3' terminus of the first end of the second nucleotide sequence, and the 5' terminus of the second end of the first nucleic acid molecule with the 3' terminus of the first end of the third nucleotide sequence. It will be recognized that other combinations of ends and topoisomerase recognition sites, or cleavage products thereof, can be used to perform such a method of the invention. Once nucleic acid molecules are joined by the methods described above, the resulting molecules may then be used in recombination reactions or other processes, such as those described elsewhere herein.

A covalently bound topoisomerase, in addition to catalyzing a ligation reaction, also can catalyze the reverse reaction, for example, religation of the 3' nucleotide of the recognition sequence, to which the type IB topoisomerase is linked through the phosphotyrosyl bond, and the nucleotide sequence that, prior to cleavage, comprised the 3' terminus of the nucleic acid molecule, and which, following cleavage, contains a free 5' hydroxy group. As such, methods have been developed for using a type IB topoisomerase to produce recombinant nucleic acid molecules. For example, cloning vectors containing a bound type IB topoisomerase have been developed and are commercially available (Invitrogen Corporation, Carlsbad, Calif.). Such cloning vectors, when linearized, contain a covalently bound type IB topoisomerase at each 3' end ("topoisomerase charged"). Nucleotide sequences such as those comprising a cDNA library, or restriction fragments, or sheared genomic DNA sequences that are to be cloned into such a vector are treated, for example, with a phosphatase to produce 5' hydroxyl termini, then are added to the linearized topoisomerase-charged vector under conditions that allow the topoisomerase to ligate the nucleotide sequences at the 5' terminus containing the hydroxyl group and the 3' terminus of the vector that contains the covalently bound topoisomerase. A nucleotide sequence such as a PCR amplification product, which is generated containing 5' hydroxyl ends, can be cloned into a topoisomerase-charged vector in a rapid joining reaction (approximately 5 minutes at room temperature). The rapid joining and broad temperature range inherent to the topoisomerase joining reaction makes the use of topoisomerase-charged vectors ideal for high throughput applications, which generally are performed using automated systems.

Type II topoisomerases have not generally been used for generating recombinant nucleic acid molecules or cloning procedures, whereas type IB topoisomerases, as indicated above, are used in a variety of procedures. As disclosed herein, type IA topoisomerases can be used in a variety of procedures similar to those described for the type IB topoisomerases. However, previously described methods of using type IB topoisomerases to ligate two or more nucleotide sequences have suffered from the disadvantage that the bound topoisomerase only effects the joining of the 3' end of the strand to which it is attached and a second strand containing a 5' hydroxyl group. Since the topoisomerase cannot ligate the complementary strands, the nucleic acid molecules that are generated contain nicks. While the presence of such nicks does not prevent the use of the recombinant molecules for transfection of a host cells, as the nicks generally are resolved intracellularly, the presence of such nicks in double stranded nucleic acid molecules significantly limits direct use of the recombinant molecules. For example, a strand of a nucleic acid molecule containing a nick cannot be amplified by PCR because the primer extension reaction terminates at the nick. Thus, nucleic acid constructs prepared using a topoisomerase according to previously described methods generally must be further treated, for example, with a DNA ligase, to obtain a ds recombinant nucleic acid molecule that is covalently linked in both strands and, therefore, useful for subsequent manipulations such as PCR.

Previously described methods for preparing nucleic acid constructs also generally required numerous steps, particularly where more than two nucleotide sequences are to be ligated, and even more so where the sequences must be ligated in a predetermined orientation. For example, the nucleotide sequences to be linked generally are ligated sequentially to produce intermediate constructs, each of which must be cloned, amplified in a host cell, isolated, and characterized. The constructs containing the correct sequences then must be isolated in a sufficient quantity and form such that the next nucleotide sequence can be ligated, and the process of cloning, amplifying, isolating and characterizing performed again to identify the proper construct. Clearly, as the number of different nucleotide sequences to be joined increases, so do the number of essentially repetitive procedures that must be performed, thus resulting in an expensive, laborious and lengthy process.

As disclosed herein, an advantage of a method of the invention for generating a ds recombinant nucleic acid molecule covalently linked in both strands is that there is no need to perform a separate ligation reaction in order to obtain a functional ds recombinant nucleic acid molecule covalently linked in both strands. In addition, a method of this aspect of the invention can be performed such that, where a number of different nucleic acid molecules are to be covalently linked in a predetermined orientation, there is no requirement that intermediate constructs be cloned, characterized and isolated before proceeding to a subsequent step. As such, the methods of this aspect of the invention provide a means to generate a ds recombinant nucleic acid molecule covalently linked in both strands much more quickly and at a substantially lower cost than was possible using previously known methods.

As an additional advantage, the generated ds recombinant nucleic acid molecules covalently linked in both strands are in a form that can be used directly in further procedures, for example, particular procedures involving extension of a primer such as a PCR amplification procedure, or other transcription or translation procedure, because the generated construct does not contain nicks at the sites where the ds nucleotides sequences have been joined. As disclosed herein, a method of the invention for generating a ds recombinant nucleic acid molecule covalently linked in one strand, in certain embodiments, also is advantageous in that the generated ds recombinant nucleic acid molecules are in a form that can be used directly in further procedures, for example, particular procedures involving extension of a primer such as a PCR amplification procedure, or other transcription or translation procedure, because in certain embodiments, the generated ds recombinant nucleic acid molecule contains one strand that does not contain a nick at the sites where the ds nucleotides sequences were joined.

Certain methods of the invention are exemplified generally herein with reference to the use of type IB topoisomerase such as the *Vaccinia* topoisomerase, or a type IA topoisomerase. However, it will be recognized that the methods also can be performed using a topoisomerase other than that exemplified, merely by adjusting the components accordingly. For example, as described in greater detail below, methods are disclosed for incorporating a type IB topoisomerase recognition site at one or both 3' termini of a linear nucleic acid molecule using a PCR primer comprising, at least in part, a nucleotide sequence complementary to the topoisomerase recognition site. In comparison, a topoisomerase recognition site for a type IA or, if desired, type II topoisomerase, can be incorporated into a nucleic acid molecule by using a PCR primer that contains the recognition site.

Cleavage of a nucleic acid molecule by a site specific type IB topoisomerase results in the generation of a 5' overhanging sequence in the strand complementary to and at the same end as that containing the covalently bound topoisomerase. Furthermore, as disclosed herein, PCR primers can be designed that can incorporate a type IB topoisomerase recognition site into a nucleic acid molecule, and that further can produce, upon cleavage of the nucleic acid molecule by the topoisomerase, a 5' overhanging sequence in the complementary strand that has a defined and predetermined sequence. As such, the methods are readily adaptable to generating a ds recombinant nucleic acid molecule having the component nucleic acid molecule operatively linked in a predetermined orientation. In view of the present disclosure, it will be recognized that PCR primers also can be designed such that a type IA topoisomerase recognition site can be introduced into a nucleic acid molecule, including a library of diverse sequences, and, if desired, such that upon cleavage by a site-specific topoisomerase, generates a 3' overhanging sequence.

A method of generating a ds recombinant nucleic acid molecule covalently linked in both strands, as disclosed herein, extends the previously known methods by providing a topoisomerase at or near the terminus of each nucleic acid molecule to be covalently linked. For example, with respect to a type IB topoisomerase, the method provides a topoisomerase recognition site, or a cleavage product thereof (i.e., a covalently bound type IB topoisomerase), at or near the 3' terminus of each linear nucleic acid molecule to be linked. As used herein, the term "topoisomerase recognition site" means a defined nucleotide sequence that is recognized and bound by a site specific topoisomerase. For example, the nucleotide sequence 5'-(C/T)CCTT-3' is a topoisomerase recognition site that is bound specifically by most poxvirus topoisomerases, including *vaccinia* virus DNA topoisomerase I, which then can cleave the strand after the 3'-most thymidine of the recognition site to produce a nucleotide sequence comprising 5'-(C/T)CCTT-$PO_4$-TOPO, i.e., a complex of the topoisomerase covalently bound to the 3' phosphate through a tyrosine residue in the topoisomerase (see Shuman, *J. Biol. Chem.* 266:11372-11379, 1991; Sekiguchi and Shuman, *Nucl. Acids Res.* 22:5360-5365, 1994; each of which is incorporated herein by reference; see, also, U.S. Pat. No. 5,766, 891; PCT/US95/16099; PCT/US98/12372). In comparison, the nucleotide sequence 5'-GCAACTT-3' is the topoisomerase recognition site for type IA *E. coli* topoisomerase III.

Topoisomerase-charged nucleic acid molecules, including those containing a topoisomerase covalently attached to a 5' terminus or 3' terminus or both, of one or both ends of the nucleic acid molecule, can be generated by any of a number of methods. In some cases and under the appropriate conditions, type I topoisomerases can cleave a single stranded nucleotide sequence. For example, a domain comprising the amino-terminal 67 kDa domain of *E. coli* topoisomerase I, which is a type IA topoisomerase, can cleave a single stranded nucleotide sequence containing the topoisomerase recognition site. Where conditions are such that the topoisomerases can cleave a single stranded nucleotide sequence, cleavage of a nucleic acid molecule containing topoisomerase recognition sites at the 5' and 3' termini of one end of nucleic acid molecule can be performed in parallel. Alternatively, where one or both of the topoisomerases requires a nucleic acid molecule for recognition and cleavage, the reactions are performed serially, wherein the more terminal (distal) of the topoisomerase recognition sites is cleaved first, then the more internal (proximal) site, which remains in a double stranded context, is cleaved. For example, a nucleic acid molecule containing an *E. coli* topoisomerase III recognition site at or near a 5' terminus of an end and a *Vaccinia* type IB topoisomerase recognition site at or near the 3' terminus of the same end, and wherein the type IB recognition site is closer to the end than the type IA recognition site, the nucleic acid molecule can be incubated with the *Vaccinia* topoisomerase, to produce a type IB topoisomerase charged nucleic acid molecule, then with the *E. coli* topoisomerase, to produce a nucleic acid molecule having the type IA topoisomerase bound to the 5' terminus and the type IB topoisomerase bound to the 3' terminus. Accordingly, the invention includes methods for producing nucleic acid molecule comprising a topoisomerase attached to one or both termini of at least one end, and further provides such topoisomerase-charged nucleic acid molecules.

As used herein, the term "cleavage product," when used in reference to a topoisomerase recognition site, refers to a nucleotide sequence that has been cleaved by a topoisomerase, generally at its recognition site, and comprises a complex of the topoisomerase covalently bound, in the case of type IA or type II topoisomerase, to the 5' phosphate group of the 5' terminal nucleotide in the topoisomerase recognition site, or in the case of a type IB topoisomerase to the 3' phosphate group of the 3' terminal nucleotide in the topoisomerase recognition site. Such a complex, which comprises a topoisomerase cleaved nucleic acid molecule having the topoisomerase covalently bound thereto, is referred to herein as a "topoisomerase-activated" or a "topoisomerase-charged" nucleotide sequence. Topoisomerase-activated nucleic acid molecules can be used in a method of the invention, as can nucleic acid molecules that contain an uncleaved topoisomerase recognition site and a topoisomerase, wherein the topoisomerase can cleave the nucleic acid molecule at the recognition site and become covalently bound thereto.

In one embodiment of a method of generating a ds recombinant nucleic acid molecule covalently linked in both strands, a topoisomerase recognition site is present at or near the 3' terminus of the end of each nucleotide sequence to be linked such that, in the presence of a type IB topoisomerase, each nucleotide sequence is cleaved to produce a 3' terminus, which contains the topoisomerase covalently bound thereto. The nucleotide sequences to be covalently linked also can contain a 5' hydroxy group at the same end as that containing the topoisomerase recognition site, or a 5' hydroxyl group can be generated using a phosphatase. Upon contact of such nucleotide sequences, the site specific topoisomerase can ligate each strand containing a 3' phosphate to a respective 5' hydroxyl group, thereby generating a ds recombinant nucleic acid molecule covalently linked in both strands, which can be produced as a linear, circular, or positively or negatively supercoiled nucleic acid molecule.

Preferably, the 5' termini of the ends of the nucleotide sequences to be linked by a type IB topoisomerase according to a method of certain aspects of the invention contain complementary 5' overhanging sequences, which can facilitate the initial association of the nucleotide sequences, including, if desired, in a predetermined directional orientation. Alternatively, the 5' termini of the ends of the nucleotide sequences to be linked by a type IB topoisomerase according to a method of certain aspects of the invention contain complementary 5' sequences wherein one of the sequences contains a 5' overhanging sequence and the other nucleotide sequence contains a complementary sequence at a blunt end of a 5' terminus, to facilitate the initial association of the nucleotide sequences through strand invasion, including, if desired, in a predetermined directional orientation. The term "5' overhang" or "5' overhanging sequence" is used herein to refer to a strand of a nucleic acid molecule that extends in a 5' direction beyond the terminus of the complementary strand of the nucleic acid molecule. Conveniently, a 5' overhang can be produced as a result of site specific cleavage of a nucleic acid molecule by a type IB topoisomerase (see Example 1).

Preferably, the 3' termini of the ends of the nucleotide sequences to be linked by a type IA topoisomerase according to a method of certain aspects of the invention contain complementary 3' overhanging sequences, which can facilitate the initial association of the nucleotide sequences, including, if desired, in a predetermined directional orientation. Alternatively, the 3' termini of the ends of the nucleotide sequences to be linked by a topoisomerase (e.g., a type IA or a type II topoisomerase) according to a method of certain aspects of the invention contain complementary 3' sequences wherein one of the sequences contains a 3' overhanging sequence and the other nucleotide sequence contains a complementary sequence at a blunt end of a 3' terminus, to facilitate the initial association of the nucleotide sequences through strand invasion, including, if desired, in a predetermined directional orientation. The term "3' overhang" or "3' overhanging sequence" is used herein to refer to a strand of a nucleic acid molecule that extends in a 3' direction beyond the terminus of the complementary strand of the nucleic acid molecule. Conveniently, a 3' overhang can be produced upon cleavage by a type IA or type II topoisomerase.

The 3' or 5' overhanging sequences can have any sequence, though generally the sequences are selected such that they allow ligation of a predetermined end of one nucleic acid molecule to a predetermined end of a second nucleotide sequence according to a method of the invention. As such, while the 3' or 5' overhangs can be palindromic, they generally are not because nucleic acid molecules having palindromic overhangs can associate with each other, thus reducing the yield of a ds recombinant nucleic acid molecule covalently linked in both strands comprising two or more nucleic acid molecules in a predetermined orientation.

A nucleic acid molecule useful in a method or kit of an aspect of the invention can be amplified by an amplification method such as PCR to contain a topoisomerase recognition site at a 3' or 5' terminus of an end. Furthermore, one or both primers used for PCR can be designed such that, upon cleavage of an amplified nucleic acid molecule, the cleaved nucleic acid molecule contains a 5' or 3' overhang at one or both ends. In one embodiment, PCR primers are designed such that the 5' overhanging sequence on a first nucleic acid molecule is complementary to a 5' overhanging sequence on a second (or other) nucleic acid molecule, thereby facilitating the association of the nucleotide sequences, preferably in a predetermined orientation, whereupon they can be covalently linked according to a method of the invention. In accordance with the invention, by designing unique overhanging sequences for the different nucleic acid molecule to be linked, any number of nucleic acid molecules can be linked in a desired order and/or orientation.

It should be recognized that PCR is used in two ways with respect to the methods of the invention. In one aspect, PCR primers are designed to impart particular characteristics to a desired nucleic acid molecule, for example, a nucleic acid molecule that encodes a transcriptional or translational regulatory element or a coding sequence of interest such as an epitope tag or cell compartmentalization domain. In this aspect, the PCR primers can be designed such that, upon amplification, the nucleic acid molecule contains a topoisomerase recognition site at one or both ends, as desired. As disclosed herein, the PCR primer also can include an additional sequence such that, upon cleavage of the amplification product by a site specific topoisomerase, the cleaved nucleic acid molecule contains a 5' or 3' overhanging sequence at the topoisomerase cleaved end. In an embodiment of the invention involving a topoisomerase that binds and cleaves a 5' terminus (e.g., an embodiment involving a type IA topoisomerase), the PCR primers can be designed to contain a bridging phosphorothioate linkage (see above), which can block religation after topoisomerase cleavage and can assist in the generation of a topoisomerase charged amplification product.

Overhanging sequences generated using PCR can include a single nucleotide overhang that is generated as an artifact of the PCR reaction. For example, a polymerase such at Taq, which does not have a proof-reading function and has an inherent terminal transferase activity, is commonly used, and produces PCR products containing a single, non-template derived 3' A overhang at each end. These amplification products can be linked to topoisomerase charged nucleic acid molecules containing a single 3' T overhang or a single 3' dU overhang, which, for a T/A cloning reaction, can be a vector (see U.S. Pat. Nos. 5,487,993 and 5,856,144, each of which is incorporated herein by reference), at one or both ends, using the methods of the invention.

PCR may also be used to amplify a covalently linked ds recombinant nucleic acid molecule covalently linked in one or both strands, generated by a method of the invention. A method of the invention can generate an expressible ds recombinant nucleic acid molecule from three substrate nucleic acid molecules, including a nucleotide sequence comprising a promoter, a nucleotide sequence comprising a coding sequence, and a nucleotide sequence comprising a polyadenylation signal. The generation of the ds recombinant nucleic acid molecule can be facilitated by the incorporation of complementary 3' (or 5') overhanging sequences at the ends of the ds nucleotides sequences to be joined. For example, the expressible ds recombinant nucleic acid molecule can be generated by contacting a first nucleic acid molecule having a type IA topoisomerase at a 5' terminus of a first end and a type IB topoisomerase at a 3' terminus of a second end with a second nucleic acid molecule and a third double stranded nucleotide sequence. By designing a PCR primer pair containing a first primer that is specific for a portion of the nucleotide sequence comprising the promoter that is upstream from the promoter, and a second primer that is specific for a portion of the nucleotide sequence comprising the polyadenylation signal that is down stream of the signal, only a full length functional ds recombinant nucleic molecule containing the promoter, coding sequence and polyadenylation signal in the correct (predetermined) orientation will be amplified. In particular, partial reaction products, for example, containing only a promoter linked to the coding sequence, and reaction products containing nicks are not amplified. Thus, PCR can be used to specifically design a nucleic acid molecule such that it is useful in a method of the invention, and to selectively amplify only those reaction products having the desired components and characteristics.

As used herein, the term "covalently linked," when used in reference to a ds recombinant nucleic acid molecule, means that the nucleic acid molecule is generated from at least two nucleic acid molecules that are ligated together, in both strands, by a topoisomerase mediated ligation. It should be recognized, for example, that a topoisomerase covalently bound to one of the nucleic acid molecules to be covalently linked can be the same as or different from the topoisomerase covalently bound to the other nucleic acid molecule. Thus, a Vaccinia topoisomerase can be covalently bound to one nucleic acid molecule and another poxvirus or eukaryotic nuclear type IB topoisomerase can be bound to the other strand. Generally, however, the topoisomerases, where different, are members of the same family, for example, type IA or type IB or type II, although, where the topoisomerases are covalently bound, for example, to a 5' phosphate and generate complementary 3' overhangs, the topoisomerase can be from different families, for example, type IA and type II.

The term "covalently linked" also is used herein in reference to a single stranded or double stranded nucleic acid molecule that is generated from at least two nucleotide sequences that are ligated together in one strand. For example, a ds recombinant nucleic acid molecule that is generated when a first topoisomerase-charged nucleic acid molecule that includes one topoisomerase bound at or near a 5' terminus contacts a second ds nucleotide sequence under conditions such that the topoisomerases can covalently link the 5' terminus of the first nucleic acid molecule to which it is bound, to the 3' terminus of the second nucleic acid molecule, can generate a ds recombinant nucleic acid molecule covalently linked in one strand.

In one embodiment, a ds recombinant nucleic acid molecule covalently linked in both strands generated according to a method of the invention does not contain a nick in either strand at the site where two nucleotide sequences are ligated, although it can contain nicks elsewhere in the molecule. In a method for generating a ds recombinant nucleic acid molecule covalently linked in one strand, a ds recombinant nucleic acid molecule is generated that contains a nick at least at the position where ends were linked in the complementary strands. This nicked ds recombinant nucleic acid molecule can be converted to a ds recombinant nucleic acid molecule covalently linked in both strands by introducing the nicked ds recombinant nucleic acid molecule into a cell, or by subjecting the ds recombinant nucleic acid molecule to a ligation reaction, such as using a ligase, as is well known in the art.

The term "recombinant" is used herein to refer to a nucleic acid molecule that is produced by linking at least two nucleotide sequences according to a method of the invention. As such, a ds recombinant nucleic acid molecule encompassed within the present invention is distinguishable from a nucleic acid molecule that may be produced in nature, for example, during meiosis. For example, a ds recombinant nucleic acid molecule covalently linked in both strands generated according to a method of certain aspects of the invention can be identified by the presence of the two topoisomerase recognition sites, one present in each of the complementary strands, at or near the site at which the nucleic acid molecules were joined.

A method of the invention can be performed by contacting a first nucleic acid molecule having a first end and a second end, wherein at the first end or second end or both, the first nucleic acid molecule has a topoisomerase recognition site, or cleavage product thereof, at or near the 3' terminus and has (or can be made to have, for example, by contact with a phosphatase) a hydroxyl group at the 5' terminus of the same end; at least a second nucleic acid molecule having a first end and a second end, wherein at the first end or second end or both, the at least second nucleic acid molecule has a topoisomerase recognition site, or cleavage product thereof, at or near the 3' terminus and has (or can be made to have) a hydroxyl group at the 5' terminus of the same end; and a topoisomerase, under conditions such that the components are in contact and the topoisomerase can effect its activity. Upon contact of the topoisomerase with the first and second (or other) nucleic acid molecules, and cleavage, where necessary, each nucleotide sequence comprises at the cleavage site a covalently bound topoisomerase at the 3' terminus and has, or can have, a hydroxyl group at the 5' terminus such that, upon contact, the first and at least second nucleotide sequences are covalently linked in both strands. Accordingly, the invention provides a ds recombinant nucleic acid molecule covalently linked in both strands produced by such a method.

As used herein, the term "at or near," when used in reference to the proximity of a topoisomerase recognition site to the 3' (type IB) or 5' (type IA or type II) terminus of a nucleotide sequence, means that the site is within about 1 to 100 nucleotides from the 3' terminus or 5' terminus, respectively, generally within about 1 to 20 nucleotides from the terminus, and particularly within about 2 to 12 nucleotides from the respective terminus. An advantage of positioning the topoisomerase recognition site within about 10 to 15 nucleotides of a terminus is that, upon cleavage by the topoisomerase, the portion of the sequence downstream of the cleavage site can spontaneously dissociate from the remaining nucleotide sequence, which contains the covalently bound topoisomerase (referred to generally as "suicide cleavage"; see, for example, Shuman, supra, 1991; Andersen et al., supra, 1991). Where a topoisomerase recognition site is greater than about 12 to 15 nucleotides from the terminus, the nucleotide sequence upstream or downstream of the cleavage site can be induced to dissociate from the remainder of the sequence by modifying the reaction conditions, for example, by providing an incubation step at a temperature above the melting temperature of the portion of the duplex including the topoisomerase cleavage site.

An additional advantage of constructing a first or second (or other) nucleic acid molecule to comprise, for example, a type IB topoisomerase recognition site about 2 to 15 nucleotides from one or both ends is that a 5' overhang is generated following cleavage of the nucleic acid molecule by a site specific topoisomerase. Such a 5' overhanging sequence, which would contain 2 to 15 nucleotides, respectively, can be designed using a PCR method as disclosed herein to have any sequence as desired. Thus, where a cleaved first nucleic acid molecule is to be covalently linked to a selected second (or other) nucleic acid molecule according to a method of the invention, and where the selected sequence has a 5' overhanging sequence, the 5' overhang on the first nucleic acid molecule can be designed to be complementary to the 5' overhang on the selected second (or other) ds sequence such that the two (or more) sequences are covalently linked in a predetermined orientation due to the complementarity of the 5' overhangs. As discussed above, similar methods can be utilized with respect to 3' overhanging sequences generated upon cleavage by, for example, a type IA or type II topoisomerase.

As used herein, reference to a nucleotide sequence having "a first end" and "a second end" means that the nucleotide sequence is linear. A substrate nucleic acid molecule can be linear or circular, including supercoiled, although, as a result of cleavage by one or more topoisomerases, a linear topoisomerase-charged nucleic acid molecule generally is produced. For example, a circular nucleic acid molecule containing two type IB topoisomerase recognition sites within about 100 nucleotides of each other and in the complementary strands, preferably within about twenty nucleotides of each other and in the complementary strands, can be contacted with a site specific type IB topoisomerase such that each strand is cleaved and the intervening sequence dissociates, thereby generating a linear nucleic acid molecule having a topoisomerase covalently bound to each end.

It should be recognized that reference to a first end or a second end of a nucleic acid molecule is not intended to imply any particular orientation of the nucleotide sequence, and is not intended to imply a relative importance of the ends with respect to each other. Where a nucleotide sequence having a first end and second end is a double stranded nucleotide sequence, each end contains a 5' terminus and a 3' terminus. Thus, reference is made herein, for example, to a nucleotide sequence containing a topoisomerase recognition site at a 3' terminus and a hydroxyl group at the 5' terminus of the same end, which can be the first end or the second end.

A method of the invention can be performed using only a first nucleic acid molecule and a second nucleic acid molecule, or can additionally include a third, fourth or more nucleic acid molecules as desired. Generally, each such nucleotide sequence contains a topoisomerase recognition site, or a cleavage product thereof, at or near at least one 3' or 5' terminus, and can contain a hydroxyl group at the 5' terminus of the same end, or a hydroxyl group can be generated using a phosphatase. Where a nucleotide sequence does not contain a topoisomerase recognition site at or near an end to be linked to a second nucleotide sequence, a topoisomerase recognition site can be introduced into the nucleotide sequence using a method as disclosed herein, for example, by PCR amplification of the sequence using a primer comprising a complement of the topoisomerase recognition site.

The terms "first nucleotide sequence," "second nucleotide sequence," "third nucleotide sequence," and the like, are used herein only to provide a means to indicate which of several nucleotide sequences is being referred to. Thus, absent any specifically defined characteristic with respect to a particular nucleotide sequence, the terms "first," "second," "third" and the like, when used in reference to a nucleotide sequence, or a population or plurality of nucleotide sequences, are not intended to indicate any particular order, importance or other information about the nucleotide sequence. Thus, where an exemplified method refers, for example, to using PCR to amplify a first nucleic acid molecule such that the amplification product contains a topoisomerase recognition site at one or both ends, it will be recognized that, similarly, a second (or other) nucleic acid molecule also can be so amplified.

The term "at least a second nucleotide sequence" is used herein to mean one or more nucleotide sequences in addition to a first nucleotide sequence. Thus, the term can refer to only a second nucleotide sequence, or to a second nucleotide sequence and a third nucleotide sequence (or more). As such, the term "second (or other) nucleotide sequence" or second (and other) nucleotide sequences" is used herein in recognition of the fact that the term "at least a second nucleotide sequence" can refer to a second, third or more nucleotide sequences. It should be recognized that, unless indicated otherwise, a nucleotide sequence encompassed within the meaning of the term "at least a second nucleotide sequence" can be the same or substantially the same as a first nucleotide sequence. For example, a first and second nucleic acid molecule can be the same except for having complementary 5' overhanging sequences produced upon cleavage by a topoisomerase such that the first and second nucleic acid molecules can be covalently linked using a method of the invention. As such, a method of the invention can be used to produce a concatenate of first and second nucleic acid molecules, which, optionally, can be interspersed, for example, by a third nucleic acid molecule such as a regulatory element, and can contain the covalently linked sequences in a predetermined directional orientation, for example, each in a 5' to 3' orientation with respect to each other.

As disclosed herein, a method of the invention provides a means to covalently link, two or more ds nucleotides in a predetermined directional orientation. The term "directional orientation" or "predetermined directional orientation" or "predetermined orientation" is used herein to refer to the covalent linkage, of two or more nucleotide sequences in a particular order. Thus, a method of the invention provides a means, for example, to covalently link, a promoter regulatory element upstream of a coding sequence, and to covalently link a polyadenylation signal downstream of the coding region to generate a functional expressible ds recombinant nucleic acid molecule; or to covalently link two coding sequences such that they can be transcribed and translated in frame to produce a fusion polypeptide.

A method of the invention also can be performed by contacting a first nucleic acid molecule having a first end and a second end, wherein at the first end or second end or both, the first nucleic acid molecule has a type IB topoisomerase covalently bound at the 3' terminus (topoisomerase-charged) and has (or can be made to have) a hydroxyl group at the 5' terminus of the same end; and at least a second type IB topoisomerase-charged nucleic acid molecule, which has (or can be made to have) a hydroxyl group at the 5' terminus at the same end. Upon contact of the topoisomerase-activated first and at least second nucleotide sequences at the ends containing the topoisomerase and a 5' hydroxyl group, phosphodiester bonds are formed in each strand, thereby generating a ds recombinant nucleic acid molecule covalently linked in both strands.

Substrates which particular reagents (e.g., enzymes) recognize and/or catalyze reactions with can be used in methods of the invention to produce nucleic acid molecules having particular characteristics. For example, reagents which catalyze nucleic acid modifications may recognize termini and/or generate termini having particular features. One example of such a feature is the presence or absence of a terminal phosphate group on the 3' or 5' strand. Such reagents, or combinations of such reagents, may be used to prepare, for example, nucleic acid molecules (1) from particular segments and/or (2) having a specific "pattern" of nicks (e.g., a nick in only one strand where two or more segments are joined, nicks in alternating strands where three or more segments are joined, etc.) or having no nicks in either strand.

Reagents (e.g., enzymes) which can be used in methods of the invention include, but are not limited to, the following:

ligases (e.g., DNA and RNA Ligases such as T4 DNA Ligase, T4 RNA ligase, *E. coli* DNA ligase, etc.), restriction enzymes (e.g., EcoRI, HpaII, BamHI, etc.), kinases (e.g., T4 polynucleotide kinase, etc.), phosphatases (e.g., calf intestinal alkaline phosphatase), topoisomerases, and polymerases (e.g., proof-reading polymerases such as Pfu, Pfx, THERMAL-ACE™ (Invitrogen Corp., Carlsbad, Calif.), etc.), and non-proof-reading polymerases such as Taq polymerase, Tfl polymerase, Tth polymerase, Tbr polymerase, etc.).

The cleavage of nucleic acid molecules by many endonucleases (e.g., restriction endonucleases) results in the formation of two new ends, wherein a hydroxyl group is present at the 3' terminus of one end and a phosphate group is present at the 5' terminus of the other end. Also, when exonucleases (e.g., snake venom phosphodiesterase, bovine spleen phosphodiesterase, *E. coli* exonuclease VII, lambda exonuclease, *E. coli* exonuclease III, etc.) digest nucleic acid molecules, they often generate ends with (1) 5' terminal hydroxyl groups and 3' terminal phosphate groups or (2) 3' terminal hydroxyl groups and 5' terminal phosphate groups. Further, exonucleases typically digest only a single stranded of a nucleic acid molecule but can use either single stranded and/or double stranded nucleic acids as substrates. In addition, exonucleases (e.g., exonucleases used in methods of the invention) may digest nucleic acid molecules from the 3' terminus, 5' terminus, or both the 3' and 5' termini. Also, kinases (e.g., T4 polynucleotide kinase, etc.) may be used to replace 5' and/or 3' terminal hydroxyl groups of nucleic acid molecules with phosphate groups.

Many polymerases used for the amplification of nucleic acid molecules, for example, by PCR, generate nucleic acid products having 3' terminal hydroxyl groups. In addition, the presence or absence of a phosphate group, or other chemical group, at the 5' terminus of a PCR product is typically determined by whether the primer used in the PCR reaction(s) contains a 5' terminal phosphate or other chemical group. Thus, 5' terminal phosphate groups, hydroxyl groups, or other groups can be introduced into PCR products by the use of primers which contain these groups at their 5' termini. As a result, PCR can be used to generate nucleic acid molecules (i.e., the first nucleic acid molecule referred to below) which contain a desired arrangement of hydroxyl groups, phosphate groups and/or other groups on the 5' and/or 3' termini of one or both ends of a linear nucleic acid molecule (e.g., 5' phosphate group and a 3' hydroxyl group at one end and a 5' hydroxyl group and a 3' hydroxyl group at the other end).

Each of the enzymes types listed above represents a general class of tools which can be used to generate nucleic acid molecules having particular characteristics (e.g., having a desired arrangement of hydroxyl, phosphate and/or other groups on the 3' and/or 5' termini of one or more ends). For example, double stranded, linear nucleic acid molecules may be prepared in which the 5' terminus and the 3' terminus at one end each contain terminal hydroxyl groups and the 5' terminus and the 3' terminus at the other end each contain terminal phosphate groups. Such ends may be prepared using the enzymes discussed above and/or other reagents and methods known in the art.

Thus, the present invention contemplates the construction and use of nucleic acid segments having particular characteristics (e.g., having a desired arrangement of hydroxyl, phosphate and/or other groups on the 3' and/or 5' termini of one or more ends). Such nucleic acids include, but are not limited to, double-stranded, linear nucleic acid molecules which have first and second ends with the characteristics set out in Table 4.

TABLE 4

| First End | | Second End | |
|---|---|---|---|
| 5' Terminus | 3' Terminus | 5' Terminus | 3' Terminus |
| Phosphate Group | Phosphate Group | Phosphate Group | Phosphate Group |
| Phosphate Group | Phosphate Group | Phosphate Group | Hydroxyl Group |
| Phosphate Group | Phosphate Group | Hydroxyl Group | Phosphate Group |
| Phosphate Group | Phosphate Group | Hydroxyl Group | Hydroxyl Group |
| Hydroxyl Group | Hydroxyl Group | Phosphate Group | Phosphate Group |
| Hydroxyl Group | Hydroxyl Group | Phosphate Group | Hydroxyl Group |
| Hydroxyl Group | Hydroxyl Group | Hydroxyl Group | Phosphate Group |
| Hydroxyl Group | Hydroxyl Group | Hydroxyl Group | Hydroxyl Group |
| Hydroxyl Group | Phosphate Group | Phosphate Group | Phosphate Group |
| Hydroxyl Group | Phosphate Group | Phosphate Group | Hydroxyl Group |
| Hydroxyl Group | Phosphate Group | Hydroxyl Group | Phosphate Group |
| Hydroxyl Group | Phosphate Group | Hydroxyl Group | Hydroxyl Group |
| Phosphate Group | Hydroxyl Group | Phosphate Group | Phosphate Group |
| Phosphate Group | Hydroxyl Group | Phosphate Group | Hydroxyl Group |
| Phosphate Group | Hydroxyl Group | Hydroxyl Group | Phosphate Group |
| Phosphate Group | Hydroxyl Group | Hydroxyl Group | Hydroxyl Group |

Nucleic acid molecules having a desired arrangement of hydroxyl, phosphate and/or other groups on the 3' and/or 5' termini of one or more ends can be directionally linked to other nucleic acid molecules using linking reactions which require, for example, the presence of a particular group on one or more termini of the molecule (e.g., either a 5' hydroxyl group or a 5' phosphate group and/or a 3' hydroxyl group or a 3' phosphate group).

A number of reagents which catalyze the linkage of nucleic acid segments to each other will generally only recognize termini with particular chemical groups (e.g., a hydroxyl group or a phosphate group) present. For example, T4 DNA ligase will catalyze the ligation of the 3' terminus of an end of a nucleic acid molecule to the 5' terminus of a separate end of the same nucleic acid molecule or of a different nucleic acid molecule, when the 5' terminus contains a terminal phosphate group. Further, a number of topoisomerases (e.g., a type IB topoisomerases) will cleave and bind to the 3' terminus of the end of a nucleic acid molecule and catalyze the linkage of this 3' terminus to the 5' terminus of the end of the same nucleic acid molecule or of a different nucleic acid molecule, when the 5' end contains a terminal hydroxyl group. Additionally, a number of topoisomerases (e.g., a type IA topoisomerases) will cleave and bind to the 5' terminus of the end of a nucleic acid molecule and catalyze the linkage of this 5' terminus to the 3' terminus of the end of the same nucleic acid molecule or of a different nucleic acid molecule, when the 3' end contains a terminal hydroxyl group.

One example of such a linking reaction is where a first nucleic acid molecule having a desired arrangement of groups on one or more termini (for example, a 5' phosphate on one terminus and a 5' hydroxyl on the other terminus) is linked to a second nucleic acid molecule that contains a type IB topoisomerase molecule covalently attached to a phosphate group at the 3' terminus of only one end of the molecule, i.e., attached to the 3' terminus of one strand of a double-stranded nucleic acid molecule. In such an instance, the 3' terminus of the end of the second nucleic acid molecule that contains the bound topoisomerase can only be joined to the 5' terminus of the end of the first nucleic acid molecule that contains the hydroxyl group. Thus, these two nucleic acid molecules can only be covalently linked in one orientation.

A linear double stranded nucleic acid molecule which has phosphate groups at both of the 5' and 3' termini at both ends (see Table 4) may be generated by any number of methods. One example of methods which may be used to produce such molecules involves chemical synthesis of both strands of the double stranded nucleic acid molecule. These individual strands may then be mixed under conditions which allow for the formation of the double stranded molecule.

Using reagents referred to above, as well as other reagents, nucleic acid molecules with various chemical groups at their termini can be covalently linked to each other in one or both strands. For example, a first nucleic acid segment which contains a 5' terminal phosphate group and a 3' terminal phosphate group with a type IB topoisomerase bound to it at one end may be linked in both strands to a second nucleic acid segment which contains 5' and 3' terminal hydroxyl groups at one end. In this instance, the 3' terminus of first nucleic acid segment which contains the topoisomerase molecule bound to it may be joined to the 5' terminus of the end of the second nucleic acid molecule. This linking reaction may be catalyzed by the bound topoisomerase molecule. Further, the 5' terminus of the same end of the first nucleic acid segments may be covalently linked to the 3' terminus of the end of the second nucleic acid segment to which it is joined by a ligase (e.g., T4 DNA ligase). As a second example, a first nucleic acid segments is prepared with a "sticky end" (i.e., an overhang) generated by digestion with a restriction endonuclease that leaves a 5' terminal phosphate group present on the "sticky end". The first nucleic acid segment is contacted with a second nucleic acid segment which contains a compatible "sticky end" and a topoisomerase molecule bound to the 5' terminus of this "sticky end". The result is the covalent connection of these two nucleic acid segments in a single strand. Further, the nick in the other strand at the junction point may be sealed by the inclusion of a ligase, such as T4 DNA ligase, in the reaction mixture.

Any number of variations of the above are possible depending on the available ends and the reagents used to prepare nucleic acid segments with ends for ligation by particular mechanisms or catalyzed by particular reagents. One example of such a variation is where the 5' terminus of the "sticky end" of the first nucleic acid molecule referred contains a hydroxyl group (e.g., the 5' phosphate is removed by a phosphatase) and the second nucleic acid molecule contain a type IB topoisomerase bound to the 3' terminus of the compatible "sticky end".

Methods

Compositions of the invention may be used in any number of processes. Typically, these processes will include methods in which two primer binding sites are employed. Examples of such processes include amplification reactions, sequencing reactions, RT-PCR, and reverse transcription reactions.

For example, the invention includes methods for amplifying nucleic acid segments (e.g., by PCR) which are flanked by primer binding sites. Typically, these primer binding sites will differ in sequence by one or more nucleotides. Also, in many instances, a single primer will be used in methods of the invention which will bind to both primer binding sites but will only mediate amplification when bound to one of the sites. Amplification reactions which employ such primers and primer binding sites can be used to produce copies of only one strand of a double stranded nucleic acid segment. In other words, only one strand of a double stranded nucleic acid molecule is generated in the reaction mixture from each melting and a synthesis cycle. Thus, the invention provides methods for producing a composition comprising single stranded nucleic acid molecules corresponding to one strand of a double stranded nucleic acid segment, as well as compositions comprising such nucleic acid molecules. In particular instances, the ratio of amplified to unamplified strands in such compositions will be determined by the number of amplification reactions which take place in which only one primer mediates 5' to 3' extension. Such ratios include ranges such as 2:1 to 200:1, 2:1 to 100:1, 2:1 to 50:1, 2:1 to 25:1, 2:1 to 15:1, 2:1 to 10:1, 5:1 to 200:1, 5:1 to 100:1, 5:1 to 50:1, 5:1 to 25:1, 5:1 to 15:1, 5:1 to 10:1, 10:1 to 200:1, 10:1 to 100:1, 10:1 to 50:1, 10:1 to 25:1, 10:1 to 15:1, etc. In particular embodiments, the invention includes methods for performing amplification reactions using two primers which bind to primer binding sites flanking a nucleic acid segment and function in amplification reactions to generated double stranded nucleic acid molecules, followed by additional rounds of amplification of the nucleic acid molecules under conditions which allow for only one strand to be amplified. These conditions include the following: (1) purification of amplified double stranded nucleic acid molecules followed by additional amplification in the presence of a single primer and (2) essentially complete consumption of one of the two primers during the amplification process resulting in initial amplification reactions generating double stranded nucleic acid molecules followed by later rounds of amplification resulting in the production of single stranded nucleic acid molecules.

The invention also includes methods for amplifying nucleic acid molecules which employ two or more primers which differ in nucleotide sequence by at least one nucleotide. In particular embodiments, the invention includes for amplifying nucleic acid segments flanked by primer binding sites which differ in nucleotide sequence. In many instances, such methods employ two primers each of which will bind to and mediate nucleic acid synthesis only when bound to of the two primer bind sites. In particular embodiments, both of the sequence primers will bind to both of the primer binding sites but will mediate nucleic acid synthesis only when bound to one of the two primer binding sites.

Nucleic acid amplification reactions and methods are well known in the art and are described, for example, in U.S. Pat. Nos. 4,683,202, 5,681,741, 6,544,782, 6,566,067, and 6,630,333, the entire disclosures of which are incorporated herein by reference.

The invention further includes methods for sequencing nucleic acid segments. Typically, these nucleic acid segments will be flanked by primer binding sites. In many instances, these primer binding sites will be identical in nucleotide sequence expect for one, two, three, four, or five nucleotides. Similar to above for nucleic acid amplification reactions, in many embodiments, the a single primer will bind to both primer binding sites by will only mediate nucleic acid synthesis or extension when bound to one of the primer binding sites.

Any number of methods may be used to sequence nucleic acid molecules of the invention. One such methods is referred to as the chain termination method or the Sanger method. Typically, the Sanger sequencing process begins by converting double stranded DNA which contain the nucleic acid to be sequenced into single stranded DNA. This can be done, for example, by denaturing the double stranded DNA with NaOH. Sequencing reaction mixtures typically comprise the following: single stranded DNA to be sequenced, a labeled primer which will is complementary to and capable of hybridizing to the single stranded DNA, a mixture of a particular ddNTP (e.g., ddATP, ddGTP, ddCTP, ddTTP) with its normal dNTP counterpart (e.g., dATP, dGTP, dCTP, dTTP), the other three dNTPs. Polymerase mediated 5' to 3' primer extension takes place and terminates in individual nucleic acid molecules whenever a ddNTP is incorporated into the growing strand. Three similar reaction mixtures are typically set up with mixtures of the other ddNTPs and their dNTP counterparts. The ratio of the ddNTP to dNTP in each reaction mixture dictates what percentage of the nucleic acid chains being synthesized terminate with each incorporation of the dd/dNTP.

When all of the reactions are completed, typically the sizes of the labeled fragments are assessed by polyacrylamide gel electrophoresis (PAGE) and lanes containing products of the reaction mixtures are compared against each other. Alternating banding patterns are generally read of photographic film to which has been exposed to the gel allows one to "read" the nucleotide sequence of the nucleic acid molecule. Nucleic acid sequencing methods are described in numerous sources, including U.S. Pat. No. 5,654,149, the entire disclosure of which is incorporated herein by reference.

Host Cells

The invention also relates to host cells comprising one or more of the nucleic acid molecules invention containing one or more nucleic acid sequences encoding a polypeptide having a detectable activity and/or one or more other sequences of interest (e.g., two, three, four, five, seven, ten, twelve, fifteen, twenty, thirty, fifty, etc.). Representative host cells that may be used according to this aspect of the invention include, but are not limited to, bacterial cells, yeast cells, plant cells and animal cells. In particular embodiments, bacterial host cells include *Escherichia* spp. cells (particularly *E. coli* cells and most particularly *E. coli* strains DH10B, Stbl2, DH5α, DB3, DB3.1 (e.g., *E. coli* LIBRARY EFFICIENCY® DB3.1™ Competent Cells; Invitrogen Corporation, Carlsbad, Calif.), DB4, DB5, JDP682 and ccdA-over (see U.S. Application Ser. No. 09/518,188, filed Mar. 2, 2000, and U.S. provisional Application No. 60/475,004, filed Jun. 3, 2003, by Louis Leong et al., entitled "Cells Resistant to Toxic Genes and Uses Thereof," the disclosures of which are incorporated by reference herein in their entireties); *Bacillus* spp. cells (particularly *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells). Suitable animal host cells include insect cells (most particularly *Drosophila melanogaster* cells, *Spodoptera frugiperda* Sf9 and Sf21 cells and *Trichoplusa* High-Five cells), nematode cells (particularly *C. elegans* cells), avian cells, amphibian cells (particularly *Xenopus laevis* cells), reptilian cells, and mammalian cells (most particularly NIH3T3, 293, CHO, COS, VERO, BHK and human cells). Suitable yeast host cells include *Saccharomyces cerevisiae* cells and *Pichia pastoris* cells. These and other suitable host cells are available commercially, for example, from Invitrogen Corporation, (Carlsbad, Calif.), American Type Culture Collection (Manassas, Va.), and Agricultural Research Culture Collection (NRRL; Peoria, Ill.).

Vectors of the invention, for example, may be propagated in any number of suitable cells. Examples of such cells include TOP10 cells (see, e.g., Invitrogen Corp. Carlsbad, Calif., cat. nos. C404003, C404052, and C409601), TOP10F' cells (see, e.g., Invitrogen Corp. Carlsbad, Calif., cat. no. C303006), and MACH 1 cells (see, e.g., Invitrogen Corp. Carlsbad, Calif., cat. nos. C862003 and C869601). Data indicates that when vectors which contain a ccdB cassette have undergone recombination reactions and are introduced into TOP10 and MACH 1 cells, lower background is seen with the MACH 1 cells. These data suggest that MACH 1 cells are more sensitive to the ccdB gene expression product that TOP10 cells. In other words, it may be more desirable to use MACH 1 cells instead of TOP10 cells to obtain vectors which have undergone recombination reactions and contain nucleic acid regions which have replaced a ccdB cassette.

Nucleic acid molecules to be used in the present invention may comprise one or more origins of replication (ORIs), and/or one or more selectable markers. In some embodiments, molecules may comprise two or more ORIs at least two of which are capable of functioning in different organisms (e.g., one in prokaryotes and one in eukaryotes). For example, a nucleic acid may have an ORI that functions in one or more prokaryotes (e.g., *E. coli*, *Bacillus*, etc.) and another that functions in one or more eukaryotes (e.g., yeast, insect, mammalian cells, etc.). Selectable markers may likewise be included in nucleic acid molecules of the invention to allow selection in different organisms. For example, a nucleic acid molecule may comprise multiple selectable markers, one or more of which functions in prokaryotes and one or more of which functions in eukaryotes.

Methods for introducing the nucleic acids molecules of the invention into the host cells described herein, to produce host cells comprising one or more of the nucleic acids molecules of the invention, will be familiar to those of ordinary skill in the art. For instance, the nucleic acid molecules of the invention may be introduced into host cells using well known techniques of infection, transduction, electroporation, transfection, and transformation. The nucleic acid molecules of the invention may be introduced alone or in conjunction with other nucleic acid molecules and/or vectors and/or proteins, peptides or RNAs. Alternatively, the nucleic acid molecules of the invention may be introduced into host cells as a precipitate, such as a calcium phosphate precipitate, or in a complex with a lipid. Electroporation also may be used to introduce the nucleic acid molecules of the invention into a host. Likewise, such molecules may be introduced into chemically competent cells such as *E. coli*. If the vector is a virus, it may be packaged in vitro or introduced into a packaging cell and the packaged virus may be transduced into cells. Thus nucleic acid molecules of the invention may contain and/or encode one or more packaging signal (e.g., viral packaging signals that direct the packaging of viral nucleic acid molecules). Hence, a wide variety of techniques suitable for introducing the nucleic acid molecules and/or vectors of the invention into cells in accordance with this aspect of the invention are well known and routine to those of skill in the art. Such techniques are reviewed at length, for example, in Sambrook, J., et al., *Molecular Cloning, a Laboratory Manual,* 2nd Ed., Cold Spring Harbor, N.Y.: Cold Spring Harbor Laboratory Press, pp. 16.30-16.55 (1989), Watson, J. D., et al., *Recombinant DNA,* 2nd Ed., New York: W. H. Freeman and Co., pp. 213-234 (1992), and Winnacker, E.-L., *From Genes to Clones,* New York: VCH Publishers (1987), which are illustrative of the many laboratory manuals that detail these techniques and which are incorporated by reference herein in their entireties for their relevant disclosures.

Kits

In another aspect, the invention provides kits that may be used in conjunction with methods the invention. Kits according to this aspect of the invention may comprise one or more containers, which may contain one or more components selected from the group consisting of one or more nucleic acid molecules (e.g., one or more nucleic acid molecules comprising one or more nucleic acid sequence encoding a polypeptide having a detectable activity) of the invention, one or more primers, the molecules and/or compounds of the invention, one or more polymerases, one or more reverse transcriptases, one or more recombination proteins (or other enzymes for carrying out the methods of the invention), one or more topoisomerases, one or more buffers, one or more detergents, one or more restriction endonucleases, one or more nucleotides, one or more terminating agents (e.g., ddNTPs), one or more transfection reagents, pyrophosphatase, and the like. Kits of the invention may also comprise written instructions for carrying out one or more methods of the invention.

The present invention also provides kits that contain components useful for conveniently practicing the methods of the invention. In one embodiment, a kit of the invention contains a first nucleic acid molecule, which comprises a nucleic acid sequence encoding a polypeptide having a detectable activity, and contains one or more topoisomerase recognition sites and/or one or more covalently attached topoisomerase enzymes. Nucleic acid molecules according to this aspect of the invention may further comprise one or more recombination sites. In some embodiments, the nucleic acid molecule comprises a topoisomerase-activated nucleotide sequence. The topoisomerase-charged nucleic acid molecule may comprise a 5' overhanging sequence at either or both ends and, the overhanging sequences may be the same or different. Optionally, each of the 5' termini comprises a 5' hydroxyl group.

In one embodiment, a kit of the invention contains a first nucleic acid molecule, which comprises a nucleic acid sequence encoding a polypeptide having a detectable activity, and contains one or more recombination sites. Nucleic acid molecules according to his aspect of the invention may further comprise one or more topoisomerase sites and/or topoisomerase enzymes.

In addition, the kit can contain at least a nucleotide sequence (or complement thereof) comprising a regulatory element, which can be an upstream or downstream regulatory element, or other element, and which contains a topoisomerase recognition site at one or both ends. In particular embodiments, kits of the invention contain a plurality of nucleic acid molecules, each comprising a different regulatory element or other element, for example, a sequence encoding a tag or other detectable molecule or a cell compartmentalization domain. The different elements can be different types of a particular regulatory element, for example, constitutive promoters, inducible promoters and tissue specific promoters, or can be different types of elements including, for example, transcriptional and translational regulatory elements, epitope tags, and the like. Such nucleic acid molecules can be topoisomerase-activated, and can contain 5' overhangs or 3' overhangs that facilitate operatively covalently linking the elements in a predetermined orientation, particularly such that a polypeptide such as a selectable marker is expressible in vitro or in one or more cell types.

The kit also can contain primers, including first and second primers, such that a primer pair comprising a first and second primer can be selected and used to amplify a desired ds recombinant nucleic acid molecule covalently linked in one or both strands, generated using components of the kit. For example, the primers can include first primers that are complementary to elements that generally are positioned at the 5' end of a generated ds recombinant nucleic acid molecule, for example, a portion of a nucleic acid molecule comprising a promoter element, and second primers that are complementary to elements that generally are positioned at the 3' end of a generated ds recombinant nucleic acid molecule, for example, a portion of a nucleic acid molecule comprising a transcription termination site or encoding an epitope tag. Depending on the elements selected from the kit for generating a ds recombinant nucleic acid molecule covalently linked in both strands, the appropriate first and second primers can be selected and used to amplify a full length functional construct.

In another embodiment, a kit of the invention contains a plurality of different elements, each of which can comprise one or more recombination sites and/or can be topoisomerase-activated at one or both ends, and each of which can contain a 5'-overhanging sequence or a 3'-overhanging sequence or a combination thereof. The 5' or 3' overhanging sequences can be unique to a particular element, or can be common to plurality of related elements, for example, to a plurality of different promoter element. In particular embodiments, the 5' overhanging sequences of elements are designed such that one or more elements can be operatively covalently linked to provide a useful function, for example, an element comprising a Kozak sequence and an element comprising a translation start site can have complementary 5' overhangs such that the elements can be operatively covalently linked according to a method of the invention.

The plurality of elements in the kit can comprise any elements, including transcription or translation regulatory elements; elements required for replication of a nucleotide sequence in a bacterial, insect, yeast, or mammalian host cell; elements comprising recognition sequences for site specific nucleic acid binding proteins such as restriction endonucleases or recombinases; elements encoding expressible products such as epitope tags or drug resistance genes; and the like. As such, a kit of the invention provides a convenient source of different elements that can be selected depending, for example, on the particular cells that a construct generated according to a method of the invention is to be introduced into or expressed in. The kit also can contain PCR primers, including first and second primers, which can be combined as described above to amplify a ds recombinant nucleic acid molecule covalently linked in one or both strands, generated using the elements of the kit. Optionally, the kit further contains a site specific topoisomerase in an amount useful for covalently linking in at least one strand, a first nucleic acid molecule comprising a topoisomerase recognition site to a second (or other) nucleic acid molecule, which can optionally be topoisomerase-activated nucleic acid molecules or nucleotide sequences that comprise a topoisomerase recognition site.

In still another embodiment, a kit of the invention contains a first nucleic acid molecule, which comprises a nucleic acid sequence encoding a polypeptide having a detectable activity, and contains a topoisomerase recognition site and/or a recombination site at each end; a first and second PCR primer pair, which can produce a first and second amplification products that can be covalently linked in one or both strands, to the first nucleic acid molecule in a predetermined orientation according to a method of the invention.

Kits of the invention may further comprise (1) instructions for performing one or more methods described herein and/or (2) a description of one or more compositions described herein. These instructions and/or descriptions may be in printed form. For example, these instructions and/or descriptions may be in the form of an insert which is present in kits of the invention.

Exemplary product literature of the invention is attached hereto as Appendix A. The invention includes product literature which describes how to perform methods of the invention, as well as how to make and/or use compositions of the invention.

It will be understood by one of ordinary skill in the relevant arts that other suitable modifications and adaptations to the methods and applications described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

In this example, we describe the creation and testing of a new TOPO T/A cloning system. pCR8/GW/TOPO is a T/A Topo vector which contains attL sequences flanking TOPO cloning sites. This vector displays the same high cloning efficiency seen in pCR2.1/TOPO (see, e.g., Invitrogen Corporation, Carlsbad, Calif., cat. nos. K4500-01, K4500-40, K4520-01, K4520-40, K4550-01, K4550-40, K4560-01, and K4560-40) along with the efficient LR recombination activity seen in current GATEWAY® ENTRY vectors. A novel sequencing primer design was employed for this vector that allows priming of reactions within the attL sites minimizing the amount of vector sequence read in each reaction. Cloning and propagation of pCR8/GW/TOPO in MACH I and TOP10 cells and faithful LR transfer and expression of Entry clones in pBAD DEST 49 were also demonstrated.

Introduction

GATEWAY® cloning is a powerful tool for transferring open reading frames (ORFs) from Entry vectors to Destination vectors, ultimately creating expression constructs. The first step in a GATEWAY® cloning experiment is to either obtain or create an Entry clone containing an insert of choice. Currently there are three methods available to construct Entry vectors: 1) standard restriction enzyme digestion and ligation of an insert into one of the pENTR vectors; 2) BP recombination of an attB appended PCR product with a Donor vector; or 3) directional TOPO ligation of a CACC-appended PCR product with one of the pENTR D-TOPO vectors. The latter PCR method requires the addition of fewer bases to the primers and achieves cloning in a five minute, bench-top reaction. Once the Entry clone is constructed and validated, the ORF may be transferred to any Destination vector with an LR recombination reaction.

We have generated of a new vector system that contains attL as well as Topo T/A cloning sites. The vectors of this system are able to perform all the functions of the pCR family of vectors while maintaining the attributes of an Entry vector. These attributes include ease of sequence verification and efficient transfer of DNA fragments into Destination vectors. Efficient sequencing of inserts in the pCR vectors is possible because the placement of efficient primer binding sites close to the cloning site. To achieve this in pCR8/GW/TOPO, mutations in the attL2 site were made which allowed for complete annealing of sequencing primers to the attL2 sites that do not anneal sufficiently to attL1 sites and these mutations were also designed to not affect LR recombination. These new sites support robust DNA sequencing reactions originating much closer to the insert than allowed by the current Donor or Entry vectors. This allows the pCR8/GW/TOPO perform as well as the pCR series in cloning and sequencing efficiency and gives the researcher the ability to transfer the insert to any appropriate Destination vector for downstream analysis.

Materials and Methods

Figure 3:
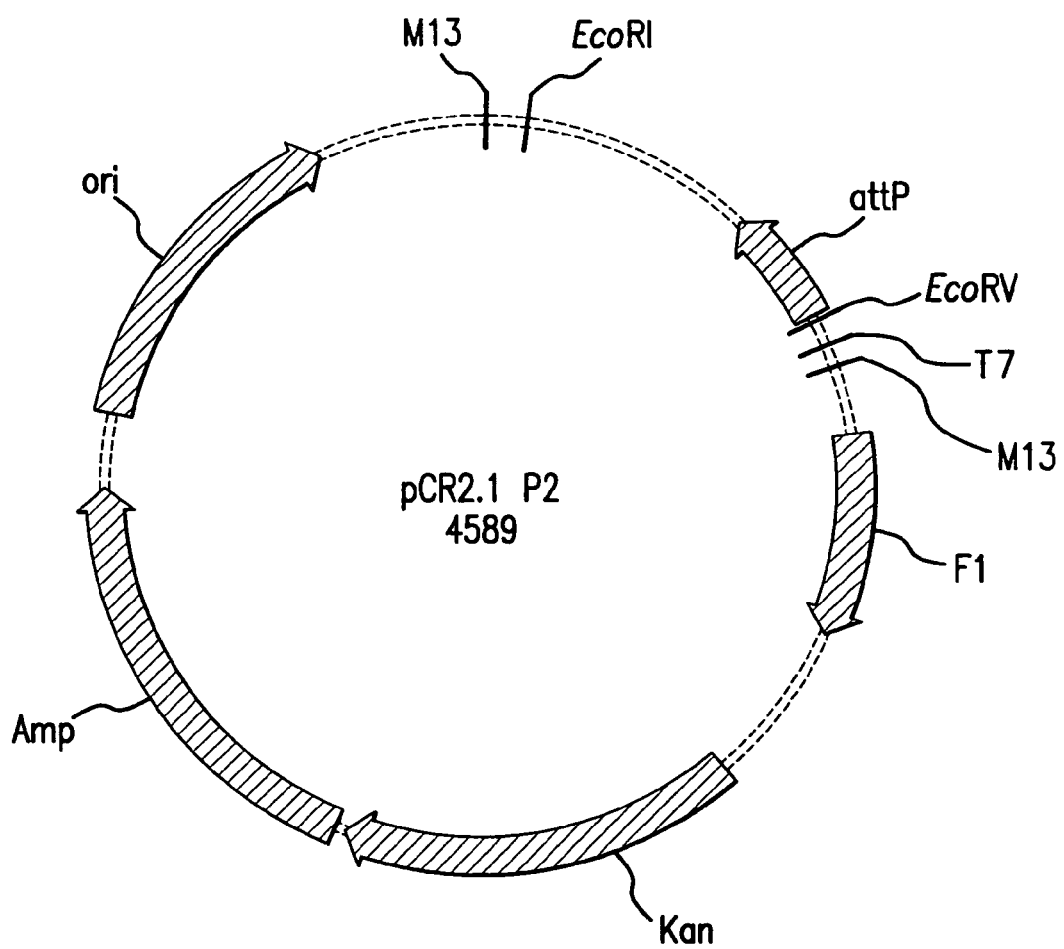

Mutagenesis of the attP2 site. The attP2 site was excised from pDONR221 (Invitrogen Corporation, Carlsbad, Calif., cat. nos. 12535-019, 12536-017) with an EcoRI and EcoRV endonuclease digest. The resulting 711 bp fragment was cloned into the EcoRI and EcoRV sites of pCR2.1 (Invitrogen Corporation, Carlsbad, Calif., cat. no. K2000-01) to create pCR2.1 P2 EcoRI/RV (FIG. 3).

Figure 4:
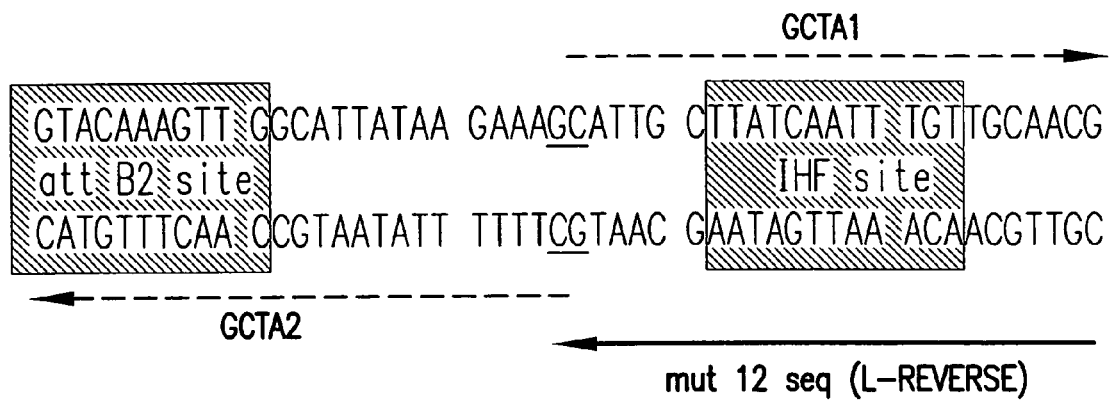
Figure 5A:
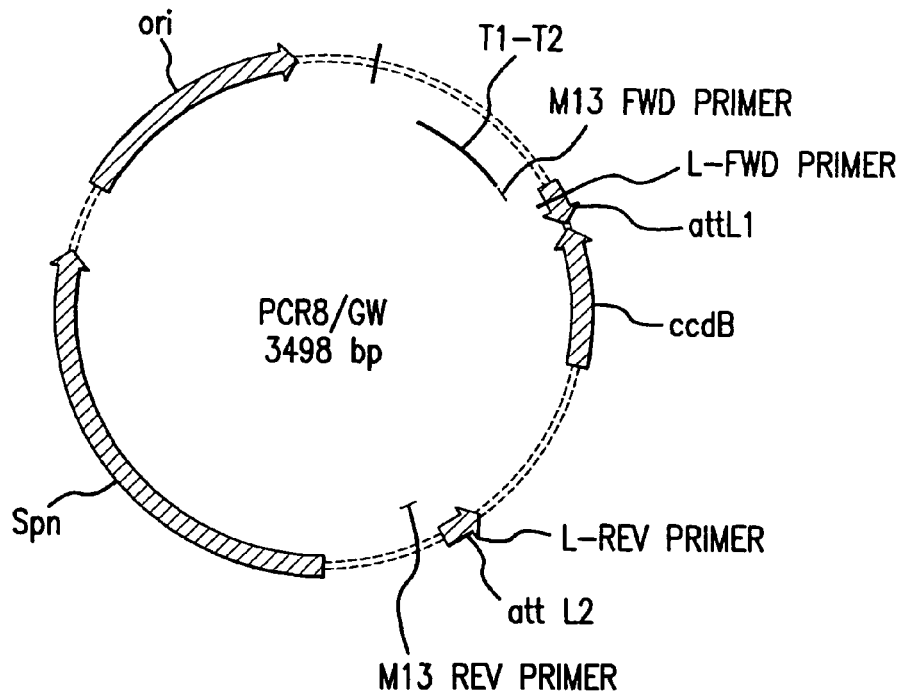
Figure 5B:
Figure 5B:
Figure 6A:
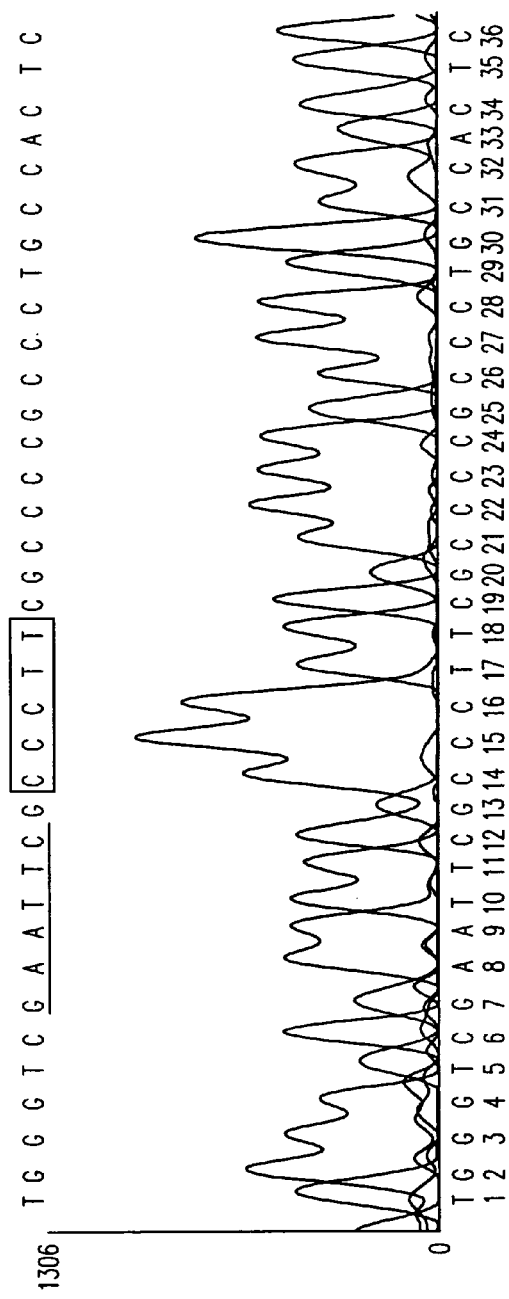
Figure 6A:
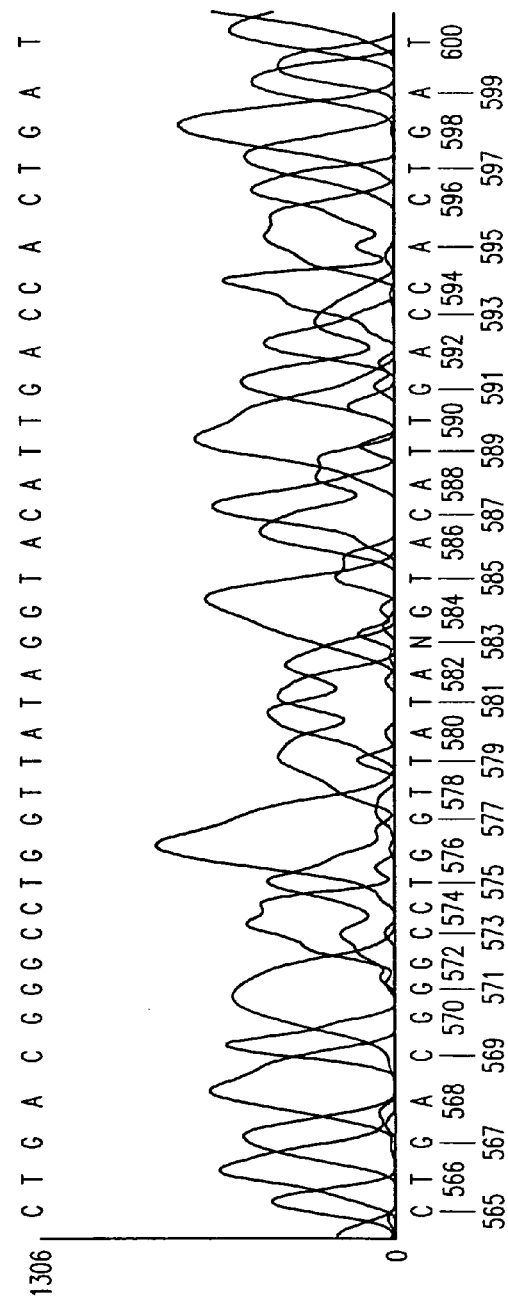
Figure 6B:
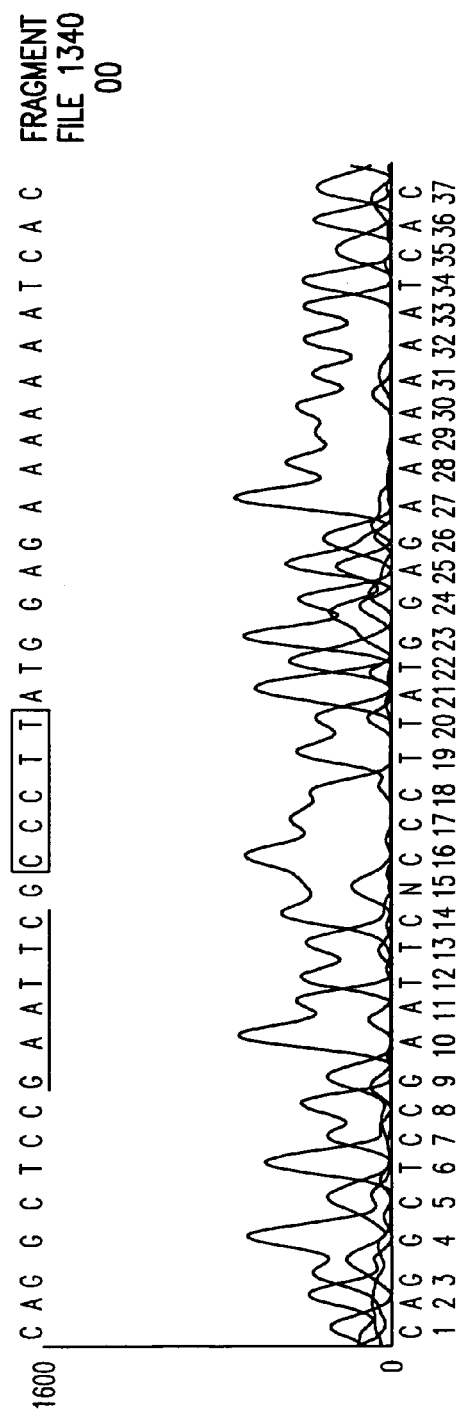
Figure 6B:
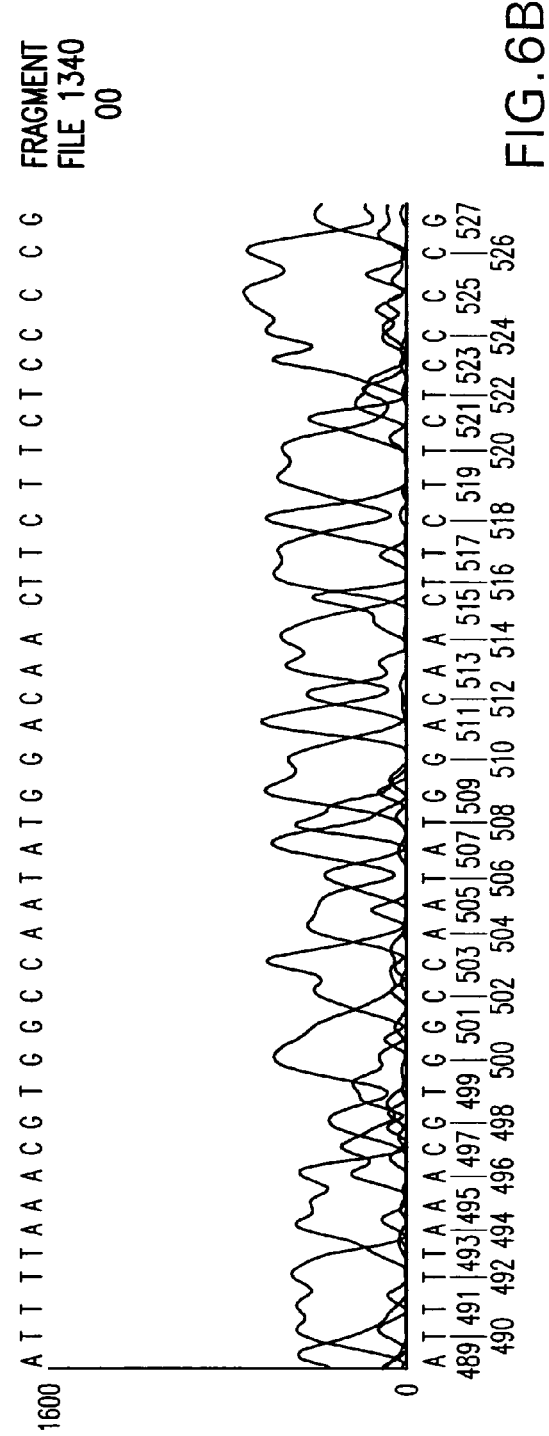

Two mutants were constructed converting GC pairs to TA pairs too allow specific annealing of primers in the nearly identical attP/L sites. The mutagenesis sites chosen were in spacer regions between CLONASE™ protein binding sites (FIG. 4). The mutagenic primers were designed to extend away from the mutated site with the 5' most nucleotide of the oligonucleotide dictating the base change. To create mutant 12 (mut 12) the phosphorylated primers GCTA1 and GCTA2 were used with pCR2.1 P2 EcoRI/RV as a template in a polymerase chain reaction. The resulting PCR product was gel purified and ligated with T4 DNA ligase. An aliquot of this ligation was transformed into TOP10 cells and plasmid DNA isolated from the resulting colonies. Positive clones were screened by DNA sequence analysis. The 711 bp EcoR1/EcoRV fragment was excised from the positive clones and ligated with the EcoRI and EcoRV sites of pDONR223 (FIG. 9) to create pDONR223 mut12. The pDONR223 mut34 mutant was created with a similar method using the phosphorylated primers GCTA3 (5'-AAATG CTTTT TTATA ATGCC AACTT TG-3') (SEQ ID NO: 12) and GCTA4 (5'-ATCAT CAATT TGTTG CAACG AACAG G-3') (SEQ ID NO: 13). As already noted, no legible sequencing data was obtained from a sequencing reaction employing the Mut34 primer (5'-TGTTC GTTGC AACAA ATTGA TGAT-3') (SEQ ID NO: 14).

Construction of attB ccdB/CmR cassette. pDEST15 (Invitrogen Corp., Carlsbad, Calif., cat. no. 11802-014) was used as a template for PCR with oligo 5' ccdB and oligo 435. The resulting PCR product was TOPO cloned into pCR2.1 to generate pCR2.1-ccdB/CM. pCR2.1-ccdB/CM was used as a template for PCR with oligonucleotides 5' GWTA-tcc and GWT ccmR, generating a PCR product containing attB sites. The PCR product was gel purified before use in the BP reaction.

Construction of pCR8/GW/TOPO. To construct pCR8/GW/TOPO, pDONR223 mut 12 was linearized with EcoRI, treated with calf intestine alkaline phosphatase (New England Biolabs), and gel purified from a 1.2% agarose E-gel using a SNAP gel purification kit (Invitrogen Corporation, Carlsbad, Calif. cat. no. K199925). The resulting DNA fragment was used in a BP reaction with a PCR product consisting of a ccdB/Cm cassette modified to contain EcoRI restriction sites as described above. The 20 µl BP reaction consisted of 4 µl (~100 ng) of the attB ccdB/Cm cassette PCR product, 300 ng of linearized pDONR 223 mut 12, 4 µl 5× BP CLONASE™ buffer (Invitrogen Corporation, Carlsbad, Calif., cat. no. 11789013), and 4 µl of BP CLONASE™ mix (Invitrogen Corporation, Carlsbad, Calif., cat. no. 11789-013). The reaction was incubated at room temperature for 1 hour. Two microliters of the reaction were used to transform chemically competent DB3.1 cells. After 1 hour out growth, the cells were plated on LB agar plates containing spectinomycin (100 µg/mL). Positive clones were verified by restriction digest analysis and the presence of insert was verified by sequence analysis.

pCR8/GW/TOPO mut12 was subsequently digested with BamHI to delete the CmR gene and generate pCR8/GW/TOPO. This was done because of concern that an EcoRI site within the CmR gene might interfere with TOPO adaptation. The vector was run on 1.2% E-gel, excised and purified using SNAP purification kit. Five nanograms of the purified vector was ligated overnight and then used to transform DB3.1 cells.

TABLE 5

Primers:

| | | |
|---|---|---|
| oligo 5'ccdB | 5'-TTCTTATATTCCCCAGAACAT | (SEQ ID: 57) |
| oligo 435 | 5'-GAGGCTTTACACTTTATGCTTCC | (SEQ ID: 58) |
| 5'GWTA-tcc | 5'GGGGACAAGTTTGTACAAAAAAGCAGGCTCC GAATTCTTATATTCCCCAGAACA | (SEQ ID: 59) |
| GWT ccmR | 5'-GGGACCACTTTGTACAAGAAAGCTGGGT CGAATTCCAGGCTTTACACTTTATGCTT | (SEQ ID NO:60) |
| GCTA1 | 5'-AATTGCTCATCAATTTGTTGCAACG | (SEQ ID NO:61) |
| GCTA2 L1S9 | 5'-ATTTTTTATAATGCCAACTTTGTAC | (SEQ ID NO:62) |
| (L-forward) mut12 seq | 5'-GTTGCAACAAATTGATGAGCAATGC | (SEQ ID NO:63) |
| (L-reverse) | 5'-GTTGCAACAAATTGATGAGCAATTA | (SEQ ID NO:64) |

Mach I growth analysis. Three lacI entry clones (ORF=lacI) were created with standard BP reactions using either pDONR221 (KanR), pDONR223 (SpecR) or pDONR228 (FIG. 10) (AmpR) and used to transform TOP10 (Invitrogen Corporation, Carlsbad, Calif., cat. no. C404003) or MACH1 (Invitrogen Corporation, Carlsbad, Calif., cat. no. C862003) cells. Colonies from these transformations were used to inoculate 3 ml of LB media (plus respective antibiotic) and grown overnight at 37° C. with shaking. $OD_{600}$ was measured after 4.5 and 7 hours. A second experiment was conducted using stationary (overnight) cultures of the above mentioned transformants as well as pENTR D-TOPO—CAT and pCR8/GW/TOPO—CAT in both cell strains. These cultures were normalized to $OD_{600}$=2.0 and diluted 1:50 in LB with either 100 μg/ml ampicillin, 50 μg/ml kanamycin, or 100 μg/ml spectinomycin. The diluted cultures were incubated at 37° C. with shaking and $OD_{600}$ measurements were taken at 1, 3, 4, and 5 hours post inoculation.

Vector preparation for TOPO charging. Fifty micrograms of pCR8/GW/TOPO was digested in 400 μl of 1× EcoRI digestion buffer (New England Biolabs) containing 300 Units of EcoRI for 3 hours at 37° C. An additional 100 Units of EcoRI was added at the 3 hour time point and incubation at 37° C. continued for another hour. The digest was extracted with 200 μl phenol/chloroform, pH 7.5 with gentle vortexing for 2 minutes. The aqueous phase was separated with centrifugation at 14000×g and transferred to a fresh tube. The digested DNA was precipitated with sodium acetate and ethanol and the DNA pelleted by centrifugation at 14000×g for 10 minutes. The pellet was washed twice with 70% ethanol, air dried, and resuspended in 45 μl of water. Typical recoveries were about 40 μg of DNA.

Ligation of TOPO oligonucleotides and TOPO adaptation. Twenty micrograms of TOPO-1 (5'-AATTC GCCCT TATTC CGATA GTG-3') (SEQ ID NO: 65) and 6 μg of TOPO-4 (5'-AGGGCG-3') oligonucleotides were initially combined with the 45 μl of digested DNA. Eight microliters of 10× ligase buffer (Invitrogen Corporation, Carlsbad, Calif., cat. no. 15224017) was added and the reaction volume adjusted to 80 μl with water. The reaction was started by addition of 5 Units of T4 DNA ligase (Invitrogen) and allowed to incubate for 16 hours at 12° C. After the incubation period the ligation reaction volume was increased to 400 μl with TE, extracted with 200 μl of phenol/chloroform, and the DNA precipitated with sodium acetate and ethanol. The DNA pellet was washed twice with 50 μl of 70% ethanol and air dried. The DNA pellet was resuspended in 40 μl of TE and quantified spectrophotometrically. Typical recoveries were about 16 μg of DNA.

TOPO charging. To 5 μg of ligated DNA, 3 μg of TOPO-5 oligonucleotide (5'-CAACA CTATC GGAAT A-3' (SEQ ID NO: 66), phosphorylated on the 5' end), 10 μl 5× NEB #1 (New England Biolabs, Inc., Beverly, Mass. cat. no. M0202S), and 5 μg of Vaccinia Topoisomerase I was added and the volume adjusted to 50 μl with water. This reaction was incubated at 37° C. for 15 minutes before addition of 5 μl of 10× TOPO Stop Buffer (1 M Tris-HCl, pH 7.5, 500 mM EDTA). The TOPO adapted vector was then gel purified and quantified using the Hoechst dye assay.

Testing of TOPO cloning efficiency. TOPO cloning efficiency was determined using a 500 bp PCR fragment containing a bacterial lac promoter driving the lacZ alpha fragment, this positive control fragment is found in some of Invitrogen's TOPO T/A cloning kits, for example, cat. no. K4300-01. Cloning of this fragment generated blue colonies on X-gal plates and colonies without the cloned fragment were white. The ratio of the total number of blue colonies to the total number of colonies was representative of the efficiency of the TOPO reaction. Twenty nanograms of the Taq polymerase generated 500 bp PCR product was used per TOPO reaction.

TOPO Cloning with other ORFs. ORFs chosen for TOPO cloning with pCR8/GW/TOPO were CAT (0.8 kb) and GUS (1.8 kb). The primers used for PCR amplification of these ORFs are listed below in Table 7. PCR amplified fragments were quantified with a qualified molecular weight mass ladder. For the TOPO cloning reactions, 1 μl of the PCR product was used and TOP10 cells were transformed.

TABLE 6

Primers:

| | | |
|---|---|---|
| CAT TA 3' | 5'-ATGGAGAAAAAAATCACTGG | (SEQ ID NO: 67) |
| CAT TA 5' | 5'-CGCCCCGCCCTGCCACTCAT | (SEQ ID NO: 68) |

TABLE 6-continued

Primers:

GUS TA 3' 5'-TTGTTTGCCTCCCTGCTGCG (SEQ ID NO: 69)

GUS TA 5' 5'-ATGGTCCGTCCTGTAGAAAC (SEQ ID NO: 70)

Transfer and expression of two TOPO cloned ORFs. Clones bearing the CAT and GUS genes (in both orientations) were transferred to pBAD DEST49 (Invitrogen Corporation, Carlsbad, Calif., cat. no. 12283-016) by LR reaction. An aliquot of the LR reaction was then used to transform TOP10 cells. Plasmid DNAs were isolated from the resulting colonies and analyzed by restriction enzyme digestion to screen for positive clones. Positive colonies were used to inoculate 3 ml of LB-Amp (100 µg/ml) and grown at 37° C. with shaking until the $OD_{600}$ reached 0.5. The culture was then split to two 1.5 ml cultures. To one of the cultures arabinose was added to a final weight to volume percentage of 0.2%. Both cultures were then incubated at 37° C. with shaking for 16 hours. The cultures were harvested by centrifugation, the cell pellets were resuspended in 600 µl of BugBuster HT (Novagen, Madison, Wis., cat. no. 70750) and incubated for 10 minutes at room temperature. Fifteen microliters of the whole cell lysates were mixed with 15 µl of 2× sample buffer containing reducing agent and boiled for 10 minutes. The samples were analyzed on a 12% Tri Glycine SDS PAGE.

Results

One of the key features of the pCR8/GW/TOPO (FIG. 8) vector is its ability to support efficient sequencing of inserts while containing attL sites flanking the insert. With current DONR/ENTR vectors, sequencing primer binding sites lie outside of the attL sequences. The reason for this is that the attL sites are nearly identical (the difference between attL1 and attL2 is only three bases). This homology would lead to primers annealing to (and extending from) both sites, resulting in ambiguous and unreadable results. The placement of primer sites outside of the attL sites brings with it two disadvantages: 1) the sequencing reaction must proceed through the entire 125 bp attL site before insert sequence can be read; and 2) often a significant amount of signal is lost as the sequencing reaction proceeds through the attL site. In cases where the purity of the DNA or the quality of the sequencing reaction leads to low signal at the outset, the signal loss through the att site can result in unreadable sequence downstream. This problem is minimized, however, in pCR8/GW/TOPO. By making a 2-base change in the attL2 site, primers can be designed that anneal to both the attL1 or attL2 sites but only extend from their specific site. The two attL primers (L-forward [GW-1] and L-reverse [GW-2]) are identical in sequence except for their two 3' bases. This difference in the 'extension end' of the primers is sufficient to direct specific annealing and extension from the correct attL site (FIG. 6). The site for the base change was chosen to be within a 'spacer region' of the attL site, which lies between the proximal IHF binding site and the attB core (Int binding) region so as not to affect the LR recombinational activity (Landy, A., *Annu. Rev. Biochem.*, 58:913-949 (1989)) or the translation of the attB2 sequence (FIG. 4).

Figure 8:
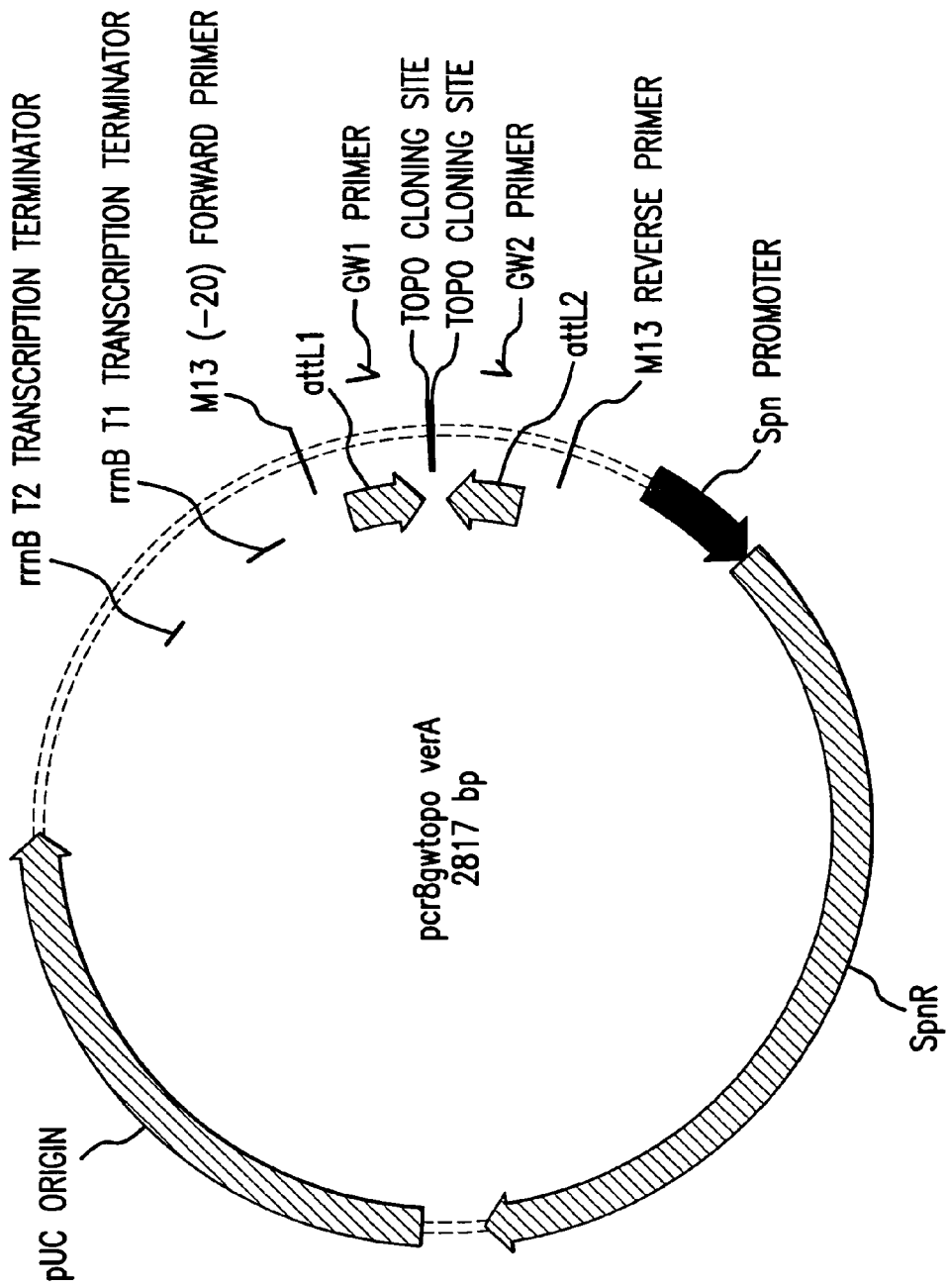
Figure 9:
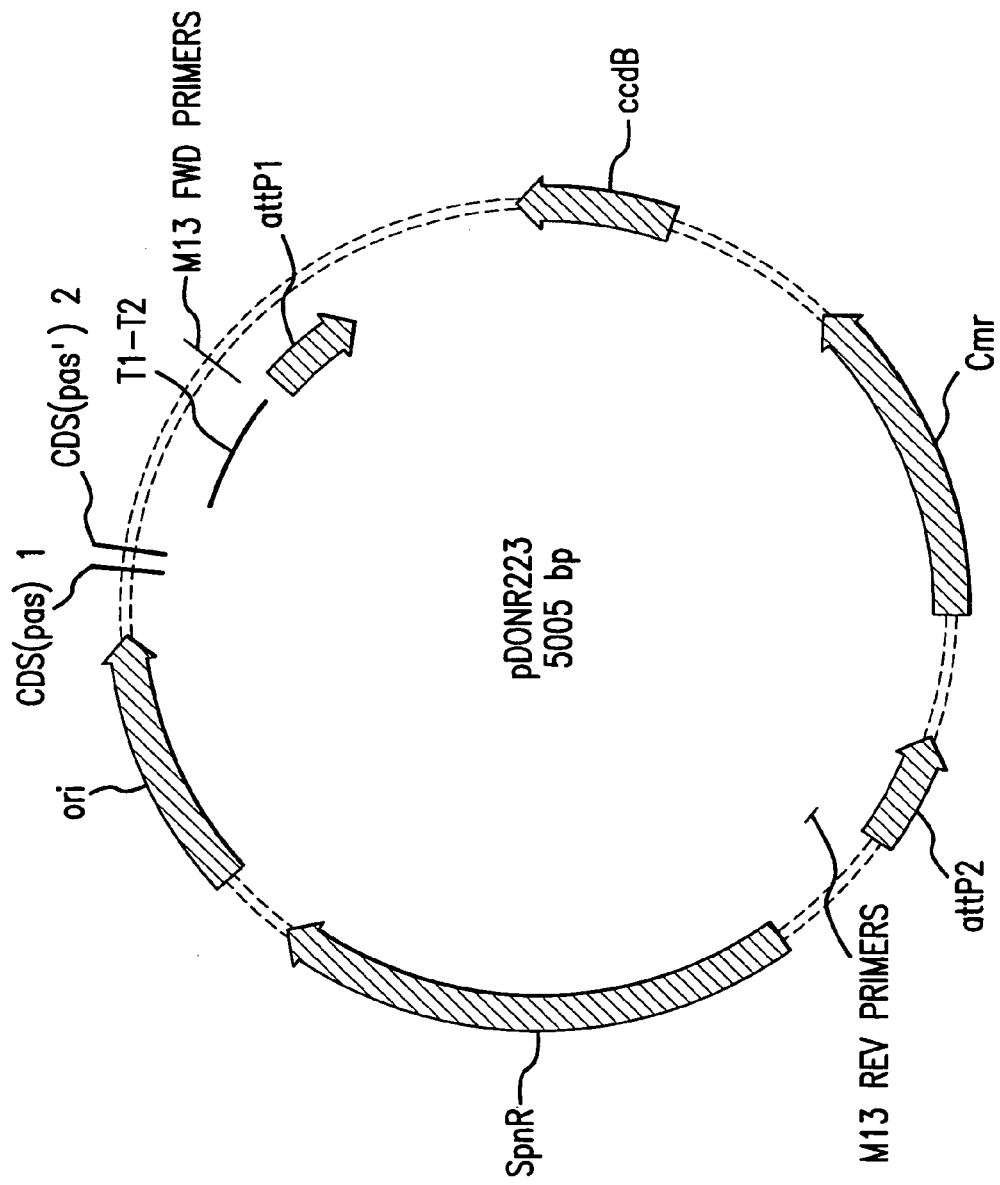
FIG. 9 shows a vector map of pDONR223 and particular features of this vector.
Figure 10:
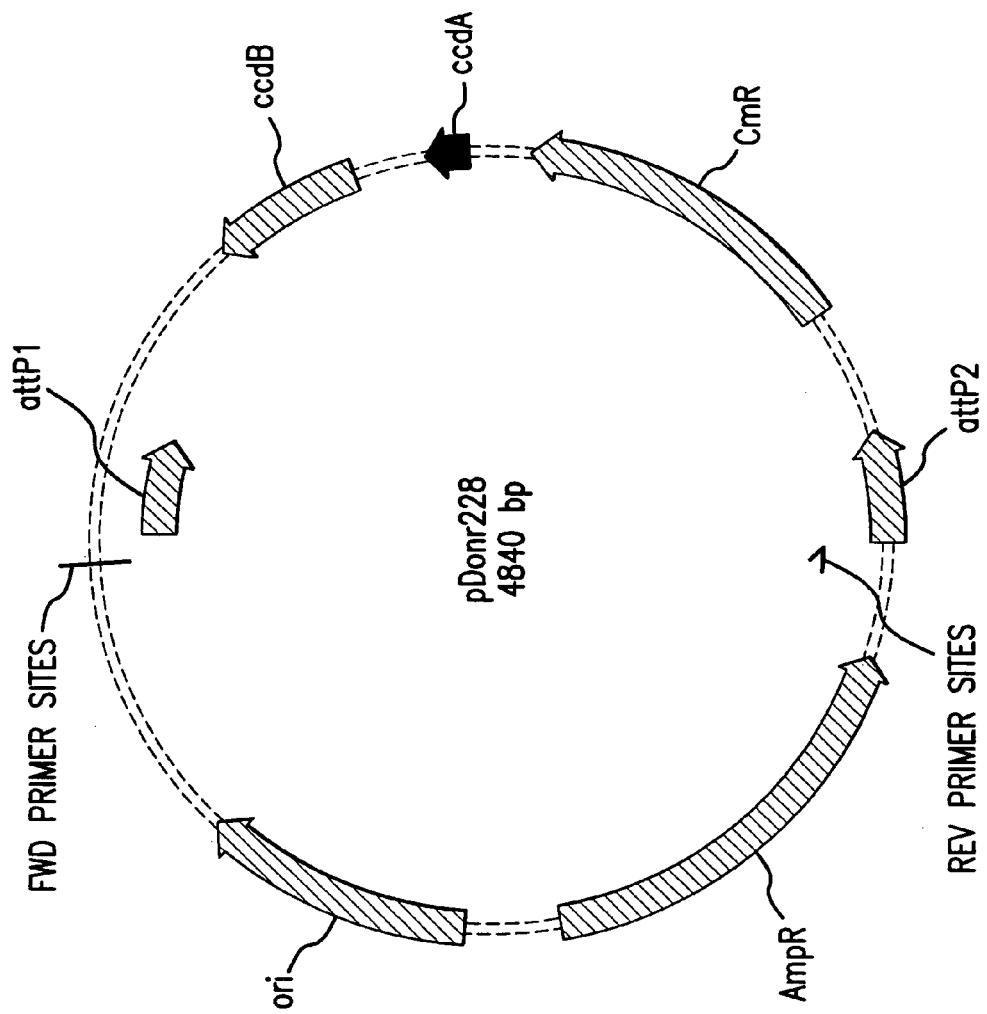
FIG. 10 shows a vector map of pDOR228 and particular features of this vector.

Vector construction. pCR8/GW/TOPO was constructed in sequential steps. First, the attP2 site of pDonor221 was mutated to allow for selective and specific annealing of sequencing primers. Once efficient sequencing from these sites was confirmed, the mutated attP site was subcloned into pDONR 223. Finally, a multiple cloning site was added via BP reaction creating pCR8/GW, which was then T/A TOPO adapted using standard procedures to create pCR8/GW/TOPO (FIG. 8).

T/A TOPO QC testing. The pCR8/GW/TOPO system was tested by TOPO cloning a Platinum taq-generated 500 bp test insert and selected ORFs into pCR8/GW/TOPO. TOPO cloning efficiency was measured using standard QC procedures. The test insert, a 500 bp lacZ-alpha ORF with it's own promoter, cloned efficiently and the vector showed low background. Initially, two lots of supercoiled DNA and adapter oligonucleotides were tested. The standard QC TOPO efficiency cutoff is 95% (5% background). One of the test lots cloned within MFG QC specs (95.1% efficiency) while the other was just under (93.6%) (Table 8). These results show that the system is capable of supporting cloning efficiency within the QC specification but suggest some variation in DNA preparation or adapter oligo quality can affect the outcome.

TABLE 7

T/A TOPO Cloning with pCR8/GW/TOPO

| Vector | Total Blue | Total White | Background (Bl/Bl + Wht.) | Vector Only | Background (Vector only) | Vector conc./ reaction |
|---|---|---|---|---|---|---|
| pCR8 #1 | 17258 | 1193 | 6.4% | 1233 | 6.6% | 13 ng/µl |
| pCR8 #2 | 13356 | 684 | 4.9% | 648 | 4.6% | 10 ng/µl |

Sequencing from pCR8/GW/TOPO. Several inserts were sequenced using the new attL primers (L forward and L reverse) described in "Materials and Methods." While DNA quality had an effect on sequence clarity and length, clean mini-prep DNA generally resulted in clear and long sequencing reads of 600 bp or greater. A representative sequencing reaction result from pCR8/GW/TOPO/CAT is shown in FIG. 6.

Figure 7A:
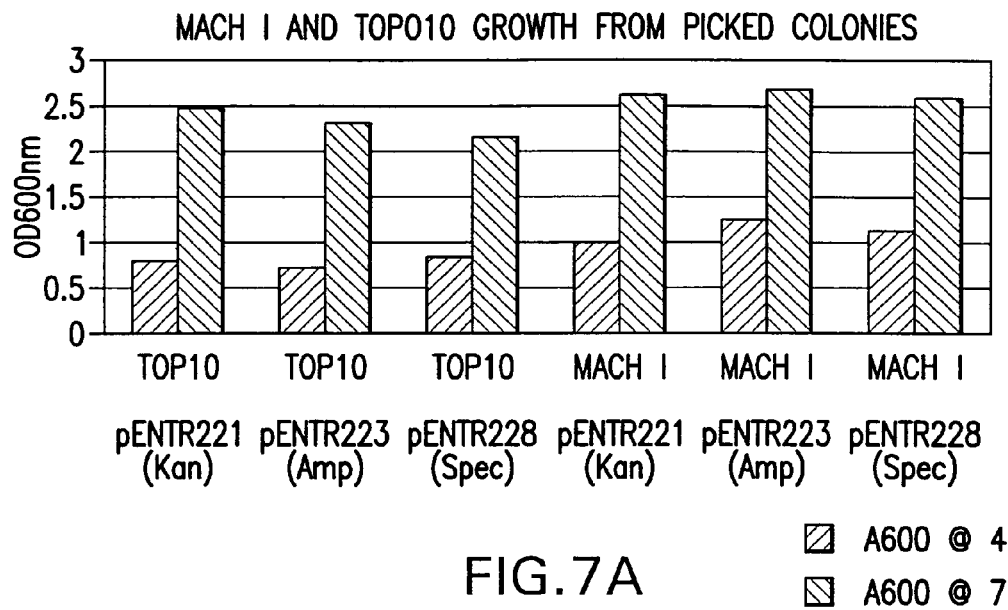

Compatibility of Mach I Cells with spectinomycin selection. One important feature of pCR8/GW/TOPO is that it's propagation is compatible with the Mach I cell strain. This strain is reported to support faster growth of ampicillin resistant plasmids but no data existed that demonstrated Mach I growth with either kanamycin of spectinomycin. The first test of this compatibility was to transform both Mach I and Top10 cells with pENTR vectors (all containing lacI as a test ORF) encoding for kanamycin (pENTR221), ampicillin (pENTR223) and spectinomycin (pENTR228) and check colony growth on solid medium. When culture plates were examined after a 16 hour incubation at 37° C., no significant difference in colony size was noted between selectable markers or between Mach I and TOP10 cells (data not shown). Colonies from these plates were picked and propagated in liquid culture and the optical density was measured at 4.5 and 7 hours (FIG. 7A). In this experiment, Mach I cells supported approximately 30% greater cell density under kanamycin and spectinomycin selection and approximately 40% greater cell density under ampicillin selection after 4.5 hours.

Figure 7B:
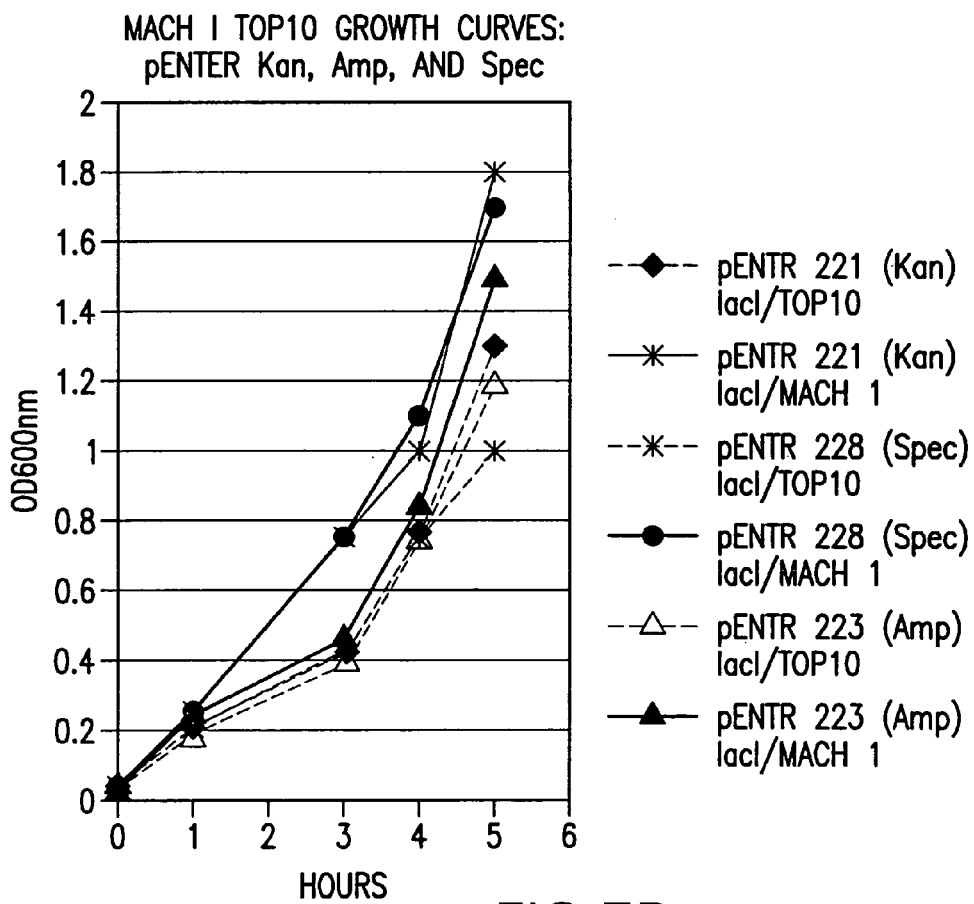

In the next experiment, stationary phase cultures of the Entry vectors described above were normalized to an $O.D._{600}$ of 2.0 then diluted 1/50 into their respective selective media. These cultures were incubated at 37° C. for 5 hours with shaking. Density measurements during the incubation suggested that there was only a modest increase in growth rates gained from propagating these vectors in Mach I cells. Mach I transformants containing pENTR 221 (Kan) and pENTR 228 (Spc) grew at slightly faster rates than did pENTR 223 (Amp) in this experiment (FIG. 7B).

Figure 7C:
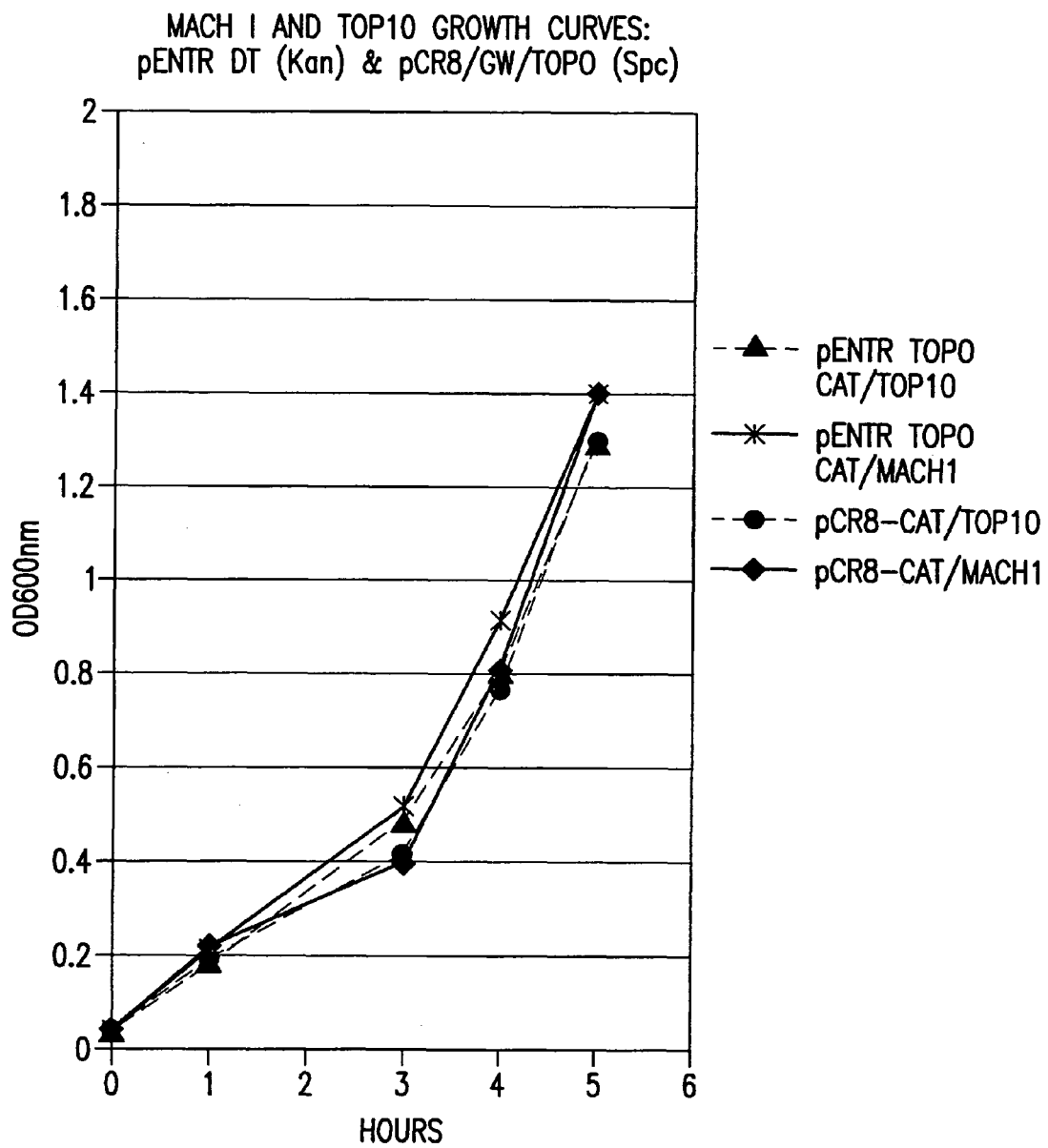

Finally, growth rates of pCR8/GW/TOPO—CAT (Spc) were compared with pENTR D-TOPO-CAT (Kan) in both Mach I and TOP10 cells. In this experiment using normalized cultures as described above, no difference in growth rate was observed between any of the vector/cell combinations tested (FIG. 7C).

Inserts in pCR8/GW/TOPO (along with GUS in pENTR221 (Invitrogen Corporation, Carlsbad, Calif., cat. no. 11824-026) were then transferred to pET-DEST49 (Invitrogen Corp., Carlsbad, Calif., cat. no. 12283-016) via LR recombination. Functionality of the attL sites was confirmed as the total colonies per reaction with pCR8-GUS was essentially identical to the number of colonies obtained from the pENTR221-GUS reaction (Table 8).

TABLE 8

LR Recombination Efficiency with pCR8/GW/TOPO.

| LR reaction | Average colonies/plate | Colonies/reaction |
| --- | --- | --- |
| pENTRGUS × pBAD-DEST49 (1) | 420 | 92400 |
| pENTRGUS × pBAD-DEST49 (2) | 428 | 157247 |
| pCR8-GUS × pBAD-DEST49 (1) | 638 | 234401 |
| pCR8-GUS × pBAD-DEST49 (2) | 483 | 106260 |

Bacterial expression of ORFs transferred from pCR8/GW/TOPO. ORFs encoding CAT and GUS (in both + and − orientation) were transferred to pET-DEST49 for expression in *E. coli* (TOP10). Colonies were cultured and induced to express by addition of arabinose. Aliquots of the resulting cultures were lysed and separated by PAGE. Expression of the ORFs proceeded as expected with only the induced, positive orientation clones producing recombinant protein.

pCR8/GW-CAT and pCR8/GW-GUS (in both orientations) were transferred to pBAD DEST 49 (Invitrogen Corp., Carlsbad, Calif., cat. no. 12283-016) and were tested for expression. pBAD49-CAT and pBAD49-GUS were expressed in TOP10 cells. Cell culture lysates were separated by PAGE and stained.

Example 2

Exemplary Product Literature of the Invention

The PCR product is produced using Taq polymerase and your own protocol. The PCR reaction is ended with a final 7 to 10 minute extension step. Set up one of the following TOPO® Cloning reactions. In a preferred embodiment, the reagents are added in the order shown in Table 9. For electroporation, dilute Salt Solution 4-fold to prepare Dilute Salt Solution.

TABLE 9

| Reagent | Chemical Txn | Electroporation |
| --- | --- | --- |
| Fresh PCR product | 0.5 to 4 µl | 0.5 to 4 µl |
| Salt Solution | 1 µl | — |
| Dilute Salt Solution | — | 1 µl |
| Sterile Water | to a final volume of 5 µl | to a final volume of 5 µl |
| TOPO ® Vector | 1 µl | 1 µl |
| Total volume | 6 µl | 6 µl |

Mix gently and incubate for 5 minutes at room temperature. Place on ice and proceed to transform One Shot® chemically competent *E. coli*, below. For each transformation, thaw one vial of One Shot® *E. coli* cells on ice. Add 2 µl of the TOPO® Cloning reaction into a vial of One Shot® chemically competent *E. coli* and mix gently. Incubate on ice for 5 to 30 minutes. Heat-shock the cells for 30 seconds at 42° C. without shaking. Immediately transfer the tube to ice. Add 250 µl of room temperature S.O.C. Medium. Incubate at 37° C. for 1 hour with shaking. Spread 10-50 µl of bacterial culture on a prewarmed LB agar plate containing 100 µg/ml spectinomycin, and incubate overnight at 37° C. Control reactions are Performed using the Control PCR Template and the Control PCR Primers included with the kit. See the protocol below for instructions.

Kit Contents and Storage

The pCR®8/GW/TOPO® TA Cloning Kit is provided with *One Shot® TOP*10 *Chemically Competent E. coli* or *with One Shot® Mach*1™-*T1$^R$ Chemically Competent E. coli* (Invitrogen Catalog No. K2500-20). Each pCR®8/GW/TOPO® TA Cloning® Kit is shipped on dry ice, and contains two boxes. Box 1 contains pCR®8/GW/TOPO® Reagents and is stored at −20° C. Box 2 contains One Shot® Chemically Competent *E. coli* and is stored at −80° C. The following reagents are supplied with the pCR®8/GW/TOPO® vector (Box 1). Taq polymerase is provided by the user.

TABLE 10

| Item | Concentration | Amount |
| --- | --- | --- |
| pCR ® 8/GW/ TOPO ® vector, TOPO ®-adapted | 5-10 ng/µl linearized plasmid DNA in: 50% glycerol 50 mM Tris-HCl, pH 7.4 (at 25° C.) 1 mM EDTA 1 mM DTT 0.1% Triton X-100 100 µg/ml BSA 30 µM phenol red | 20 µl |
| 10× PCR Buffer | 100 mM Tris-HCl, pH 8.3 (at 42° C.) 500 mM KCl 25 mM MgCl$_2$ 0.01% gelatin | 100 µl |
| dNTP Mix | 12.5 mM dATP 12.5 mM dCTP 12.5 mM dGTP 12.5 mM dTTP neutralized at pH 8.0 in water | 10 µl |
| Salt Solution | 1.2 M NaCl 0.06 M MgCl$_2$ | 50 µl |
| Sterile Water | — | 1 ml |
| GW1 Primer | 0.1 µg/µl in TE Buffer, pH 8.0 | 20 µl |
| GW2 Primer | 0.1 µg/µl in TE Buffer, pH 8.0 | 20 µl |
| Control PCR Primers | 0.1 µg/µl each in TE Buffer, pH 8.0 | 10 µl |
| Control PCR Template | 0.05 µg/µl in TE Buffer, pH 8.0 | 10 µl |

The sequences of the GW1 and GW2 primers are as follows: GW1: 5'-GTTGCAACAAATTGATGAGCAATGC-3' (SEQ ID NO: 2) and GW2: 5'-GTTGCAACAAATTGATGAGCAATTA-3' (SEQ ID NO: 1). 260 pMoles of each primer is supplied. The reagents shown in Table 11 are included with the One Shot® TOP10 or Mach1™-T1$^R$ Chemically Competent *E. coli* kit (Box 2). Transformation efficiency is ≧1×10$^9$ cfu/mg plasmid DNA.

TABLE 11

| Reagent | Composition | Amount |
| --- | --- | --- |
| S.O.C. Medium (may be stored at room temperature or +4° C.) | 2% Tryptone 0.5% Yeast Extract 10 mM NaCl | 6 ml |

TABLE 11-continued

| Reagent | Composition | Amount |
|---|---|---|
| | 2.5 mM KCl | |
| | 10 mM MgCl$_2$ | |
| | 10 mM MgSO$_4$ | |
| | 20 mM glucose | |
| TOP10 or Mach1 ™-T1$^R$cells | — | 21 × 50 µl |
| pUC19 Control DNA | 10 pg/µl in 5 mM Tris-HCl, 0.5 mM EDTA, pH 8 | 50 µl |

The *E. coli* genotypes are as follows: TOP10: F$^-$ mcrA D(mrr-hsdRMS-mcrBC) F80lacZDM15 DlacC74 recA1 araD139 D(ara-leu)7697 galU galK rpsL (Str$^R$) endA1 nupG; Mach1™-T1$^R$: F$^-$ F80lacZDM15 DlacC74 hsdR(r$_k^-$, m$_k^+$) DrecA1398 endA1 tonA (confers resistance to phage T1). The parental strain of Mach1™-T1$^R$ *E. coli* is the non-K-12, wild-type W strain (ATCC #9637, S. A. Waksman). Although the parental strain is generally classified as Biosafety Level 1 (BL-1), it is recommended that you consult the safety department of your institution to verify the Biosafety Level.

The products listed in this section may be used with the pCR®8/GW/TOPO® TA Cloning® Kit. For more information, refer to our Web site (www.invitrogen.com) or call Technical Service. Some of the reagents supplied in the pCR®8/GW/TOPO® TA Cloning® Kit and other reagents suitable for use with the kits are available separately from Invitrogen. Ordering information for these reagents is provided in Table 12. Other reagent quantities may be available.

TABLE 12

| Item | Quantity | Catalog no. |
|---|---|---|
| Platinum ® Taq DNA Polymerase | 100 reactions | 10966-018 |
| | 250 reactions | 10966-026 |
| | 500 reactions | 10966-034 |
| Taq DNA Polymerase, Recombinant | 100 units | 10342-053 |
| | 250 units | 10342-012 |
| | 500 units | 10342-020 |
| Platinum ® Taq DNA Polymerase High Fidelity | 100 units | 11304-011 |
| | 500 units | 11304-029 |
| One Shot ® TOP10 Chemically Competent *E. coli* | 10 reactions | C4040-10 |
| | 20 reactions | C4040-03 |
| One Shot ® TOP10 Electrocompetent *E. coli* | 10 reactions | C4040-50 |
| One Shot ® Mach1 ™-T1$^R$ Chemically Competent *E. coli* | 20 reactions | C8620-03 |
| LB Broth | 500 ml | 10855-021 |
| LB Agar | 500 g | 22700-025 |
| PureLink ™ HQ Mini Plasmid Purification Kit | 100 reactions | K2100-01 |
| Gateway ® LR Clonase ™ Enzyme Mix | 20 reactions | 11791-019 |
| | 100 reactions | 11791-043 |
| Gateway ® LR Clonase ™ Plus Enzyme Mix | 20 reactions | 12538-013 |
| MultiSite Gateway ® Three-Fragment Vector Construction Kit | 1 kit | 12537-023 |

For selection of pCR®8/GW/TOPO® transformants in *E. coli*, you will need to obtain spectinomycin. Spectinomycin Dihydrochloride is available from Sigma (Catalog No. S4014). For a recipe to prepare spectinomycin for use, see below.

The pCR®8/GW/TOPO® TA Cloning® Kit combines Invitrogen's TOPO® Cloning and Gateway® technologies to facilitate 5-minute, one-step cloning of Taq polymerase-amplified PCR products into a plasmid vector with ≧95% efficiency. As is the case with other pCR® vectors (e.g. pCR®2.1-TOPO®), clones may be easily sequenced and characterized. Once characterized, clones may also be transferred from the pCR®08/GW/TOPO® entry vector to a Gateway® or MultiSite Gateway® destination vector of choice for expression of the gene of interest in virtually any system. For more information about how TOPO® Cloning works and the Gateway® and MultiSite Gateway® technologies, see the rest of this section.

Using the pCR®8/GW/TOPO® vector for cloning applications provides the following advantages:

The vector is TOPO®-adapted to allow highly efficient, 5-minute cloning of Taq polymerase-amplified PCR products. No ligase, post-PCR procedures, or restriction enzymes are required.

The vector contains primer binding sites that are located within 55 base pairs of the TOPO® Cloning site to facilitate sequencing of the PCR product while minimizing the amount of vector-encoded DNA that needs to be read.

The vector is Gateway®-adapted to allow easy recombination-based transfer of the PCR product of interest into any Gateway® destination vector for downstream analysis.

EcoRI sites flank the TOPO® Cloning to simplify excision of the cloned PCR product.

The vector contains the spectinomycin resistance marker for efficient selection in *E. coli*. Use of this particular marker also allows recombination-based transfer of the PCR product into ampicillin- or kanamycin-resistant Gateway® destination vectors.

Using the pCR®8/GW/TOPO® vector for cloning applications provides the following advantages:

The vector is TOPO®-adapted to allow highly efficient, 5-minute cloning of Taq polymerase-amplified PCR products. No ligase, post-PCR procedures, or restriction enzymes are required.

The vector contains primer binding sites that are located within 55 base pairs of the TOPO® Cloning site to facilitate sequencing of the PCR product while minimizing the amount of vector-encoded DNA that needs to be read.

The vector is Gateway®-adapted to allow easy recombination-based transfer of the PCR product of interest into any Gateway® destination vector for downstream analysis.

EcoRI sites flank the TOPO® Cloning to simplify excision of the cloned PCR product.

The vector contains the spectinomycin resistance marker for efficient selection in *E. coli*. Use of this particular marker also allows recombination-based transfer of the PCR product into ampicillin- or kanamycin-resistant Gateway® destination vectors.

Features of the pCR®8/GW/TOPO® vector include: TOPO® Cloning site for rapid and efficient cloning of Taq-amplified PCR products (see the next page for more information); attL1 and attL2 sites for recombination-based transfer of the gene of interest into any Gateway® destination vector; specifically designed primer binding sites within the attL1 and attL2 sites for sequencing using the GW1 and GW2 primers; rrnB transcription termination sequences to prevent basal expression of the PCR product of interest in *E. coli*; spectinomycin resistance gene for selection in *E. coli*; and pUC origin for high-copy replication of the plasmid in *E. coli*.

The pCR®8/GW/TOPO® vector is supplied linearized with single 3'-thymidine (T) overhangs for TA Cloning® and topoisomerase I covalently bound to the vector (referred to as "activated" vector). Taq polymerase has a non-template-dependent terminal transferase activity that adds a single deoxyadenosine (A) to the 3' ends of PCR products. The linearized vector supplied in this kit has single, overhanging 3' deoxythymidine (T) residues. This allows PCR inserts to ligate efficiently with the vector.

Topoisomerase I from *Vaccinia* virus binds to duplex DNA at specific sites (CCCTT) and cleaves the phosphodiester backbone in one strand (Shuman, *Proc. Natl. Acad. Sci. U.S.A.* 88:10104-10108, 1991). The energy from the broken phosphodiester backbone is conserved by formation of a covalent bond between the 3' phosphate of the cleaved strand and a tyrosyl residue (Tyr-274) of topoisomerase I. The phosphotyrosyl bond between the DNA and enzyme can subsequently be attacked by the 5' hydroxyl of the original cleaved strand, reversing the reaction and releasing topoisomerase (Shuman, supra., 1994). TOPO® Cloning exploits this reaction to efficiently clone PCR products.

The Gateway® Technology is a universal cloning system that takes advantage of the site-specific recombination properties of bacteriophage lambda (Landy, 1989) to provide a rapid and highly efficient way to move your gene of interest into multiple vector systems. To express your gene of interest using the Gateway® Technology, simply:

1. TOPO® Clone your Taq-amplified PCR product into pCR®8/GW/TOPO® to generate an entry clone.
2. Generate an expression construct by performing an LR recombination reaction between the entry clone and a Gateway® destination vector of choice.
3. Introduce your expression construct into the appropriate host (e.g. bacterial, mammalian, yeast, insect) and express your recombinant protein.

For more information about the Gateway® Technology, refer to the Gateway® Technology manual, or call Technical Service. The Gateway® Technology manual is available for downloading from our Web site or by contacting Technical Service.

Inserts cloned into most Gateway® entry vectors (e.g. pENTR™/D-TOPO®) can be sequenced using M13 forward (−20) and M13 reverse primers. The M13 forward (−20) and M13 reverse primer binding sites are located upstream and downstream of the attL1 and attL2 sites, respectively, requiring that at least 130 base pairs of vector-encoded DNA be read before reaching the insert DNA. To facilitate more efficient sequencing and to minimize the amount of vector-encoded DNA that needs to be read, three nucleotides within the attL2 site of pCR®8/GW/TOPO® have been mutated. This results in the following:

Allows robust and efficient sequencing of inserts cloned into pCR®8/GW/TOPO® using the GW1 and GW2 primers.

The GW1 and GW2 primer binding sites are located within the attL1 and attL2 sites, thereby minimizing the amount of vector-encoded DNA that needs to be read to less than 55 base pairs.

Does not affect the efficiency of LR recombination between pCR®8/GW/TOPO® and Gateway® destination vectors.

The pCR®8/GW/TOPO® vector also contains the M13 forward (−20) and M13 reverse primer binding sites to allow sequencing using the M13 forward (−20) and M13 reverse primers, if desired.

The MultiSite Gateway® Technology uses modifications of the site-specific recombination reactions of the Gateway® Technology (see the previous page) to allow simultaneous cloning of multiple DNA fragments in a defined order and orientation. The MultiSite Gateway® Three-Fragment Vector Construction Kit available from Invitrogen (Catalog no. 12537-023) facilitates simultaneous cloning of DNA fragments in three entry vectors to create your own expression clone. For more information about the MultiSite Gateway® Technology and the MultiSite Gateway® Three-Fragment Vector Construction Kit, refer to the MultiSite Gateway® Three-Fragment Vector Construction Kit manual, which is available for downloading from our Web site or by contacting Technical Service.

Figure 11:
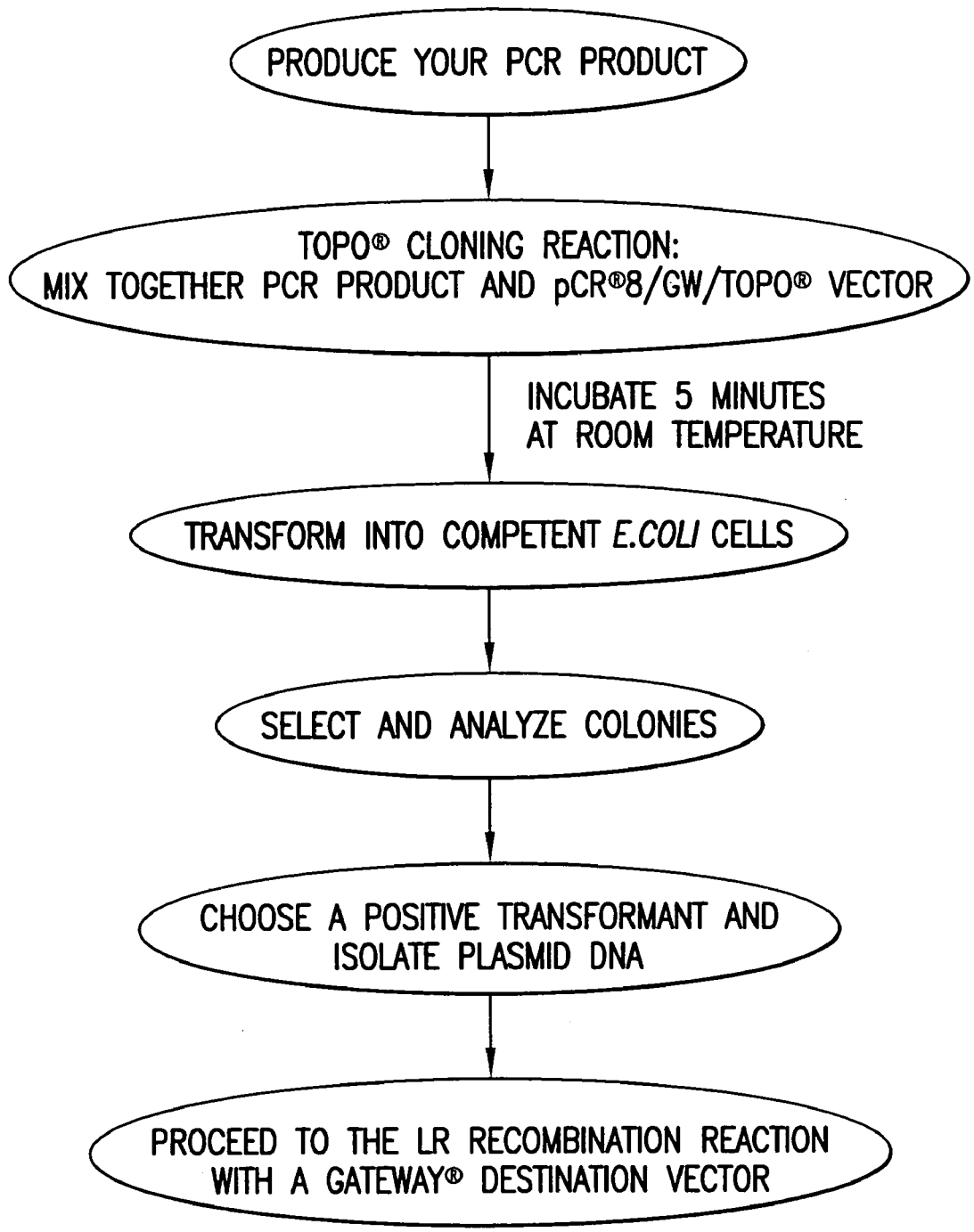
FIG. 11 is a flow chart describing the production and TOPO cloning of a Taq-amplified PCR product.

The flow chart shown in FIG. 11 describes the general steps involved in the production and TOPO cloning of your Taq-amplified PCR product.

Methods

Designing PCR Primers

Before the pCR®8/GW/TOPO® TA Cloning® Kit is used, PCR primers are designed and the PCR product is produced. Guidelines for designing PCR primers are described below. The proper design of PCR primers will ensure that you obtain the PCR product you need for your studies. Consider the following when designing your PCR primers:

If you plan to transfer your PCR product into a Gateway® destination vector for downstream expression studies, remember to include the sequences required for proper translation initiation and termination of your PCR product.

If you wish to fuse your PCR product to an N- or C-terminal tag after recombination of your entry clone with a Gateway® destination vector, remember to design your PCR primers such that your PCR product will be in frame with the appropriate tag (see Tips below). Make sure that the PCR product includes or lacks a Kozak consensus sequence or stop codon, as appropriate to permit proper expression of your recombinant protein. Note that the first three base pairs of the PCR product will constitute a functional codon.

The diagram on the next page may be used to help design your PCR primers and your PCR strategy.

Tips

If you wish to fuse your PCR product to an N- or C-terminal tag after recombination of your entry clone with a destination vector, use the tips below as appropriate to design your forward or reverse PCR primer.

Tip 1: To fuse your PCR product in frame with an N-terminal tag after recombination of your entry clone with a destination vector, keep the -AAA-AAA- triplets in the attL1 site in frame with the translation reading frame of the fusion protein (see bolded nucleotides in the diagram on the next page).

Tip 2: To fuse your PCR product in frame with a C-terminal tag after recombination of your entry clone with a destination vector, keep the -TTT-GTA (TAC-AAA on the complementary strand) triplets in the attL2 site in frame with the translation reading frame of the fusion protein (see bolded nucleotides in the diagram on the next page).

In one embodiment, when synthesizing PCR primers, 5' phosphates should not be added to the primers as this will prevent the synthesized PCR product from ligating into the pCR®8/GW/TOPO® vector.

TOPO® Cloning Site for pCR®8/GW/TOPO®

Figure 12:
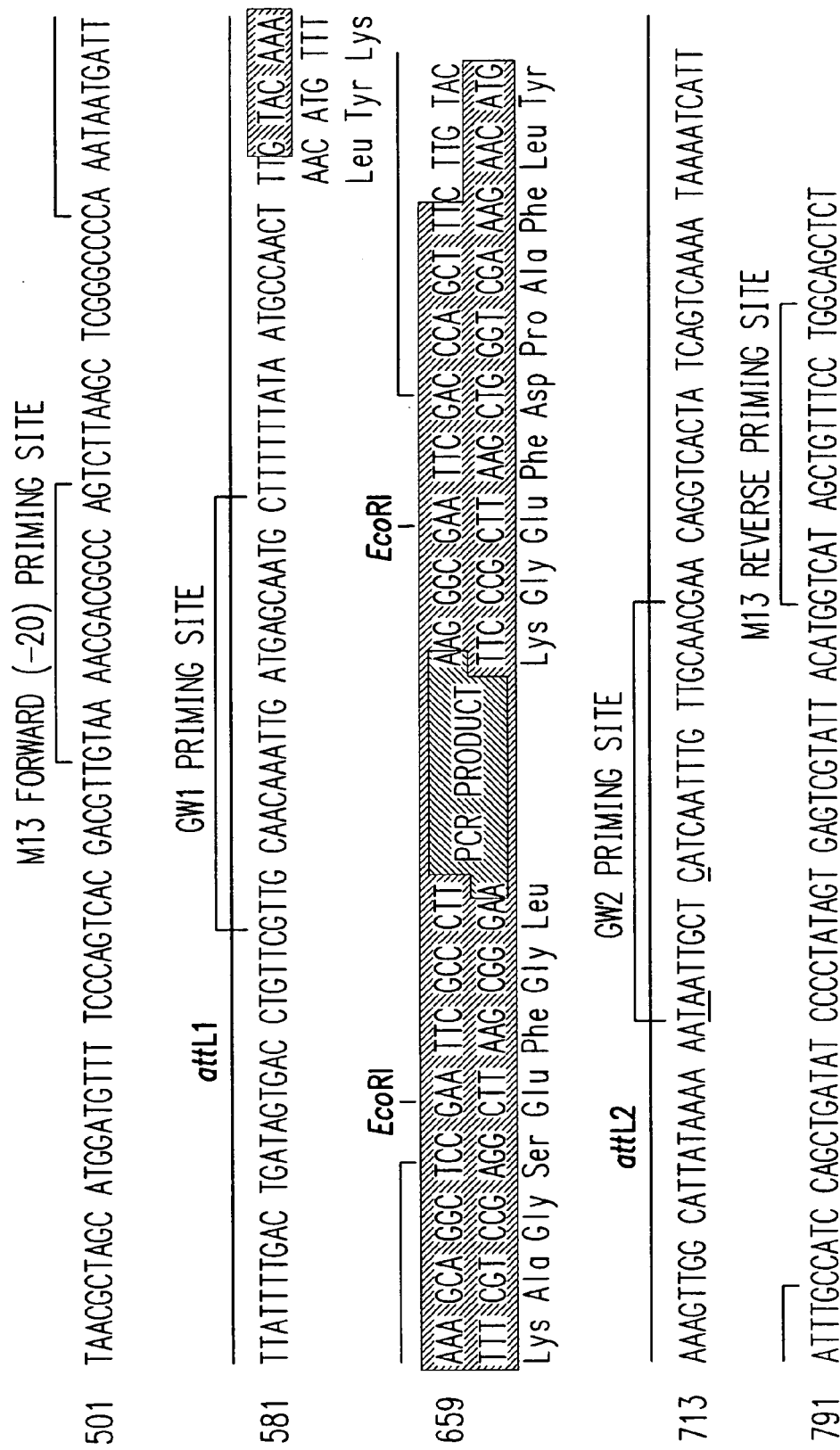
FIG. 12 shows the TOPO® cloning region (SEQ ID NO: 11) of pCR®8/GW/TOPO®. A portion of the protein sequence of the cloning region is also shown. (SEQ ID NO: 72)

The diagram shown in FIG. 12 may be used to help design PCR primers and produce PCR products for TOPO® Cloning into pCR®8/GW/TOPO®.

Features of the TOPO® Cloning Region:

Restriction sites are labeled to indicate the actual cleavage site.

The primer binding sites for the GW1 and GW2 primers included with the kit are labeled. The nucleotides that were mutated in the attL2 site to facilitate sequencing using the GW2 primer are underlined.

The shaded region corresponds to the DNA sequences that will be transferred from the clone into the Gateway® destination vector following LR recombination.

If you plan to fuse your PCR product in frame with an N- or C-terminal tag after recombination with a destination vector, remember to keep the translation reading frame of the fusion protein in frame with the triplets indicated in bold, as appropriate.

The sequence of pCR®8/GW/TOPO® is available for downloading from our Web site (www.invitrogen.com) or by contacting Technical Service. For more information about pCR®8/GW/TOPO®, see below.

Producing PCR Products

Introduction

Once you have synthesized appropriate PCR primers, you may use the primers and a suitable DNA polymerase to produce your PCR product. In a referred embodiment, the PCR product has single 3' A-overhangs.

Materials Supplied by the User

The following reagents and equipment are used for PCR. dNTPs (adjusted to pH 8) are provided in the kit.

Taq polymerase or other suitable DNA polymerase

Note: In one embodiment, Platinum® Taq DNA Polymerase available from Invitrogen is used to generate the PCR product.

Thermocycler

DNA template and primers to produce the PCR product.

Polymerase Mixtures

A polymerase mixture containing Taq polymerase and a proofreading polymerase may be used to produce the PCR product. In a preferred embodiment, the mixture contains a ratio of Taq polymerase:proofreading polymerase in excess of 10:1 to ensure the presence of 3' A-overhangs on the PCR product. Platinum® Taq DNA Polymerase High Fidelity (Invitrogen) may be used. If polymerase mixtures that do not have enough Taq polymerase are used or a proofreading polymerase only, 3' A-overhangs may be added to the PCR product using the method described below.

Producing PCR Products

Set up the following 50 µl PCR reaction: 10-100 ng DNA template, 5 µl 10× PCR buffer, 0.5 µl dNTP mix (50 mM), PCR primers (100-200 ng each), sterile water to a final volume of 49 µl and Taq polymerase (1 U/µl) for a total volume of 50 µl. Use less DNA if you are using plasmid DNA as a template and more DNA if you are using genomic DNA as a template. Use the cycling parameters suitable for your primers and template. A 7 to 30 minute extension at 72° C. is performed after the last cycle to ensure that all PCR products are full-length and 3' adenylated.

Electrophoresis, for example agarose gel electrophoresis, is used to verify the quality of your PCR product. You should see a single, discrete band of the correct size. If you do not obtain a single, discrete band from your PCR, optimize your PCR to eliminate multiple bands and smearing (Innis et al., PCR Protocols: A Guide to Methods and Applications, Academic Press, San Diego, 1990). The PCR Optimizer™ Kit available from Invitrogen (Catalog no. K1220-01) incorporates many of the recommendations found in this reference. For more information contact Technical Service. Gel-purify your fragment using, for example, one of the methods provided below. Take special care to avoid sources of nuclease contamination.

Setting Up the TOPO® Cloning Reaction

Introduction

Once you have produced the desired PCR product, you are ready to TOPO® Clone it into the pCR®8/GW/TOPO® vector and transform the recombinant vector into One Shot® competent E. coli. You should have everything you need set up and ready to use to ensure that you obtain the best possible results. We suggest that you read this section and the section entitled Transforming One Shot® Competent E. coli (below) before beginning. If this is the first time you have TOPO® Cloned, perform the control reactions described herein in parallel with your samples.

It has been found that including salt (200 mM NaCl, 10 mM $MgCl_2$) in the TOPO® Cloning reaction can increase the number of transformants 2- to 3-fold. In addition, incubating the reaction mixture for greater than 5 minutes in the presence of salt can also increase the number of transformants. This is in contrast to earlier experiments without salt where the number of transformants decreases as the incubation time increases beyond 5 minutes. Including salt in the TOPO® Cloning reaction allows for longer incubation times because it prevents topoisomerase I from rebinding and potentially nicking the DNA after ligating the PCR product and dissociating from the DNA. The result is more intact molecules, leading to higher transformation efficiencies.

Using Salt Solution in the TOPO® Cloning Reaction

You will perform TOPO® Cloning in a reaction buffer containing salt (i.e. using the stock salt solution provided in the kit). Note that the amount of salt added to the TOPO® Cloning reaction varies depending on whether you plan to transform chemically competent cells (provided) or electrocompetent cells. If you are transforming chemically competent E. coli, use the stock Salt Solution as supplied and set up the TOPO® Cloning reaction as directed on the next page. If you are transforming electrocompetent E. coli, the amount of salt in the TOPO® Cloning reaction may be reduced to 50 mM NaCl, 2.5 mM $MgCl_2$ to prevent arcing during electroporation. Dilute the stock Salt Solution 4-fold with water to prepare a 300 mM NaCl, 15 mM $MgCl_2$ Dilute Salt Solution. Use the Dilute Salt Solution to set up the TOPO® Cloning reaction as directed on the next page.

Materials Needed

You should have the following materials on hand before beginning:

Your PCR product (freshly prepared)

pCR®8/GW/TOPO® vector (supplied with the kit, Box 1; keep at −20° C. until use)

Salt Solution (supplied with the kit, Box 1) or Dilute Salt Solution as appropriate Sterile water (supplied with the kit, Box 1)

Performing the TOPO® Cloning Reaction

The procedure below may be used to perform the TOPO® Cloning reaction. Set up the TOPO® Cloning reaction using the reagents shown in Table 13, and depending on whether you plan to transform chemically competent E. coli or electrocompetent E. coli. In a preferred embodiment, the reagents are combined in the order shown. The red color of the TOPO® vector solution is normal and is used to visualize the solution.

TABLE 13

| Reagent* | Chemically Competent E. coli | Electrocompetent E. coli |
|---|---|---|
| Fresh PCR product | 0.5 to 4 μl | 0.5 to 4 μl |
| Salt Solution | 1 μl | — |
| Dilute Salt Solution (1:4) | — | 1 μl |
| Sterile Water | add to a final volume of 5 μl | add to a final volume of 5 μl |
| TOPO ® vector | 1 μl | 1 μl |
| Final volume | 6 μl | 6 μl |

*Store all reagents at −20° C. when finished. Salt solution and water can be stored at room temperature or +4° C.

Mix reaction gently and incubate for 5 minutes at room temperature (22-23° C.). For most applications, 5 minutes will yield a sufficient number of colonies for analysis. Depending on your needs, the length of the TOPO® Cloning reaction can be varied from 30 seconds to 30 minutes. For routine subcloning of PCR products, 30 seconds may be sufficient. For large PCR products (>1 kb) or if you are TOPO® Cloning a pool of PCR products, increasing the reaction time may yield more colonies. Place the reaction on ice and proceed to Transforming One Shot® Competent E. coli, as described below. You may store the TOPO® Cloning reaction at −20° C. overnight.

Transforming One Shot® Competent E. coli

Introduction

Once you have performed the TOPO® Cloning reaction, you will transform your pCR®8/GW/TOPO® construct into competent E. coli. One Shot® TOP10 or Mach1™-T1$^R$ Chemically Competent E. coli (Box 2) are included with the kit to facilitate transformation. You may also transform electrocompetent cells, if desired. Protocols to transform chemically competent or electrocompetent E. coli are provided in this section.

Selecting a One Shot® Chemical Transformation Protocol

Two protocols are provided to transform One Shot® TOP10 or Mach1™-T1$^R$ chemically competent E. coli. Consider the following factors and choose the protocol that best suits your needs. If you wish to maximize the number of transformants or clone large PCR products (>1000 bp), the regular chemical transformation protocol is used. If you wish to obtain transformants as quickly as possible, the rapid chemical transformation protocol is used, although the total number of transformants obtained may be lower than with the chemical transformation protocol.

Materials Needed

In addition to general microbiological supplies (i.e. plates, spreaders), you will need the following reagents and equipment:

TOPO® Cloning reaction (from Step 2, previous page)
One Shot® TOP10 or Mach1™-T1$^R$ chemically competent E. coli (supplied with the kit, Box 2)
S.O.C. Medium (included with the kit, Box 2)
pUC19 positive control (to verify transformation efficiency, if desired, Box 2)
42° C. water bath (or electroporator with cuvettes, optional)
15 ml sterile, snap-cap plastic culture tubes (for electroporation only)
LB plates containing 100 μg/ml spectinomycin (two for each transformation)
LB plates containing 100 μg/ml ampicillin (if transforming pUC19 control)
37° C. shaking and non-shaking incubator There is no blue-white screening for the presence of inserts. Most transformants will contain recombinant plasmids with the PCR product of interest cloned into the vector. The GW1 and GW2 primers are included in the kit to allow you to sequence across an insert in the TOPO® Cloning site to confirm orientation and reading frame.

For each transformation, you will need one vial of One Shot® competent cells and two selective plates.

Equilibrate a water bath to 42° C. (for chemical transformation) or set up your electroporator if you are using electrocompetent E. coli.

Warm the vial of S.O.C. Medium from Box 2 to room temperature.

Warm LB plates containing 100 μg/ml spectinomycin at 37° C. for 30 minutes. If you are including the pUC19 positive control, prewarm LB plates containing 100 μg/ml ampicillin as well.

Thaw on ice one vial of One Shot® cells for each transformation. If you are performing the rapid chemical transformation protocol, your LB plates containing 100 μg/ml spectinomycin should be prewarmed prior to spreading.

The following protocol is used to transform One Shot® TOP10 or Mach1™-T1$^R$ chemically competent E. coli.

1. Add 2 μl of the TOPO® Cloning reaction from Performing the TOPO® Cloning Reaction into a vial of One Shot® Chemically Competent E. coli and mix gently. Do not mix by pipetting up and down. If you are transforming the pUC19 control plasmid, use 10 pg (1 μl).
2. Incubate on ice for 5 to 30 minutes. Longer incubations on ice seem to have a minimal effect on transformation efficiency. The length of the incubation is at the user's discretion. Longer incubations on ice seem to have a minimal effect on transformation efficiency. The length of the incubation is at the user's discretion.
3. Heat-shock the cells for 30 seconds at 42° C. without shaking.
4. Immediately transfer the tubes to ice.
5. Add 250 μl of room temperature S.O.C. Medium.
6. Cap the tube tightly and shake the tube horizontally (200 rpm) at 37° C. for 1 hour.
7. Spread 10-50 μl from each transformation on a prewarmed selective plate and incubate overnight at 37° C. To ensure even spreading of small volumes, add 20 μl of S.O.C. Medium. We recommend that you plate two different volumes to ensure that at least one plate will have well-spaced colonies.
8. An efficient TOPO® Cloning reaction should produce several hundred colonies. Pick 10 colonies for analysis (see "Analyzing Transformants").

Rapid One Shot® Chemical Transformation Protocol

The alternative protocol below is used to rapidly transform One Shot® TOP10 or Mach1™-T1$^R$ chemically competent

*E. coli*. Before beginning, LB agar plates containing 100 µg/ml spectinomycin are prewarmed at 37° C. for 30 minutes.

1. Add 4 µl of the TOPO® Cloning reaction from "Performing the TOPO® Cloning Reaction", Step 2 into a vial of One Shot® Chemically Competent *E. coli* and mix gently. Do not mix by pipetting up and down.
2. Incubate on ice for 5 minutes.
3. Spread 50 µl of cells on a prewarmed selective plate and incubate overnight at 37° C.
4. An efficient TOPO® Cloning reaction should produce several hundred colonies. Pick 10 colonies for analysis (see Analyzing Transformants).

One Shot® Electroporation Protocol

It is preferred that electrocompetent cells be used for electroporation to avoid arcing. One Shot® TOP10 or Mach1™-T1$^R$ chemically competent cells are not used for electroporation.

1. Add 2 µl of the TOPO® Cloning reaction from "Performing the TOPO® Cloning Reaction", Step 2, into a sterile microcentrifuge tube containing 50 µl of electrocompetent *E. coli* and mix gently. Do not mix by pipetting up and down. Avoid formation of bubbles. Transfer the cells to a 0.1 cm cuvette.
2. Electroporate your samples using your own protocol and your electroporator.
If you have problems with arcing, see below.
3. Immediately add 250 µl of room temperature S.O.C. Medium.
4. Transfer the solution to a 15 ml snap-cap tube (i.e. Falcon) and shake for at least 1 hour at 37° C. to allow expression of the spectinomycin resistance gene.
5. Spread 10-50 µl from each transformation on a prewarmed selective plate and incubate overnight at 37° C. To ensure even spreading of small volumes, add 20 µl of S.O.C. Medium. We recommend that you plate two different volumes to ensure that at least one plate will have well-spaced colonies.

An efficient TOPO® Cloning reaction should produce several hundred colonies. Pick 10 colonies for analysis (see Analyzing Transformants).

Analyzing Transformants
Analyzing Positive Clones

Pick 10 colonies and culture them overnight in LB or SOB medium containing 100 µg/ml spectinomycin. If you transformed One Shot® Mach1™-T1$^R$ competent *E. coli*, you may inoculate overnight-grown colonies and culture them for only 4 hours in pre-warmed LB medium containing 100 µg/ml spectinomycin before isolating plasmid. For optimal results, we recommend inoculating as much of a single colony as possible. Isolate plasmid DNA using your method of choice. If you need ultra-pure plasmid DNA for automated or manual sequencing, we recommend using Invitrogen's PureLink™ HQ Mini Plasmid Purification Kit (Catalog no. K2100-01). Analyze the plasmids by, for example, restriction analysis or PCR to confirm the presence and correct orientation of the insert. pCR®8/GW/TOPO® contains EcoRI sites flanking the TOPO® Cloning site. You may use EcoRI digestion to check for the presence of inserts, if desired.

Sequencing

Once you have identified the correct clone(s), you may sequence your construct to confirm that your gene is cloned in the correct orientation. The GW1 and GW2 primers are included in the kit to help you sequence your. For the complete sequence of the pCR®8/GW/TOPO® vector, see Table 11, or call Technical Service.

The GW1 and GW2 primer sites are located less than 55 nucleotides from the PCR product insertion site, and fall within the attL1 and attL2 sites, respectively of pCR®8/GW/TOPO®. Although Invitrogen offers other Gateway® entry vectors containing attL1 and attL2 sites, the GW1 and GW2 primers are only suitable for use in sequencing inserts cloned into pCR®8/GW/TOPO®. This is because three nucleotides within the attL2 site in pCR®8/GW/TOPO® have been mutated. These mutations allow GW1 and GW2 primer-based sequencing, but do not affect the LR recombination efficiency.

Long-Term Storage

Once you have identified the correct clone, be sure to purify the colony and make a glycerol stock for long-term storage at −20° C.

1. Streak the original colony out for single colonies on an LB plate containing 100 µg/ml spectinomycin.
2. Isolate a single colony and inoculate into 1-2 ml of LB containing 100 µg/ml spectinomycin.
3. Grow until culture reaches stationary phase.
4. Mix 0.85 ml of culture with 0.15 ml of sterile glycerol and transfer to a cryovial.

Store at −80° C.

Guidelines to Perform the LR Recombination Reaction
Introduction

Once you have obtained your entry clone, you may perform an LR recombination reaction using Gateway® LR Clonase™ enzyme mix (Invitrogen Catalog No.11789-013) to transfer your gene of interest from the pCR®8/GW/TOPO® construct into any Gateway® destination vector of choice to generate an expression clone. In addition, you may perform a MultiSite Gateway® LR recombination reaction with 5' and 3' entry clones, the appropriate MultiSite Gateway® destination vector, and LR Clonase™ Plus enzyme mix (Invitrogen Catalog No. 12538-013) to generate an expression clone. General guidelines are provided below.

For most applications the LR recombination reaction or the MultiSite Gateway® LR recombination reaction is performed using Supercoiled entry clone(s) or Supercoiled destination vector. A large selection of Gateway® destination vectors is available from Invitrogen to facilitate expression of your gene of interest in virtually any protein expression system. For more information about the vectors available call Technical Service. Manuals supporting all of the destination vectors are available for downloading from our Web site or by contacting Technical Service.

*E. coli* Host

Once you have performed the LR recombination reaction or the MultiSite Gateway® LR recombination reaction, you will transform the reaction mixture into competent *E. coli* and select for expression clones. You may use any recA, endA *E. coli* strain including TOP10, Mach1™-T1$^R$, DH5α™, DH10B™, or equivalent for transformation. Do not transform the Gateway® or MultiSite Gateway® LR reaction mixture into *E. coli* strains that contain the F' episome (e.g. TOP10F'). These strains contain the ccdA gene and will prevent negative selection with the ccdB gene.

Performing the LR Recombination Reaction

To perform the Gateway® LR recombination reaction, you will need:

Purified plasmid DNA of the entry clone containing your gene of interest
A destination vector of choice
LR Clonase™ enzyme mix
5× LR Clonase™ Reaction Buffer (supplied with the LR Clonase™ enzyme mix)
2 µg/µl Proteinase K solution (supplied with the LR Clonase™ enzyme mix)
TE Buffer, pH 8.0 (10 mM Tris-HCl, pH 8.0, 1 mM EDTA)

Appropriate chemically competent *E. coli* host and growth media for expression

Appropriate selective plates

For instructions to perform the LR recombination reaction, refer to the Gateway® Technology manual or to the manual for the destination vector you are using.

Performing the MultiSite Gateway® LR Recombination Reaction

Before you can perform the MultiSite Gateway® LR recombination reaction, you will first need to generate 5' and 3' entry clones using Invitrogen's MultiSite Gateway® Three-Fragment Vector Construction Kit (Catalog no. 12537-023). Once you have generated the 5' and 3' entry clones, you will use the 5' and 3' entry clones, the entry clone containing your gene of interest, and the other reagents supplied in the MultiSite Gateway® Three-Fragment Vector Construction Kit (including LR Clonase™ Plus enzyme mix and the pDEST™R4-R3 destination vector) in a MultiSite Gateway® LR recombination reaction to generate an expression clone. For instructions to generate 5' and 3' entry clones and to perform the MultiSite Gateway® LR recombination reaction, refer to the MultiSite Gateway® Three-Fragment Vector Construction Kit manual.

Troubleshooting

TOPO® Cloning Reaction and Transformation

Table 14 lists some potential problems and possible solutions that may help you troubleshoot the TOPO® Cloning and transformation reactions. To help evaluate your results, we recommend that you perform the control reactions (see below) in parallel with your samples.

TABLE 14

| Problem | Reason | Solution |
|---|---|---|
| Few or no colonies obtained from sample reaction and the transformation control gave colonies | Incomplete extension during PCR | Include a final extension step of 7 to 30 minutes during PCR. Longer PCR products will need a longer extension time. |
| | Excess (or overly dilute) PCR product used in the TOPO ® Cloning reaction | Reduce (or concentrate) the amount of PCR product. |
| | PCR primers contain 5' phosphates | Do not add 5' phosphates to your PCR primers. |
| | Used a proofreading polymerase or a Taq/proofreading polymerase mixture for PCR | Use Taq polymerase or another DNA polymerase that leaves 3' A-overhangs to produce your PCR product. Add 3' A-overhangs to your blunt PCR product by incubating with Taq poly-merase. |
| | Large PCR product | Increase the amount of PCR product used in the TOPO ® Cloning reaction. Increase the incubation time of the TOPO ® Cloning reaction from 5 minutes to 30 minutes. Gel-purify the PCR product to remove primer-dimers and other artifacts. |
| | PCR reaction contains artifacts (i.e. does not run as a single band on an agarose gel) | Optimize your PCR conditions. Gel-purify your PCR product. |
| | Cloning large pool of PCR products or a toxic gene | Increase the incubation time of the TOPO ® reaction from 5 minutes to 30 minutes. |
| Few or no colonies obtained from sample reaction and the transformation control gave colonies, continued | PCR product does not contain sufficient 3' A-overhangs even though you used Taq polymerase | Increase the final extension time to ensure that all 3' ends are adenylated. Taq polymerase is most efficient at adding a non-template 3' A next to a C, and less efficient at adding a nontemplate 3' A next to another A. You may have to re-design your primers so that they contain a 5' G instead of a 5' T (Brownstein et al. Bio Techniques 20: 1004-1010, 1996). |
| Large number of incorrect inserts cloned | PCR cloning artifacts | Gel-purify your PCR product to remove primer-dimers and smaller PCR products. Optimize your PCR conditions. Include a final extension step of 7 to 30 minutes during PCR. Longer PCR products will need a longer extension time. |

TABLE 14-continued

| Problem | Reason | Solution |
|---|---|---|
| Few or no colonies obtained from sample reaction and the transformation control gave no colonies | One Shot ® competent E. coli stored incorrectly | Store One Shot ® competent E. coli at −80° C. If you are using another E. coli strain, follow the manufacturer's instructions. |
| | Did not perform the 1 hour grow-out period before plating the transformation mixture | After the heat-shock step, add S.O.C. Medium and incubate the transformation mixture for 1 hour at 37° C. before plating. |
| | Insufficient amount of E. coli plated | Increase the amount of E. coli plated. |
| | Transformants plated on selective plates containing the wrong antibiotic | Use the appropriate antibiotic for selection. |

Performing the Control Reactions

We recommend performing the following control TOPO® Cloning reactions the first time you use the kit to help you evaluate your results. Performing the control reactions involves producing a control PCR product containing the lac promoter and the LacZα fragment using the reagents included in the kit. Successful TOPO® Cloning of the control PCR product in either direction will yield blue colonies on LB agar plates containing spectinomycin and X-gal. For each transformation, prepare two LB plates containing 100 µg/ml spectinomycin and X-gal (recipes provided herein). Use the procedure below to produce the 500 bp control PCR product using Taq polymerase.

1. In a 0.5 ml microcentrifuge tube, set up the 50 µl PCR reaction shown in Table 15:

TABLE 15

| Reagent | Amount |
|---|---|
| Control DNA Template (50 ng) | 1 µl |
| 10× PCR Buffer | 5 µl |
| dNTP Mix | 0.5 µl |
| Control PCR Primers (0.1 µg/µl each) | 1 µl |
| Sterile water | 41.5 µl |
| Taq polymerase (1 U/µl) | 1 µl |
| Total volume | 50 µl |

2. Overlay with 70 µl (1 drop) of mineral oil, if required.
3. Amplify using the following cycling parameters Table 16:

TABLE 16

| Step | Time | Temperature | Cycles |
|---|---|---|---|
| Initial Denaturation | 2 minutes | 94° C. | 1X |
| Denaturation | 1 minute | 94° C. | 25X |
| Annealing | 1 minute | 60° C. | |
| Extension | 1 minute | 72° C. | |
| Final Extension | 7 minutes | 72° C. | 1X |

4. Remove 10 µl from the reaction and analyze by agarose gel electrophoresis. A discrete 500 bp band should be visible. Proceed to the "Control TOPO® Cloning Reactions" as described below.

Control TOPO® Cloning Reactions

Using the control PCR product produced on the previous page and the pCR®8/GW/TOPO® vector, set up two 6 µl TOPO® Cloning reactions as described below.

1. Set up control TOPO® Cloning reactions (Table 17):

TABLE 17

| Reagent | "Vector Only" | "Vector + PCR Insert" |
|---|---|---|
| Sterile Water | 4 µl | 3 µl |
| Salt Solution | 1 µl | 1 µl |
| Control PCR Product | — | 1 µl |
| pCR ® 8/GW/TOPO ® vector | 1 µl | 1 µl |
| Total volume | 6 µl | 6 µl |

2. Incubate at room temperature for 5 minutes and place on ice.
3. Transform 2 µl of each reaction into separate vials of One Shot® competent cells using the procedure described above.
4. Spread 10-50 µl of each transformation mix onto LB plates containing 100 µg/ml spectinomycin and X-gal. When plating small volumes, add 20 µl of S.O.C. Medium to ensure even spreading. Be sure to plate two different volumes to ensure that at least one plate has well-spaced colonies.
5. Incubate overnight at 37° C.

What You Should See

The "vector+PCR insert" reaction should be produce hundreds of colonies. Greater than 95% of these will be blue. The "vector only" reaction should yield very few colonies (<5% of the vector+PCR insert plate) and these should be white.

Transformation Control pUC19 plasmid is included to check the transformation efficiency of the One Shot® TOP10 or Mach1™-T1$^R$ competent cells. Transform one vial of One Shot® TOP10 or Mach1™-T1$^R$ cells with 10 pg of pUC19 using the protocol described above. Plate 10 µl of the transformation mixture plus 20 µl of S.O.C. Medium on LB plates containing 100 µg/ml ampicillin. Transformation efficiency should be ≧ 1×10$^9$ cfu/µg DNA.

Gel Purifying PCR Products

Introduction

Smearing, multiple banding, primer-dimer artifacts, or large PCR products (>3 kb) may necessitate gel purification. If you wish to purify your PCR product, be extremely careful to remove all sources of nuclease contamination. There are many protocols to isolate DNA fragments or remove oligonucleotides. Refer to Current Protocols in Molecular Biology, Unit 2.6 (Ausubel et al., Current Protocols in Molecular Biology, Greene Publishing and Wiley Interscience, New York, 1994) for the most common protocols. Three simple protocols are provided below. The cloning efficiency may decrease with purification of the PCR product (e.g. PCR product too dilute). You may wish to optimize your PCR to produce a single band (see "Producing PCR Products", above).

Using the S.N.A.P.™ Gel Purification Kit

The S.N.A.P.™ Gel Purification Kit available from Invitrogen (Catalog no. K1999-25) allows you to rapidly purify PCR products from regular agarose gels.

1. Electrophorese amplification reaction on a 1 to 5% regular TAE agarose gel. Do not use TBE to prepare agarose gels. Borate interferes with the sodium iodide step, below.
2. Cut out the gel slice containing the PCR product and melt it at 65° C. in 2 volumes of the 6 M sodium iodide solution.
3. Add 1.5 volumes Binding Buffer.
4. Load solution (no more than 1 ml at a time) from Step 3 onto a S.N.A.P.™ column. Centrifuge 1 minute at 3000 ×g in a microcentrifuge and discard the supernatant.
5. If you have solution remaining from Step 3, repeat Step
6. Add 900 µl of the Final Wash Buffer.
7. Centrifuge 1 minute at full speed in a microcentrifuge and discard the flow-through.
8. Repeat Step 7.
9. Elute the purified PCR product in 40 µl of TE or sterile water. Use 4 µl for the TOPO® Cloning reaction.

Quick S.N.A.P.™ Method

An even easier method is to simply cut out the gel slice containing your PCR product, place it on top of the S.N.A.P.™ column bed, and centrifuge at full speed for 10 seconds. Use 1-2 µl of the flow-through in the TOPO® Cloning reaction. The gel slice should be as small as possible for best results.

Low-Melt Agarose Method

If you prefer to use low-melt agarose, use the procedure below. Note that gel purification will result in a dilution of your PCR product and a potential loss of cloning efficiency.
1. Electrophorese as much as possible of your PCR reaction on a low-melt agarose gel (0.8 to 1.2%) in TAE buffer.
2. Visualize the band of interest and excise the band.
3. Place the gel slice in a microcentrifuge tube and incubate the tube at 65° C. until the gel slice melts.
4. Place the tube at 37° C. to keep the agarose melted.
5. Add 4 µl of the melted agarose containing your PCR product to the TOPO® Cloning reaction as described herein.
6. Incubate the TOPO® Cloning reaction at 37° C. for 5 to 10 minutes. This is to keep the agarose melted.
7. Transform 2 to 4 µl directly into One Shot® competent cells using the method described herein.

The cloning efficiency may decrease with purification of the PCR product. You may wish to optimize your PCR to produce a single band.

Addition of 3' A-Overhangs Post-Amplification

Introduction

Direct cloning of DNA amplified by proofreading polymerases into TOPO TA Cloning® vectors is often difficult because proofreading polymerases remove the 3' A-overhangs necessary for TA Cloning®. Invitrogen has developed a simple method to clone these blunt-ended fragments. You will need Taq polymerase, a heat block equilibrated to 72° C., and optionally one or more of the following: phenol-chloroform, 3 M sodium acetate, 100% ethanol, 80% ethanol and TE buffer.

Procedure

This is just one method for adding 3' adenines. Other protocols may be suitable.

16. After amplification with a proofreading polymerase, place vials on ice and add 0.7-1 unit of Taq polymerase per tube. Mix well. It is not necessary to change the buffer. A sufficient number of PCR products will retain the 3' A-overhangs.
17. Incubate at 72° C. for 8-10 minutes (do not cycle).
18. Place on ice and use immediately in the TOPO® Cloning reaction.

If you plan to store your sample overnight before proceeding with TOPO® Cloning, extract your sample with an equal volume of phenol-chloroform to remove the polymerases. Ethanol-precipitate the DNA and resuspend in TE buffer using the starting volume of the PCR. You may also gel-purify your PCR product after amplification with a proofreading polymerase. After purification, add Taq polymerase buffer, dATP, and 0.5 unit of Taq polymerase. Incubate the reaction for 10-15 minutes at 72° C. and use in the TOPO® Cloning reaction.

Features of pCR®8/GW/TOPO® pCR®8/GW/TOPO® (2817 bp) contains the following elements (Table 18). All features have been functionally tested.

TABLE 18

| Feature | Benefit |
| --- | --- |
| rrnB T1 and T2 transcription termination sequences | Reduces potential toxicity in *E. coli* by preventing basal expression of the PCR product. |
| M13 forward (−20) priming site | Allows sequencing of the insert. |
| GW1 priming site | Allows sequencing of the insert. |
| attL1 and attL2 sites | Bacteriophage λ-derived recombination sequences that allow recombinational cloning of a gene of interest in the entry construct with a Gateway ® destination vector (Landy, Ann. Rev. Biochem. 58: 913–949, 1989). |
| TOPO ® Cloning site | Allows rapid cloning of your Taq-amplified PCR product. |
| GW2 priming site | Allows sequencing of the insert. |
| M13 reverse priming site | Allows sequencing of the insert. |
| Spectinomycin promoter | Allows expression of the spectinomycin resistance gene in *E. coli*. |
| Spectinomycin resistance gene (aadA1) | Allows selection of the plasmid in *E. coli* (Liebert et al., 1999). |
| pUC origin of replication (ori) | Allows high-copy replication and maintenance in *E. coli*. |

Recipes

LB (Luria-Bertani) Medium and Plate

Composition: 1.0% Tryptone, 0.5% yeast extract, 1.0% NaCl. pH 7.0. For 1 liter, dissolve 10 g tryptone, 5 g yeast extract and 10 g NaCl in 950 ml distilled water. Adjust the pH of the solution to 7.0 with NaOH and bring the volume up to 1 liter. Autoclave on liquid cycle for 20 minutes. Allow solution to cool to about 55° C. and add antibiotic, if needed. Store at room temperature or at 4° C.

For LB agar plates. Prepare LB medium as above, but add 15 g/L agar before autoclaving. Autoclave on liquid cycle for 20 minutes. After autoclaving, add antibiotic and pour into 10 cm plates. Let harden, then invert and store at 4° C. in the dark. To add X-gal to the plate, warm the plate to 37° C. Pipette 40 µl of the 40 mg/ml X-gal stock solution (see below), spread evenly, and let dry for 15 minutes. Protect plates from light.

A 10 mg/ml stock solution of spectinomycin is prepared as follows. Spectinomycin (50 mg, Sigma Catalog No. S4014) is resuspended in 5 ml of sterile, deionized water, filter-sterilized and stored at 4° C. for up to 2 weeks. For long-term storage, the solution is stored at −20° C.

A 40 mg/ml stock solution of X-gal is prepared by dissolving 400 mg of X-gal in 10 ml dimethylformamide. The solution is stored at −20° C., protected from light.

Described here is the creation and testing of a new cloning system that combines the time tested reliability of T/A TOPO cloning with the power and versatility of GATEWAY® technology. In constructing this vector, a novel design for sequencing primers that allows sequencing of entry clones from primer sites within the attL regions. This resulted in clean sequence reads of 600 to 700 bases from mini-prep DNA without the inclusion of unnecessary vector sequence. Also, the use of ccdB negative selection cassette in the TOPO adaptation site, maintained the high foreground and low background cloning associated with the pCR2.1 series vectors. Further, spectinomycin positive selection was used in pCR8/GW/TOPO instead of kanamycin, which is used in most ENTRY vectors. This will allow users to use this ENTRY vector with kanamycin selectable DEST vectors, which are popular in plant expression systems. PCR8/GW/TOPO was also demonstrated to be compatible with Mach I E. coli propagation. This cell lines has previously been reported to support faster colony generation and liquid medium growth compared with other cell strains. In this study, only a modest increase in culture density was observed at 4.5 hours when various selectable markers were tested in either Mach I or Top10 cells.

In summary, pCR8/GW/TOPO combines attributes of the pCR2.1/TOPO-T/A cloning system while adding the ability to transfer DNA elements into other systems via GATEWAY® technology.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

TABLE 19

Annotated Nucleotide Sequence of pCR8/GW (SEQ ID NO: 71).

```
  1 CTTTCCTGCG TTATCCCCTG ATTCTGTGGA TAACCGTATT ACCGCCTTTG

GAAAGGACGC AATAGGGGAC TAAGACACCT ATTGGCATAA TGGCGGAAAC

CDS(pas)_1

51 AGTGAGCTGA TACCGCTCGC CGCAGCCGAA CGACCGAGCG CAGCGAGTCA

TCACTCGACT ATGGCGAGCG GCGTCGGCTT GCTGGCTCGC GTCGCTCAGT

CDS(pas')_2

101 GTGAGCGAGG AAGCGGAAGA GCGCCCAATA CGCAAACCGC CTCTCCCCGC

CACTCGCTCC TTCGCCTTCT CGCGGGTTAT GCGTTTGGCG GAGAGGGGCG

151 GCGTTGGCCG ATTCATTAAT GCAGCTGGCA CGACAGGTTT CCCGACTGGA

CGCAACCGGC TAAGTAATTA CGTCGACCGT GCTGTCCAAA GGGCTGACCT

201 AAGCGGGCAG TGAGCGCAAC GCAATTAATA CGCGTACCGC TAGCCAGGAA

TTCGCCCGTC ACTCGCGTTG CGTTAATTAT GCGCATGGCG ATCGGTCCTT

T1-T2
251 GAGTTTGTAG AAACGCAAAA AGGCCATCCG TCAGGATGGC CTTCTGCTTA

CTCAAACATC TTTGCGTTTT TCCGGTAGGC AGTCCTACCG GAAGACGAAT

T1-T2
301 GTTTGATGCC TGGCAGTTTA TGGCGGGCGT CCTGCCCGCC ACCCTCCGGG

CAAACTACGG ACCGTCAAAT ACCGCCCGCA GGACGGGCGG TGGGAGGCCC
```

TABLE 19-continued

Annotated Nucleotide Sequence of pCR8/GW (SEQ ID NO: 71).

```
                       T1-T2
351 CCGTTGCTTC ACAACGTTCA AATCCGCTCC CGGCGGATTT GTCCTACTCA
    GGCAACGAAG TGTTGCAAGT TTAGGCGAGG GCCGCCTAAA CAGGATGAGT
    ~~~~~~~~~~~~~~~~~~~~~~~~~~~~~~~~~~~~~~~~~~~~~~~~~~~~
                       T1-T2
401 GGAGAGCGTT CACCGACAAA CAACAGATAA AACGAAAGGC CCAGTCTTCC
    CCTCTCGCAA GTGGCTGTTT GTTGTCTATT TTGCTTTCCG GGTCAGAAGG
    ~~~~~~~~~~~~~~~~~~~~~~~~~~~~~~~~~~~~~~~~~~~~~~~~~~~~
                       T1-T2
451 GACTGAGCCT TTCGTTTTAT TTGATGCCTG GCAGTTCCCT ACTCTCGCGT
    CTGACTCGGA AGCAAAATA AACTACGGAC CGTCAAGGGA TGAGAGCGCA
    ~~~~~~~~~~~~~~~~~~~~~~~~~~~~~~~~~~~~~~~~~~~~~~~~~~~~
                       T1-T2
                              M13 fwd primers
                       ~~~~~~~~~~~~~~~~~~~~~~~~~~~~~~~~~~
501 TAACGCTAGC ATGGATGTTT TCCCAGTCAC GACGTTGTAA AACGACGGCC
    ATTGCGATCG TACCTACAAA AGGGTCAGTG CTGCAACATT TTGCTGCCGG ~~~~~~~~~~
       T1-T2
    M13 fwd primers                       att L1
    ~~~                ~~~~~~~~~~~~~~~~~~~~~~~~~~~~~~~~~~
551 AGTCTTAAGC TCGGGCCCCA AATAATGATT TTATTTTGAC TGATAGTGAC
    TCAGAATTCG AGCCCGGGGT TTATTACTAA AATAAAACTG ACTATCACTG
    ~~~~~~~~~~~~~~~~~~~~~~~~~~~~~~~~~~~~~~~~~~~~~~~~~~~~
                       att L1
601 CTGTTCGTTG CAACAAATTG ATGAGCAATG CTTTTTTATA ATGCCAACTT
    GACAAGCAAC GTTGTTTAAC TACTCGTTAC GAAAAAATAT TACGGTTGAA
        att L1
    ~~~~~~~~~~~~~~~~
651 TGTACAAAAA AGCAGGCTCC GAATTCTTAT ATTCCCCAGA ACATCAGGTT
    ACATGTTTTT TCGTCCGAGG CTTAAGAATA TAAGGGGTCT TGTAGTCCAA
                                      ~~~~~~~~~~~~~~~~~~
                                                     ccdB
701 AATGGCGTTT TGATGTCAT TTTCGCGGTG GCTGAGATCA GCCACTTCTT
    TTACCGCAAA AACTACAGTA AAAGCGCCAC CGACTCTAGT CGGTGAAGAA
    ~~~~~~~~~~~~~~~~~~~~~~~~~~~~~~~~~~~~~~~~~~~~~~~~~~~~
                    ccdB
751 CCCCGATAAC GGAGACCGGC ACACTGGCCA TATCGGTGGT CATCATGCGC
    GGGGCTATTG CCTCTGGCCG TGTGACCGGT ATAGCCACCA GTAGTACGCG
    ~~~~~~~~~~~~~~~~~~~~~~~~~~~~~~~~~~~~~~~~~~~~~~~~~~~~
                    ccdB
801 CAGCTTTCAT CCCCGATATG CACCACCGGG TAAAGTTCAC GGGAGACTTT
    GTCGAAAGTA GGGGCTATAC GTGGTGGCCC ATTTCAAGTG CCCTCTGAAA
    ~~~~~~~~~~~~~~~~~~~~~~~~~~~~~~~~~~~~~~~~~~~~~~~~~~~~
                    ccdB
851 ATCTGACAGC AGACGTGCAC TGGCCAGGGG GATCACCATC CGTCGCCCGG
    TAGACTGTCG TCTGCACGTG ACCGGTCCCC CTAGTGGTAG GCAGCGGGCC
    ~~~~~~~~~~~~~~~~~~~~~~~~~~~~~~~~~~~~~~~~~~~~~~~~~~~~
                    ccdB
901 GCGTGTCAAT AATATCACTC TGTACATCCA CAAACAGACG ATAACGGCTC
    CGCACAGTTA TTATAGTGAG ACATGTAGGT GTTTGTCTGC TATTGCCGAG
    ~~~~~~~~~~~~~~~~~~~~~~~~~~~~~~~~~~~~~~~~~~~~~~~~~~~~
```

TABLE 19-continued

Annotated Nucleotide Sequence of pCR8/GW (SEQ ID NO: 71).

```
             ccdB
 951 TCTCTTTTAT AGGTGTAAAC CTTAAACTGC ATTTCACCAG CCCCTGTTCT

AGAGAAAATA TCCACATTTG GAATTTGACG TAAAGTGGTC GGGGACAAGA

~~~~~~~~~~~~~~~~~~~~~~~~~~~~~~~~~~~~~~
             ccdB
1001 CGTCAGCAAA AGAGCCGTTC ATTTCAATAA ACCGGGCGAC CTCAGCCATC

GCAGTCGTTT TCTCGGCAAG TAAAGTTATT TGGCCCGCTG GAGTCGGTAG

1051 CCTTCCTGAT TTTCCGCTTT CCAGCGTTCG GCACGCAGAC GACGGGCTTC

GGAAGGACTA AAAGGCGAAA GGTCGCAAGC CGTGCGTCTG CTGCCCGAAG

1101 ATTCTGCATG GTTGTGCTTA CCAGACCGGA GATATTGACA TCATATATGC

TAAGACGTAC CAACACGAAT GGTCTGGCCT CTATAACTGT AGTATATACG

1151 CTTGAGCAAC TGATAGCTGT CGCTGTCAAC TGTCACTGTA ATACGCTGCT

GAACTCGTTG ACTATCGACA GCGACAGTTG ACAGTGACAT TATGCGACGA

1201 TCATAGCATA CCTCTTTTTG ACATACTTCG GGTATACATA TCAGTATATA

AGTATCGTAT GGAGAAAAAC TGTATGAAGC CCATATGTAT AGTCATATAT

1251 TTCTTATACC GCAAAAATCA GCGCGCAAAT ACGCATACTG GTATCTGGCT

AAGAATATGG CGTTTTTAGT CGCGCGTTTA TGCGTATGAC CATAGACCGA

1301 TTTAGTAAGC CGGATCCTAA CTCAAAATCC ACACATTATA CGAGCCGGAA

AAATCATTCG GCCTAGGATT GAGTTTTAGG TGTGTAATAT GCTCGGCCTT

1351 GCATAAAGTG TAAAGCCTGG AATTCGACCC AGCTTTCTTG TACAAAGTTG

CGTATTTCAC ATTTCGGACC TTAAGCTGGG TCGAAAGAAC ATGTTTCAAC

~~~~~~~~~~~~~~~~~~~~
                                                       att L2
1401 GCATTATAAA AAATAATTGC TCATCAATTT GTTGCAACGA ACAGGTCACT

CGTAATATTT TTTATTAACG AGTAGTTAAA CAACGTTGCT TGTCCAGTGA

~~~~~~~~~~~~~~~~~~~~~~~~~~~~~~~~~~~~~~~~~~~~~~~~
                            att L2
1451 ATCAGTCAAA ATAAAATCAT TATTTGCCAT CCAGCTGATA TCCCCTATAG

TAGTCAGTTT TATTTTAGTA ATAAACGGTA GGTCGACTAT AGGGGATATC

~~~~~~~~~~~~~~~~~~~~~~~~~~                    ~~~
              att L2                           M13 rev primers
1501 TGAGTCGTAT TACATGGTCA TAGCTGTTTC CTGGCAGCTC TGGCCCGTGT

ACTCAGCATA ATGTACCAGT ATCGACAAAG GACCGTCGAG ACCGGGCACA

~~~~~~~~~~~~~~~~~~~~~~~~~~~~~~~~~~~~
            M13 rev primers
1551 CTCAAAATCT CTGATGTTAC ATTGCACAAG ATAAAAATAT ATCATCATGC

GAGTTTTAGA GACTACAATG TAACGTGTTC TATTTTTATA TAGTAGTACG

1601 CTCCTCTAGA CCAGCCAGGA CAGAAATGCC TCGACTTCGC TGCTGCCCAA

GAGGAGATCT GGTCGGTCCT GTCTTTACGG AGCTGAAGCG ACGACGGGTT

1651 GGTTGCCGGG TGACGCACAC CGTGGAAACG GATGAAGGCA CGAACCCAGT

CCAACGGCCC ACTGCGTGTG GCACCTTTGC CTACTTCCGT GCTTGGGTCA

SpnR
                                                      ~~~~~~
1701 GGACATAAGC CTGTTCGGTT CGTAAGCTGT AATGCAAGTA GCGTATGCGC

CCTGTATTCG GACAAGCCAA GCATTCGACA TTACGTTCAT CGCATACGCG
```

TABLE 19-continued

Annotated Nucleotide Sequence of pCR8/GW (SEQ ID NO: 71).

SpnR
1751 TCACGCAACT GGTCCAGAAC CTTGACCGAA CGCAGCGGTG GTAACGGCGC
     AGTGCGTTGA CCAGGTCTTG AACTGGCTT GCGTCGCCAC CATTGCCGCG

SpnR
1801 AGTGGCGGTT TTCATGGCTT GTTATGACTG TTTTTTTGGG GTACAGTCTA
     TCACCGCCAA AAGTACCGAA CAATACTGAC AAAAAAACCC CATGTCAGAT

SpnR
1851 TGCCTCGGGC ATCCAAGCAG CAAGCGCGTT ACGCCGTGGG TCGATGTTTG
     ACGGAGCCCG TAGGTTCGTC GTTCGCGCAA TGCGGCACCC AGCTACAAAC

SpnR
1901 ATGTTATGGA GCAGCAACGA TGTTACGCAG CAGGGCAGTC GCCCTAAAAC
     TACAATACCT CGTCGTTGCT ACAATGCGTC GTCCCGTCAG CGGGATTTTG

SpnR
1951 AAAGTTAAAC ATCATGAGGG AAGCGGTGAT CGCCGAAGTA TCGACTCAAC
     TTTCAATTTG TAGTACTCCC TTCGCCACTA GCGGCTTCAT AGCTGAGTTG

SpnR
2001 TATCAGAGGT AGTTGGCGTC ATCGAGCGCC ATCTCGAACC GACGTTGCTG
     ATAGTCTCCA TCAACCGCAG TAGCTCGCGG TAGAGCTTGG CTGCAACGAC

SpnR
2051 GCCGTACATT TGTACGGCTC CGCAGTGGAT GGCGGCCTGA AGCCACACAG
     CGGCATGTAA ACATGCCGAG GCGTCACCTA CCGCCGGACT TCGGTGTGTC

SpnR
2101 TGATATTGAT TTGCTGGTTA CGGTGACCGT AAGGCTTGAT GAAACAACGC
     ACTATAACTA AACGACCAAT GCCACTGGCA TTCCGAACTA CTTTGTTGCG

SpnR
2151 GGCGAGCTTT GATCAACGAC CTTTTGGAAA CTTCGGCTTC CCTGGAGAG
     CCGCTCGAAA CTAGTTGCTG GAAAACCTTT GAAGCCGAAG GGACCTCTC

SpnR
2201 AGCGAGATTC TCCGCGCTGT AGAAGTCACC ATTGTTGTGC ACGACGACAT
     TCGCTCTAAG AGGCGCGACA TCTTCAGTGG TAACAACACG TGCTGCTGTA

SpnR
2251 CATTCCGTGG CGTTATCCAG CTAAGCGCGA ACTGCAATTT GGAGAATGGC
     GTAAGGCACC GCAATAGGTC GATTCGCGCT TGACGTTAAA CCTCTTACCG

SpnR
2301 AGCGCAATGA CATTCTTGCA GGTATCTTCG AGCCAGCCAC GATCGACATT
     TCGCGTTACT GTAAGAACGT CCATAGAAGC TCGGTCGGTG CTAGCTGTAA

SpnR
2351 GATCTGGCTA TCTTGCTGAC AAAAGCAAGA GAACATAGCG TTGCCTTGGT
     CTAGACCGAT AGAACGACTG TTTTCGTTCT CTTGTATCGC AACGGAACCA

TABLE 19-continued

Annotated Nucleotide Sequence of pCR8/GW (SEQ ID NO: 71).

SpnR
2401 AGGTCCAGCG GCGGAGGAAC TCTTTGATCC GGTTCCTGAA CAGGATCTAT

TCCAGGTCGC CGCCTCCTTG AGAAACTAGG CCAAGGACTT GTCCTAGATA

SpnR
2451 TTGAGGCGCT AAATGAAACC TTAACGCTAT GGAACTCGCC GCCCGACTGG

AACTCCGCGA TTTACTTTGG AATTGCGATA CCTTGAGCGG CGGGCTGACC

SpnR
2501 GCTGGCGATG AGCGAAATGT AGTGCTTACG TTGTCCCGCA TTTGGTACAG

CGACCGCTAC TCGCTTTACA TCACGAATGC AACAGGGCGT AAACCATGTC

SpnR
2551 CGCAGTAACC GGCAAAATCG CGCCGAAGGA TGTCGCTGCC GACTGGGCAA

GCGTCATTGG CCGTTTTAGC GCGGCTTCCT ACAGCGACGG CTGACCCGTT

SpnR
2601 TGGAGCGCCT GCCGGCCCAG TATCAGCCCG TCATACTTGA AGCTAGACAG

ACCTCGCGGA CGGCCGGGTC ATAGTCGGGC AGTATGAACT TCGATCTGTC

SpnR
2651 GCTTATCTTG ACAAGAAGA AGATCGCTTG GCCTCGCGCG CAGATCAGTT

CGAATAGAAC CTGTTCTTCT TCTAGCGAAC CGGAGCGCGC GTCTAGTCAA

SpnR
2701 GGAAGAATTT GTCCACTACG TGAAAGGCGA GATCACCAAG GTAGTCGGCA

CCTTCTTAAA CAGGTGATGC ACTTTCCGCT CTAGTGGTTC CATCAGCCGT

SpnR
2751 AATAACCCTC GAGCCACCCA TGACCAAAAT CCCTTAACGT GAGTTACGCG

TTATTGGGAG CTCGGTGGGT ACTGGTTTTA GGGAATTGCA CTCAATGCGC

2801 TCGTTCCACT GAGCGTCAGA CCCCGTAGAA AAGATCAAAG GATCTTCTTG

AGCAAGGTGA CTCGCAGTCT GGGGCATCTT TTCTAGTTTC CTAGAAGAAC

2851 AGATCCTTTT TTTCTGCGCG TAATCTGCTG CTTGCAAACA AAAAAACCAC

TCTAGGAAAA AAAGACGCGC ATTAGACGAC GAACGTTTGT TTTTTTGGTG ori
2901 CGCTACCAGC GGTGGTTTGT TTGCCGGATC AAGAGCTACC AACTCTTTTT

GCGATGGTCG CCACCAAACA AACGGCCTAG TTCTCGATGG TTGAGAAAAA ori
2951 CCGAAGGTAA CTGGCTTCAG CAGAGCGCAG ATACCAAATA CTGTCCTTCT

GGCTTCCATT GACCGAAGTC GTCTCGCGTC TATGGTTTAT GACAGGAAGA ori
3001 AGTGTAGCCG TAGTTAGGCC ACCACTTCAA GAACTCTGTA GCACCGCCTA

TCACATCGGC ATCAATCCGG TGGTGAAGTT CTTGAGACAT CGTGGCGGAT

TABLE 19-continued

Annotated Nucleotide Sequence of pCR8/GW (SEQ ID NO: 71).

```
                            ori
          ~~~~~~~~~~~~~~~~~~~~~~~~~~~~~~~~~~~~~~~~
3051 CATACCTCGC TCTGCTAATC CTGTTACCAG TGGCTGCTGC CAGTGGCGAT GTATGGAGCG AGACGATTAG GACAATGGTC ACCGACGACG GTCACCGCTA
                       ori
          ~~~~~~~~~~~~~~~~~~~~~~~~~~~~~~~~~~
3101 AAGTCGTGTC TTACCGGGTT GGACTCAAGA CGATAGTTAC CGGATAAGGC TTCAGCACAG AATGGCCCAA CCTGAGTTCT GCTATCAATG GCCTATTCCG
                            ori
          ~~~~~~~~~~~~~~~~~~~~~~~~~~~~~~~~~~~~~~~~
3151 GCAGCGGTCG GGCTGAACGG GGGGTTCGTG CACACAGCCC AGCTTGGAGC CGTCGCCAGC CCGACTTGCC CCCCAAGCAC GTGTGTCGGG TCGAACCTCG
                            ori
          ~~~~~~~~~~~~~~~~~~~~~~~~~~~~~~~~~~~~~~~~
3201 GAACGACCTA CACCGAACTG AGATACCTAC AGCGTGAGCA TTGAGAAAGC CTTGCTGGAT GTGGCTTGAC TCTATGGATG TCGCACTCGT AACTCTTTCG
                            ori
          ~~~~~~~~~~~~~~~~~~~~~~~~~~~~~~~~~~~~~~~~
3251 GCCACGCTTC CCGAAGGGAG AAAGGCGGAC AGGTATCCGG TAAGCGGCAG CGGTGCGAAG GCTTCCCTC TTTCCGCCTG TCCATAGGCC ATTCGCCGTC
                            ori
          ~~~~~~~~~~~~~~~~~~~~~~~~~~~~~~~~~~~~~~~~
3301 GGTCGGAACA GGAGAGCGCA CGAGGGAGCT TCCAGGGGGA AACGCCTGGT CCAGCCTTGT CCTCTCGCGT GCTCCCTCGA AGGTCCCCCT TTGCGGACCA
                            ori
          ~~~~~~~~~~~~~~~~~~~~~~~~~~~~~~~~~~~~~~~~
3351 ATCTTTATAG TCCTGTCGGG TTTCGCCACC TCTGACTTGA GCGTCGATTT TAGAAATATC AGGACAGCCC AAAGCGGTGG AGACTGAACT CGCAGCTAAA
                     ori
          ~~~~~~~~~~~~~~~~~~~~~~~~~~~~~~~~~~~~~~~~
3401 TTGTGATGCT CGTCAGGGGG GCGGAGCCTA TGGAAAAACG CCAGCAACGC AACACTACGA GCAGTCCCCC CGCCTCGGAT ACCTTTTTGC GGTCGTTGCG
3451 GGCCTTTTTA CGGTTCCTGG CCTTTTGCTG GCCTTTTGCT CACATGTT

CCGGAAAAAT GCCAAGGACC GGAAAACGAC CGGAAAACGA GTGTACAA
```

TABLE 20

Annotated Nucleotide Sequence of pCR8/GW/TOPO (SEQ ID NO: 10).

```
  1 CTTTCCTGCG TTATCCCCTG ATTCTGTG-
    GA TAACCGTATT ACCGCCTTTG AGTGAGCTGA TACCGCTCGC

CGCAGCCGAA CGACCGAGCG CAGCGAGT-
    CA GAAAGGACGC AATAGGGGAC TAAGACACCT ATTGGCATAA

TGGCGGAAAC TCACTCGACT ATGGCGAGCG GCGTCGGCTT GCTGGCTCGC GTCGCTCAGT

101 GTGAGCGAGG AAGCGGAAGA GCGC-
    CCAATA CGCAAACCGC CTCTCCCCGC GCGTTGGCCG ATTCATTAAT

GCAGCTGGCA CGACAGGTTT CCCGACTG-
    GA CACTCGCTCC TTCGCCTTCT CGCGGGTTAT GCGTTTGGCG

GAGAGGGGCG CGCAACCGGC TAAGTAATTA CGTCGACCGT GCTGTCCAAA GGGCTGACCT
```

TABLE 20-continued

Annotated Nucleotide Sequence of pCR8/GW/TOPO (SEQ ID NO: 10).

```
                                        rrnB T2 transcription terminator
                                        ~~~~~~~~~~~~~~~~~~~~~~~~~~~~~~~~
201 AAGCGGGCAG TGAGCGCAAC GCAAT-
    TAATA CGCGTACCGC TAGCCAGGAA GAGTTTGTAG AAACGCAAAA AGGCCATCCG TCAGGATGGC CTTCTGCT-
    TA TTCGCCCGTC ACTCGCGTTG CGTTAATTAT GCGCATGGCG

ATCGGTCCTT CTCAAACATC TTTGCGTTTT TCCGGTAGGC AGTCCTACCG GAAGACGAAT

301 GTTTGATGCC TGGCAGTTTA TG-
    GCGGGCGT CCTGCCCGCC ACCCTCCGGG CCGTTGCTTC ACAACGTTCA

AATCCGCTCC CGGCGGATTT GTCCTACT-
    CA CAAACTACGG ACCGTCAAAT ACCGCCCGCA GGACGGGCGG

TGGGAGGCCC GGCAACGAAG TGTTGCAAGT TTAGGCGAGG GCCGCCTAAA CAGGATGAGT

401 GGAGAGCGTT CACCGACAAA CAACA-
    GATAA AACGAAAGGC CCAGTCTTCC GACTGAGCCT TTCGTTTTAT

TTGATGCCTG GCAGTTC-
    CCT ACTCTCGCGT CCTCTCGCAA GTGGCTGTTT GTTGTCTATT TTGCTTTCCG

GGTCAGAAGG CTGACTCGGA AAGCAAAATA AACTACGGAC CGTCAAGGGA TGAGAGCGCA

~~~~~~~~~~~~~~~~~~~~~~~~~~~~~~~~~~~~~~~~~~~~~~~
           rrnB T1 transcription terminator
           M13 (-20) forward primer           attL1
           ~~~~~~~~~~~~~~~~~~~~               ~~~~~~~~~~~~~~~~~~~~~~~~~~~~
501 TAACGCTAGC ATGGATGTTT TCCCAGT-
    CAC GACGTTGTAA AACGACGGCC AGTCTTAAGC TCGGGCCCCA AATAATGATT TTATTTTGAC TGATAGT-
    GAC ATTGCGATCG TACCTACAAA AGGGTCAGTG CTGCAACATT

TTGCTGCCGG TCAGAATTCG AGCCCGGGGT TTATTACTAA AATAAAACTG ACTATCACTG

GW1 primer                          TOPO Cloning site
           ~~~~~~~~~~~~~~~~~~~~~~~~~~~         ~~~~~
               attL1                           TOPO Cloning site
           ~~~~~~~~~~~~~~~~~~~~~~~~~~~~~~~~~~  ~~~~~
601 CTGTTCGTTG CAACAAATTG ATGAG-
    CAATG CTTTTTTATA ATGCCAACTT TGTACAAAAA AGCAGGCTCC GAATTCGCCC TTAAGGGCGA ATTCGAC-
    CCA GACAAGCAAC GTTGTTTAAC TACTCGTTAC GAAAAAATAT

TACGGTTGAA ACATGTTTTT TCGTCCGAGG CTTAAGCGGG AATTCCCGCT TAAGCTGGGT attL2
                   GW2 primer
                   ~~~~~~~~~~~~~~~~~~~~~
701 GCTTTCTTGT ACAAAGTTGG CAT-
    TATAAAA AATAATTGCT CATCAATTTG TTGCAACGAA CAGGTCACTA TCAGTCAAAA TAAAATCATT ATTTGC-
    CATC CGAAAGAACA TGTTTCAACC GTAATATTTT TTATTAACGA

GTAGTTAAAC AACGTTGCTT GTCCAGTGAT AGTCAGTTTT ATTTTAGTAA TAAACGGTAG

~~~~~~~~~~~~~~~~~~~~~~~~~~~~~~~~~~~~~~~~~~~~~~~~~~~~~~~~~~~~~~
                              attL2
801 CAGCTGATAT CCCCTATAGT GAGTCG-
    TATT ACATGGTCAT AGCTGTTTCC TGGCAGCTCT GGCCCGTGTC TCAAAATCTC TGATGTTACA TTGCACAA-
    GA GTCGACTATA GGGGATATCA CTCAGCATAA TGTACCAGTA

TCGACAAAGG ACCGTCGAGA CCGGGCACAG AGTTTTAGAG ACTACAATGT AACGTGTTCT

~~~~~~~~~~~~~~~~~~
                        M13 reverse primer
                   Spn promoter
                   ~~~~~~~~~~~~~~~~~~~~~~~~~~~~~~~~~~~~~~~~~~~~~~~~~~~~
901 TAAAAATATA TCATCATGCC TCCTCTA-
    GAC CAGCCAGGAC AGAAATGCCT CGACTTCGCT GCTGCCCAAG
```

TABLE 20-continued

Annotated Nucleotide Sequence of pCR8/GW/TOPO (SEQ ID NO: 10).

```
     GTTGCCGGGT GACGCACACC GTG-
     GAAACGG ATTTTTATAT AGTAGTACGG AGGAGATCTG GTCGGTCCTG

TCTTTACGGA GCTGAAGCGA CGACGGGTTC CAACGGCCCA CTGCGTGTGG CACCTTTGCC
                              Spn promoter
                              ~~~~~~~~~~~~~~~~~~~~~~~~~~~~~~~~~~~~~~
                                                                       SpnR
                                                                       ~~~~~~~~~~~~~~~~~~~~~~~~~~~~~~
1001 ATGAAGGCAC GAACCCAGTG GACAT-
     AAGCC TGTTCGGTTC GTAAGCTGTA ATGCAAGTAG CGTATGCGCT CACGCAACTG GTCCAGAACC TTGAC-
     CGAAC TACTTCCGTG CTTGGGTCAC CTGTATTCGG ACAAGCCAAG CATTCGACAT TACGTTCATC GCATACGCGA GTGCGTTGAC CAGGTCTTGG AACTGGCTTG
                                              SpnR
     ~~~~~~~~~~~~~~~~~~~~~~~~~~~~~~~~~~~~~~~~~~~~~~~~~~~~~~~~~~~~~~~~
1101 GCAGCGGTGG TAACGGCGCA GTGGCG-
     GTTT TCATGGCTTG TTATGACTGT TTTTTTGGGG TACAGTCTAT GCCTCGGGCA TCCAAGCAGC AAGCGCGT-
     TA CGTCGCCACC ATTGCCGCGT CACCGCCAAA AGTACCGAAC AATACTGACA AAAAAACCCC ATGTCAGATA CGGAGCCCGT AGGTTCGTCG TTCGCGCAAT
                                              SpnR
     ~~~~~~~~~~~~~~~~~~~~~~~~~~~~~~~~~~~~~~~~~~~~~~~~~~~~~~~~~~~~~~~~
1201 CGCCGTGGGT CGATGTTTGA TGTTATG-
     GAG CAGCAACGAT GTTACGCAGC AGGGCAGTCG CCCTAAAACA AAGTTAAACA TCATGAGGGA AGCGGT-
     GATC GCGGCACCCA GCTACAAACT ACAATACCTC GTCGTTGCTA CAATGCGTCG TCCCGTCAGC GGGATTTTGT TTCAATTTGT AGTACTCCCT TCGCCACTAG
                                              SpnR
     ~~~~~~~~~~~~~~~~~~~~~~~~~~~~~~~~~~~~~~~~~~~~~~~~~~~~~~~~~~~~~~~~
1301 GCCGAAGTAT CGACTCAACT ATCAGAGG-
     TA GTTGGCGTCA TCGAGCGCCA TCTCGAACCG ACGTTGCTGG CCGTACATTT GTACGGCTCC GCAGTG-
     GATG CGGCTTCATA GCTGAGTTGA TAGTCTCCAT CAACCGCAGT AGCTCGCGGT AGAGCTTGGC TGCAACGACC GGCATGTAAA CATGCCGAGG CGTCACCTAC
                                              SpnR
     ~~~~~~~~~~~~~~~~~~~~~~~~~~~~~~~~~~~~~~~~~~~~~~~~~~~~~~~~~~~~~~~~
1401 GCGGCCTGAA GCCACACAGT GATAT-
     TGATT TGCTGGTTAC GGTGACCGTA AGGCTTGATG AAACAACGCG GCGAGCTTTG ATCAACGACC TTTTG-
     GAAAC CGCCGGACTT CGGTGTGTCA CTATAACTAA ACGACCAATG CCACTGGCAT TCCGAACTAC TTTGTTGCGC CGCTCGAAAC TAGTTGCTGG AAAACCTTTG
                                              SpnR
     ~~~~~~~~~~~~~~~~~~~~~~~~~~~~~~~~~~~~~~~~~~~~~~~~~~~~~~~~~~~~~~~~
1501 TTCGGCTTCC CCTGGAGAGA GCGAGAT-
     TCT CCGCGCTGTA GAAGTCACCA TTGTTGTGCA CGACGACATC ATTCCGTGGC GTTATCCAGC TAAGCGC-
     GAA AAGCCGAAGG GGACCTCTCT CGCTCTAAGA GGCGCGACAT CTTCAGTGGT AACAACACGT GCTGCTGTAG TAAGGCACCG CAATAGGTCG ATTCGCGCTT
                                              SpnR
     ~~~~~~~~~~~~~~~~~~~~~~~~~~~~~~~~~~~~~~~~~~~~~~~~~~~~~~~~~~~~~~~~
1601 CTGCAATTTG GAGAATGGCA GCGCAAT-
     GAC ATTCTTGCAG GTATCTTCGA GCCAGCCACG ATCGACATTG ATCTGGCTAT CTTGCTGACA AAAGCAA-
     GAG GACGTTAAAC CTCTTACCGT CGCGTTACTG TAAGAACGTC

CATAGAAGCT CGGTCGGTGC TAGCTGTAAC TAGACCGATA GAACGACTGT TTTCGTTCTC
```

TABLE 20-continued

Annotated Nucleotide Sequence of pCR8/GW/TOPO (SEQ ID NO: 10).

SpnR
```
1701 AACATAGCGT TGCCTTGGTA GGTC-
     CAGCGG CGGAGGAACT CTTTGATCCG GTTCCTGAAC AGGATCTATT

TGAGGCGCTA AATGAAACCT TAACGC-
     TATG TTGTATCGCA ACGGAACCAT CCAGGTCGCC GCCTCCTTGA

GAAACTAGGC CAAGGACTTG TCCTAGATAA ACTCCGCGAT TTACTTTGGA ATTGCGATAC
```

SpnR
```
1801 GAACTCGCCG CCCGACTGGG CTGGCGAT-
     GA GCGAAATGTA GTGCTTACGT TGTCCCGCAT TTGGTACAGC

GCAGTAACCG GCAAAATCGC GCCGAAG-
     GAT CTTGAGCGGC GGGCTGACCC GACCGCTACT CGCTTTACAT

CACGAATGCA ACAGGGCGTA AACCATGTCG CGTCATTGGC CGTTTTAGCG CGGCTTCCTA
```

SpnR
```
1901 GTCGCTGCCG ACTGGGCAAT GGAGCGC-
     CTG CCGGCCCAGT ATCAGCCCGT CATACTTGAA GCTAGACAGG

CTTATCTTGG ACAAGAAGAA GATCGCT-
     TGG CAGCGACGGC TGACCCGTTA CCTCGCGGAC GGCCGGGTCA

TAGTCGGGCA GTATGAACTT CGATCTGTCC GAATAGAACC TGTTCTTCTT CTAGCGAACC
```

SpnR
```
2001 CCTCGCGCGC AGATCAGTTG GAA-
     GAATTTG TCCACTACGT GAAAGGCGAG ATCACCAAGG TAGTCGGCAA

ATAACCCTCG AGCCACCCAT GAC-
     CAAAATC GGAGCGCGCG TCTAGTCAAC CTTCTTAAAC AGGTGATGCA

CTTTCCGCTC TAGTGGTTCC ATCAGCCGTT TATTGGGAGC TCGGTGGGTA CTGGTTTTAG
``` pUC origin
```
2101 CCTTAACGTG AGTTACGCGT CGTTC-
     CACTG AGCGTCAGAC CCCGTAGAAA AGATCAAAGG ATCTTCTTGA GATCCTTTTT TTCTGCGCGT AATCTGCT-
     GC GGAATTGCAC TCAATGCGCA GCAAGGTGAC TCGCAGTCTG

GGGCATCTTT TCTAGTTTCC TAGAAGAACT CTAGGAAAAA AAGACGCGCA TTAGACGACG
``` pUC origin
```
2201 TTGCAAACAA AAAAACCACC GCTAC-
     CAGCG GTGGTTTGTT TGCCGGATCA AGAGCTACCA ACTCTTTTTC CGAAGGTAAC TGGCTTCAGC AGAGCGCA-
     GA AACGTTTGTT TTTTTGGTGG CGATGGTCGC CACCAAACAA

ACGGCCTAGT TCTCGATGGT TGAGAAAAAG GCTTCCATTG ACCGAAGTCG TCTCGCGTCT
``` pUC origin
```
2301 TACCAAATAC TGTCCTTCTA GTGTAGC-
     CGT AGTTAGGCCA CCACTTCAAG AACTCTGTAG CACCGCCTAC ATACCTCGCT CTGCTAATCC TGTTAC-
     CAGT ATGGTTTATG ACAGGAAGAT CACATCGGCA TCAATCCGGT

GGTGAAGTTC TTGAGACATC GTGGCGGATG TATGGAGCGA GACGATTAGG ACAATGGTCA
``` pUC origin
```
2401 GGCTGCTGCC AGTGGCGATA AGTCGT-
     GTCT TACCGGGTTG GACTCAAGAC GATAGTTACC GGATAAGGCG CAGCGGTCGG GCTGAACGGG GGGTTCGT-
     GC CCGACGACGG TCACCGCTAT TCAGCACAGA ATGGCCCAAC

CTGAGTTCTG CTATCAATGG CCTATTCCGC GTCGCCAGCC CGACTTGCCC CCCAAGCACG
```

TABLE 20-continued

Annotated Nucleotide Sequence of pCR8/GW/TOPO (SEQ ID NO: 10).

pUC origin

```
2501 ACACAGCCCA GCTTGGAGCG AACGAC-
     CTAC ACCGAACTGA GATACCTACA GCGTGAGCAT TGAGAAAGCG

CCACGCTTCC CGAAGGGAGA AAGGCGGA-
     CA TGTGTCGGGT CGAACCTCGC TTGCTGGATG TGGCTTGACT

CTATGGATGT CGCACTCGTA ACTCTTTCGC GGTGCGAAGG GCTTCCCTCT TTCCGCCTGT
``` pUC origin

```
2601 GGTATCCGGT AAGCGGCAGG GTCGGAA-
     CAG GAGAGCGCAC GAGGGAGCTT CCAGGGGGAA ACGCCTGGTA

TCTTTATAGT CCTGTCGGGT TTCGCCAC-
     CT CCATAGGCCA TTCGCCGTCC CAGCCTTGTC CTCTCGCGTG

CTCCCTCGAA GGTCCCCCTT TGCGGACCAT AGAAATATCA GGACAGCCCA AAGCGGTGGA
``` pUC origin

```
2701 CTGACTTGAG CGTCGATTTT TGTGAT-
     GCTC GTCAGGGGGG CGGAGCCTAT GGAAAAACGC CAGCAACGCG

GCCTTTTTAC GGTTCCTGGC-
     CTTTTGCTGG GACTGAACTC GCAGCTAAAA ACACTACGAG CAGTCCCCCC

GCCTCGGATA CCTTTTTGCG GTCGTTGCGC CGGAAAAATG CCAAGGACCG GAAAACGACC
``` pUC origin

```
2801 CCTTTTGCTC ACATGTT

GGAAAACGAG TGTACAA
```

---

What is claimed is:

1. A method for sequencing all or part of a nucleic acid segment, the method comprising:
   (a) providing a first nucleic acid molecule comprising the nucleic acid segment flanked by a first attP recombination site and a second attP recombination site which can not recombine with each other and wherein the first and the second attP recombination sites each have a sequencing primer binding site located within 30 nucleotides of the nucleic acid segment wherein the sequencing primer binding sites encompass the IHF site of the first and the second attP site and wherein the sequencing primer binding sites differ from each other by one, two, three or four nucleotides,
   (b) providing a second nucleic acid molecule comprising a first attB recombination site and a second attB recombination site which can not recombine with each other,
   (c) combining the first and the second nucleic acid molecules in the presence of one or more recombinases under conditions which allow for site specific recombination in trans between,
       (1) the first attP recombination site and the first attB recombination site and,
       (2) the second attP recombination site and the second attB recombination site,
       such that a product nucleic acid molecule is generated which contains the nucleic acid segment flanked by a first and a second attL recombination sites, wherein the product attL recombination sites comprise the unique binding sites encompassing the IHF site from the attP recombination sites,
   (d) sequencing all or part of a first strand of the product nucleic acid molecules comprising the attL sites with a sequencing primer which mediates 5' to 3' extension from the unique sequencing primer binding site located within the first attL recombination site, and
   (e) sequencing all or part of a second strand of the nucleic acid segment comprising the attL sites with a sequencing primer which mediates 5' to 3' extension from the sequencing primer binding site located within the second attL site specific recombination site.

2. The method of claim 1, wherein, when the sequencing primer binding sites differ from each other by two, three or four nucleotides, the nucleotides which are different are located adjacent to each other.

3. A method for sequencing all or part of a nucleic acid segment comprising:
   (a) providing in a recombination reaction, a first nucleic acid comprising the nucleic acid segment flanked by att recombination sites which do not recombine with each other, wherein the att recombination sites each comprise an IHF site, a second nucleic acid molecule comprising two att recombination sites which cannot recombine with each other but can recombine with the att recombination sites in the first nucleic acid, one or more recombinases, wherein the two att recombination sites within the second nucleic acid molecule each comprise sequencing primer binding sites that encompass the IHF sites wherein the recombination reaction is effective to generate a product nucleic acid molecule comprising the two sequencing primer binding sites flanking the nucleic acid segment wherein the two sequencing primer sites are within 30 nucleotides of the nucleic acid segment and wherein the two sequencing primer binding sites differ from each other in nucleotide sequence by one, two, three, or four nucleotides and allow for sequencing of the nucleic acid segment from either end;
   (b) contacting a composition comprising the product nucleic acid molecule of (a), comprising the sequencing primer binding sites, with a first sequencing primer wherein the first sequencing primer binds to both sequencing primer binding sites but mediates 5' to 3' extension only when bound to one of the two sequencing primer binding sites; and
   (c) sequencing from the end of the nucleic acid segment comprising the bound first primer.

4. The method of claim 3, further comprising the steps of:
   (d) contacting a second composition comprising the product nucleic acid molecule of (a), comprising the sequencing primer binding sites, with a second sequencing primer wherein the second sequencing primer binds to both sequencing primer binding sites but mediates 5' to 3' extension only from the sequencing primer binding site located at the opposite end of the nucleic acid segment from which the first sequencing primer mediates 5' to 3' extension; and
   (e) sequencing from the end of the nucleic acid segment comprising the bound second primer.

5. The method of claim 4, wherein the first sequencing primer and the second sequencing primer are each between 15 and 45 nucleotides in length.

6. The method of claim 5, wherein the first sequencing primer and the second sequencing primer differ in nucleotide sequence at their 3' termini.

7. The method of claim 6, wherein the first sequencing primer comprises the nucleotide sequence 5' GTTGCAACAAATTGATGAGCAATTA 3' (SEQ ID NO: 1) and the second sequencing primer comprises the nucleotide sequence 5' GTTGCAACAAATTGATGAGCAATGC 3' (SEQ ID NO: 2).

* * * * *

SEQUENCE LISTING

<160> NUMBER OF SEQ ID NOS: 72

<210> SEQ ID NO 1
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: GW1 primer

<400> SEQUENCE: 1
gttgcaacaa attgatgagc aatta                                           25

<210> SEQ ID NO 2
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: GW2 Primer

<400> SEQUENCE: 2
gttgcaacaa attgatgagc aatgc                                           25

<210> SEQ ID NO 3
<211> LENGTH: 10
<212> TYPE: DNA
<213> ORGANISM: Artificial Sequence
<220> FEATURE:

```
<223> OTHER INFORMATION: Chemically Synthesized
<220> FEATURE:
<223> OTHER INFORMATION: Nucleic acid molecule

<400> SEQUENCE: 3
gaaaatattg                                                            10

<210> SEQ ID NO 4
<211> LENGTH: 50
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP2 mut12 site

<400> SEQUENCE: 4
gtacaaagtt ggcattataa gaaagcattg cttatcaatt tgttgcaacg                50

<210> SEQ ID NO 5
<211> LENGTH: 50
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP2 mut12 site

<400> SEQUENCE: 5
cgttgcaaca aattgataag caatgctttt ttataatgcc aactttgtac                50

<210> SEQ ID NO 6
<211> LENGTH: 59
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: L-forward primer

<400> SEQUENCE: 6
agcaatgctt ttttataatg ccaactttgt acaaaaaagc aggctccgaa ttcgccctt     59

<210> SEQ ID NO 7
<211> LENGTH: 58
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: L reverse primer

<400> SEQUENCE: 7
tcgttaataa agaatattac ggttgaaaca tgttctttcg acccagctta agcgggaa      58

<210> SEQ ID NO 8
<211> LENGTH: 72
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL-forward primer

<400> SEQUENCE: 8
tgggtcgaat tgcccttcg ccccgccctg ccactcctga cgggcctggt tataggtaca     60
ttgaccactg at                                                        72
```

```
<210> SEQ ID NO 9
<211> LENGTH: 76
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL reverse primer

<400> SEQUENCE: 9
caggctccga attcgccctt atggagaaaa aaatcacatt ttaaacgtgg ccaatatgga     60
caacttcttc tccccg                                                    76

<210> SEQ ID NO 10
<211> LENGTH: 2817
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: pCR8/GW/TOPO vector

<400> SEQUENCE: 10
ctttcctgcg ttatcccctg attctgtgga taaccgtatt accgcctttg agtgagctga     60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca atccgctcc cggcggattt gtcctactca ggagagcgtt caccgacaaa   420
caacagataa acgaaaggc ccagtcttcc gactgagcct ttcgttttat ttgatgcctg   480
gcagttccct actctcgcgt taacgctagc atggatgttt tcccagtcac gacgttgtaa   540
aacgacggcc agtcttaagc tcgggcccca aataatgatt ttattttgac tgatagtgac   600
ctgttcgttg caacaaattg atgagcaatg ctttttttata atgccaactt tgtacaaaaa   660
agcaggctcc gaattcgccc ttaagggcga attcgaccca gctttcttgt acaaagttgg   720
cattataaaa aataattgct catcaatttg ttgcaacgaa caggtcacta tcagtcaaaa   780
taaaatcatt atttgccatc cagctgatat cccctatagt gagtcgtatt acatggtcat   840
agctgtttcc tggcagctct ggcccgtgtc tcaaaatctc tgatgttaca ttgcacaaga   900
taaaaatata tcatcatgcc tcctctagac cagccaggac agaaatgcct cgacttcgct   960
gctgcccaag ttgccgggt gacgcacacc gtggaaacgg atgaaggcac gaacccagtg  1020
gacataagcc tgttcggttc gtaagctgta atgcaagtag cgtatgcgct cacgcaactg  1080
gtccagaacc ttgaccgaac gcagcggtgg taacggcgca gtggcggttt tcatggcttg  1140
ttatgactgt tttttggggg tacagtctat gcctcgggca tccaagcagc aagcgcgtta  1200
cgccgtgggt cgatgtttga tgttatggag cagcaacgat gttacgcagc agggcagtcg  1260
ccctaaaaca aagttaaaca tcatgaggga agcggtgatc gccgaagtat cgactcaact  1320
atcagaggta gttggcgtca tcgagcgcca tctcgaaccg acgttgctgg ccgtacattt  1380
gtacggctcc gcagtggatg gcggcctgaa gccacacagt gatattgatt tgctggttac  1440
ggtgaccgta aggcttgatg aaacaacgcg gcgagctttg atcaacgacc ttttggaaac  1500
ttcggcttcc cctggagaga gcgagattct ccgcgctgta gaagtcacca ttgttgtgca  1560
```

-continued

```
cgacgacatc attccgtggc gttatccagc taagcgcgaa ctgcaatttg gagaatggca    1620
gcgcaatgac attcttgcag gtatcttcga gccagccacg atcgacattg atctggctat    1680
cttgctgaca aaagcaagag aacatagcgt tgccttggta ggtccagcgg cggaggaact    1740
ctttgatccg gttcctgaac aggatctatt tgaggcgcta aatgaaacct taacgctatg    1800
gaactcgccg cccgactggg ctggcgatga gcgaaatgta gtgcttacgt tgtcccgcat    1860
ttggtacagc gcagtaaccg gcaaaatcgc gccgaaggat gtcgctgccg actgggcaat    1920
ggagcgcctg ccggcccagt atcagcccgt catacttgaa gctagacagg cttatcttgg    1980
acaagaagaa gatcgcttgg cctcgcgcgc agatcagttg gaagaatttg tccactacgt    2040
gaaaggcgag atcaccaagg tagtcggcaa ataaccctcg agccacccat gaccaaaatc    2100
ccttaacgtg agttacgcgt cgttccactg agcgtcagac cccgtagaaa agatcaaagg    2160
atcttcttga gatccttttt ttctgcgcgt aatctgctgc ttgcaaacaa aaaaaccacc    2220
gctaccagcg gtggtttgtt tgccggatca agagctacca actctttttc cgaaggtaac    2280
tggcttcagc agagcgcaga taccaaatac tgtccttcta gtgtagccgt agttaggcca    2340
ccacttcaag aactctgtag caccgcctac atacctcgct ctgctaatcc tgttaccagt    2400
ggctgctgcc agtggcgata gtcgtgtct taccggggttg gactcaagac gatagttacc    2460
ggataaggcg cagcggtcgg gctgaacggg gggttcgtgc acacagccca gcttggagcg    2520
aacgacctac accgaactga gatacctaca gcgtgagcat tgagaaagcg ccacgcttcc    2580
cgaagggaga aaggcggaca ggtatccggt aagcggcagg gtcggaacag gagagcgcac    2640
gagggagctt ccaggggaa acgcctggta tctttatagt cctgtcgggt ttcgccacct    2700
ctgacttgag cgtcgatttt tgtgatgctc gtcaggggg cggagcctat ggaaaaacgc    2760
cagcaacgcg gccttttttac ggttcctggc cttttgctgg ccttttgctc acatgtt     2817
```

<210> SEQ ID NO 11
<211> LENGTH: 360
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: TOPO cloning region of pCR8/GW/TOPO

<400> SEQUENCE: 11

```
taacgctagc atggatgttt tcccagtcac gacgttgtaa aacgacggcc agtcttaagc     60
tcgggcccca aataatgatt ttattttgac tgatagtgac ctgttcgttg caacaaattg    120
atgagcaatg cttttttata atgccaactt tgtacaaaaa agcaggctcc gaattcgccc    180
ttaagggcga attcgaccca gctttcttgt acaaagttgg cattataaaa aataattgct    240
catcaatttg ttgcaacgaa caggtcacta tcagtcaaaa taaaatcatt atttgccatc    300
cagctgatat cccctatagt gagtcgtatt acatggtcat agctgtttcc tggcagctct    360
```

<210> SEQ ID NO 12
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: Primer GCTA3

<400> SEQUENCE: 12

```
aaatgctttt ttataatgcc aactttg                                         27
```

```
<210> SEQ ID NO 13
<211> LENGTH: 26
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: Primer GCTA4

<400> SEQUENCE: 13
atcatcaatt tgttgcaacg aacagg                                          26

<210> SEQ ID NO 14
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: mut34 sequencing primer

<400> SEQUENCE: 14
tgttcgttgc aacaaattga tgat                                            24

<210> SEQ ID NO 15
<211> LENGTH: 15
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: wild-type att site

<400> SEQUENCE: 15
gcttttttat actaa                                                      15

<210> SEQ ID NO 16
<211> LENGTH: 21
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: Reference sequence

<400> SEQUENCE: 16
caactttttt atacaaagtt g                                               21

<210> SEQ ID NO 17
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attB1 site

<400> SEQUENCE: 17
agcctgcttt tttgtacaaa cttgt                                           25

<210> SEQ ID NO 18
<211> LENGTH: 233
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP1 site
```

-continued

```
<400> SEQUENCE: 18
tacaggtcac taataccatc taagtagttg attcatagtg actggatatg ttgtgtttta      60
cagtattatg tagtctgttt tttatgcaaa atctaattta atatattgat atttatatca     120
ttttacgttt ctcgttcagc ttttttgtac aaagttggca ttataaaaaa gcattgctca     180
tcaatttgtt gcaacgaaca ggtcactatc agtcaaaata aaatcattat ttg            233

<210> SEQ ID NO 19
<211> LENGTH: 100
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL1 site

<400> SEQUENCE: 19
caaataatga ttttattttg actgatagtg acctgttcgt tgcaacaaat tgataagcaa      60 tgcttttta taatgccaac tttgtacaaa aaagcaggct                            100

<210> SEQ ID NO 20
<211> LENGTH: 125
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR1 site

<400> SEQUENCE: 20
acaagtttgt acaaaaaagc tgaacgagaa acgtaaaatg atataaatat caatatatta      60
aattagattt tgcataaaaa acagactaca taatactgta aaacacaaca tatccagtca     120
ctatg                                                                 125

<210> SEQ ID NO 21
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attB0 site

<400> SEQUENCE: 21
agcctgcttt tttatactaa cttgagc                                          27

<210> SEQ ID NO 22
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP0 site

<400> SEQUENCE: 22
gttcagcttt tttatactaa gttggca                                          27

<210> SEQ ID NO 23
<211> LENGTH: 27
<212> TYPE: DNA
<213> ORGANISM: Artificial Sequence
<220> FEATURE:
<223> OTHER INFORMATION: Chemically Synthesized
<220> FEATURE:
```

<223> OTHER INFORMATION: attL0 site

<400> SEQUENCE: 23
agcctgcttt tttatactaa gttggca                                              27

<210> SEQ ID NO 24
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR0 site

<400> SEQUENCE: 24
gttcagcttt tttatactaa cttgagc                                              27

<210> SEQ ID NO 25
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attB1 site

<400> SEQUENCE: 25
agcctgcttt tttgtacaaa cttgt                                                25

<210> SEQ ID NO 26
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP1 site

<400> SEQUENCE: 26
gttcagcttt tttgtacaaa gttggca                                              27

<210> SEQ ID NO 27
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL1 site

<400> SEQUENCE: 27
agcctgcttt tttgtacaaa gttggca                                              27

<210> SEQ ID NO 28
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR1 site

<400> SEQUENCE: 28
gttcagcttt tttgtacaaa cttgt                                                25

<210> SEQ ID NO 29
<211> LENGTH: 25
<212> TYPE: DNA

```
<213> ORGANISM: Artificial Sequence
<220> FEATURE:
<223> OTHER INFORMATION: Chemically Synthesized
<220> FEATURE:
<223> OTHER INFORMATION: attB2 site

<400> SEQUENCE: 29
acccagcttt cttgtacaaa gtggt                                         25

<210> SEQ ID NO 30
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP2 site

<400> SEQUENCE: 30
gttcagcttt cttgtacaaa gttggca                                       27

<210> SEQ ID NO 31
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL2 site

<400> SEQUENCE: 31
acccagcttt cttgtacaaa gttggca                                       27

<210> SEQ ID NO 32
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR2 site

<400> SEQUENCE: 32
gttcagcttt cttgtacaaa gtggt                                         25

<210> SEQ ID NO 33
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attB5 site

<400> SEQUENCE: 33
caactttatt atacaaagtt gt                                            22

<210> SEQ ID NO 34
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP5 site

<400> SEQUENCE: 34
gttcaacttt attatacaaa gttggca                                       27
```

```
<210> SEQ ID NO 35
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL5 site

<400> SEQUENCE: 35
caactttatt atacaaagtt ggca                                          24

<210> SEQ ID NO 36
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR5 site

<400> SEQUENCE: 36
gttcaacttt attatacaaa gttgt                                         25

<210> SEQ ID NO 37
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attB11 site

<400> SEQUENCE: 37
caacttttct atacaaagtt gt                                            22

<210> SEQ ID NO 38
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP11 site

<400> SEQUENCE: 38
gttcaacttt tctatacaaa gttggca                                       27

<210> SEQ ID NO 39
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL11 site

<400> SEQUENCE: 39
caacttttct atacaaagtt ggca                                          24

<210> SEQ ID NO 40
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR11 site
```

```
<400> SEQUENCE: 40
gttcaacttt tctatacaaa gttgt                                        25

<210> SEQ ID NO 41
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attB17 site

<400> SEQUENCE: 41
caacttttgt atacaaagtt gt                                           22

<210> SEQ ID NO 42
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP17 site

<400> SEQUENCE: 42
gttcaacttt tgtatacaaa gttggca                                      27

<210> SEQ ID NO 43
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL17 site

<400> SEQUENCE: 43
caacttttgt atacaaagtt ggca                                         24

<210> SEQ ID NO 44
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR17 site

<400> SEQUENCE: 44
gttcaacttt tgtatacaaa gttgt                                        25

<210> SEQ ID NO 45
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attB19 site

<400> SEQUENCE: 45
caactttttc gtacaaagtt gt                                           22

<210> SEQ ID NO 46
<211> LENGTH: 27
<212> TYPE: DNA
<213> ORGANISM: Artificial Sequence
<220> FEATURE:
```

<223> OTHER INFORMATION: Chemically Synthesized
<220> FEATURE:
<223> OTHER INFORMATION: attP19 site

<400> SEQUENCE: 46
gttcaacttt ttcgtacaaa gttggca                                               27

<210> SEQ ID NO 47
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL19 site

<400> SEQUENCE: 47 caacttttc gtacaaagtt ggca                                                   24

<210> SEQ ID NO 48
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR19 site

<400> SEQUENCE: 48
gttcaacttt ttcgtacaaa gttgt                                                 25

<210> SEQ ID NO 49
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attB20 site

<400> SEQUENCE: 49 caacttttg gtacaaagtt gt                                                     22

<210> SEQ ID NO 50
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP20 site

<400> SEQUENCE: 50
gttcaacttt ttggtacaaa gttggca                                               27

<210> SEQ ID NO 51
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL20 site

<400> SEQUENCE: 51 caacttttg gtacaaagtt ggca                                                   24

<210> SEQ ID NO 52

```
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR20 site

<400> SEQUENCE: 52
gttcaacttt ttggtacaaa gttgt                                              25

<210> SEQ ID NO 53
<211> LENGTH: 22
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attB21 site

<400> SEQUENCE: 53
caacttttta atacaaagtt gt                                                 22

<210> SEQ ID NO 54
<211> LENGTH: 27
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attP21 site

<400> SEQUENCE: 54
gttcaacttt ttaatacaaa gttggca                                            27

<210> SEQ ID NO 55
<211> LENGTH: 24
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attL21 site

<400> SEQUENCE: 55
caacttttta atacaaagtt ggca                                               24

<210> SEQ ID NO 56
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: attR21 site

<400> SEQUENCE: 56
gttcaacttt ttaatacaaa gttgt                                              25

<210> SEQ ID NO 57
<211> LENGTH: 21
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: oligo 5'ccdB primer

<400> SEQUENCE: 57
```

| ttcttatatt ccccagaaca t | 21 |

<210> SEQ ID NO 58
<211> LENGTH: 23
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: oligo 435 primer

<400> SEQUENCE: 58

| caggctttac actttatgct tcc | 23 |

<210> SEQ ID NO 59
<211> LENGTH: 54
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: 5'GWTA-tcc primer

<400> SEQUENCE: 59

| ggggacaagt ttgtacaaaa aagcaggctc cgaattctta tattccccag aaca | 54 |

<210> SEQ ID NO 60
<211> LENGTH: 56
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: GWT ccmR primer

<400> SEQUENCE: 60

| gggaccactt tgtacaagaa agctgggtcg aattccaggc tttacactttt atgctt | 56 |

<210> SEQ ID NO 61
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: GCTA1 primer

<400> SEQUENCE: 61

| aattgctcat caatttgttg caacg | 25 |

<210> SEQ ID NO 62
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: GCTA2 primer

<400> SEQUENCE: 62

| attttttata atgccaactt tgtac | 25 |

<210> SEQ ID NO 63
<211> LENGTH: 25
<212> TYPE: DNA
<213> ORGANISM: Artificial Sequence
<220> FEATURE:
<223> OTHER INFORMATION: Chemically Synthesized
<220> FEATURE:

<223> OTHER INFORMATION: L1S9 L-forward mut12 sequence

<400> SEQUENCE: 63
gttgcaacaa attgatgagc aatgc                                    25

<210> SEQ ID NO 64
<211> LENGTH: 25
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: L1S9 L-reverse mut12 sequence

<400> SEQUENCE: 64
gttgcaacaa attgatgagc aatta                                    25

<210> SEQ ID NO 65
<211> LENGTH: 23
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: TOPO-1

<400> SEQUENCE: 65
aattcgccct tattccgata gtg                                      23

<210> SEQ ID NO 66
<211> LENGTH: 16
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: TOPO-5

<400> SEQUENCE: 66
caacactatc ggaata                                              16

<210> SEQ ID NO 67
<211> LENGTH: 20
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: CAT TA 3' primer

<400> SEQUENCE: 67
atggagaaaa aaatcactgg                                          20

<210> SEQ ID NO 68
<211> LENGTH: 20
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: CAT TA 5' primer

<400> SEQUENCE: 68
cgccccgccc tgccactcat                                          20

<210> SEQ ID NO 69
<211> LENGTH: 20
<212> TYPE: DNA

```
<213> ORGANISM: Artificial Sequence
<220> FEATURE:
<223> OTHER INFORMATION: Chemically Synthesized
<220> FEATURE:
<223> OTHER INFORMATION: GUS TA 3' primer

<400> SEQUENCE: 69
ttgtttgcct ccctgctgcg                                               20

<210> SEQ ID NO 70
<211> LENGTH: 20
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: GUS TA 5' primer

<400> SEQUENCE: 70
atggtccgtc ctgtagaaac                                               20

<210> SEQ ID NO 71
<211> LENGTH: 3498
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: pCR8/GW vector

<400> SEQUENCE: 71
ctttcctgcg ttatcccctg attctgtgga taaccgtatt accgcctttg agtgagctga    60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca aatccgctcc cggcggattt gtcctactca ggagagcgtt caccgacaaa   420
caacagataa aacgaaaggc ccagtcttcc gactgagcct ttcgttttat ttgatgcctg   480
gcagttccct actctcgcgt taacgctagc atggatgttt tcccagtcac gacgttgtaa   540
aacgacggcc agtcttaagc tcgggcccca ataatgatt ttattttgac tgatagtgac   600
ctgttcgttg caacaaattg atgagcaatg ctttttttata atgccaactt tgtacaaaaa   660
agcaggctcc gaattcttat attccccaga acatcaggtt aatggcgttt ttgatgtcat   720
tttcgcggtg gctgagatca gccacttctt ccccgataac ggagaccggc acactggcca   780
tatcggtggt catcatgcgc cagctttcat ccccgatatg caccaccggg taaagttcac   840
gggagacttt atctgacagc agacgtgcac tggccagggg gatcaccatc cgtcgcccgg   900
gcgtgtcaat aatatcactc tgtacatcca caaacagacg ataacggctc tctctttat    960 aggtgtaaac cttaaactgc atttcaccag cccctgttct cgtcagcaaa agagccgttc  1020
atttcaataa accgggcgac ctcagccatc ccttcctgat tttccgcttt ccagcgttcg  1080
gcacgcagac gacgggcttc attctgcatg gttgtgctta ccagaccgga gatattgaca  1140
tcatatatgc cttgagcaac tgatagctgt cgctgtcaac tgtcactgta atacgctgct  1200
tcatagcata cctcttttg acatacttcg ggtatacata tcagtatata ttcttatacc  1260
gcaaaaatca gcgcgcaaat acgcatactg gtatctggct tttagtaagc cggatcctaa  1320
```

-continued

```
ctcaaaatcc acacattata cgagccggaa gcataaagtg taaagcctgg aattcgaccc    1380
agctttcttg tacaaagttg gcattataaa aataattgc tcatcaattt gttgcaacga     1440
acaggtcact atcagtcaaa ataaaatcat tatttgccat ccagctgata tccctatag     1500 tgagtcgtat tacatggtca tagctgtttc ctggcagctc tggcccgtgt ctcaaaatct    1560
ctgatgttac attgcacaag ataaaaatat atcatcatgc ctcctctaga ccagccagga    1620
cagaaatgcc tcgacttcgc tgctgcccaa ggttgccggg tgacgcacac cgtggaaacg    1680
gatgaaggca cgaacccagt ggacataagc ctgttcggtt cgtaagctgt aatgcaagta    1740
gcgtatgcgc tcacgcaact ggtccagaac cttgaccgaa cgcagcggtg gtaacggcgc    1800
agtggcggtt ttcatggctt gttatgactg ttttttggg gtacagtcta tgcctcgggc     1860
atccaagcag caagcgcgtt acgccgtggg tcgatgtttg atgttatgga gcagcaacga    1920
tgttacgcag cagggcagtc gccctaaaac aaagttaaac atcatgaggg aagcggtgat    1980
cgccgaagta tcgactcaac tatcagaggt agttggcgtc atcgagcgcc atctcgaacc    2040
gacgttgctg gccgtacatt tgtacggctc cgcagtggat ggcggcctga agccacacag    2100
tgatattgat ttgctggtta cggtgaccgt aaggcttgat gaaacaacgc ggcgagcttt    2160
gatcaacgac cttttggaaa cttcggcttc ccctggagag agcgagattc tccgcgctgt    2220
agaagtcacc attgttgtgc acgacgacat cattccgtgg cgttatccag ctaagcgcga    2280
actgcaattt ggagaatggc agcgcaatga cattcttgca ggtatcttcg agccagccac    2340
gatcgacatt gatctggcta tcttgctgac aaaagcaaga gaacatagcg ttgccttggt    2400
aggtccagcg gcggaggaac tctttgatcc ggttcctgaa caggatctat ttgaggcgct    2460
aaatgaaacc ttaacgctat ggaactcgcc gcccgactgg gctggcgatg agcgaaatgt    2520
agtgcttacg ttgtcccgca tttggtacag cgcagtaacc ggcaaaatcg cgccgaagga    2580
tgtcgctgcc gactgggcaa tggagcgcct gccggcccag tatcagcccg tcatacttga    2640
agctagacag gcttatcttg acaagaaga agatcgcttg gcctcgcgcg cagatcagtt    2700
ggaagaattt gtccactacg tgaaaggcga gatcaccaag gtagtcggca ataaccctc     2760 gagccaccca tgaccaaaat cccttaacgt gagttacgcg tcgttccact gagcgtcaga    2820
ccccgtagaa aagatcaaag gatcttcttg agatcctttt tttctgcgcg taatctgctg    2880
cttgcaaaca aaaaaaccac cgctaccagc ggtggtttgt ttgccggatc aagagctacc    2940 aactctttt ccgaaggtaa ctggcttcag cagagcgcag ataccaaata ctgtccttct    3000
agtgtagccg tagttaggcc accacttcaa gaactctgta gcaccgccta catacctcgc    3060
tctgctaatc ctgttaccag tggctgctgc cagtggcgat aagtcgtgtc ttaccgggtt    3120
ggactcaaga cgatagttac cggataaggc gcagcggtcg ggctgaacgg ggggttcgtg    3180
cacacagccc agcttggagc gaacgaccta caccgaactg agatacctac agcgtgagca    3240
ttgagaaagc gccacgcttc ccgaagggag aaaggcggac aggtatccgg taagcggcag    3300
ggtcggaaca ggagagcgca cgagggagct tccaggggga aacgcctggt atctttatag    3360
tcctgtcggg tttcgccacc tctgacttga gcgtcgattt tgtgatgct cgtcagggg      3420 gcggagccta tggaaaaacg ccagcaacgc ggcctttta cggttcctgg ccttttgctg    3480
gccttttgct cacatgtt                                                   3498
```

<210> SEQ ID NO 72
<211> LENGTH: 21
<212> TYPE: PRT
<213> ORGANISM: Artificial Sequence
<220> FEATURE:

<223> OTHER INFORMATION: Chemically Synthesized
<220> FEATURE:
<223> OTHER INFORMATION: TOPO cloning region of pCR8/GW/TOPO

<400> SEQUENCE: 72

Leu Tyr Lys Lys Ala Gly Ser Glu Phe Gly Leu Lys Gly Glu Phe Asp
1               5                   10                  15

Pro Ala Phe Leu Tyr
            20